United States Patent
Eggers et al.

(10) Patent No.: US 6,993,394 B2
(45) Date of Patent: Jan. 31, 2006

(54) SYSTEM METHOD AND APPARATUS FOR LOCALIZED HEATING OF TISSUE

(75) Inventors: Philip E. Eggers, Dublin, OH (US); John L. Ridihalgh, Columbus, OH (US)

(73) Assignee: Calfacion Corporation, Dublin, OH (US)

( * ) Notice: Subject to any disclaimer, the term of this patent is extended or adjusted under 35 U.S.C. 154(b) by 183 days.

(21) Appl. No.: 10/246,347

(22) Filed: Sep. 18, 2002

(65) Prior Publication Data

US 2003/0139787 A1 Jul. 24, 2003

Related U.S. Application Data

(63) Continuation-in-part of application No. 10/201,353, filed on Jul. 23, 2002, now abandoned.
(60) Provisional application No. 60/349,593, filed on Jan. 18, 2002.

(51) Int. Cl.
 *A61F 2/00* (2006.01)

(52) U.S. Cl. .................................. 607/103; 623/1.15
(58) Field of Classification Search ............... 623/1.15, 623/1.2, 1.42–1.43; 607/96, 103
See application file for complete search history.

(56) References Cited

U.S. PATENT DOCUMENTS

| | | | |
|---|---|---|---|
| 2,958,664 A | 11/1960 | Vassiliev et al. |
| 3,252,913 A | 5/1966 | Van Gils et al. |
| 3,422,816 A | 1/1969 | Robinson et al. |
| 3,587,583 A | 6/1971 | Greenberg |
| 3,653,385 A | 4/1972 | Burton |

(Continued)

FOREIGN PATENT DOCUMENTS

| | | |
|---|---|---|
| DE | 34 06 565 C2 | 4/1995 |
| DE | 44 33 502 A1 | 3/1996 |
| EP | 0152963 A2 | 2/1985 |
| EP | 0 152 963 A2 | 8/1985 |
| EP | 0 392 837 A2 | 10/1990 |

(Continued)

OTHER PUBLICATIONS

(38) Magnetic Sensors and Magnetometers, edited by P. Ripka, Artech House, Inc., Norwood, MA, pp 75–127, and 380–391 (2001).
(10) Falk, et al., "Hyperthermia in oncology" *Int. J. Hyperthermia*, 17 (1): 1–18 (2001).
Janetski, et al., "Immunization of cancer patients with autologous cancer–derived heat shock protein gp96 preparations: A pilot study." *Int. J. Cancer* 88: 232–238 (2000).

(Continued)

*Primary Examiner*—Roy D. Gibson
(74) *Attorney, Agent, or Firm*—Mueller and Smith, LPA

(57) ABSTRACT

System method and apparatus for accurately carrying out the in situ heating of a targeted tissue. Small implants are employed with the targeted tissue which exhibit an abrupt change of magnetic permeability at an elected Curie temperature. The permeability state of the implant is monitored utilizing a magnetometer. The implants may be formed as a setpoint temperature determining component combined with a non-magnetic heater component to enhance the tissue heating control of the system. With the system, a very accurate quantum of heat energy can be supplied to a neoplastic lesion or tissue carrying infectious disease so as to maximize the induction of heat shock proteins. The system also may be utilized in conjunction with non-magnetic arterially implanted stents for the hyperthermia therapy treatment of restenosis and in conjunction with the mending of boney tissue.

102 Claims, 53 Drawing Sheets

U.S. PATENT DOCUMENTS

| | | | |
|---|---|---|---|
| 3,837,910 | A | 9/1974 | Van der Laan, et al. |
| 3,948,785 | A | 4/1976 | Berchtold |
| 4,074,249 | A | 2/1978 | Minasy |
| 4,091,813 | A | 5/1978 | Shaw et al. |
| 4,138,998 | A | 2/1979 | Nowogrodzki |
| 4,207,896 | A | 6/1980 | Shaw |
| 4,209,017 | A | 6/1980 | Shaw |
| 4,323,056 | A | 4/1982 | Borrelli et al. |
| 4,364,377 | A | 12/1982 | Smith |
| 4,364,390 | A | 12/1982 | Shaw |
| 4,369,345 | A | 1/1983 | Czerlinski |
| 4,520,249 | A | 5/1985 | Czerlinski |
| 4,545,368 | A | 10/1985 | Rand et al. |
| 4,574,782 | A | 3/1986 | Borrelli et al. |
| 4,690,130 | A | 9/1987 | Mirell |
| 4,695,713 | A | 9/1987 | Krumme |
| 4,798,215 | A | 1/1989 | Turner |
| 4,807,620 | A | 2/1989 | Strul et al. |
| 4,846,496 | A | 7/1989 | Wiksell et al. |
| 4,869,247 | A | 9/1989 | Howard, III et al. |
| 4,979,518 | A | 12/1990 | Itoh et al. |
| 4,979,948 | A | 12/1990 | Geddes et al. |
| 4,983,159 | A | 1/1991 | Rand |
| 5,057,095 | A | 10/1991 | Fabian |
| 5,067,952 | A | 11/1991 | Gudov et al. |
| 5,078,736 | A | 1/1992 | Behl |
| 5,087,256 | A | 2/1992 | Taylor et al. |
| 5,098,429 | A | 3/1992 | Sterzer |
| 5,099,756 | A | 3/1992 | Franconi et al. |
| 5,108,359 | A | 4/1992 | Granov et al. |
| 5,133,710 | A | 7/1992 | Carter, Jr. et al. |
| 5,134,370 | A | 7/1992 | Jefferts et al. |
| 5,197,940 | A | 3/1993 | Sievert et al. |
| 5,203,782 | A | 4/1993 | Gudov et al. |
| 5,251,645 | A | 10/1993 | Fenn |
| 5,300,750 | A * | 4/1994 | Carter et al. ............. 219/605 |
| 5,329,085 | A | 7/1994 | Cowell et al. |
| 5,378,879 | A | 1/1995 | Monovoukas |
| 5,425,731 | A | 6/1995 | Daniel et al. |
| 5,429,583 | A | 7/1995 | Paulus et al. |
| 5,433,708 | A | 7/1995 | Nichols et al. |
| 5,447,843 | A | 9/1995 | McGuire et al. |
| 5,456,718 | A | 10/1995 | Szymaitis |
| 5,468,210 | A | 11/1995 | Matsui et al. |
| 5,490,840 | A | 2/1996 | Uzgiris et al. |
| 5,494,035 | A | 2/1996 | Leuthold et al. |
| 5,527,337 | A | 6/1996 | Stack et al. |
| 5,571,153 | A | 11/1996 | Wallsten |
| 5,611,798 | A | 3/1997 | Eggers |
| 5,690,847 | A | 11/1997 | LaValley et al. |
| 5,715,837 | A | 2/1998 | Chen |
| 5,810,888 | A | 9/1998 | Fenn |
| 5,824,005 | A | 10/1998 | Motamedi et al. |
| 5,830,179 | A | 11/1998 | Mikus et al. |
| 5,830,464 | A | 11/1998 | Srivastava |
| 5,853,752 | A | 12/1998 | Unger et al. |
| 5,906,636 | A | 5/1999 | Casscells et al. |
| 5,919,479 | A | 7/1999 | Zhang et al. |
| 5,928,217 | A | 7/1999 | Mikus et al. |
| 5,935,576 | A | 8/1999 | Srivastava |
| 5,976,067 | A | 11/1999 | Tucker et al. |
| 6,007,474 | A | 12/1999 | Rydell |
| 6,022,308 | A | 2/2000 | Williams |
| 6,074,337 | A | 6/2000 | Tucker et al. |
| 6,081,749 | A | 6/2000 | Ingle et al. |
| 6,083,148 | A | 7/2000 | Williams |
| 6,139,536 | A | 10/2000 | Mikus et al. |
| 6,143,019 | A | 11/2000 | Motamedi et al. |
| 6,165,209 | A | 12/2000 | Patterson et al. |
| 6,167,313 | A * | 12/2000 | Gray et al. ............... 607/103 |
| 6,174,276 | B1 | 1/2001 | Blackwell |
| 6,176,872 | B1 | 1/2001 | Miksza |
| 6,179,789 | B1 | 1/2001 | Tu et al. |
| 6,179,824 | B1 | 1/2001 | Eggers et al. |
| 6,179,867 | B1 | 1/2001 | Cox |
| 6,030,618 | A1 | 2/2001 | Srivastava |
| 6,183,409 | B1 | 2/2001 | Armini |
| 6,186,941 | B1 | 2/2001 | Blackwell |
| 6,187,037 | B1 | 2/2001 | Satz |
| 6,187,312 | B1 | 2/2001 | Srivastava |
| 6,190,302 | B1 | 2/2001 | Mosseri et al. |
| 6,190,355 | B1 | 2/2001 | Hastings |
| 6,190,379 | B1 | 2/2001 | Heuser et al. |
| 6,190,404 | B1 | 2/2001 | Palmaz et al. |
| 6,192,095 | B1 | 2/2001 | Sekine et al. |
| 6,193,669 | B1 | 2/2001 | Degany et al. |
| 6,195,411 | B1 | 2/2001 | Dinsmore |
| 6,196,996 | B1 | 3/2001 | Teirstein |
| 6,197,051 | B1 | 3/2001 | Zhong |
| 6,197,296 | B1 | 3/2001 | Davies et al. |
| 6,200,259 | B1 | 3/2001 | March |
| 6,200,307 | B1 | 3/2001 | Kasinkas et al. |
| 6,203,508 | B1 | 3/2001 | Ren et al. |
| 6,206,916 | B1 | 3/2001 | Furst |
| 6,245,347 | B1 | 6/2001 | Zhang et al. |
| 6,303,142 | B1 | 10/2001 | Zhang et al. |
| 6,319,242 | B1 | 11/2001 | Patterson et al. |
| 6,319,251 | B1 | 11/2001 | Tu et al. |
| 6,451,044 | B1 | 9/2002 | Naghavi et al. |
| 6,497,647 | B1 | 12/2002 | Tucker |
| 6,565,887 | B1 | 5/2003 | Gray et al. |
| 2002/0008336 | A1 | 1/2002 | Otobe et al. |
| 2002/0183829 | A1 * | 12/2002 | Doscher et al. ............. 623/1.15 |
| 2003/0163187 | A1 * | 8/2003 | Weber ....................... 623/1.2 |

FOREIGN PATENT DOCUMENTS

| | | |
|---|---|---|
| EP | 0 459 520 A2 | 4/1991 |
| EP | 0 459 520 A3 | 4/1991 |
| EP | 0 970 724 A2 | 1/2000 |
| EP | 1 036 574 A1 | 9/2000 |
| GB | 2 102 127 A | 1/1983 |
| RU | 2082458 C1 | 6/1997 |
| WO | WO 00/38602 | 7/2000 |
| WO | WO 00/57818 | 10/2000 |

OTHER PUBLICATIONS

Yedavelli, S.P.K., et al., "Preventive and therapeutic effect of tumor derived heat shock protein, gp96, in an experimental prostate cancer model." *Int. J. Molecular Med.* 4: 243–248 (1999).

Cetas, et al., "A Ferrite Corel Metallic Sheath Thermoseed for Interstitial Thermal Therapies", *IEEE Trans. On Biomed. Eng.*, 45 (1) (1998).

(37) Ajishi, Yoshifumi, et al., "Preparation and Evaluation of Temperature Sensitive Magnetic Thin film With Low Curie Temperature", *T. IEEE Japan*, vol. 118–A, (2): 158–163 (1998).

Paulus, et al., "Thermal Ablation of Canine Prostate Using Interstitial Temperature Self–Regulating Seeds: New Treatment for Prostste Cancer", *J. of Endourology* 11 (4)s: 295–300 (1997).

(7) Arkin, H. et al., "Recent Development in Modeling Heat Transfer in Blood Perfused Tissue," *IEEE Transactions on Bio–Medical Engineering* 41 (2) 97–107 (1994).

Wu, B., et al., "Antitumor effects of Interleukin 7 in combination with local hyperthermia in mice bearing B 16a melnoma cells." *Stem Cells* 11: 412–421 (1993) [Abstract Only].

Haider, Shah A., et al, "Power Absorption in Ferromagnetic Implants from Radio Frequency Magnetic Fields and the Problem of Optimization", IEEE Transactions on Microwave Theory and Techniques, vol. 39, No. 11 (1991).

(36) Hynynen, et al., "Hyperthermia in Cancer Treatment" *Investigative Radiology* 25: 824–834 (1990).

Stuchly, et al., "Measurements of Electromagnetic Fields in Biomedical Applications", *CRC Critical Reviews in Biomedical Engineering*, 14 (3): 241–288 (1987).

(5) Brezovich, et al., "Practical Aspects of Ferromagnetic Thermoseed Hyperthermia," *Radiologic Clinics of North America* 27:589–682 (1989).

(4) Holman, R. A., Letter "Hyperthermia and Cancer", *Lancet*, pp. 1027–1029 (May 3, 1975).

(2) Strom, et al., "The Biochemical Mechanism of Selective Heat Sensitivity of Cancer Cells—IV. Inhibition of RNA Synthesis." *Europ. J. Cancer* 9:103–112 (1973).

Castagna, et al., "Studies on the Inhibition by Ethionine of Aminoazo Dye Carcinogenesis in Rat Liver." *Cancer Research* 32:1960–1965 (1972).

(1) Muckle, et al., "The Selective Inhibitory Effect of Hyperthermia on the Metabolism and Growth of Malignant Cells" *Brit J. of Cancer* 25:771–778 (1971).

Niernz, M.H., Laser–Tissue Interactions, Fundamentals and Applications Springer, pp. 77–80 (2002).

(10) Falk, et al., "Hyperthermia In Oncology", *Int. J. Hyperthermia* 17: 1–18 (2001).

(8), (39) Kong, et al., "Efficiency of Liposomes and Hyperthermia in a Human Tumor Xenograft Model: Importance of Triggered Drug Release", *Cancer Research 60*: 6950–6957 (2000).

(9) Chung, J.E., et al., "Thermo–Responsive Drug Delivery From Polymeric Micelles Using Block Co–Polymers of Poly (N–isopropylaerylamide–b–butylmethaerylate) and Poly (butylmethacrylate)," *Journal of Controlled Release* (Netherlands), 62 (2): 115–127 (Nov. 1, 1999).

Henriques, F.C. "Studies of Thermal Injury: V. The predictability and the significance of thermally induced rate processes leading to irreversible epidermal injury." *Archives of Pathology* 4: 489–502 (1947).

(47) Ito, A., Shinkai, M., Honda, H., Wakabayashi, T., Yoshida, J., and Kobayashi, T., "Augmentation of MHC Class I Antigen Presentation via Heat Shock Protein Expression by Hyperthermia." *Cancer Immunol. Immunother.*, 50: 515–522 (2001).

Schiaffonati, et al., "Hyperthermia induces gene expression of heat shock protein 70 and phosphorylation of mitogen activated protein kinases in the rat cerebellum", *Neuros, Ltrs* 312: 75–78 (2001).

Wang et al., "Characterization of Heat Shock Protein 110 and Glucose–Regulated Protein 170 as Cancer Vaccines and the Effect of Fever–Range Hyperthermia on Vaccine Activity", *J. of Imm.* 165: 490–497 (2001).

(12) Anderson, et al., "Heat, heat shock, heat shock protein and death: a central link in innate and adaptive immune responses" *Immunology Letters*, 74: 35–39 (2000).

Braiden, et al., "Eradication of Breast Cancer Xenografts by Hyperthermic Suicide Gene Therapy under the Control of the Heat Shock Protein Promoter", *Human Gene Therapy* 11: 2453–2463 (2000).

(48) Jolly, Caroline and Morimoto, Richard I., "Review: Role of the Heat Shock Response and Molecular Chaperones in Oncogenesis and Cell Death." *Journal of the National Cancer Institute*, 92 (19): pp 1564–1572 (Oct. 4, 2000).

Binder, et al., "CD91: a receptor for heat shock protein gp96", *Nature Immunology*, 1 (2): 151–155 (2000).

(52) Basu, Sreyashi, Binder, Robert J., Suto, Ryuichiro, Anderson, Kirstin M. and Srivastava, Pramod K., "Necrotic but not Apoptotic Cell Death Releases Heat Shock Proteins, Which Deliver a Partial Maturation Signal to Dendritic Cells and Activate the NF–κβ pathway." *International Immunology*, 12 (11): 1539–1546 (2000).

Huang, et al., "Heat–induced Gene Expression as a Novel Targeted Cancer Gene Therapy Strategy", *Cancer Research* 60: 3435–3439 (Jul. 2000).

Ito, et al., "Induction of TNF–a Gene Expression by Heat Inducible Promoter gadd 153", Jpn. J.Hyperthermic Oncol. 16 (2) (2000).

(44) Morrison, A.J., Rush, S.J., and Brown, I.R., "Heat Shock Transcription Factors and the hsp70 Induction Response in Brain and Kidney of the Hyperthermic Rat During Postnatal Development." *Journal of Neurochemistry*, 75: 363–372 (2000).

Wells, et al., "Heat shock proteins, tumor immunogenicity and antigen presentation: an integrated view", Immunology today, 21 (3): 129–132 (2000).

Vekris et al., "Control of transgene expression using local hyperthermia in combination with a heat–sensitive promoter", *J of Gene Med* 2: 89:96 (2000).

Fehrenbach, et al., "Role of Heat Shock Proteins in the Exercise Response", *Exercise Immunology Review*, 5: 57–77 (1999).

Dressel, et al., "Enhanced susceptibility to cytotoxic T lymphocytes without increase of MHC class I antigen expression after conditional overexpression of heat shock protein 70 in target cells", *Eur. J. Immunol.* 29: 3925–3935 (1999).

Housby, et al., "Non–Steroidal Anti–Inflammatory Drugs Inhibit The Expression Of Cytokines And Induce HSP70 In Human Monocytes", *CYTOKINE*, 11 (5) 347–358 (May 1999).

(13) Srivastava, et al., "Heat Shock Proteins Come of Age: Primitive Functions Acquire New Role in an Adaptive World" *Immunity*, 8 (6), pp 657–665 (1998).

Edwards, "Apoptosis, the heat shock response, hyperthermia, birth defects, disease and cancer. Where are the common links?", *Cell Stress of Chaperones* 3 (4): 213–220 (1998).

Ménoret, et al., "Heat–Shock Protein–Based Anticancer Immunotherapy: An Idea Whose Time Has Come", *Sem. In Oncology* 25 (6) 654–660 (Dec. 1998).

(43) Yanase, et al., "Antitumor Immunity Induction by Intracellular Hyperthermia Using Magnetite Cationic Liposomes", *Jpn J. Cancer Res.* 89: 775–782, (Jul. 1998).

(49) Melcher, A. Todryk, S, Hardwick, N., Ford, M., Jacobson, M., Vile, R.G., "Tumor Immunogenicity is Determined by the Mechanism of Cell Death via Induction of Heat Shock Protein Expression." *Nature Medicine*, 4 (5): 581–587 (1998).

Satyal, et al., "Negative regulation of the heat shock transcriptional response by HSPBI", *Genes & Development* 12: 1962–1974 (1998).

(50) Albert, M.L. et al., "Dendritic Cells Acquire Antigen from Apoptotic Cells and Induce Class I Restricted CTLs." *Nature*, 392: 86–89 (Mar. 5, 1998).

Xu, et al., "Intracellular distribution of hsp70 during long duration moderate hyperthermia", *Int. J. Hyperthermia* 14 (2): 211–225 (1998).

Wells, et al., "Hsp72—mediated augmentation of MHC class I surface expression and endogenous antigen presentation", *International Immunology*, 10 (5): 609–617(1998).

Peper, et al., "A mathematical model of the hsp70 regulation in the cell", *Int. J. of Hyperthermia*, 14 (1): 97–124 (1998).

Benndorf, et al., "Cellular Stress Response: Stress Proteins—Physiology and Implications for Cancer", *Recent Results in Cancer Research*, 143: 129–144 (1997).

Speiser et al., "Self Antigens Expressed by Solid Tumors Do Not Efficiently Stimulate Naïve or Activated T Cells: Implications for Immunotherapy", *J. Exp. Med.* 186 (5): 645–653 (1997).

(46) Tanabe, M., Nakai, A., Kawazoe, Y., and Nagata, K., "Different Thresholds in the Responses of Two Heat Shock Transcription Factors, HSF1 and HSF3*." *Journal of Biological Chemistry*, 272: 15389–15395 (1997).

Peng, et al., "Purification of immunogenic heat shock protein 70–peptide com–plexes by ADP–affinity chromatography" *J. of Imm. Meth.* 204: 13–21(1997).

Freeman, et al., "Immune system in suicide–gene therapy" (Commentary) *The Lancet*, 349: 2–3 (Jan. 4, 1997).

Blachere, et al., "Heat Shock Protein—Peptide Complexes, Reconstituted In Vitro, Elicit Peptide–specific Cytotoxic T Lymphocyte Response and Tumor Immunity", *J. Exp. Med*, 186 (8): 1315–1322 (1997).

(40) Tamura, Y., Peng, P., Liu, K., Daou, M. and Srivastava, P.K., "Immunotherapy of Tumors with Autologous Tumor–Derived Heat Shock Protein Preparations." *Science*, 278: 117–120 (1997).

Cahill, et al., "Transcriptional Repression of the Prointerleukin 1B Gene by Heat Shock Factor 1*", *Biological Chem.*, 271 (40): 24874–2487 (1996).

Wei, et al., "Induction of Autologous Tumor Killing by Heat Treatment of Fresh Human Tumor Cells: Involvement of γδ T–cells and Heat Shock Protein 70", *Cancer Research*, 56: 1104–1110 (1996).

Liu, et al., "Letter to Editor", *Int. J. Hyperthermia*, 12 (2): 301–302 (1996).

(33) Morimoto, R.I., et al., "The transcriptional regulation of heat shock genes: A plethora of heat shock factors and regulatory conditions." in *Stress Inducible Responses*, ed. by Feige et al., Springer Verlag, Boston pp. 120, 139–163 (1996).

Arnold, et al., "Cross–priming of minor histocompatibility antigen–specific cytotoxic T cells upon immunization with the heat shock protein gp96", *J. of Ex. Med.* 182: 885–889 (1995).

(41) Suto, R. & Srivastava, P.K., "A Mechanism for the Specific Immunogenicity of Heat Shock Protein–Chaperoned Peptides." *Science*, 269: 1585–1588 (1995).

Li, et al., "Heat shock proteins, thermotolerance, and their relevance to clinical hyperthermia", *Int J. Hyperthermia* 11 (4) 459–488 (1995).

(27) Columbano, A., "Cell Death: Current Difficulties in Discriminating Apoptosis From Necrosis in the Context of Pathological Processes in Vivo", *Journal of Cellular Biochemistry*, 58; 181–190 (1995).

(31) Matzinger, "Tolerance and Danger and the Extended Family"; *Annu. Rev. Immunol.*, 12: 991–1044 (1994).

Craig, et al., "Heat Shock Proteins and Molecular Chaperones: Mediators of Protein Conformation and Turnover in the Cell" (Meeting Review), *Cell*, 78: 365–372 (Aug. 12, 1994).

Huang, et al., "Role of Bone Marrow—Derived Cells in Presenting MHC Class I—Restricted Tumor Antigens", *Science* 264: 961–965 (May 3, 1994).

Udono, et al., "Cellular requirements for tumor–specific immunity elicited by heat shock proteins: Tumor rejection antigen gp96 primes CD8+ T cells in vivo", *Proc. Natl. Acad. Sci. USA*, 91: 3077–3081 (1994).

Fajardo, et al., "Endothelial cells and hyperthermia", *Int. J. Hyperthermia*, 10 (3): 347–353 (1994).

(28) Georgopoulos, C., Welch, W.J. "Role of the Major Heat Shock Proteins as Molecular Chaperones." *Annu. Rev. of Cell Biol.*, 9: 601–634 (1993).

(29) Hendrick, J.P. and Hartl, F.U., "Molecular Chaperone Functions of Heat–Shock Proteins." *Annu. Rev. of Biochem.*, 62: 349–84 (1993).

(34) Parsell, D.A. & Lindquist, S., "The Function of Heat–Shock Proteins in Stress Tolerance: Degradation and Reactivation of Damaged Proteins." *Annu. Rev. of Genet.*, 27: 437–496 (1993).

Li, Z., and Srivastava, P.K., "Tumor rejection antigen gp96/grp94 is an ATPase: implications for protein folding and antigen presentation." *EMBO Journal* 12 (8): 3143–3151 (1993).

Udono, et al., "Heat shock protein 70–associated peptides elicit specific cancer immunity", *J. of Exp. Med.* 178: 1391–1396 (1993).

Marquez, et al., "HSP 70 Synthesis In Clinical Hyperthermia Patients: Preliminary Results of A New Technique", *J. Radiation Oncology Biol Phys.* 28: 425–430 (1993).

Blachere, et al., "Heat Shock Protein Vaccines Against Cancer", *J. of Immunology* 14: 352–356 (1993).C62.

Paulus, et al., "Heat Shock Protein Response in a Prostate Tumor Model to Interstitial Thermotherapy: Implications for Clinical Treatment", *The Prostate* 23: 263–270 (1993).

(32) Morimoto R.I., "Perspective: Cells in Stress: Transcriptional Activation of Heat Shock Genes." *Science* 259: 1409–10 (1993).

Ciocca, et al., "Response of human breast cancer cells to heat shock and chemotherapeutic drugs." *Cancer Res.* 52: 3648–3654 (Jul. 1, 1992).

Davidoff, et al., "Immune response to p53 is dependent upon p53/HSP70 complexes in breast cancers", *Proc. Natl. Acad. Sci USA* 89: 3439–3442 (Apr. 1992).

(35) Schlesinger, M.J., "Minireview: Heat Shock Proteins." *Journal of Biological Chemistry* 265: 12111–12114 (1990).

Nowak, Jr., "Heat Shock RNA Levels in Brain and Other Tissues After Hyperthermia and Transient Ischemia", *J. of Neurochem.* 54: 451–458 (1990).

(30) Lindquist, S., "The Heat Shock Response." *Annu. Rev. Biochem.*, 55: 1151–91 (1986).

Srivastava, et al., "Tumor Rejection Antigens of Chemically Induced Sarcomas of Inbred Mice", *Proc. Natl. Acad Sci USA* 83 (10) 3407–3411 (1986).

Tomasovic, et al., "Heat stress proteins and experimental cancer metastasis", *Int. J. Hyperthermia* 2(3) 253–266 (1986).

Li, "Thermal Biology and Physiology in Clinical Hyperthermia: Current Status and Future Needs", *Cancer Rev.* (suppl.) 44: 4886s–4893s (1984).

(11) Ritossa, "A New Puffing Pattern Induced By Temperature shock and DNP in Drosophilia" *Experientia*, 18; 571–573 (1962).

(56) "Drug–Coated Stents Poised for Growth", *Cardiovasular Device Update* 7: 8–10 (Sep. 2001).

(55) Simonsen, "Percutaneous intervention arena still expanding for heart disease." *Cardiovascular Device Update* 7 (5): 1–7 (May 2001).

(15) Holmes, Jr., "In–Stent Restenosis", *Reviews in Cardiovascular Medicine*, 2: 115–119 (2001)

(52) Stefanadis, C., et al., "Hyperthermia of Arterial Stented Segments by Magnetic Force: A New Method to Eliminate Initimal Hyperplasia", *Journal of the American College of Cardiology* 37 (2) Supp. A: 2A–3A (2001).

(57) Thury, et al., "Initial Experience With Intravascular Sonotherapy for Prevention of In–Stent Restenosis Safety and Feasibility", *J. of Am. College of Cardiology* 37 (2) Supplement A (2000).

Neschis, et al., "Thermal Preconditioning Before Rat Arterial Balloon Injury", *Arterioscler Thromb Vasc. Biol.* 18: 120–126 (1998).

Lafont, et al., "Remodeling: therapeutic opportunities", *Semin. Intervent. Cardiol.* 2: 177–182 (1997).

Mukherjee, et al., "Association of Antibodies to Heat–Shock Protein–65 with Percutaneous Transluminal Coronary Angioplasty and Subsequent Restinosis", *Lancet* 75 (2): 258–260 (1996).

(17) Meyer, et al., "Stent Wire Cutting During Coronary Directional Artherectomy", *Clin. Cardiol.* 16: 450–452 (1993).

(14) Kaplan, et al., "Healing After Arterial Dilation With Radiofrequency Thermal and Non–Thermal Baloon Angioplasty Systems", *Journal of Investigative Surgery* 6: 33–52 (1993).

(16) Bowerman, et al., "Disruption of Coronary Stent During Artherectomy for Restenosis", *Catherization and Cardio Vascular Diagnosis* 24: 248–251 (1990).

(21) Shui, C., and Scutt, A., "Mild Heat Shock Induces Proliferation, Alkaline Phosphatase Activity, and Mineralization in Human Bone Marrow Stromal Cells and Mg–63 Cells In Vitro." *Journal of Bone and Mineral Research* 16: 731–741 (2001).

Meyer, R.A., et al., "Delayed union of femoral fractures in older rats: decreased gene expression." *BMC Musculoskeletal Disorders* 2: 2, available at http;//www.biomedcentral.com/1471–2474/2/2 (2001).

(22) Huang, C.–C., Chang, W.H., and Liu, H.–C.. "Study on the Mechanism of Enhancing Callus Formation of Fracture by Ultrasonic Stimulation and Microwave Hyperthermia." *Biomed. Eng. Appl. Basis Comm.* 10: 14–17 (1998).

Farley, D., "New Ways to Heal Broken Bones", *FDA Consumer Mag.* at http://www.fda.gov/folac/features/396_bone.html (1996).

Ohashi, "The effect of drilling parameters on bone", *J. of Materials Sci.: Materials in Medl*, 5:225–231 (1994).

(20) Leon, et al., "Effects of Hyperthermia on Bone. II. Heating of Bone in vivo and Stimulation of Bone Growth." *Int. J. Hyperthermia* 9: 77–87 (1993).

(19) Wootton, R., Jennings, P., King–Underwood, C., and Wood, S. J., "The Effect of Intermittent Local Heating on Fracture Healing in the Distal Tibia of the Rabbit" *International Orthopedics*, 14:189–193 (1990).

Giffin, D.J., "The Effect of Power Instrumentation on Bone Healing" *J. of Foot Surg.* 20 (2); 81–83 (1981).

Jacobs et al., "The Effect of Heat on Bone Healing", *Arch. Surg.*, 104; 687–691 (1972).

(25) Zugel, U., Sponaas, A.M., Neckermann, J., Schoel, B., and Kaufmann, S. H.E., "gp96–Peptide Vaccination of Mice Against Intracellular Bacteria." *Infection and Immunity*, 69: 4164–4167 (2001).

Sponaas, et al., "Immunization with gp96 from *Listeria monocytogenes*—Infected Mice is Due to N–Formylated Listerial Peptides", *J. of Immun.* 167:6480–6486 (2001).

Fan, et al., "Recognition of a Sequestered Self Peptide by Influenza Virus—Specific CD8+ Cytolytic T Lymphocytes", *J. of Imm.* 164: 1669–1680 (2000).

(26) Zugel, U., and Kaufmann, S.H.E., "Role of Heat Shock Proteins in Protection from and Pathogenesis of Infectious Diseases." *Clinical Microbiology Reviews*, 12: 19–39 (1999).

Rosenkrands, et al., "Differential T–Cell Recognition of Native and Recombinant Mycobacterium tuberculosis GroES", *Infection and Imm.* 67 (11): 5552–5558 (1999).

(24) Heikema, A., Agsteribbe, E., Wilschut, J., Huckriede, A., "Generation of heat shock protein–based vaccines by intracellular loading of gp96 with antigenic peptides." *Immunology Letters*, 57: 69–74. (1997).

(23) Neiland, Thomas J. F., M. C. Agnes A. Tan, Monique Monnee–van Muijen, Frits Koning, Ada M. Kruisbeek, and Grada M. van Bleek, "Isolation of an immunodominant viral peptide that is endogenously bound to stress protein gp96/GRP94." *Proc. Nat'l Acad. Sci. USA*, 93: 6135–6139 (1996).

Matsuki, H. and K. Murakami. "High Quality Soft Heating Method Utilizing Temperature Dependence of Permeability and Core Loss of Low Curie Temperature Ferrite." IEEE Transactions on Magnetics, vol. MAG–21, No. 5, Sep. 1985. pp. 1927–1929.

Matsui, T., et al., "A novel ferromagnetic thermo–stent for plaque stabilization that self–regulates the temperature," IEEE Trans. Biomed. Eng., 49(6): 621–623 (2002).

Fenn, et al., "An Adaptive Microwave Phased Array For Targeted Heating Of Deep Tumors in Intact Breast: Animal Studies Results" Int. J. Hyperthermia, vol. 15, No. 1, pp. 45–61 (1999).

Feldmann, H.J., et al., "Deep regional hyperthermia comparison between the annular phased array and the Sigma–60 applicator in the same patients.", Int. J. Radiation. Oncol. Biol. Phys. 26: 111–116 (1993).

Feldmann, H.J., et al., "Deep regional hyperthermia comparison between the annular phased array and the Sigma–60 applicator in the same patients." Int. J. Radiation. Oncol. Biol. Phys. 26: 111–116 (1993).

Murakami, K., "The characteristics of ferrite cores with low curie temperature and their application." IEEE Transactions OIn Magnetics Jun. 1965 96–100 (1965).

\* cited by examiner

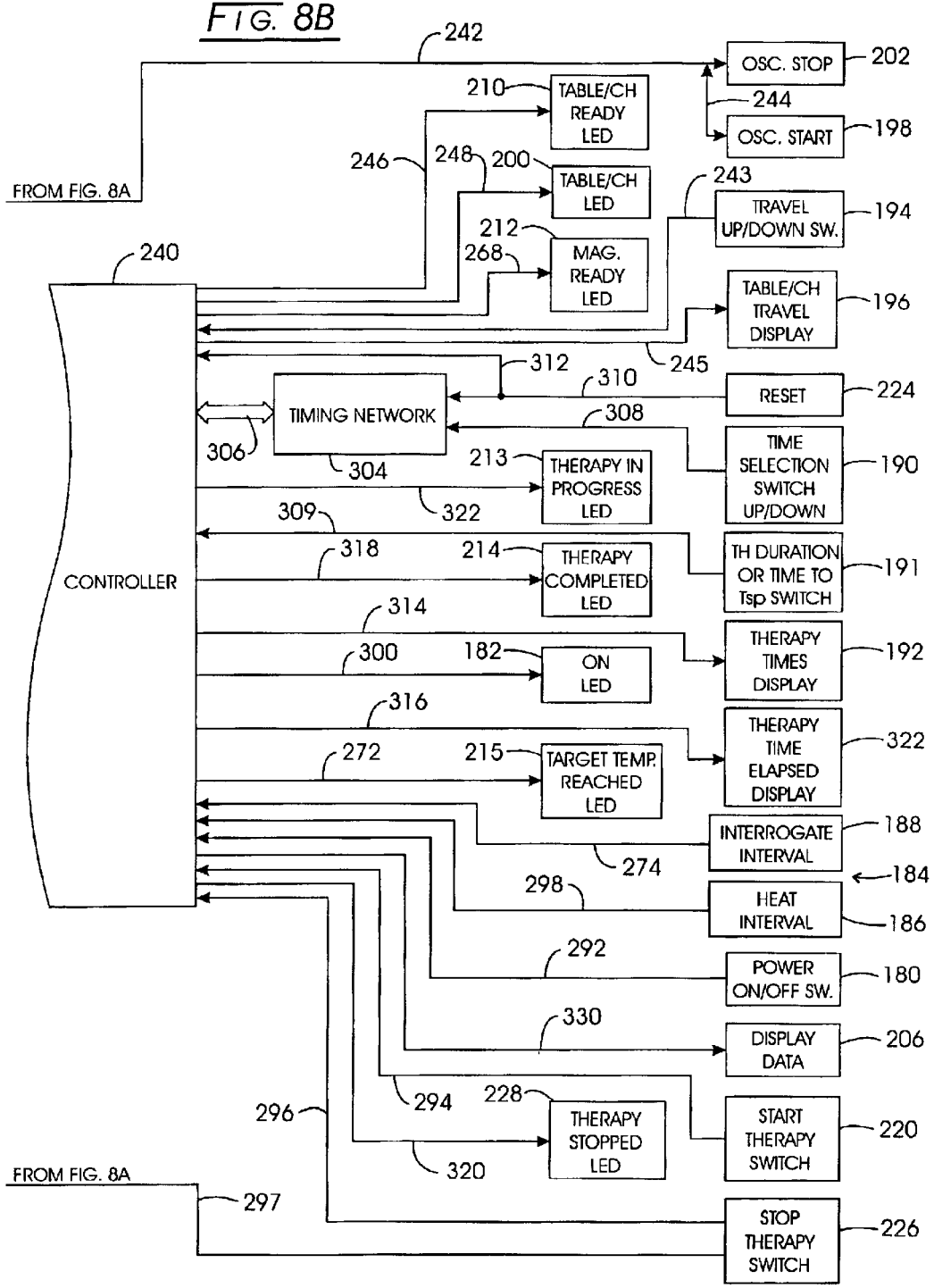

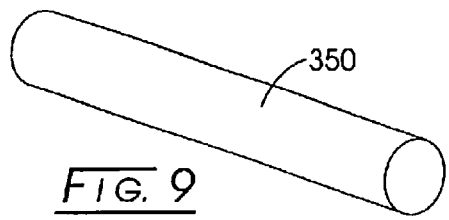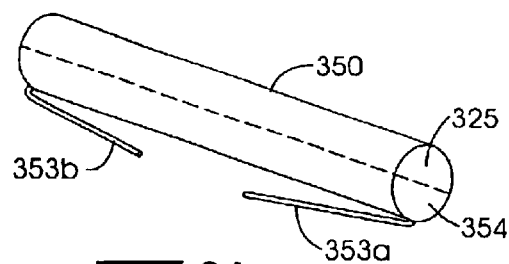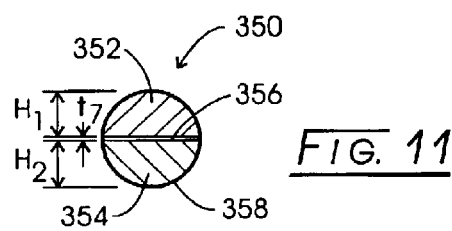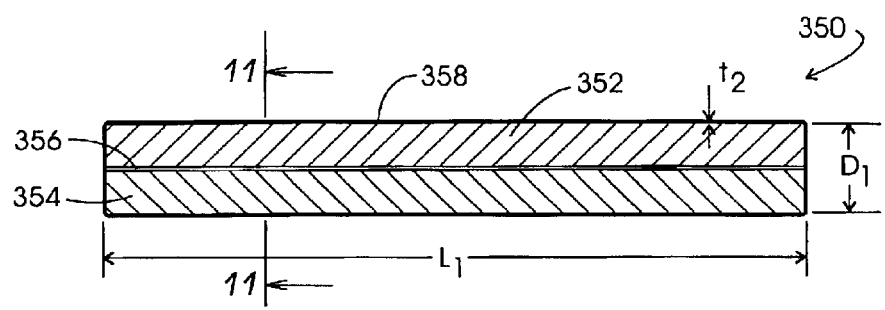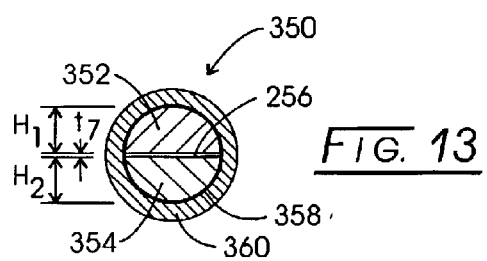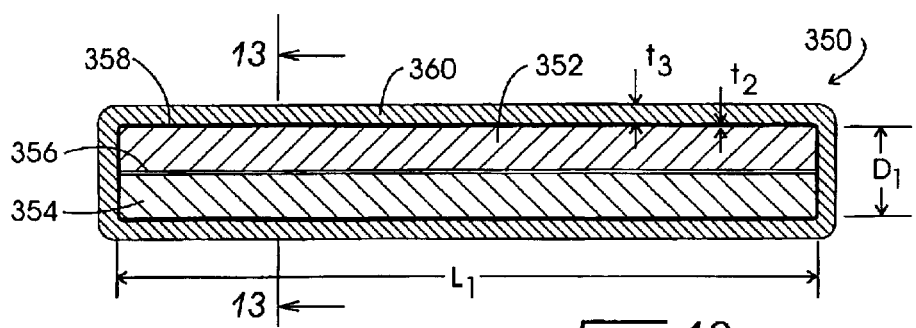

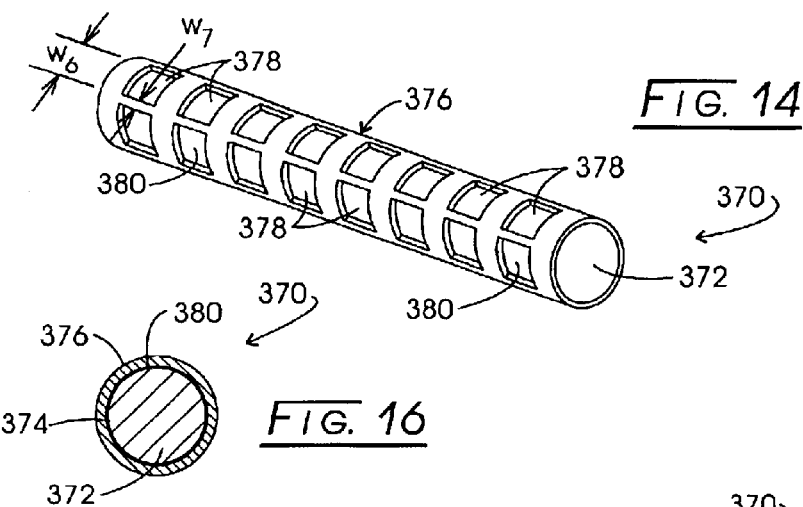
FIG. 14
FIG. 16
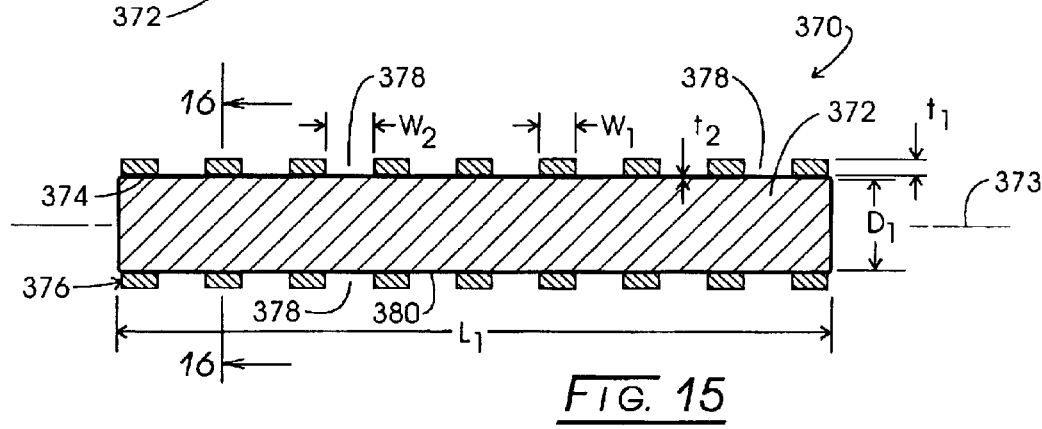
FIG. 15
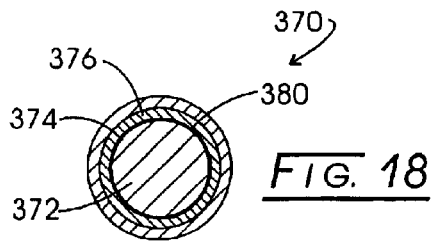
FIG. 18
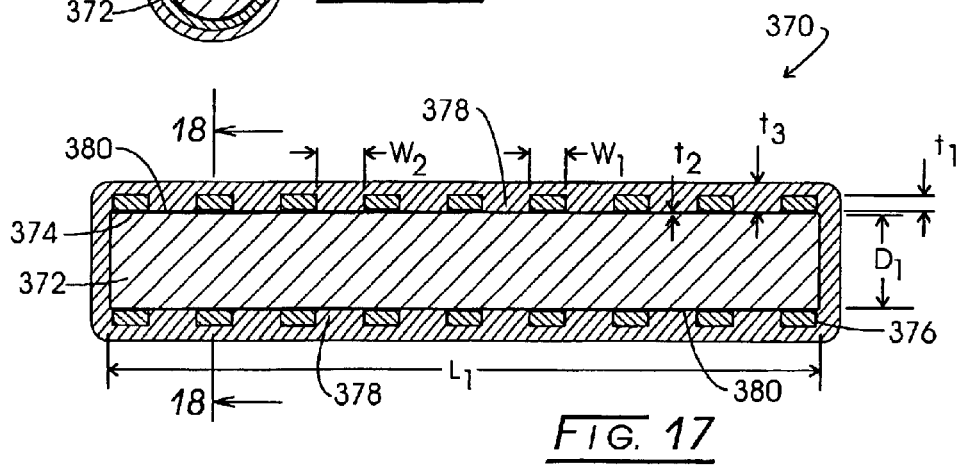
FIG. 17

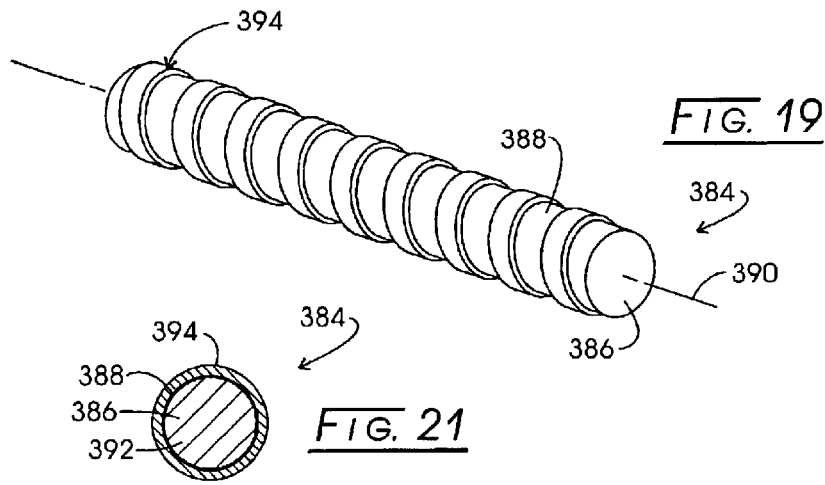
*FIG. 19*
*FIG. 21*
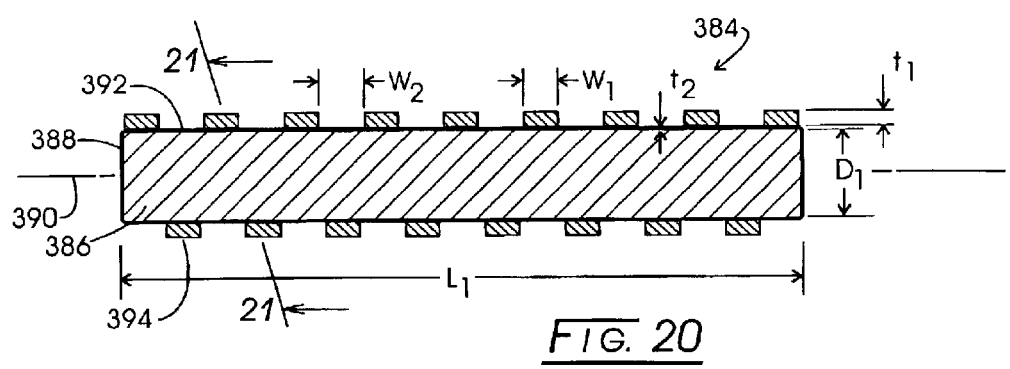
*FIG. 20*
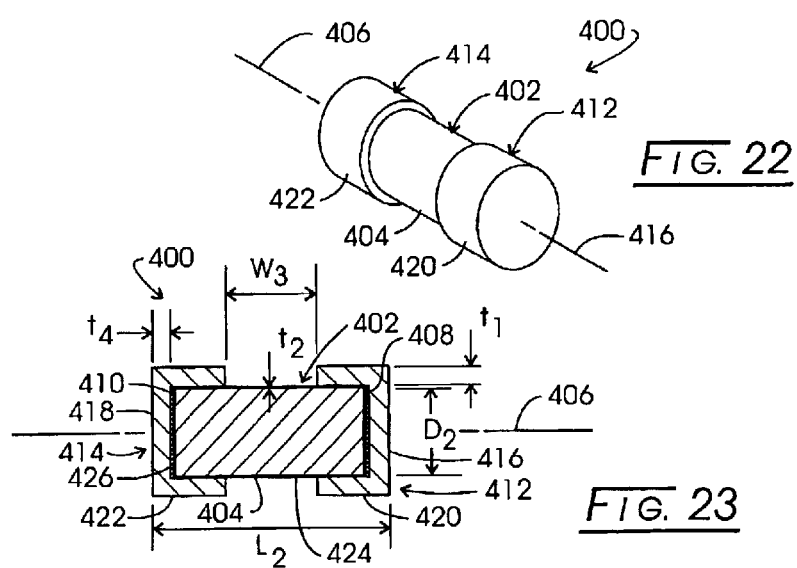
*FIG. 22*
*FIG. 23*

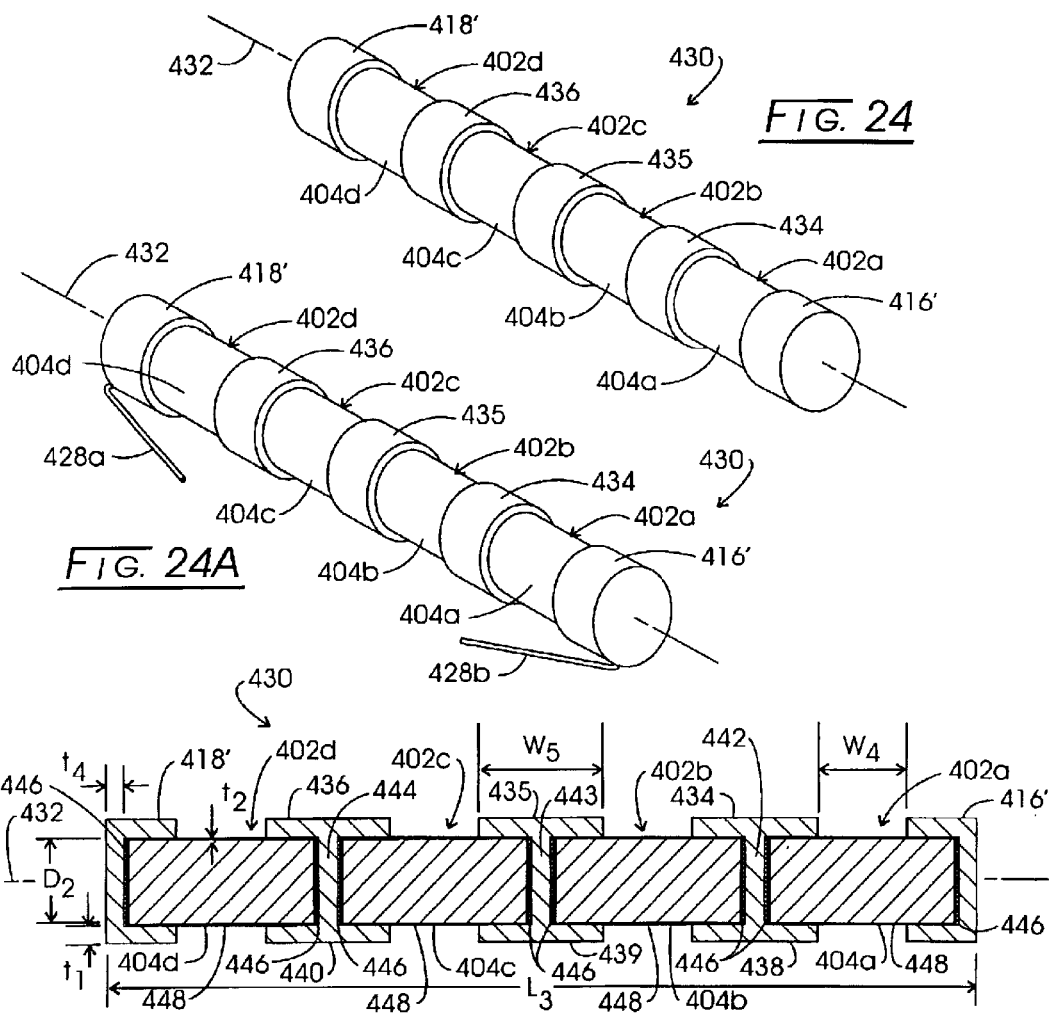
FIG. 24
FIG. 24A
FIG. 25
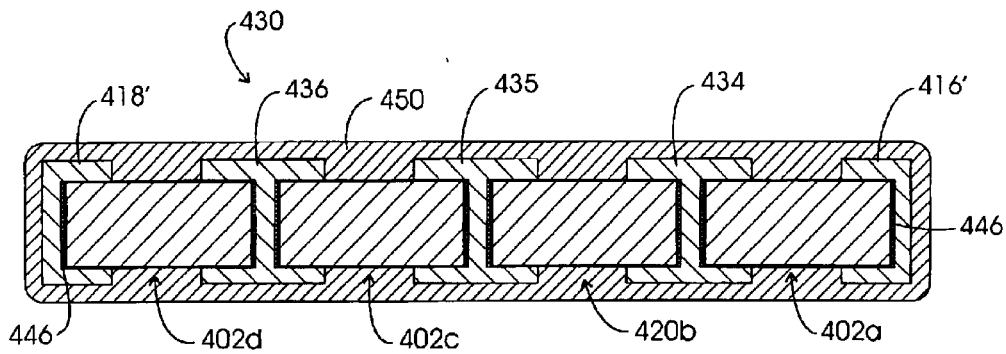
FIG. 26

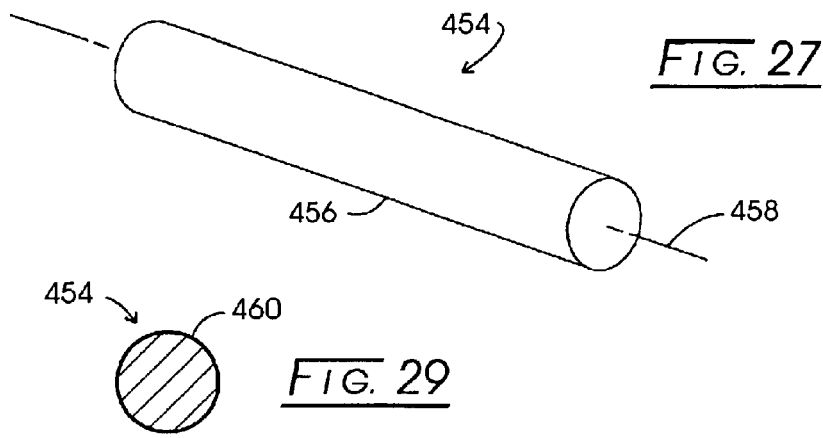
FIG. 27
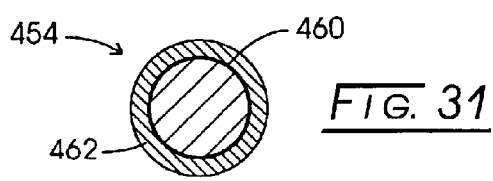
FIG. 29
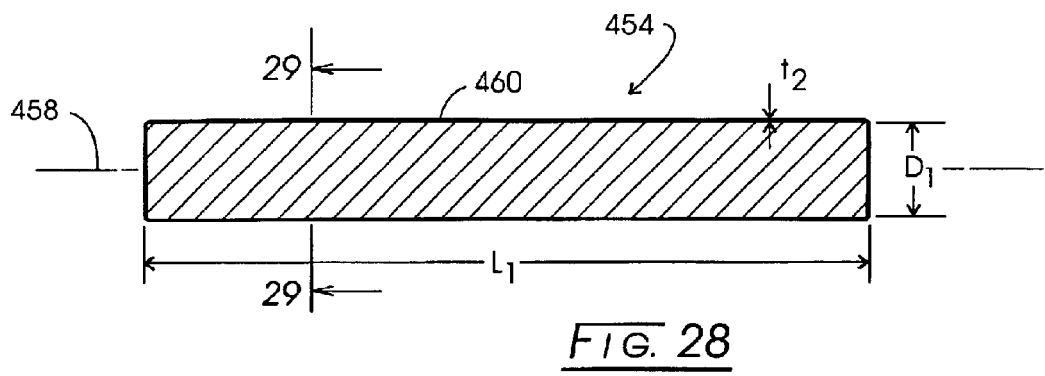
FIG. 28
FIG. 31
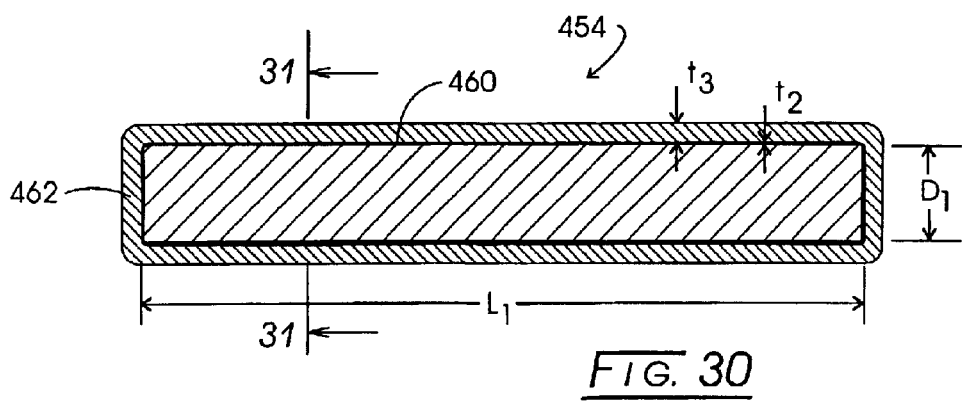
FIG. 30

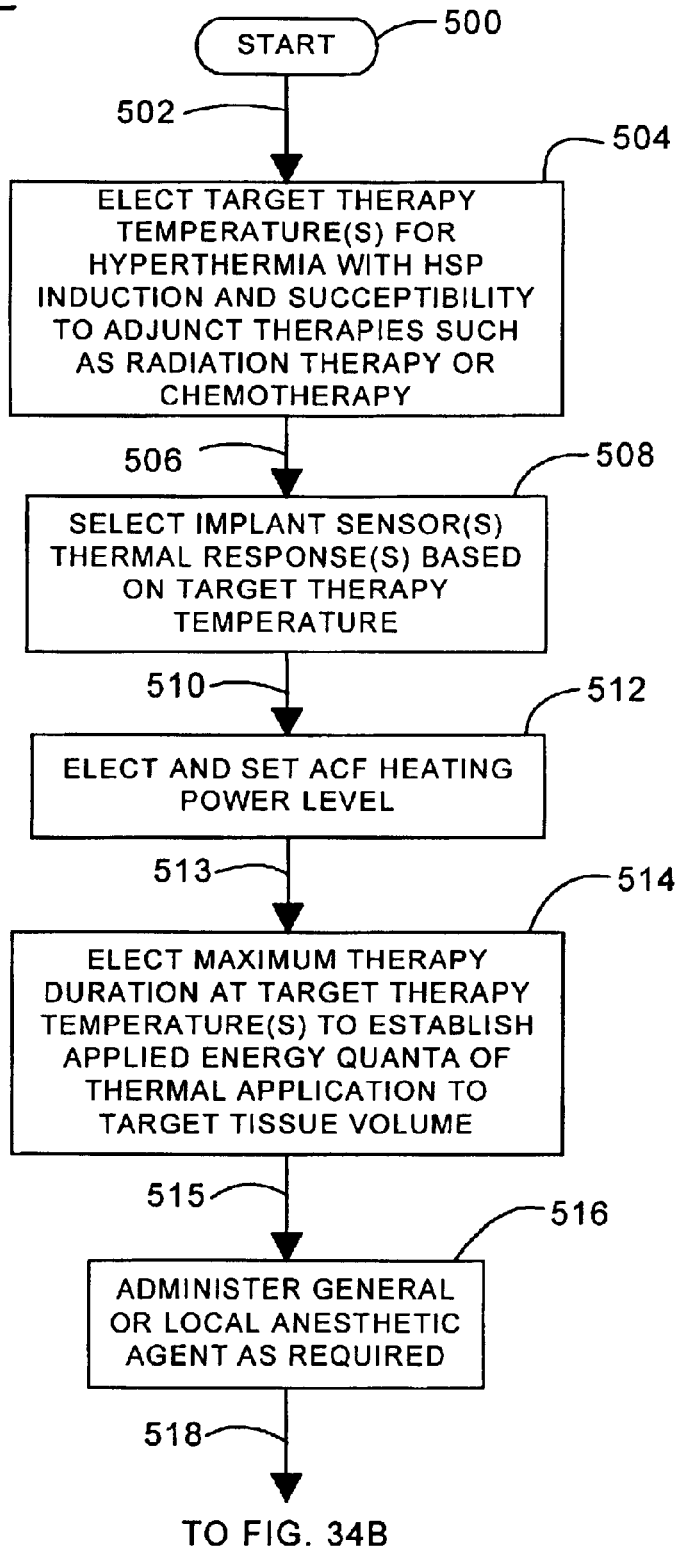

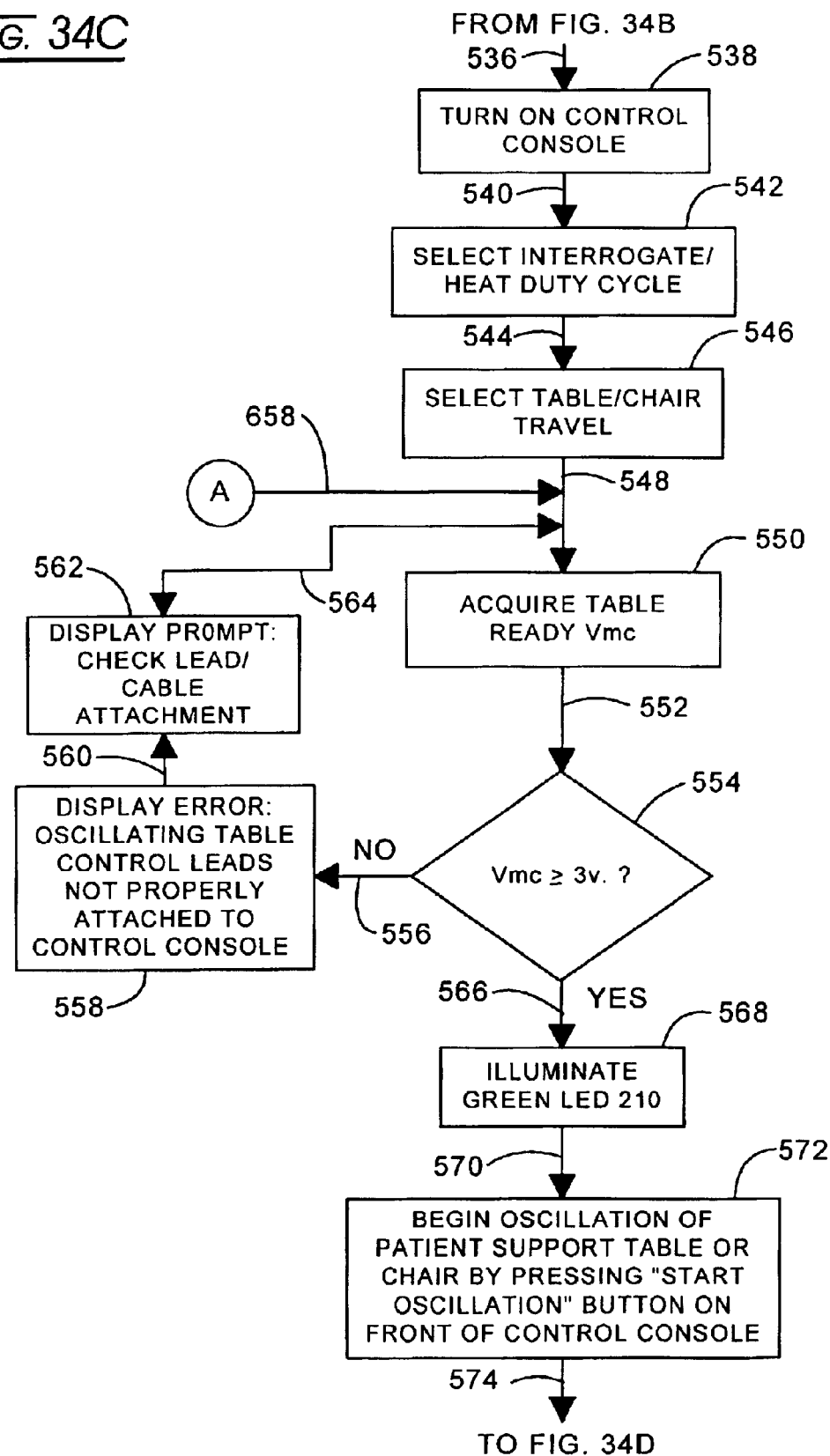

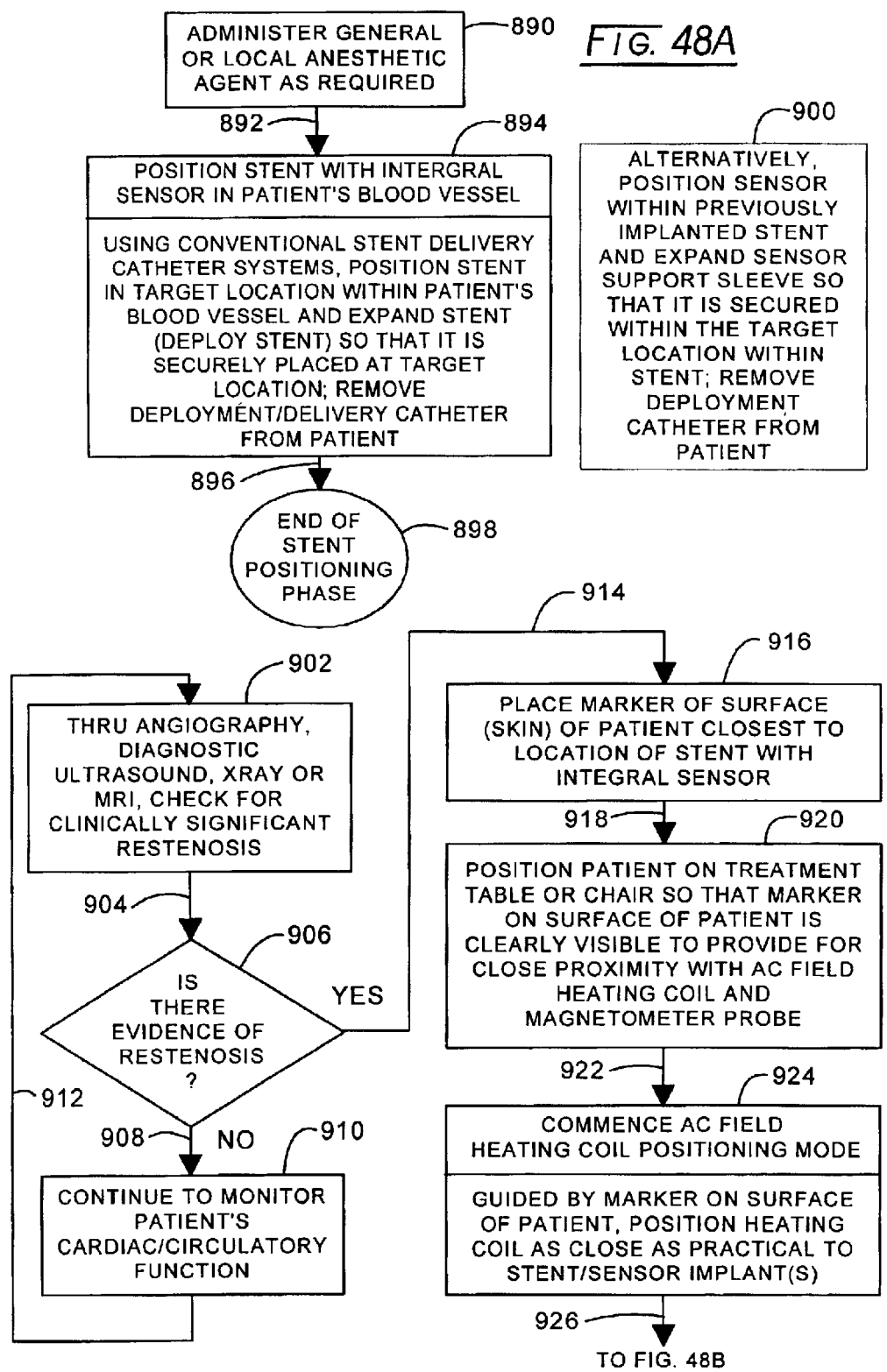

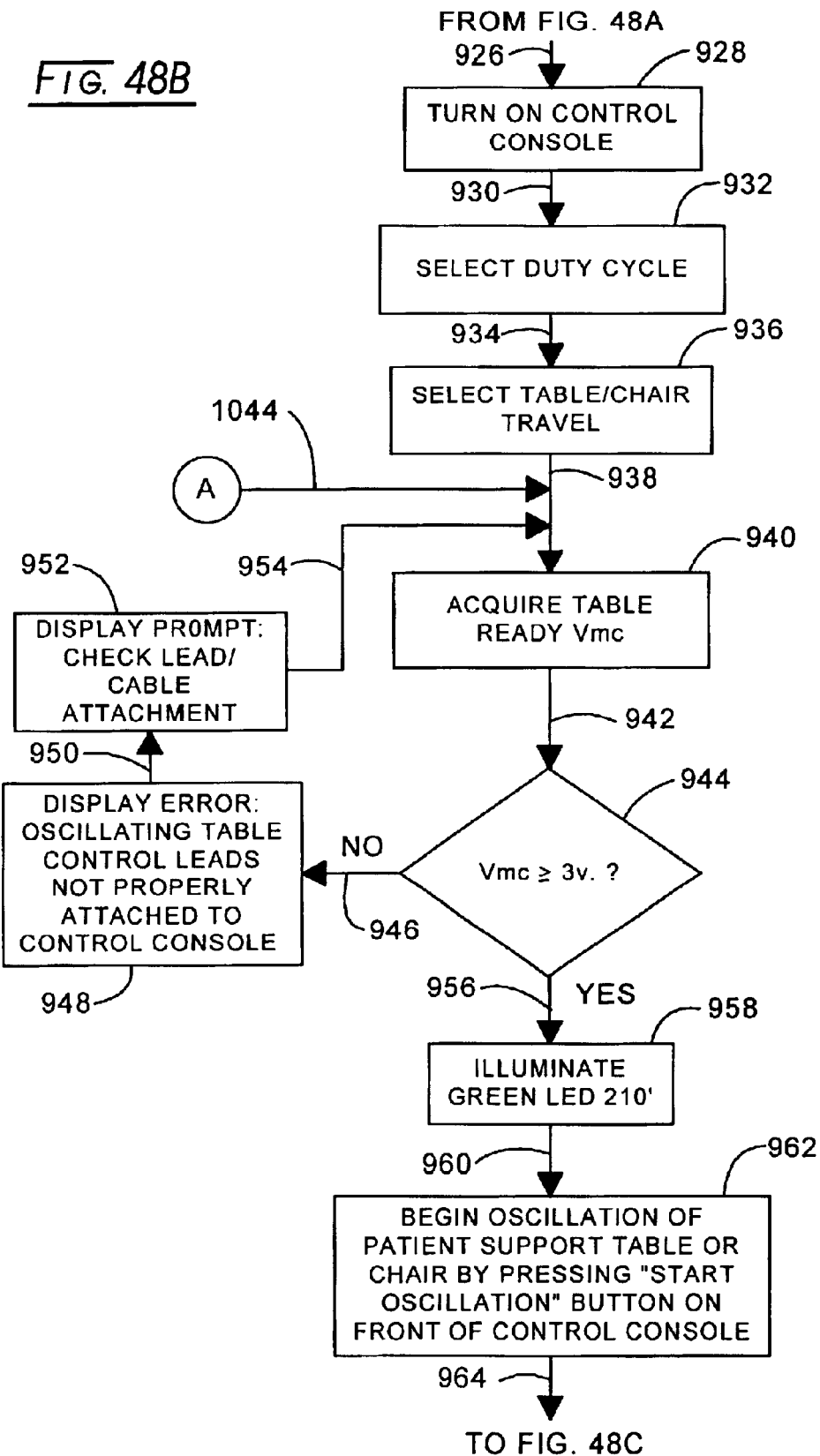

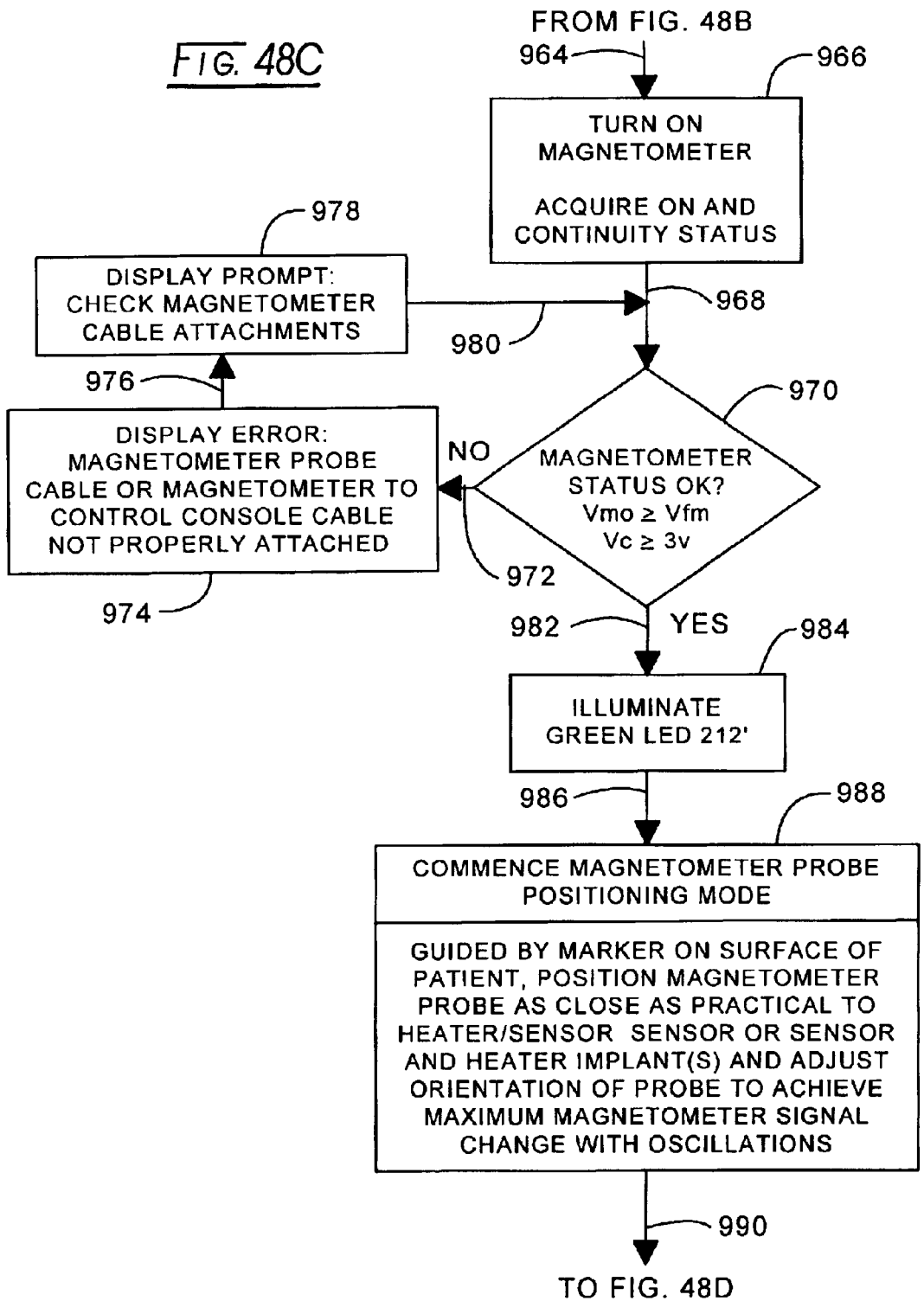

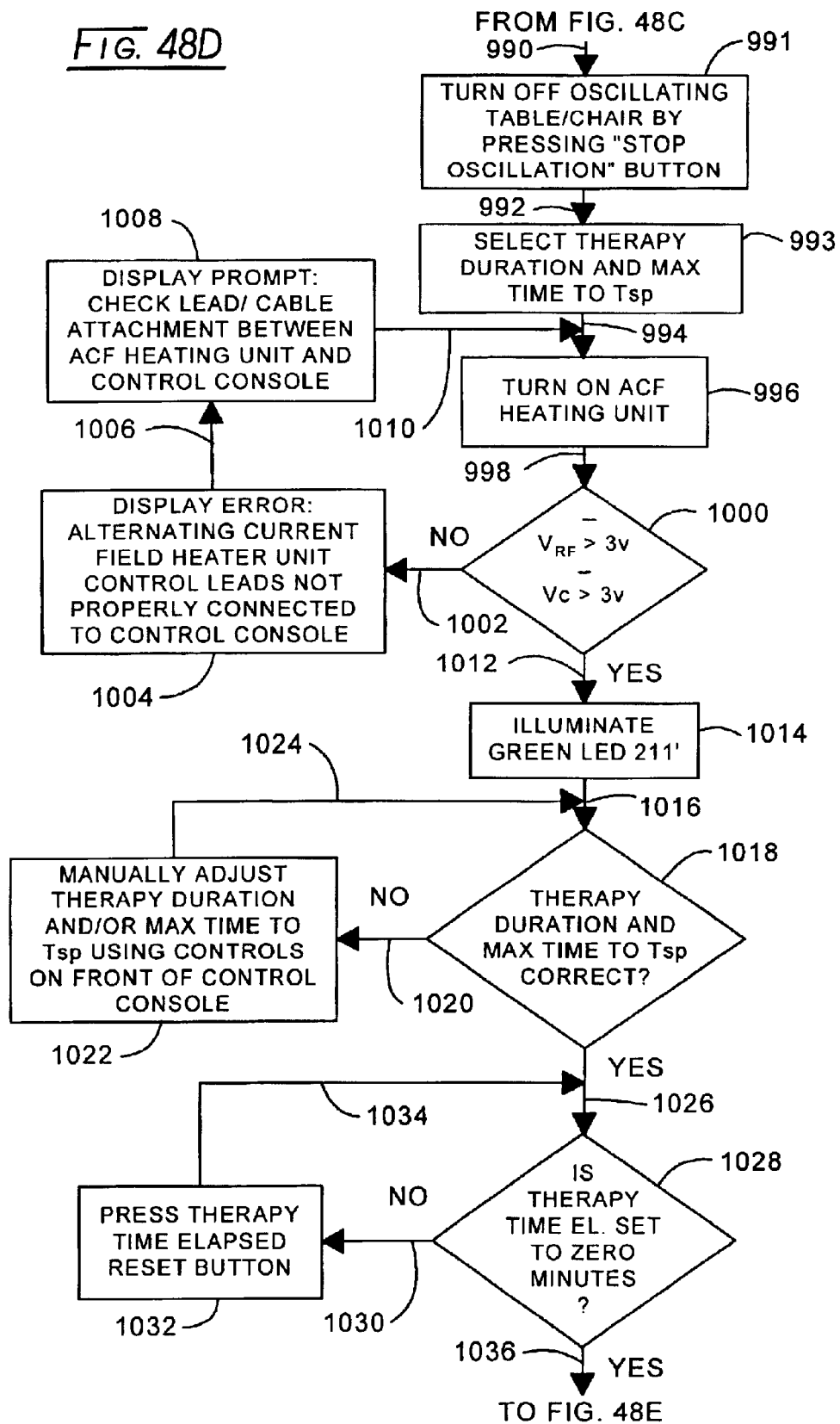

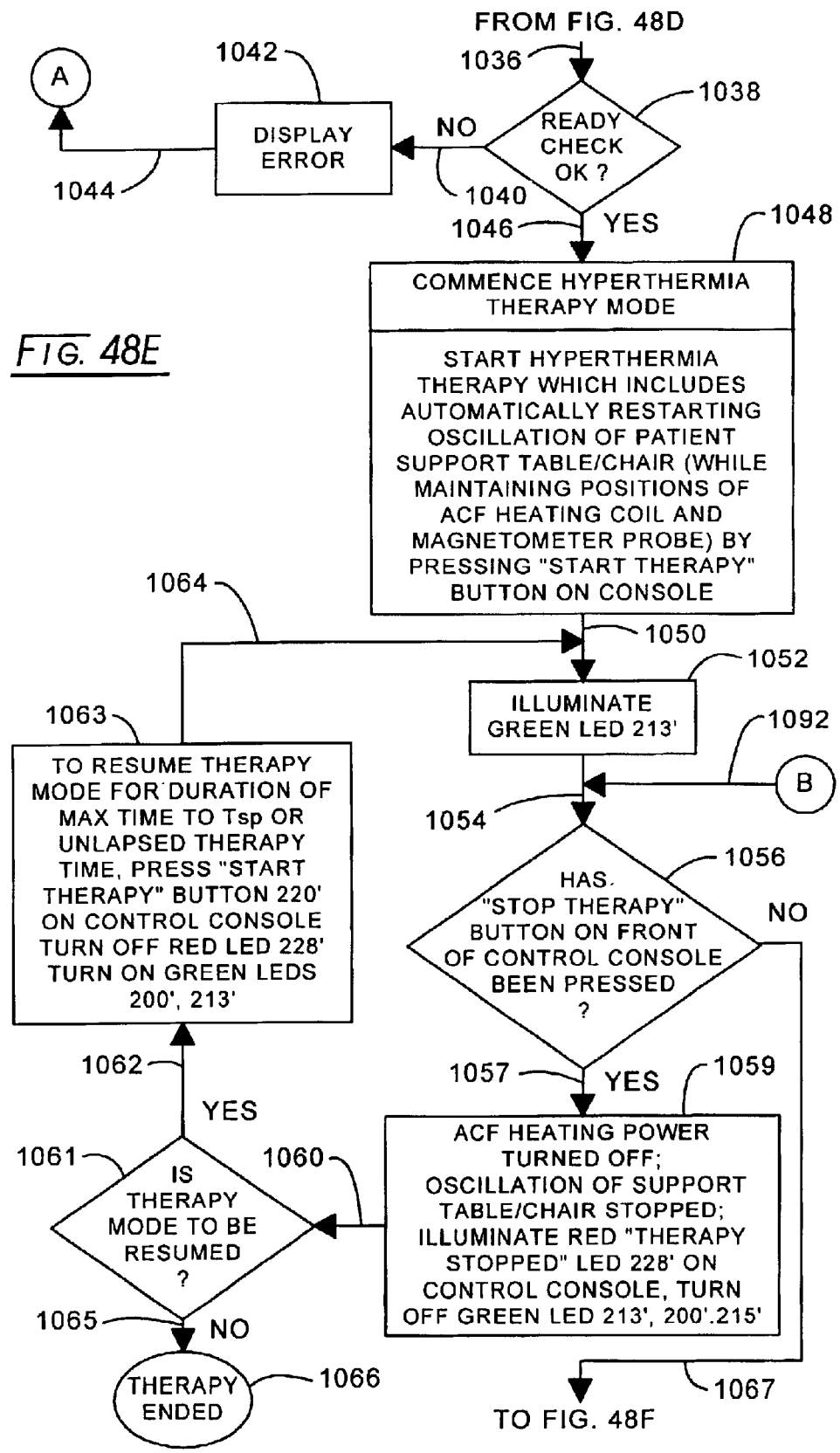

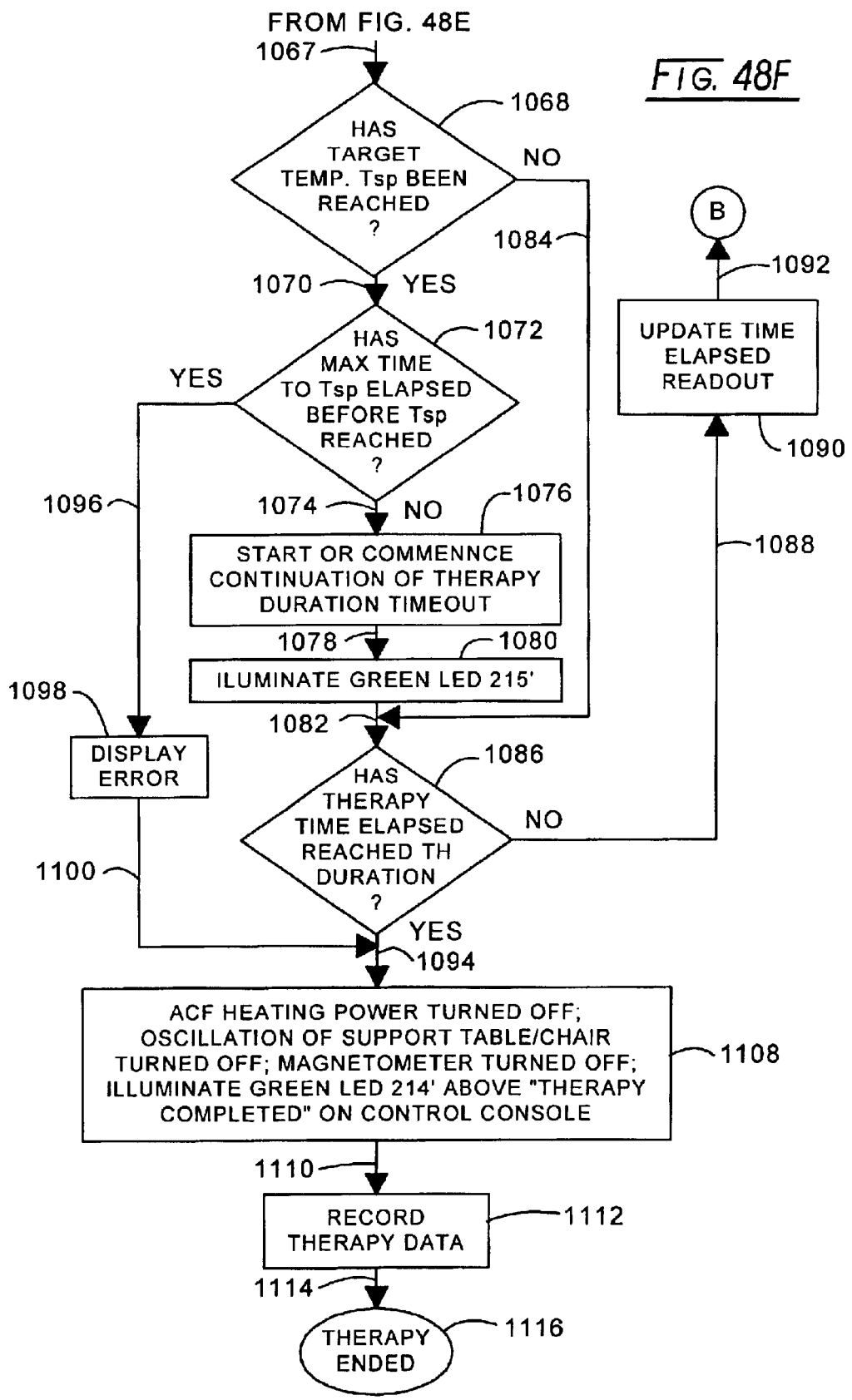

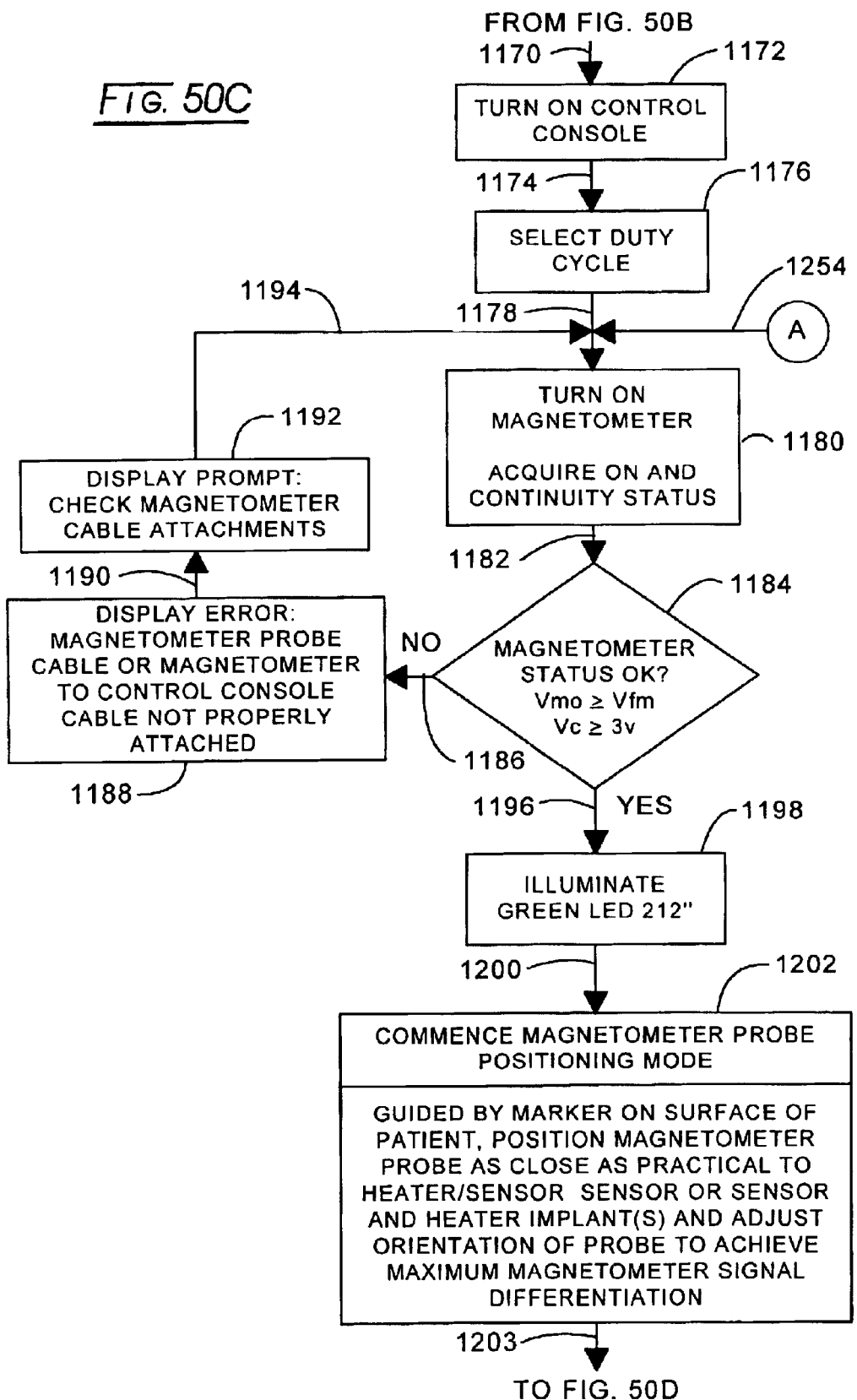

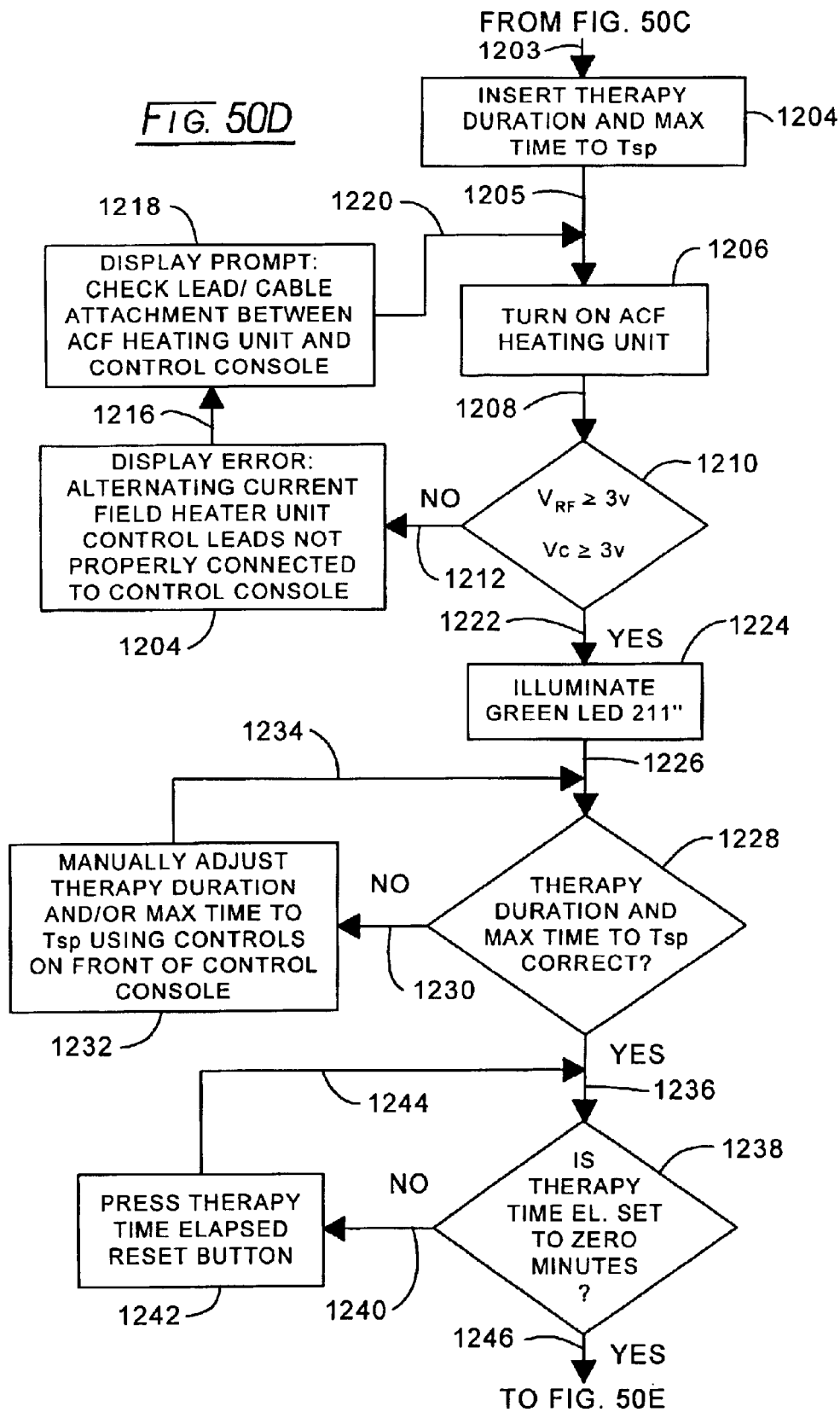

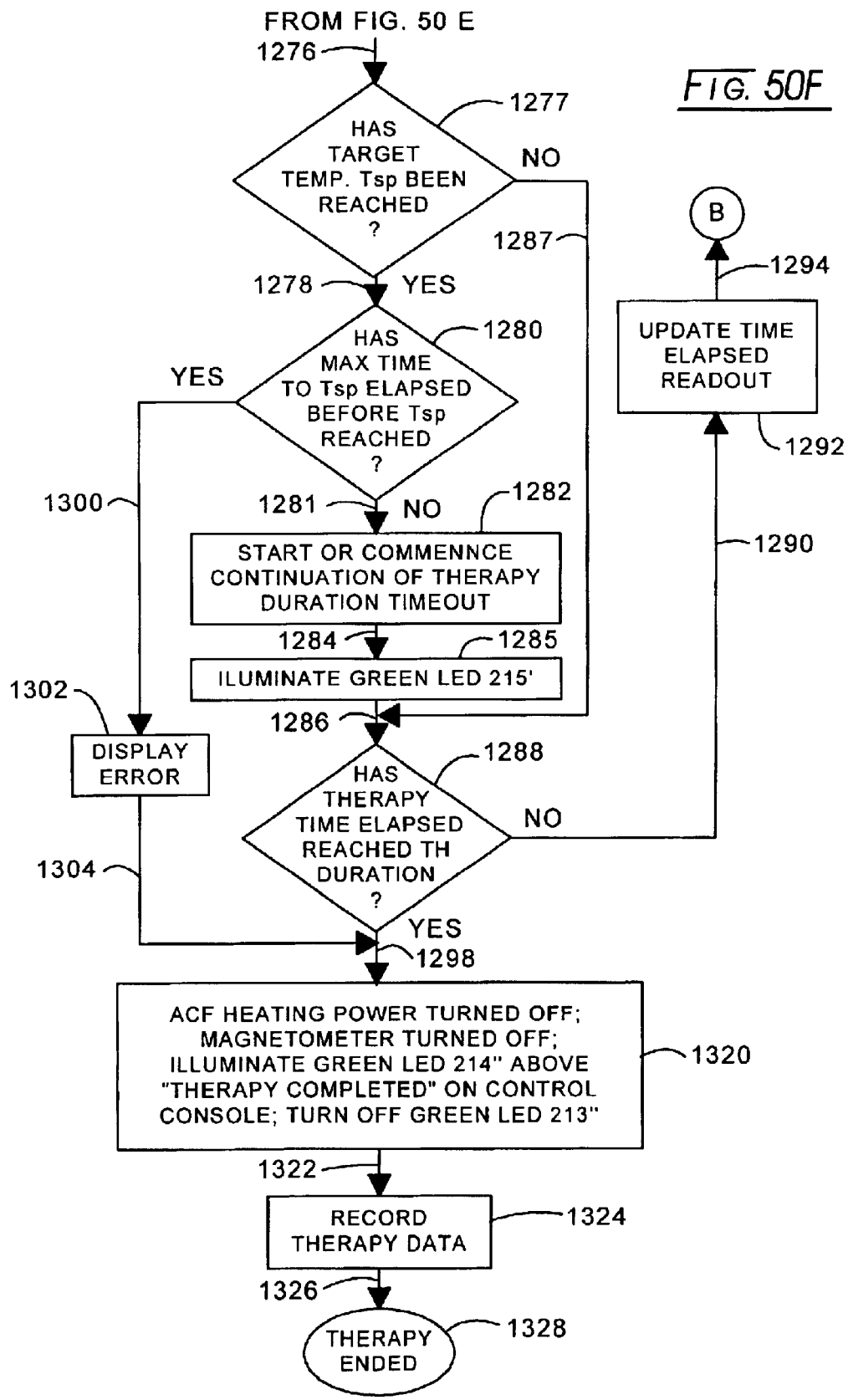

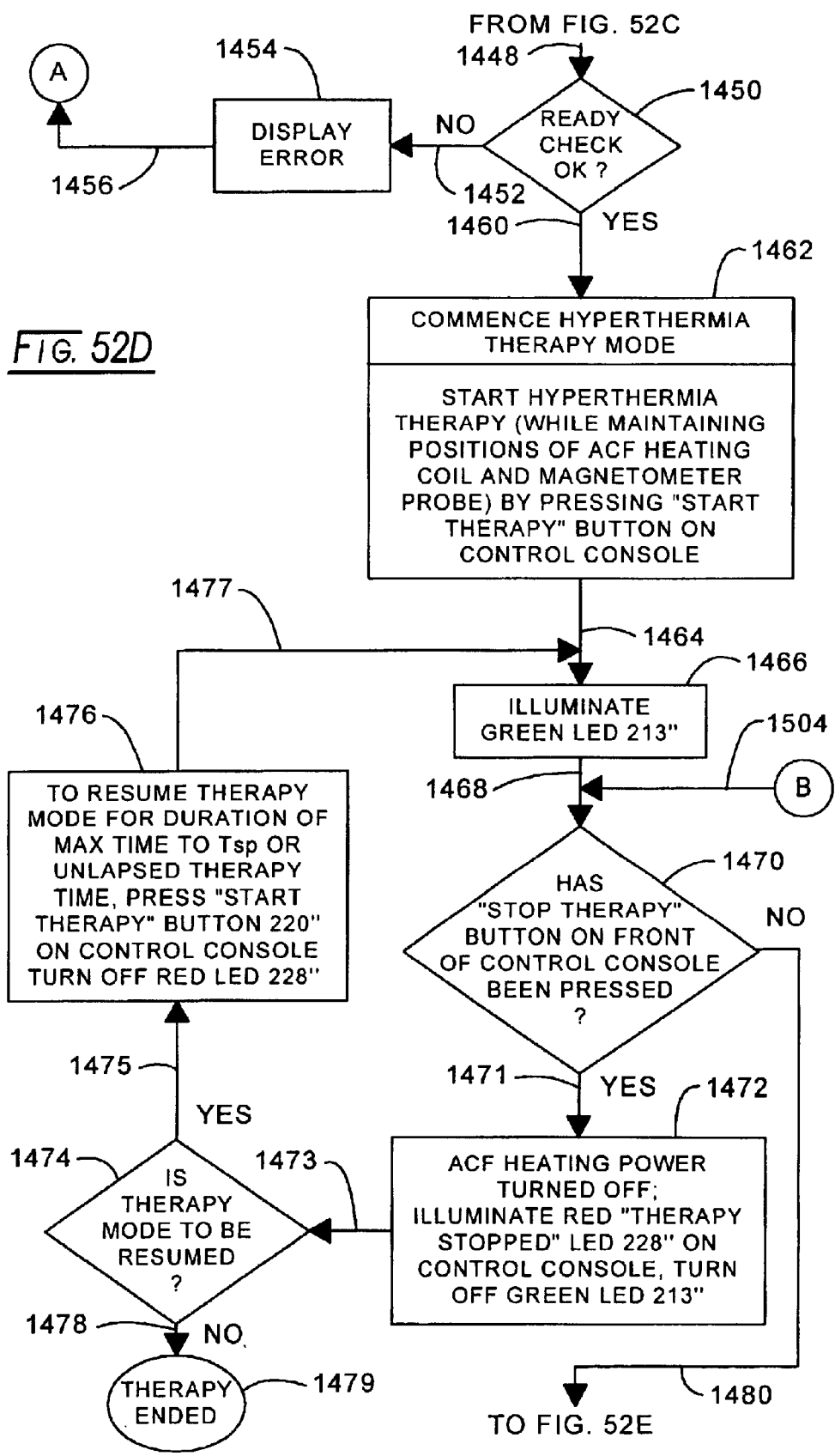

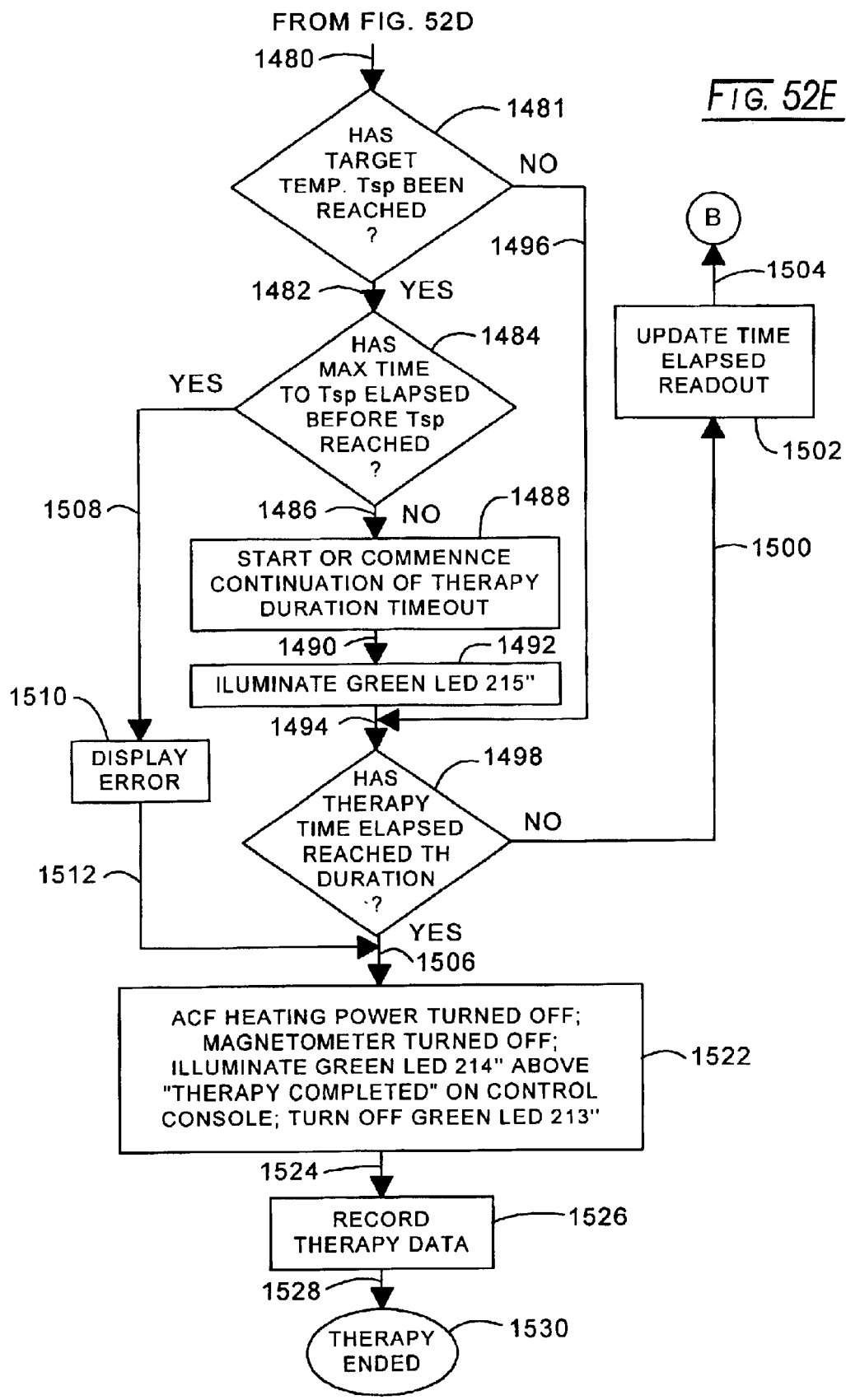

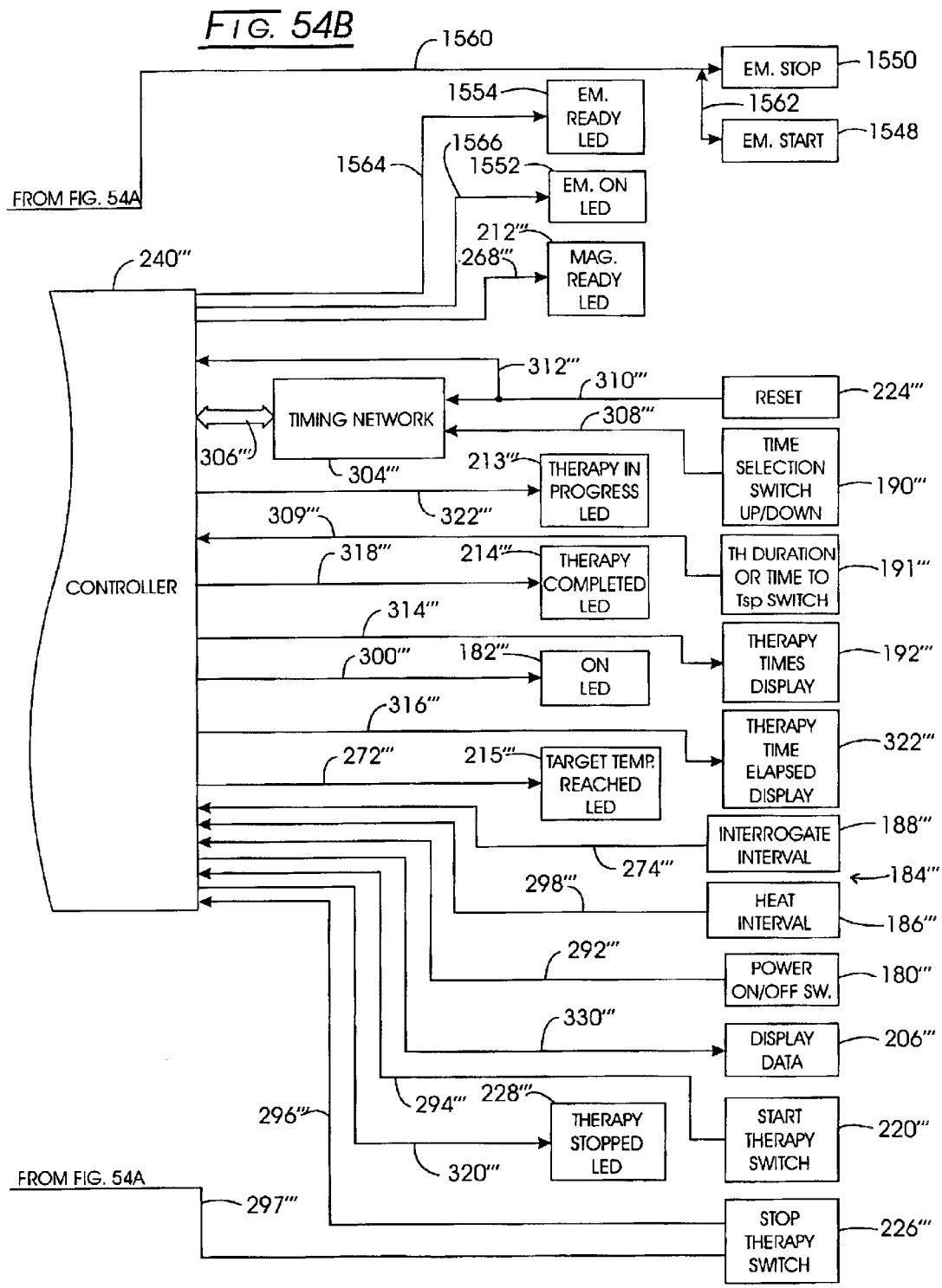

TO FIG. 55B

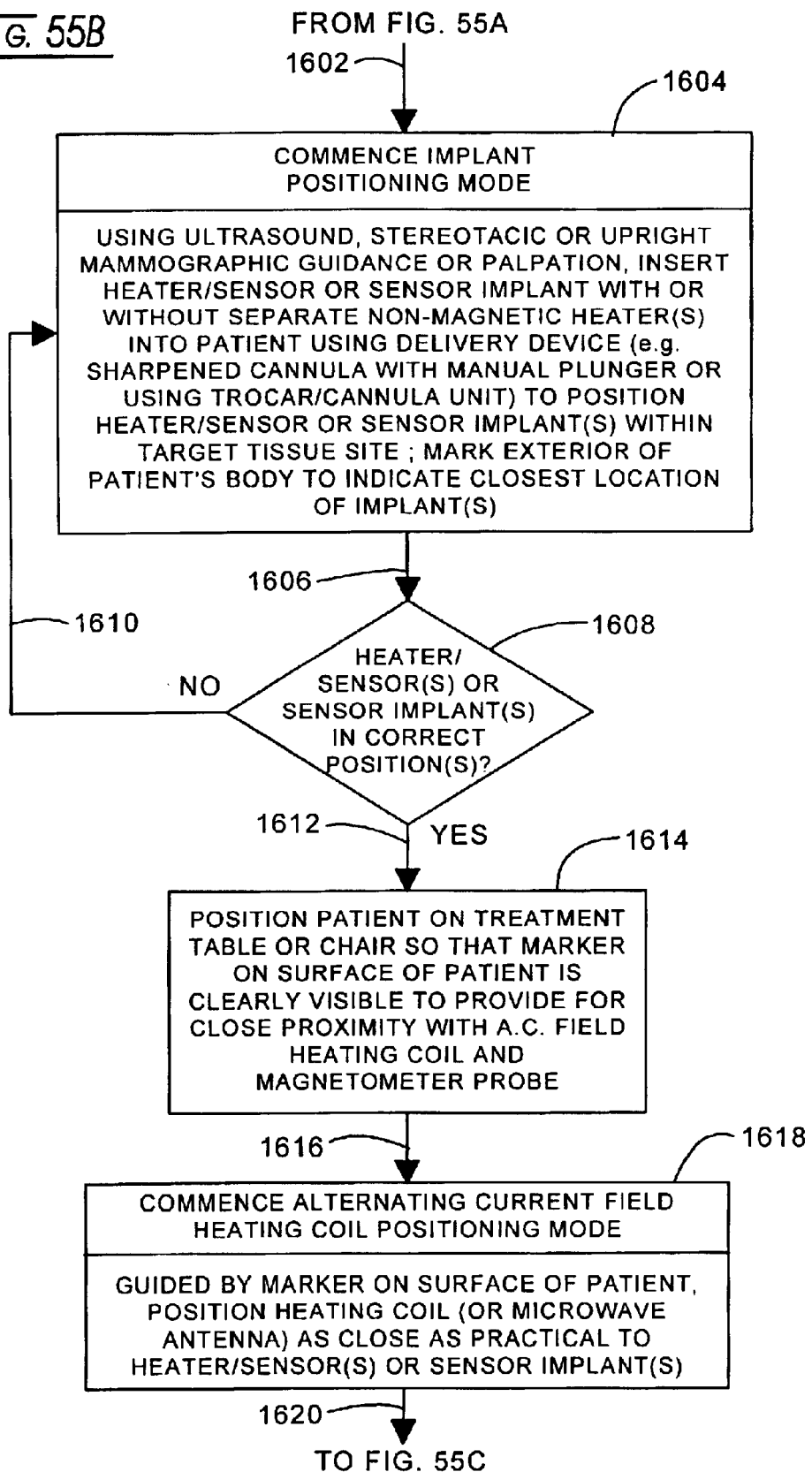

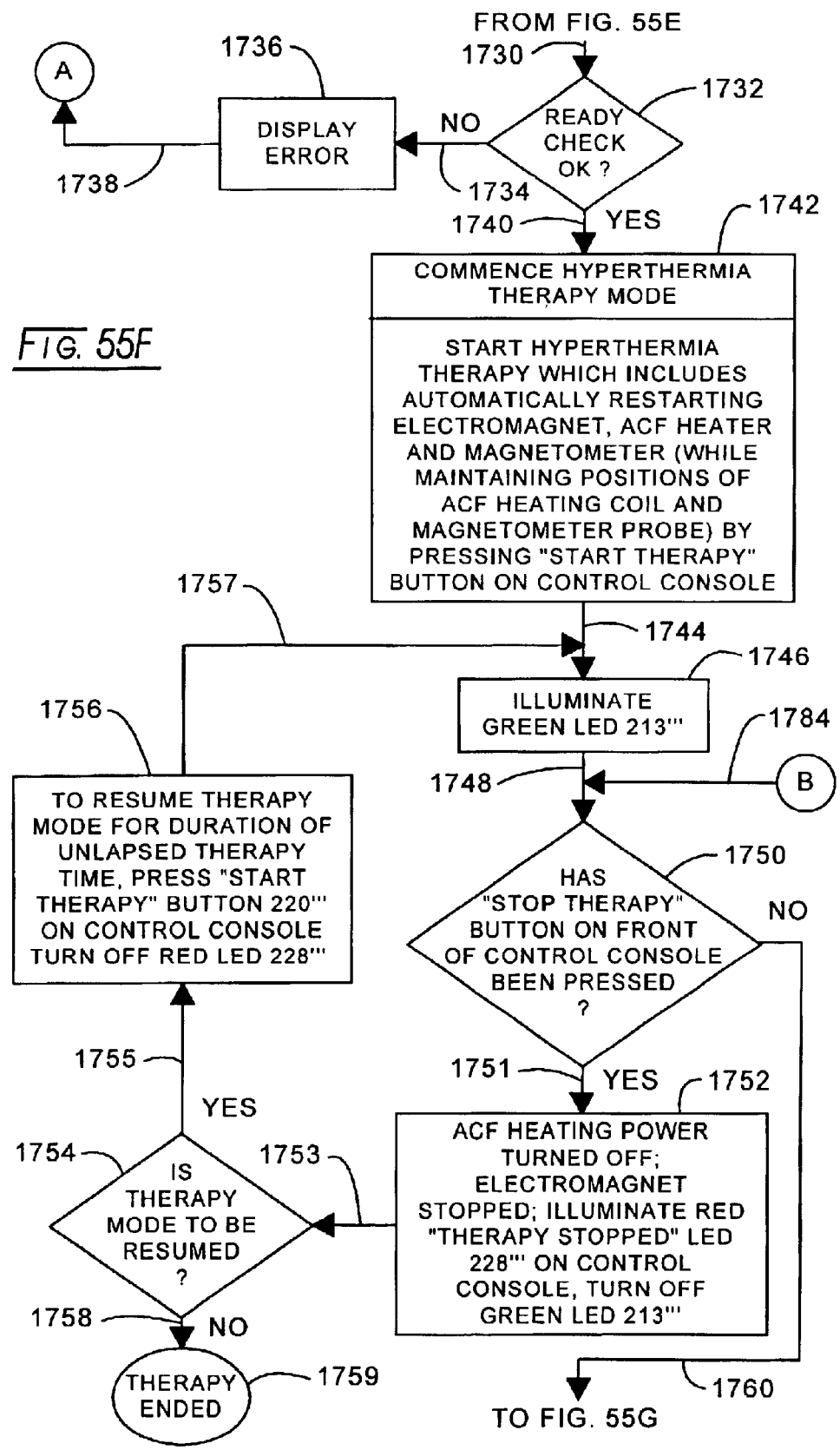

SYSTEM METHOD AND APPARATUS FOR LOCALIZED HEATING OF TISSUE

CROSS-REFERENCE TO RELATED APPLICATIONS

This application claims the benefit of U.S. Provisional Application No. 60/349,593, filed Jan 18, 2002 and is a continuation-in-part of U.S. patent application Ser. No. 10/201,363 filed Jul. 23, 2002 now abandoned.

STATEMENT REGARDING FEDERALLY SPONSORED RESEARCH

Not applicable.

BACKGROUND OF THE INVENTION

A beneficial response elicited by a heating of neoplastic tissue was reported by investigators in 1971. See the following publication in this regard:

(1) *Brit. J. of Cancer* 25:771(1971); *Cancer Research* 32:1960 (1972).

While deemed beneficial, applications of such thermotherapy initially were constrained to external surface heating. When external applications have been employed the resultant body structure heating has been described as having been uncontrolled in thermal localization resulting in temperature elevation of the whole body. Employment of diathermy has been reported with a resultant non-destructive inhibitory reaction. In general, no consensus by investigators as to the efficacy of thermotherapy with respect to tumor was present as late as the mid 1970s. See generally:

(2) *Europ. J. Cancer* 9: 103, (1973).

(3) *Ziet. fur Naturforschung* 8, 6: 359.

(4) *The Lancet*, p. 1027 (May 3, 1975).

Notwithstanding a straightforward need for more effective techniques in the confinement of thermotherapy to localized internally located target tissue regions, investigators have established that tumor cells may be physiologically inhibited by elevating their temperatures above normal body temperature, for example, 37° C. for one major population, to a range exceeding about 40° C. The compromising but beneficial results further are predicated upon that quantum of thermal exposure achieved, based upon the time interval of controlled heat application. Thus, effective thermotherapies are characterized by an applied quantum of thermal energy established within a restrictive tissue periphery or volume of application with an accurately controlled temperature over an effective component of time.

One modality of thermotherapy is termed "hyperthermia" therapy, an approach to thermal treatment at temperatures elevated within somewhat narrow confines above normal body temperature. For instance, the elevation above a normal body temperature of 37° C. typically will fall within a range of 42° C. to 45° C. While higher temperature links have been described, hyperthermia therapy conventionally looks to affecting tissue to the beneficial effect of, for instance, negating neoplastic development, while avoiding denaturization, i.e., cell death or necrosis. It follows that an embracing of this therapeutic modality calls for the application of thermal control over specific tissue volumes.

Confinement of thermotherapy to a neoplasm-suspect target tissue volume internally disposed within the body without a generation of damage to healthy surrounding tissue has been considered problematic and thus the subject of diverse investigation. A variety of approaches toward intra-body localized heat applications has evolved. Such efforts generally have been based upon the application of microwave energy (U.S. Pat. No. 4,138,998); the application of acoustic wave-based systems (ultrasound); and the application of electric fields at RF frequencies from transmitting antenna arrays including an application subset utilizing inductive systems driven at relatively lower frequencies below the RF realm. With the former approach, thermal localization has been evolved by developing constructive wave interference with annular phased-array antennas. (See U.S. Pat. No. 5,251,645).

Inductively-based approaches to thermotherapy systems have received important attention by investigators. The coil transmitted outputs of these systems generally are focused for field convergence toward the target tissue volume and the resultant, internally thermally affected tissue region has been monitored in situ by thermo-responsive sensors such as rod-mounted thermocouples and thermistors. Typically, those tethered heat sensors are inserted percutaneously into the target tissue region, being coupled by extra-body electrical leads extending to connections with temperature monitoring readouts. The invasiveness of the monitoring electrical leads extending into the patients' body for this procedure has been considered undesirable. This particularly holds where repetitive but time-spaced procedures are called for, or the therapeutic modality is employed in thermally treating tumor within the brain.

Efforts to regionalize or confine therapeutic tissue heating to predefined borders or volumetric peripheries have included procedures wherein small wire or iron-containing crystals (U.S. Pat. No. 4,323,056) are implanted strategically within the tissue region of interest. Implantation is achieved with an adapted syringe instrumentality. Electromagnetic fields then are introduced to the region to inductively heat the implanted radiative-responsive heater components and thus evoke a more regionally controlled form of thermotherapy. In one such approach, ferromagnetic thermoseeds have been employed which exhibit Curie temperature values somewhat falling within the desired temperature range for an elected thermotherapy. This achieves a form of self regulation by operation of the system about those Curie transitions. For instance, as radiative excitation drives the thermoseeds to temperatures to within the permeability based state change levels associated with attainment of a Curie temperature range, the thermoseeds become immune to further application of external excitation energy. (See generally U.S. Pat. No. 5,429,583). Unfortunately, the Curie transition temperature range of the thermoseeds is relatively broad with respect to the desired or target temperature. See generally:

(5) Brezovich, et al., "Practical Aspects of Ferromagnetic Thermoseed Hyperthermia." *Radiologic Clinics of North America*, 27: 589–682 (1989).

(6) Haider, et al., "Power Absorption in Ferromagnetic Implants from Radio Frequency Magnetic Fields and the Problem of Optimization." *IEEE Transactions On Microwave Theory And Techniques*, 39: 1817–1827 (1991).

Thermotherapeutic approaches designed to avoid the subcutaneous insertion of one or more temperature sensors have looked to the control of heating using modeling methodology. These approximating modeling methods are subject to substantial error due to differences or vagaries exhibited by the tissue of any given patient. Such differences may be due to variations in vascularity, as well as the gradual metamorphosis of a tumor mass. The latter aspect may involve somewhat pronounced variations in tissue physiologic char acteristics such as density. See generally the following publication:

(7) Arkin, H. et al., "Recent Development In Modeling Heat Transfer in Blood Perfused Tissue." *IEEE Transactions on Bio-Medical Engineering*, 41 (2): 97–107 (1994).

Some aspects of thermotherapy have been employed as an adjunct to the use of chemotherapeutic agents in the treatment of tumor. Because of the precarious blood supply or vascularity and of the high interstitial fluid presence, such agents may not be effectively delivered to achieve a 100% cell necrosis. Further the tumor vessel wall may pose a barrier to such agents, and resultant non-specific delivery may lead to significant systemic toxicities. Studies have addressed these aspects of chemotherapy, for instance, by the utilization of liposomes to encapsulate the chemotherapeutic agents to achieve preferential delivery to the tumor. However the efficiencies of such delivery approaches have been somewhat modest. Clinically hyperthermia therapy has been employed as a form of adjunct therapy to improve the efficiency of more conventional modalities such as radiation therapy and chemotherapy. For the latter applications the thermal aspect has been used to augment bloodstream borne release agents or liposome introduction to the tumor site. Hyperthermia approaches have been shown to trigger agent release from certain liposomes, making it possible to release liposome contents at a heated site (U.S. Pat. Nos. 5 490,840; 5,810,888). For any such thermotherapeutic application, an accurate temperature control at the situs of the release is mandated. See the following publications:

(8) Kong, et al., "Efficacy of Lipsomes and Hyperthermia in a Human Tumor Xenograft Model: Importance of Triggered Drug Release." *Cancer Research*, 60: 6950–6957 (2000).

(9) Chung, J. E., et al., "Thermo-Responsive Drug Delivery From Polymeric Micelles Using Block Co-Polymers of Poly (N-isopropylacrylamide-b-butylmethacrylate) and Poly (butylmethacrylate), *Journal of Controlled Release* (Netherlands), 62(2): 115–127 (Nov. 1, 1999).

Hyperthermia when used in conjunction with radiation treatment of malignant disease has been demonstrated as beneficial for destroying a specific tumor site. Clinical data has evolved demonstrating an improved efficacy associated with combined radiation and hyperthermia treatments as compared to radiation therapy alone. Such multimodal therapy concepts also have been extended to a combination of hyperthermia treatment with both radiation treatment and chemotherapy (radiochemotherapy). See generally:

(10) Falk et al., "Hyperthermia In Oncology" *Int. J. Hyperthermia*, Vol 17, pp 1–18 (2001).

Biological mechanisms at the levels of single cells activated by heat became the subject of scientific interest in the early 1960s as consequence of the apparently inadvertent temperature elevation of an incubator containing Drosophila melanogaster (fruit flies). These creatures, upon being heat shocked, showed the characteristic puffs indicative of transcriptional activity and discrete loci. See the following publication:

(11) Ritossa, "A New Puffing Pattern Induced By Temperature Shock and DNP in Drosophila." *Experientia*, 18: 571–573 (1962).

These heat shock loci encoding the heat shock proteins (HSPs), became models for the study of transcriptional regulation, stress response and evolution. The expression of HSPs may not only be induced by heat shock, but also by other mechanisms such as glucose deprivation and stress. Early recognized attributes of heat shock proteins resided in their reaction to physiologically support or reinvigorate heat damaged tissue. (See U.S. Pat. No. 5,197,940). Perforce, this would appear to militate against the basic function of thermotherapy when used to carry out the denaturization of neoplastic tissue. However, heat shock phenomena exhibit a beneficial attribute where the thermal aspects of their application can be adequately controlled. In this regard, evidence that HSPs, possess unique properties that permit their use in generating specific immune responses against cancers and infectious agents has been uncovered. Additionally, such properties have been subjects of investigation with respect to boney tissue repair, transplants and other therapies. See generally the following publications:

(12) Anderson et al., "Heat, Heat Shock, Heat Shock Protein and Death: A Central Link in Innate and Adoptive Immune Responses." *Immunology Letters*, 74: 35–39 (2000).

(13) Srivastava, et al, "Heat Shock Proteins Come of Age: Primitive Functions Acquire New Role In an Adaptive World." *Immunity*, 1998; 8(6), pp 657–665.

Beneficial thermal compromization of target tissue volumes is not entirely associated with HSP based treatments for neoplastic tissue and other applications, for instance, having been studied in connection with certain aspects of angioplasty. Catheter-based angioplasty was first intentionally employed in 1964 for providing a transluminal dilation of a stenosis of an adductor hiatus with vascular disease. Balloon angioplasty of peripheral arteries followed with cautious approaches to its implementation to the dilation of stenotic segments of coronary arteries. By 1977 the first successful percutaneous transluminal coronary angioplasty (PTCA) was carried out. While, at the time, representing a highly promising approach to the treatment of angina pectoris, subsequent experience uncovered post-procedural complications. While PTCA had been observed to be effective in 90% or more of the subject procedures, acute reclosure, was observed to occur in approximately 5% of the patients. Stenosis was observed to occur in some patients within a period of a few weeks of the dilational procedure and restenosis was observed to occur in 15% to 43% of cases within six months of angioplasty. See generally:

(14) Kaplan, et al., "Healing After Arterial Dilatation with Radiofrequency Thermal and Non-Thermal Balloon Angioplasty Systems." *Journal of Investigative Surgery*, 6: 33–52 (1993).

In general, the remedy for immediate luminal collapse has been a resort to urgent or emergency coronary bypass graft surgery. Thus, the original procedural benefits attributed to PTCA were offset by the need to provide contemporaneous standby operating room facilities and surgical personnel. A variety of modalities have been introduced to avoid post PTCA collapse, including heated balloon-based therapy, (Kaplan, et al., supra) the most predominate being the placement of a stent extending intra-luminally across the dilational situs. Such stents currently are used in approximately 80% to 90% of all interventional cardiology procedures. While effective to maintain or stabilize intra-luminal dilation against the need for emergency bypass procedures, the stents are subject to the subsequent development of in-stent stenosis or restenosis (ISR). See generally:

(15) Holmes, Jr., "In-Stent Restenosis." *Reviews in Cardiovascular Medicine*, 2: 115–119 (2001).

Debulking of the stenotic buildup has been evaluated using laser technology; rotational atherectomy; directional coronary atherectomy; dualistic stent interaction (U.S. Pat. No.

6,165,209); repeated balloon implemented dilation, the application of catheter introduced heat to the stent region (U.S. Pat. No. 6,319,251); the catheter-borne delivery of soft x-rays to the treated segment, sonotherapy; light activation and local arterial wall alcohol injection.

See additionally the following publications with respect to atherectomy for therapeutically confronting restenosis:

(16) "Bowerman, et al., "Disruption of Coronary Stent During Artherectomy for Restenosis." *Catherization and Cardio Vascular Diagnosis* 24: 248–251 (1991).

(17) Meyer, et al., "Stent Wire Cutting During Coronary Directional Atherectomy." *Clin. Coardiol,.* 16: 450–452 (1993).

In each such approach, additional percutaneous intervention is called for. See generally the following publication:

(18) Vlielstra and Holmes, Jr., *PTCA*. Philadelphia: F. A. Davis Company (Mayo Foundation) (1987).

Other approaches have been proposed including the application of electrical lead introduced electrical or RF applied energy to metallic stents, (U.S. Pat. No. 5,078,736); the incorporation of radioisotopes with the stents (U.S. Pat. Nos. 6,187,037; 6,192,095); and resort to drug releasing stents (U.S. Pat. No. 6,206,916 B1). While non-invasive control of ISR has been the subject of continued study, the development of a necessarily precise non-invasively derived control over it has remained an elusive goal.

Another application of hyperthermia is in orthopedics, as a means to stimulate bone growth and fracture healing. There are several FDA approved devices for stimulation of bone growth or healing, each with limitations and side effects. Therapies include invasive electrical stimulation, electromagnetic fields, and ultrasound stimulation. Decades old research has claimed a stimulation of bone growth by a mild increase in temperature of the boney tissue. Previous researchers have used such methods as inductive heating of implanted metal plates, or heating coils wrapped around the bone. The utility of these methods is limited by the invasive nature of the surgery needed to implant the heating elements and the inability to closely control tissue temperature. Moreover, therapeutic benefits have been inconsistent between different studies and experimental protocols. For a summary of past work, see generally:

(19) Wootton, R. Jennings, P., King-Underwood, C., and Wood, S. J., "The Effect of Intermittent local Heating on Fracture Healing in the Distal Tibia of the Rabbit." *International Orthopaedics,* 14: 189–193 (1990).

A number of protocols have demonstrated a beneficial effect of hyperthermia on bone healing. Several studies indicate temperature affects bone growth and remodeling after injury. Hyperthermia may both improve blood supply and stimulate bone metabolism and have a direct effect on bone-forming cells by inducing heat shock proteins or other cellular proteins. In one experiment, rabbit femurs were injured by drilling and insertion of a catheter. Hyperthermia treatments were given at four-day intervals for 2–3 weeks using focused microwave radiation. Bones which had suffered an insult as a result of the experimental procedure showed a greater density of osteocytes and increased bone mass when treated with hyperthermia. Injured bones treated with hyperthermia showed completely ossified calluses after two weeks, while these processes normally take four weeks in untreated injuries. One problem with microwave heating of bone mass is the difficulty in predicting heat distribution patterns and maintaining the target tissue within the appropriate heat range.

When tissue is heated at too high of temperature, there can be irreversible cytotoxic effects which could damage bone and other tissues, including osteogenic cells, rather than induce healing. Certain studies have shown that induction of mild heat shock promotes bone growth, while more severe heat shock inhibits bone growth. Therefore, control and monitoring of the temperature of the targeted bone tissue is imperative to achieve therapeutic benefit and avoid tissue damage.

See additionally the following publications with respect to hyperthermia for therapeutically promoting osteogenesis:

(20) Leon, et al., "Effects of Hyperthermia on Bone. II. Heating of Bone in vivo and Stimulation of Bone Growth." *Int. J. Hyperthermia* 9: 77–87 (1993).

(21) Shui, C., and Scutt, A., "Mild Heat Shock Induces Proliferation, Alkaline Phosphatase Activity, and Mineralization in Human Bone Marrow Stromal Cells and Mg-63 Cells In Vitro." *Journal of Bone and Mineral Research* 16: 731–741 (2001).

(22) Huang, C.-C., Chang, W. H., and Liu, H.-C. "Study on the Mechanism of Enhancing Callus Formation of Fracture by Ultrasonic Stimulation and Microwave Hyperthermia." *Biomed. Eng. Appl. Basis Comm.* 10: 14–17 (1998).

Existing protocols for therapeutically promoting osteogenesis are limited by the invasive nature and concomitant potential for infection for instance with tethered electrical stimulators; poor temperature control, and potential for tissue injury or reduced therapeutic benefit, for instance with microwave heating or other induced electromagnetic fields; difficulty in effectively applying therapy to the injured bone because of targeting difficulties or low patient compliance with prescribed repetitive therapy.

The host immune system can be activated against infectious disease by heat shock protein chaperoned peptides in a manner similar to the effect seen against metastatic tumors. Heat shock proteins chaperoning peptides derived from both viral and bacterial pathogens have been shown to be effective at creating immunity against the infectious agent. For infectious agents for which efficacious vaccines are not currently available (especially for intracellular pathogens e.g. viruses, *Mycobacerium tuberculosis* or *Plasmodium*) HSP chaperoned peptides may be useful for the development of novel vaccines. It is expected that purified HSP chaperoned peptides (e.g. gp96 complexes) used as vaccines for diseases caused by highly polymorphic infectious agents would be less effective against genetically distinct pathogen populations. For a summary of past work on HSP vaccines against infectious agents, see generally:

(23) Neiland, Thomas J. F., M. C. Agnes A. Tan, Monique Monnee-van Muijen, Frits Koning, Ada M. Kruisbeek, and Grada M. van Bleek, "Isolation of an immunodonminant viral peptide that is endogenously bound to stress protein gp96/GRP94." *Proc. Nat'l Acad. Sci. USA,* 93: 6135–6139 (1996).

(24) Heikema, A., Agsteribbe, E., Wilschut, J., Huckriede, A., "Generation of heat shock protein-based vaccines by intracellular loading of gp96 with antigenic peptides." *Immunology Letters,* 57: 69–74. (1997)

(25) Zugel, U., Sponaas, A. M., Neckermann, J., Schoel, B., and Kaufmann, S. H. E., "gp96-Peptide Vaccination of Mice Against Intracellular Bacteria." *Infection and Immunity,* 69: 4164–4167 (2001).

(26) Zugel, U., and Kaufmann, S. H. E., "Role of Heat Shock Proteins in Protection from and Pathogenesis of Infectious Diseases." *Clinical Microbiology Reviews,* 12: 19–39 (1999).

BRIEF SUMMARY OF THE INVENTION

The present invention is addressed to method, system and apparatus for accurately carrying out an in situ elevation of the temperature of a target tissue volume. Accuracy is achieved using an untethered temperature sensor implant positionable within or adjacent to the target tissue volume using minimally invasive procedures or using intraoperatively implanted sensors subsequent to surgery. Such implants may be in the form of (1) a single macroscopic device (e.g., wire shaped implant), (2) multiple macroscopic devices (e.g., wire shaped implants) and/or (3) multiple microscopic devices (e.g., devices in particulate form that can be injected into a volume of the tissue or attach preferentially systemic injection using chemical binding targeting modalities such as possible with monoclonal antibody vehicles). Positioning of macroscopic implants may be carried out utilizing an implant instrument somewhat resembling a hypodermic needle. The implant essentially sharply transitions between externally discernable states as a setpoint or target temperature is reached at the target tissue volume.

The method has broad application to thermotherapy endeavors including an in vivo induction of heat shock proteins, a procedure having important utility in the treatment of cancer, infectious diseases and other therapies. As another modality, the implant is combined with an intraluminal stent and when so combined and implanted, permits a non-invasive repeatable and accurate hyperthermia therapy for restenosis.

In situ heating is carried out using conventional alternating current field-based devices such as RF heating, inductive heating, microwave-based procedures and ultrasound, all of which are of a non-invasive nature.

In a principal embodiment, the temperature sensor which is implanted is formed of a ferromagnetic material which experiences an abrupt magnetic permeability state change at a Curie temperature selected to correspond with the determined thermotherapy setpoint temperature. For instance, the Curie transition may be experienced within a temperature range of from about 0.1° C. to about 1° C. The system is capable of detecting this permeability state transition externally of the body of the patient by monitoring a magnetic field extending through the position of the implant. That magnetic field may be the earth's magnetic field or a field generated, for example, by an electromagnet. A magnetometer, for instance, of a fluxgate sensor design is employed to monitor for the magnetic permeability state change at the implant.

The volumetrically defined heating of a target tissue may be facilitated through the utilization of implanted non-magnetic heater components. These heater components may be combined with the sensor components in intimate thermal exchange relationship. In this regard, a variety of such structures are described. In one approach, both the heater component and the temperature sensing component are each of generally semi-cylindrical form having the semi-cylindrically defined flat surfaces of such geometric structures coupled together in the noted heat exchange relationship. The entire structure may be coated with an electrically insulative biocompatible conformal coating. Additionally, the implant may carry a thermally activatable release agent layer which functions to release a therapy supporting agent at the situs of the target tissue when the heater component reaches an induced temperature at a setpoint temperature detected by the temperature sensing component. In another combined implant approach, the heater component is formed as a discontinuity containing covering of the sensor which, for instance, may assume a cylindrical geometric shape. The discontinuities permit interaction of the sensor component with the monitoring magnetic field. In another approach, the cylindrical sensor component may be surmounted by a heater component which is configured as a generally open, spiral sleeve positioned against the surface of the temperature sensor in thermal exchange relationship. This defines a helical-shaped open, outwardly exposed surface portion of the sensor component, again functioning in conjunction with a magnetic field to provide a discernable magnetic permeability state change at a desired setpoint temperature. Another geometry for the combinational implant provides a generally cylindrical temperature sensor component with combined heater components configured as metal caps which fit over the sensors adjacent the ends of their cylindrical structures. Several such sensors may be combined with such end caps and intermediately disposed heater component sleeves to, in effect, develop an implant formed of a chain of sensors which, for example, may be configured to exhibit a permeability state change at different setpoint temperatures.

The implants may perform in conjunction with a variety of system scenarios. In one approach a single channel magnetometer is employed in conjunction with a single channel pick-up. This pick-up is located externally of the patient's body at a location in somewhat close adjacency with the position of the implant. Additionally, the broadcasting component of an alternating current field heating assembly is positioned in adjacency with that targeted area. To carry out detection of the permeability state of the sensor component of the implant, the patient will be supported on an oscillative platform or chair in order to achieve single channel detection of a magnetic permeability Curie temperature state change. Either the earth's magnetic field or an applied magnetic field may be employed with this system. In another system approach a multichannel magnetometer assembly is employed incorporating an arrayed pick-up. With this arrangement the patient support may remain stationary and the magnetometer-based detection assembly determines a differentiation of magnetic field disturbance and non-disturbance. In the presence of a non-disturbance condition, the target temperature or setpoint temperature at the targeted tissue will have been achieved.

A feature of the system and method of the invention is concerned with a typical patient management regimen wherein a relatively substantial repetition of hyperthermia therapeutic procedures are called for. The implants remain in position with respect to the target tissue volume and may, in this regard, be fashioned with implant barbs or the like for the purpose of migration avoidance. Where a succession of treatments is involved, not only is there no requirement to re-install sensors, but also, the aligning of the sensing system magnetometer remains quite simple, involving the observation of signal response amplitudes on the part of the attending technician. Another aspect of this feature resides in the utilization of the pre-implanted sensors or sensor-heaters as a conventional tumor situs marker for subsequent patient evaluation imaging procedures.

While any of the above approaches may be used in connection with stents and the treatment for restenosis, where the stent along with temperature sensor is implanted in a coronary artery, then the natural beating of the heart of the patient will provide sufficient movement of the sensor itself to permit single channel detection by a magnetometer.

Control over the alternating current field (ACF) heating system preferably is achieved by controlling the actuation of the heating assembly and the magnetometer in an intermittent manner. With this approach, the heater assembly is activated for a predetermined interval of time following which the magnetometer is activated for a much shorter interval. This sequencing continues until setpoint temperature is detected, whereupon the magnetometer remains enabled while the heater remains deactuated until the temperature sensing component reverts to a higher relative permeability to again disturb the monitored magnetic field.

The implant controlled heating approach of the invention also may be applied to the field of orthopedics. In this regard, the sensor component may be combined in intimate thermal exchange relationship with non-magnetic metal bone support devices implanted within boney tissue. The setpoint temperature elected for such modality is selected to enhance the repair of the mending boney tissue.

Implant based controlled in vivo heating according to the precepts of the invention also may be employed as a vehicle for inducing immunity against or for the treatment of diseases caused by infectious agents.

Other objects of the invention will, in part, be obvious and will, in part appear hereinafter;

The invention, accordingly, comprises the method, system and apparatus possessing the construction, combination of elements, arrangement of parts and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIGS. 8A and 8B combine as labeled thereon to provide a schematic block diagram of a control feature of the invention;

FIG. 9 is a general view of an implant incorporating heater and sensor components according to the invention;

FIG. 9A is a perspective view of an implant configured in accordance with FIG. 9 but modified to incorporate extensible barb-like structures for migration avoidance;

FIG. 10 is a sectional view of the implant of FIG. 9;

FIG. 11 is a sectional view taken through the plane 11—11 shown in FIG. 10;

FIG. 12 is a sectional view of the implant of FIG. 9 showing the incorporation of a heat activated release agent coating;

FIG. 13 is a sectional view taken through the plane of 13—13 shown in FIG. 12;

FIG. 14 is a perspective view of another embodiment of an implant according to the invention with a combined heater component and sensor component;

FIG. 15 is a sectional view of the implant of FIG. 14;

FIG. 16 is a sectional view taken through the plane 16—16 shown in FIG. 15;

FIG. 17 is a sectional view of the implant of FIG. 14 showing the incorporation therewith of a heat activated release agent coating;

FIG. 18 is a sectional view taken through the plane 18—18 in FIG. 17;

FIG. 19 is another embodiment of an implant according to the invention incorporating both sensor and heater components;

FIG. 20 is a sectional view of the implant of FIG. 19;

FIG. 21 is a sectional view taken through the plane 21—21 shown in FIG. 20;

FIG. 22 is a perspective view of another implant according to the invention incorporating both sensor and heater components;

FIG. 23 is a sectional view of the implant of FIG. 22;

FIG. 24 is a perspective view of another implant embodiment according to the invention incorporating both sensor and heater component;

FIG. 24A is a perspective view of an implant configured in accordance with FIG. 24 but modified to incorporate extensible barb-like structures for migration avoidance;

FIG. 25 is a sectional view of the implant of FIG. 24;

FIG. 26 is a sectional view of the implant of FIG. 24 showing incorporation of a thermally activated release agent coating;

FIG. 27 is a perspective view of an implant according to the invention incorporating only a sensor function;

FIG. 28 is a sectional view of the implant of FIG. 27;

FIG. 29 is a sectional view of the implant of FIG. 28 taken through the plane 29—29 shown therein;

FIG. 30 is a sectional view of the implant of FIG. 27 showing the incorporation therewith of a thermally activated release agent coating;

FIG. 31 is a sectional view taken through the plane 31—31 shown in FIG. 30;

FIGS. 34A–34G combine as labeled thereon to provide a flowchart illustrating the procedure and control carried out with the system represented in FIG. 5;

FIGS. 48A–48F combine as labeled thereon to provide a procedure and control flowchart associated with the system shown in FIG. 39;

FIGS. 50A–50F combine as labeled thereon to provide a procedure and control flowchart associated with the system illustrated in connection with FIG. 49;

FIGS. 52A–52E combine as labeled thereon to describe the control and procedure associated with the system illustrated in connection with the FIG. 51;

FIGS. 54A–54B combine as labeled thereon to provide a block diagrammatic illustration of the control features of the system of FIG. 53; and FIGS. 55A–55G combine as labeled thereon to provide a procedure and control flowchart describing the system illustrated in connection with FIG. 53.

DETAILED DESCRIPTION OF THE INVENTION

Figure 1:
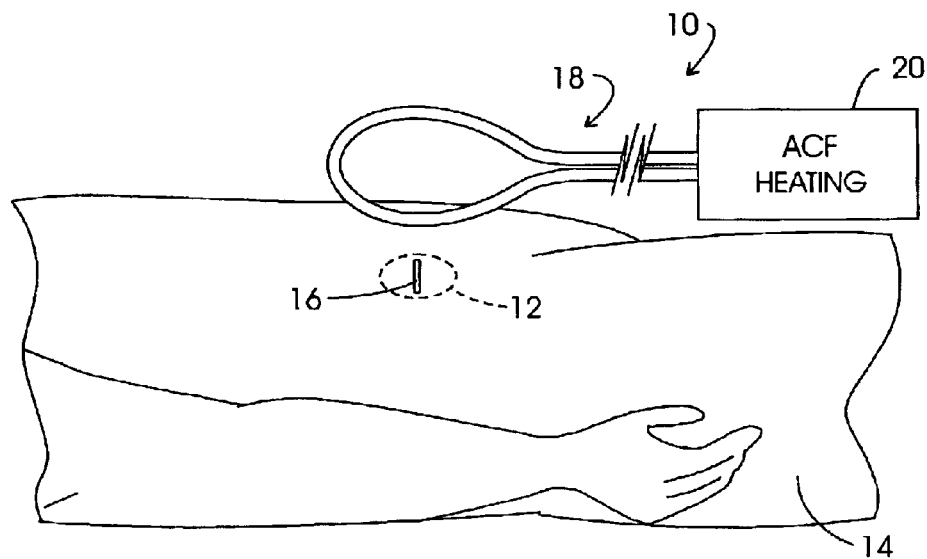
FIG. 1 is a partial schematic view of a prior art approach to heating a target tissue volume utilizing an auto-regulating heater implant.
Figure 2:
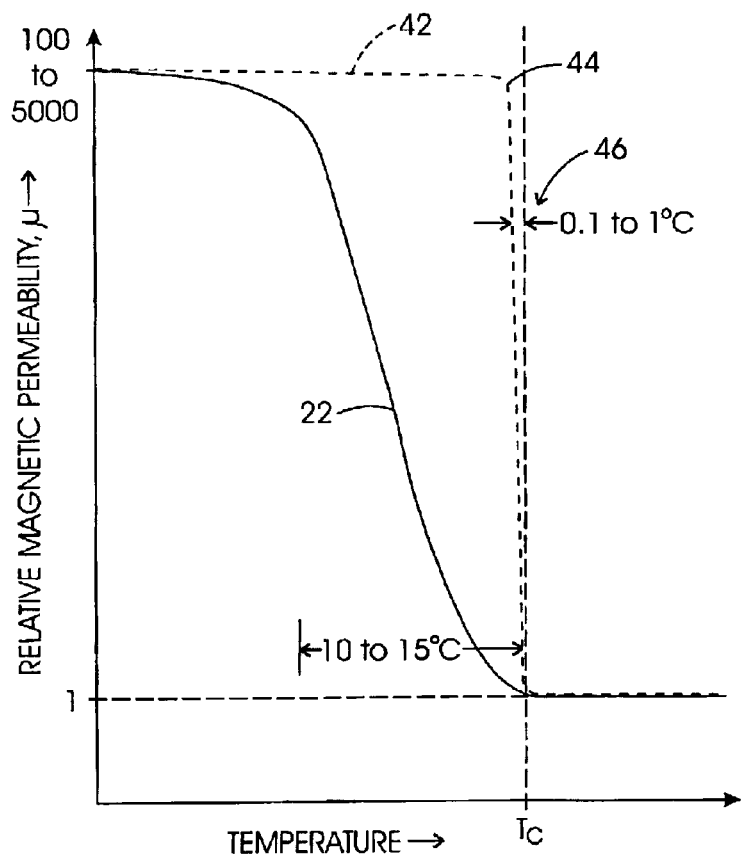
FIG. 2 shows curves relating relative permeability with temperature for ferromagnetic implants.

While a variety of techniques for evolving an effective interstitial thermotherapy of target tissue volumes have been approached by investigators, an earlier development deemed somewhat promising involved the implantation of ferromagnetic alloy heaters sometimes referred to as "ferromagnetic seeds" within that volume. The ferromagnetic alloy heaters were adapted so as to alter in exhibited magnetic permeability in consequence of temperature. For example, with this arrangement, when a Curie temperature transition range was thermally reached, permeability would, in turn, diminish over the transition range and correspondingly thermal responsiveness to an applied inductive field would diminish. Thus it was opined that a temperature auto-regulation could be achieved to optimize a thermally based implantation therapy. Such an arrangement is depicted in FIG. 1. Here, the treatment modality is represented generally at 10 wherein a target tissue volume, for example, comprised of neoplastic tissue, is shown symbolically within dashed region 12 located internally within the body of patient 14. Within the target tissue volume 12 a ferromagnetic material (e.g., having palladium cobalt additives) auto-regulating heater implant 16 is embedded which is, for instance, inductively heated from the excited inductive coil 18 of an alternating current field (ACF) heating assembly 20. The ferromagnetic implants as at 16 exhibit a temperature-related relative magnetic permeability, $\mu_r$. Such relative permeability may be represented by curve 22 shown in FIG. 2. Relative permeability is expressed as $\mu_r = \mu/\mu_o$, where $\mu$=absolute permeability (Henry/meter), $\mu_o$=a constant=magnetic permeability of free space (Henry/meter) and $\mu_r$ is therefore dimensionless but ranges from a value of unity to 100,000 or more. Curve 22 reveals that the relative magnetic permeability, $\mu_r$, decreases as the temperature of the ferromagnetic alloy heater approaches its Curie temperature, $T_c$. Since the induced electric field heating power in an object is proportional to the square root of magnetic permeability, a decrease in magnetic permeability with elevation of temperature is associated with a corresponding decrease in the heating power associated with inductive heating.

Traditionally, the change in magnetic permeability of ferromagnetic alloys with increasing temperature has not been abrupt as would be preferred for precise temperature regulation of an implanted heating component as at 16. In this regard, characteristic curve 22 reveals that a permeability transition occurs gradually over a span typically of 10° C. to 15° C. or more. As a result, the implanted heater device 16 may not reach the intended Curie temperature and resultant relative permeability of unity. Often, that elevation in temperature above normal body temperature has not been achieved. Accordingly, accommodation has been made by electing Curie temperature transition ranges falling well above what would have otherwise been a target temperature for thermotherapy with a result that critical temperature limits of the tissue being treated have been exceeded. Thermotherapeutic procedures also are prone to inaccuracies by virtue of the unknown environmental conditions within which an implant as at 16 is situated. With respect to such unknown phenomena, temperatures achieved with ferromagnetic implants will vary depending upon cooling phenomena within the tissue surrounding the device. Such phenomena occur, for example, as a consequence of the degree of vascularity in the target region and proximity of the heating element as at 16 to blood vessels. These vessels will tend to perform as inherent cooling mechanisms. Accordingly, while attempting to achieve an effective heat therapy, the auto-regulating implants as at 16 generally have been unable to establish a necessary precise temperature output for requisite therapeutic time intervals.

Now turning to the subject of the physiological consequence of elevating tissue temperature, studies have been carried out to investigate both the component of temperature elevation as well as the time component within which such asserted higher temperatures are maintained, i.e., the temporal aspect thereof. Such investigations have established critical temperature and time relationships which identify the occurrence of irreversible tissue damage effects. In this regard, looking to FIG. 3, a generalized semi-log curve 24 is presented illustrating the temporal relationship between the duration of the application of a given temperature to tissue with the value of that critical temperature at which irreversible tissue damage may occur. The system and method of the present invention are concerned, inter alia, with maintaining the treatment of target tissue volumes at accurately controlled temperatures for heat-based therapies including hyperthermia. Hyperthermia is a form of thermotherapy where there is an artificial elevation of the temperature of a group of cells, a tissue, cell culture, or a whole organism for experimental or therapeutic purposes. Heating of tissue through thermotherapy techniques can induce a variety of biologic responses, depending on the intensity of the stress induced. When a tissue is heated, certain cells near the focus of the induced heating may experience greater heat shock than cells at a distance from the focus. Therefore, within a tissue being heated, a range of responses may occur at the cellular level. These responses of tissues to hyperthermia can be broadly categorized. If the heat shock is too mild, there will be no detectable biologic changes (over the basal level of "heat shock" gene expression typical in the absence of heat shock). A mild heat shock may induce reversible cellular changes, including, for example, reversible denaturation of proteins, triggering of ion fluxes from various cellular compartments, activation of existing enzymes, and importantly, induction of alterations in gene expression.

A more severe heat shock may irreversibly damage cellular components. Under certain conditions, when a cell is damaged, an ordered process, apoptosis, is induced that leads to the death of the damaged cell. Apoptosis is considered a form of "programmed cell death," and cells undergoing apoptosis often exhibit distinctive morphologic changes. Apoptosis is also involved in many developmental processes, defensive responses to microbial infection, the homeostasis of cell populations (e.g. lymphocytes) and as means of eliminating genetically damaged cells, such as cancer cells.

It is generally accepted that apoptosis is an active, highly organized, form of cell death, requiring both RNA and protein synthesis. A classic example is the systematic death of a finite number of cells, 131, at a certain stage in the life cycle of the nematode Caenorhabditis elegans, a process controlled by the negative and positive regulation of specific genes. As demonstrated by development in C. elegans, certain genes are involved in the regulation of cell death by apoptosis. A specific example is the human gene bcl-2. In certain human follicular B-cell lymphomas, deregulation of the expression of bcl-2 has been identified as a cause of the prolonged survival of the lymphoma cells. Altered expression of bcl-2 interferes with the typical programmed cell death pattern, blocking apoptosis even when hematopoeitic growth factors are absent.

Apoptotic cells exhibit a pronounced decrease in cellular volume, modification of the cytoskeleton that results in convolution of the cell, and eventual blebbing of the cell's membrane, compaction of chromatin and its segregation within the nucleus that the cell. The DNA is degraded into small fragments, and the apoptotic cell sheds small membrane-bound apoptotic bodies which may contain intact organelles. The apoptotic bodies are phagocytosed (e.g. by macrophages) and the contents of apoptotic bodies are intracellularly degraded, with little release of the contents of the apoptotic cells. In this manner, apoptosis does not induce a localized inflammatory response.

Apoptosis is differentiated from necrosis by the general absence of inflammation. It is a physiological type of cell death, part of a homeostatic mechanism to maintain an optimal number and arrangement of cells. In certain physiological conditions, massive apoptosis is not followed by necrosis and inflammation, such as the removal of interdigital webs during early human development, the regression of liver hyperplasia following withdrawal of a primary mitogen [Columbano citing Bursch, Carcinogenesis 5: 453–458.], and cellular loss in the premenstrual endometrium.

If thermotherapy is sufficiently severe, cells and tissues may be so damaged that cellular integrity is destroyed, or the cellular machinery is so disabled that the induction of apoptosis does not occur. In contrast to apoptosis, necrosis is a type of cell death morphologically characterized by extensive cell loss, which results in the recruitment of inflammatory cells. In necrosis, injured cells may exhibit clumping of chromatin, swelling of the cell and organelles (demonstrating a loss of control of ion balance), flocculent mitochondria, and eventual bursting and disintegration of the necrotic cell. If necrosis is extensive enough, the architecture of a tissue is destroyed. Extensive necrosis is characteristic of tissue destruction induced following severe damage by toxic chemicals, invasive microorganisms or ischemia. The wholesale release of cellular components into a tissue itself can trigger a damaging inflammatory response.

When a tissue is damaged, cells may die by a combination of apoptosis and necrosis. Many agents capable of inducing necrosis also induce apoptosis. Apoptosis often precedes extensive necrosis, with apoptosis in these situations possibly acting in a self-protective manner. When the level of insult to a tissue is too great, necrotic cell death cannot be avoided. Murine mastocytoma cells have been reported to undergo apoptosis after a moderately severe heat shock, but the same cells die via necrosis when the heat shock exposure is more severe.

For a comparison of apoptosis and necrosis, see:
(27) Columbano, A., "Cell Death: Current Difficulties in Discriminating Apoptosis from Necrosis in Context of Pathological Processes in vivo." *Journal of Cellular Biochemistry,* 58: 181–190 (1995).

The cellular response to a heat-shock has been extensively studied. Certain heat shock inducible proteins such as Heat Shock Protein 70 (HSP70), HSP 90 and gp96 are expressed constitutively at low levels. During mild to moderate heat-shock, cellular proteins may undergo conformational changes. It is this alteration in the structure of proteins, or other reversible denaturation effects, which are believed to play a role in inducing the heat shock response. (Note that other stressors, such as nutrient deprivation, release of oxygen radicals, or viral infection may also induce conformational aberrations.) Following a heat shock, mRNA expression of the genes encoding HSP70, HSP 90 and gp96, for example (along with that of other heat-shock responsive genes) is induced by activating proteins called "Heat Shock Factors." The response of two "Heat Shock Factors", HSF-I and HSF-II is triggered by different levels of thermal stress. As an example, HSP70 is thought to be induced more rapidly than (by either less heat stress, or a shorter duration) HSP90. Therefore, different thermotherapy regimes will induce different panels of heat inducible genes.

For additional background on the heat shock response see:
(28) Georgopoulos, C., Welch, W. J. "Role of the Major Heat Shock Proteins as Molecular Chaperones." *Annu. Rev. of Cell Biol.*, 9: 601–634 (1993).
(29) Hendrick, J. P. and Hartl, F. U., "Molecular Chaperone Functions of Heat-Shock Proteins." *Annu. Rev. of Biochem.*, 62: 349–84 (1993).
(30) Lindquist, S., "The Heat Shock Response." *Annu. Rev. Biochem.*, 55: 1151–91 (1986).
(31) Matzinger, "Tolerance and Danger: the Sensitivity of the Immune System." *Annu. Rev. Immunol.*, 12: 991–1044 (1994).
(32) Morimoto R. I., "Perspective: Cells in Stress: Transcriptional Activation of Heat Shock Genes." *Science* 259: 1409–10 (1993).
(33) Morimoto, R. I., "Stress Inducible Responses", Springer Verlag, Boston (1996)
(34) Parsell, D. A. & Lindquist, S., "The Function of Heat-Shock Proteins in Stress Tolerance: Degradation and Reactivation of Damaged Proteins." *Annu. Rev. of Genet.*, 27: 437–496 (1993).
(35) Schlesinger, M. J., "Minireview: Heat Shock Proteins." *Journal of Biological Chemistry* 265: 12111–12114 (1990).

Initiation of a heat-shock will induce conformational changes in cellular proteins, and lead to the induction of heat shock genes. HSP70 has the ability to bind to proteins, is thought to act as a molecular chaperone, and may use an ATP dependant activity to renature stress-damaged proteins. It is thought that HSP 70 is involved in a process that 'repairs' partially denatured proteins. If the native conformation of a protein is not restored, then the denatured protein is degraded. During the degradation process, HSP70 can retain a peptide fragment derived from the degraded protein. In essence HSP 70 may then chaperone an antigenic peptide fragment of the denatured protein. These HSP70 chaperoned fragments are then processed though the cell's endoplasmic reticulum and Golgi apparatus, and can then appear on the cell surface, presented by MHC-I molecules. Antigens presented on the surface of a cell can then lead to an immune response being generated to those antigens.

In order to have processing of peptide fragments, and presentment of potentially immunogenic fragments on the cell surface, it is necessary to have a living cell. An apoptotic cell, since the cellular contents are degraded (for instance, without presenting antigens on the phagocytitic cell's surface MHC-I molecules), may have lower immunogenicity than either a heat shocked, but recovering cell or a necrotic cell.

Accordingly, with accurate temperature and time controls therapy employing heat shock protein induction becomes available. Other adjunct therapies available with accurately controlled thermotherapy are, for example, release agent systems associated with a heating instigated release, radiation treatment, chemotherapy and radiochemotherapy.

Some approaches utilized by investigators, in the use of hyperthermia therapy, have achieved accurate temperature measurement and consequent control by inserting temperature sensors such as fiber optic temperature sensors, thermocouples or thermistors into the tissue adjacent to or integrally with implanted heaters. These fiberoptic, thermocouple or thermistor-based sensors necessarily are tethered having one or more electrical or optical leads extending externally or to a surface region of the body each time a hyperthermia therapy is administered. In the latter regard, the somewhat involved procedure often must also be repeated a number of times over many weeks or months to effect the desired therapeutic results. This becomes particularly problematic where the approach is employed in thermal therapy procedures associated with the human brain. See generally:

(36) Hynynen, et al., "Hyperthermia in Cancer Treatment." *Investigative Radiology*, 25: 824–834 (1990)

Figure 4:
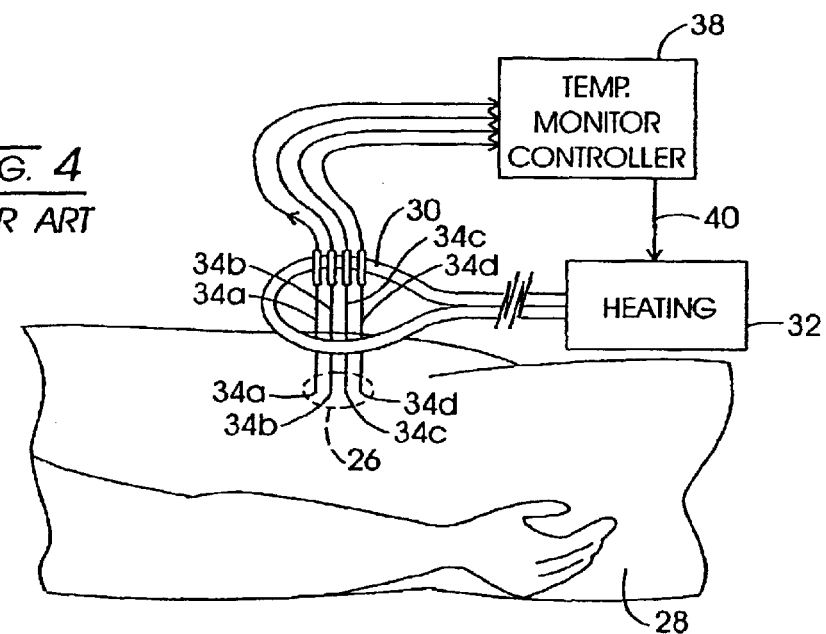
FIG. 4 is a prior art approach to heating a targeted tissue volume utilizing tethered heat sensors located within the target tissue volume.

Referring to FIG. 4, the noted tethered approach to sensing internal target tissue volume subjected to thermal therapy is illustrated schematically. In the figure, a targeted internal tissue volume 26 of patient 28 is shown to be under thermotherapy treatment. Thermal energy is applied to the target tissue volume 26 from the heating coil or antenna 30 of an ACF heating assembly employing radio frequency (RF) or microwave based heating as represented at block 32. The coil or antenna 30 typically is of a design based upon human phantom models and/or computer modeling achieving a coil/antenna structuring which evokes the sought after heating and thermal distribution at the target tissue volume 26. One or more temperature sensors 34a–34d are implanted strategically within the target tissue volume 26. Devices 34a–34d are "tethered" in that electrical leads 34a–34d extend therefrom through or adjacent to the skin to a temperature monitor/controller 38. Controller 38 additionally controls the output of the heating assembly 32 as is represented by arrow 40. In general, the heating carried out by the heating unit 32 may be enhanced through the utilization of heating elements implanted within the zone of the target tissue volume 26. A principal limitation of the technique illustrated in connection with FIG. 4 resides in the requirement that the temperature sensors 34a–34d must be inserted into and accurately positioned within the patient 28 each time thermotherapy is carried out and the procedure may be repeated often; calling for a succession of accurate sensor positionings. As noted earlier, the somewhat arduous insertion of the heat sensing elements 34a–34e becomes particularly intrusively undesirable where the procedure is carried out in conjunction with brain tumor.

Should those sensors as at 34a–34d not be utilized, the temperatures reached at the target tissue volume 26 during application of ACF radiofrequency or microwave heating can only be approximated by modeling methods which are subject to substantial error due to physical differences in the tissue of given patients. In this regard, tissues will exhibit differences in vascularity, as well as otherwise assumed average properties. As noted hereinbefore, vascularity functions as a conveyance for heat removal in the vicinity of the targeted tissue region. For further discussion of thermal modeling based methods of thermotherapy, reference is made to publication (7) supra.

The present invention generally is characterized by the partitioning of the function of heating the target tissue volume to requisite temperatures from the function of measurement of tissue temperature. For the latter function, a remotely interrogatable material property such as magnetic permeability can achieve accurate temperature measurement over very narrow temperature ranges, for example, between about 0.1° C. to about 1° C. Untethered implanted ferromagnetic sensors are employed, which are of diminutive size and can be structured to provide such a very sharp Curie transition. For example, a transition of relative magnetic permeability, $\mu_r$, from about 1000–5000 to 1 obtains. Returning to FIG. 2, this permeability/temperature characteristic extending to the Curie temperature $T_C$, is represented by dashed curve 42 having a transition at knee 44 establishing a narrow Curie transition range as shown generally at arrow pair 46. Because the sensors are of such small size the methodology of the invention can be employed in conjunction with magnetic resonant imagining (MRI) without adverse consequence. In effect, the very narrow Curie transition permits a "binary" response tuned to a particular predetermined target temperature for the involved target tissue volume. The instant system and method may provide a separate, nonmagnetic heater material which is thermally exercised from a remote non-invasive radiative source and which is brought into close thermal communication with a sensor component. In this manner, precise temperature sensing and control can be achieved, inasmuch as, for example, the ferromagnetic materials employed can be selected for their very sharp change in magnetic permeability over a narrow Curie temperature transition range. Examples of such ferromagnetic materials include ferrites having the general composition: 65% iron oxide, 14% manganese oxide, 20.7% zinc oxide and 0.3% trace quantities of other elements. See the following publication:

(37) Yoshifumi, A., et al., "Preparation and Evaluation of Temperature Sensitive Magnetic Thin Film With Low Curie Temperature", T. IEE Japan, Vol. 118-A, No. 2,1998, pp 158–163.

The heater materials employed with these sensors are selected from materials which are non-magnetic so as to permit their performance with sensors having magnetic properties. With the combination of a heating component with a sensor structure formed with a narrow Curie transition-based material, precise setpoint temperatures can be detected non-invasively using magnetometer technology in conjunction, for instance, with the earth's magnetic field as it is influenced or perturbed by the sensing component. Such magnetometer monitoring can be carried out in one approach by evoking relative movement of the target tissue volume with respect to the position of influence of the magnetometer and in another approach through the use of detector arrays. Alternately the system may perform with a derived magnetic field, for example, one which is electromagnetically generated.

Figure 5:
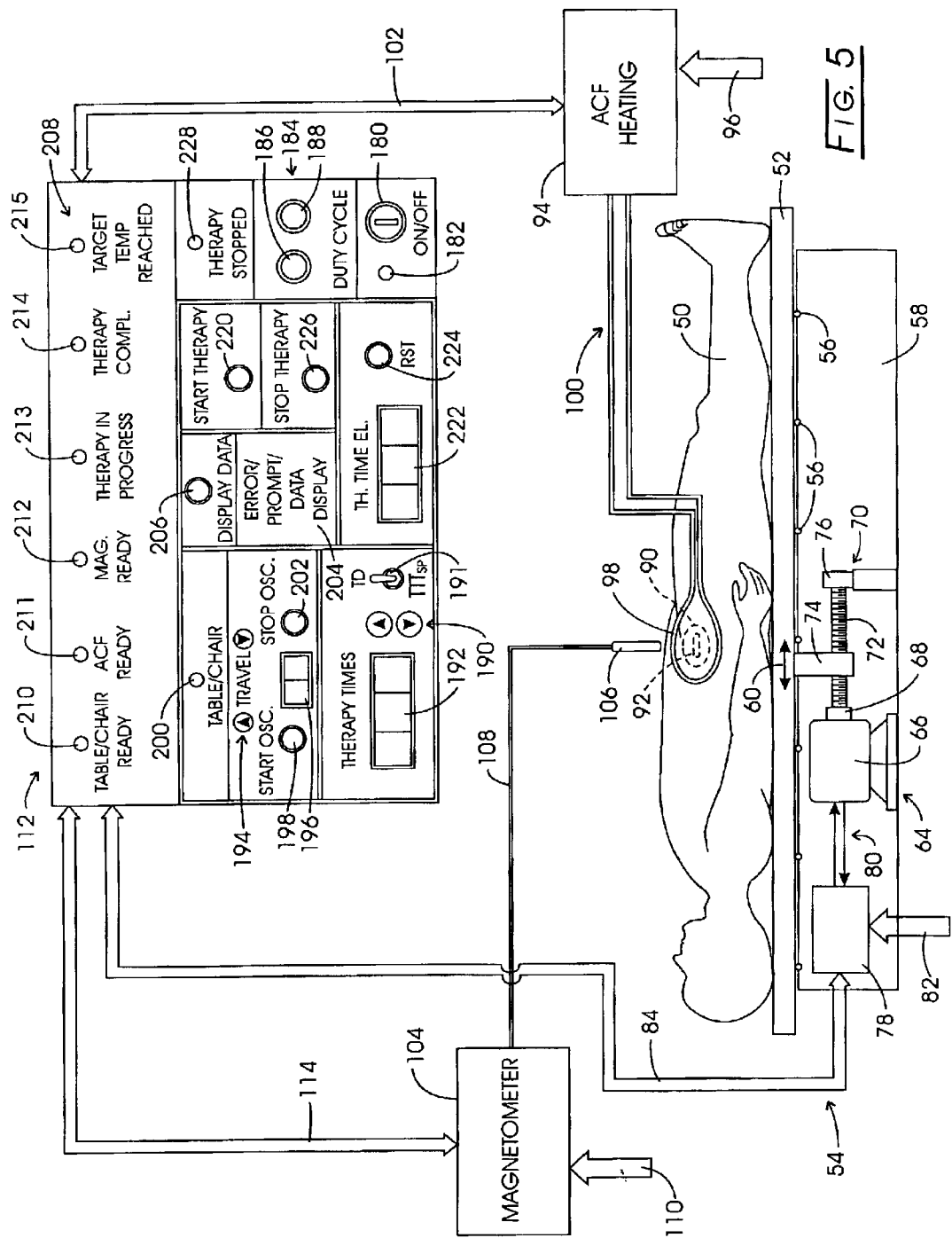
FIG. 5 is a schematic representation of one embodiment of the system of the invention utilizing a patient moving mechanism.

Referring to FIG. 5, a schematic representation of one embodiment of the system of the invention is provided. In the figure, a patient 50 is shown in a supinate position on the horizontal platform 52 of a support assemblage represented generally at 54. Platform 52 is moveably supported within the assemblage 54 by a plurality of roller bearings certain of which are identified at 56. Bearings 56, in turn, are shown mounted upon a translational support structure 58. As represented by the dual arrow 60, platform 52 may be caused to oscillate along a linear horizontal locus in consequence of its oscillatory actuation by a drive assembly represented generally at 64. Assembly 64 includes an oscillatively drivable motor 66 coupled via a drive collar 68 with a ball-screw mechanism represented generally at 70. Mechanism 70 includes a lead screw 72 which is threadably connected with a bearing-incorporating drive collar 74 fixed in turn to the platform 52. Lead screw 72 terminates in a thrust bearing 76. Oscillatory drive input to the motor 66 is provided from a motor control circuit 78 as represented by dual arrows 80. Line power is supplied to the motor 66 via the control circuit 78 as represented by arrow 82 and control input as well as status feedback information is represented by enlarged dual directional arrow 84. The oscillatory function provided by the support assemblage 54 can take a variety of support configurations depending upon, for instance, the region of tissue interest involved with the procedure. In this regard, a variety of chair structures can be implemented with the oscillatory function with patient 50 assuming other than the illustrated supinate posture. The amount of oscillation provided by the support assemblage 54 as represented by dual arrow 60 may be quite minimal, for example, an amplitude of oscillation of about 0.3 cm to about 10 cm may be provided at an oscillatory rate of about 0.1 cm to about 3 cm per second. In general, frequency is selected in accordance with the relative strength of the earths' magnetic field as will be seen to be employed with the instant embodiment, and the length of travel along the linear locus may be established in consonance with the dimensions of the target tissue volume involved. In the latter regard, the system is called upon to traverse at least that tissue volume defined distance in the presence of a magnetic field evaluation pick-up. Because the system employs a magnetometer with pick-up, pertinent components of the support system 54 are constructed of non-magnetic materials such as plastic, and the like to prevent interference with magnetic field-based measurement.

The target tissue volume of interest for the instant embodiment is represented internally within the body of patient 50 by a symbolically represented dashed boundary 90. Within this boundary 90 there is shown at least one sensor implant configured according to the invention as represented schematically at 92. However, that sensor implant or combination of such implants may be intimately combined with an internally disposed nonmagnetic heating component. Where those two components are combined in a single implant arrangement, at least a portion of the surface of both the nonmagnetic heating component and sensor component are exposed. Note that the implant 92 is untethered, having no electrical leads extending exteriorly of the patient 50.

Heating of the region of interest 90 under thermotherapy conditions and, in particular, hyperthermia conditions for the instant system, is provided from an inductive form of alternating current field (ACF) heating assembly represented at block 94. Line power input is represented as being directed to the assembly 94 as indicated at arrow 96. Substantially focused radiative heating is provided from the heating assembly 94 by a typical coil-implemented heating component represented at 98 which is positioned in close proximity to the skin of patient 50 in the vicinity of a predetermined and earlier marked location of the target tissue volume 90. Association of the component 98 with the heating assembly 94 is represented schematically by line pair 100. Preferably, the component 98 may be associated with an induction heating assemblage operating at a lower frequency within the generally identified radiofrequency range. In the latter regard, such an induction heating arrangement may be provided, for example, as a type NK-24 induction heating system marketed by Pillar Industries, Inc., of Brookfield, Wis. Other radiative heating systems will include those employing higher frequency RF, microwave or ultrasound technologies. (See $f_1$ in Table 1). As used herein, the terms "alternating current field" or "ACE" are meant to include radiofrequency (RF) systems, inductive systems, microwave systems, ultrasound systems and other noninvasive heating approaches which may perform in concert with unteathered temperature sensors.

Now looking to the magnetometer-based detection of the magnetic field disturbances evoked by the state of permeability of the sensor component at implant 92, a magnetometer control assembly is represented at block 104. The assembly 104 performs in conjunction with a remotely disposed pick-up or probe 106 oriented for discerning and/or differentiating magnetic field flux lines as they may be affected by the implant or implants as at 92. The association of probe or pick-up 106 with the assembly 104 is represented at cable 108. Assembly 104 is seen receiving line power, as represented by arrow 110, and is controlled and provides outputs to a console mounted control assembly represented generally at 112 as indicated at arrow 114. It may be noted that the control assembly 112 also is in communication with the motor control 78 as represented at arrow 84 and with the ACF heating assembly 94 as represented at arrow 102. While the magnetometer assembly 104 with its probe 106 may perform with a generated and applied magnetic field, for the instant embodiment, the field utilized is the earth's magnetic field. This magnetic field is considered to be a field of medium intensity. Because of the on/off or binary nature of the temperature sensing function of implant 92, relative amplitudes or variations and declinations in contemplated areas of use of the instant system will have no particular effect with respect to the use of this earth involved magnetic field.

For the instant application, magnetometer assemblies as at 104 and associated probes or pick-ups 106 are configured in the manner of fluxgate sensors. The basic fluxgate sensor principal is schematically illustrated in connection with FIG. 6. Looking momentarily to that figure, the soft magnetic material of a sensor core 120 is periodically saturated in both polarities by an ac excitation field evolved from a source 122 which is produced by the excitation current $I_{exc}$ through an excitation coil 124. In consequence, the core permeability changes and the dc flux associated with the measured dc magnetic field, Bo is modulated, the "gating" of the flux that occurs when the core is saturated evolving the term describing the sensor. The device output is usually the voltage, $V_{ind}$ induced into the sensing (pick-up) coil at the second and higher harmonics of the excitation frequency. This voltage is proportional to the magnetic field.

Concerning the earth's magnetic field with which the instant embodiment performs, it may be recalled that earth has a crust, a metal and a metallic core. The inner part of that core is solid and complex processes are associated with the increase of the inner core together with the earth's rotational drive, the earth's so-called magnetic dynamo which is believed to cause the earth's magnetic field. That field has a dipole character with a north magnetic pole displaced from the geographical north pole by about 1000 km. That pole, paradoxically, is a south pole of an equivalent bar magnet, inasmuch as it attracts the north pole of a magnet needle. The earth's field is changing in time, for example, the amplitude is decreasing by 0.1% each year and the pole is drifting westward by 0.1° per year. The tilt of the dipole axis is decreasing by 0.2° per year.

A magnetometer which may be employed to carry out the functions of magnetometer assembly 104 and associated probe or pick-up 106 may be provided, for example, as a multipurpose precision magnetometer identified as a type (MPN) 4.0 marketed by Walker LDJ Scientific, Inc. of Troy, Mich. For a further discourse concerning magnetic sensors and magnetometers, reference is made to the following publication:

(38) *Magnetic Sensors and Magnetometers*, edited by P. Ripka, Artech House, Inc., Norwood, Mass., pp 75–127, 380–391 (2001).

While the tissue heating function of alternating current field (ACF) assembly 94 may be carried out simultaneously with the temperature monitoring function of magnetometer assembly 104, such coincident operation necessarily requires that the monitoring function be effectively shielded or protected from electromagnetic interference. An approach to avoiding this interference is to intermit the operation of these assemblies, for instance, such that the ACF heating assembly 94 is enabled for about 100 milliseconds to about 1000 milliseconds (ms) and the magnetometer assembly 104 then is enabled for a sequential 10 ms to about 100 ms. This provides an almost continuous noise-free monitoring and the off interval for the ACF heating assembly 94 permits a modicum of accommodation for thermal inertia resulting "overshoot" which may be encountered within the heating components of implants as at 92 as they reach target temperature or Curie transition temperature. With the instant system, the duty cycles of these functions can be established by the operator or may be preset at time of manufacture of the control system.

Figure 7:
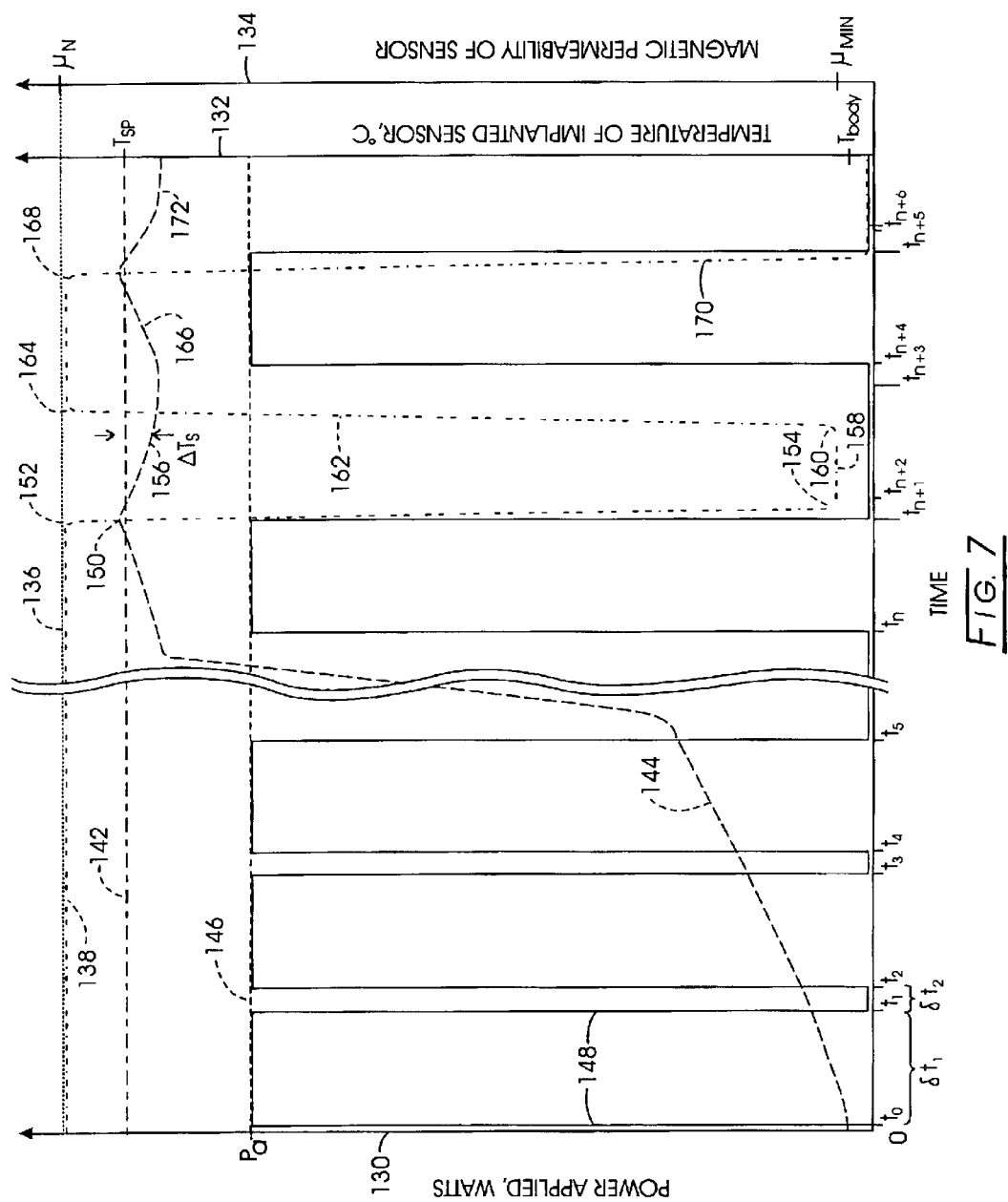
FIG. 7 is a chart illustrating the intermittent heating and interrogating features of the system of the invention, the chart being broken along its timeline in the interest of clarity.

A graphic illustration of the performance of the ACF heating function 94 and magnetometer function 104 is provided in connection with FIG. 7. Referring momentarily to that figure, it may be noted that the graph is sectioned in terms of time along its abscissa, while power applied to the heater components or tissue is represented along a left ordinate. Illustrated as a rightward ordinate is the temperature of the implanted sensor and the relative permeability of that sensor corresponding with such temperature. The noted power is seen to be identified along ordinate 130 as extending in value essentially from zero to applied power $P_a$; temperature of the implanted sensor is shown at ordinate 132 extending from body temperature, $T_{body}$ to a setpoint corresponding with Curie temperature, $T_{SP}$; and the related permeability of the implanted sensor is represented along ordinate 134 as extending from $\mu_{MIN}$ (unity value for relative permeability) and extends to generally starting relative permeability which may fall within a substantial range, for example, to values of about 100 to 10,000. A maximum relative permeability level for the given sensor at hand is represented at dotted horizontal line 136, while the relative permeability of the ferromagnetic sensor component employed with the implant or as the implant is represented at dashed curve 138. Set-point temperature, $T_{SP}$, is represented at the horizontal dashed line 142 and the gradually increasing temperature of the implant heater component, which influences the temperature elevation of involved tissue is represented by dashed line 144. Because of the proximity of the sensor implant with discrete heater components, the temperatures of those two components generally will be substantially equal. The level of power applied, $P_a$ is represented by the dashed line 146 which initially exhibits a horizontal orientation.

Now considering the intermittent activation or duty cycle-defined application of power and enablement of sensing features, it may be observed that power is represented as initially being applied as shown at power curve 148 between times $t_0$ and $t_1$, representing a power application increment of time $\delta t_1$. Following this power application interval, ACF heating function 94 is turned off for a sensing or interrogation interval extending between times $t_1$, $t_2$, representing an increment of measurement time, $\delta t_2$. Note that during the intervals, $\delta t_1$ and $\delta t_2$, the temperature value of the implanted sensor as indexed along ordinate 132 and shown at dashed curve 144 commences to rise and is seen to exhibit a modicum of thermal inertia during interrogation interval $\delta t_2$. This power-on-power-off-interrogation sequence continues, for example, a power-on condition being applied between times $t_2$ and $t_3$ with an interrogation interval occurring between times $t_3$ and $t_4$. As these power-on and sensing or interrogation intermitting cycles continue, curve 144 is seen to rise, eventually approaching the setpoint temperature $T_{SP}$. For illustrative convenience, note that the figure is broken following time, $t_5$. Setpoint temperature at line 142 is shown being acquired during the heating interval $t_n$ to $t_{n+1}$. At the termination of that power application time interval, $t_{n+1}$, Curie temperature is achieved with a slight thermal over-shoot as represented at point 150 of curve 144. Note, as this occurs, that a permeability curve 138 knee 152 change of state is experienced and the relative permeability of the implanted sensor component drops dramatically, essentially to a unity value as represented at curve 138 inflexion point 154 occurring at time $t_{n+2}$. Under the ensuing time element, until the temperature of the sensing component drops, for example, as represented at temperature drop identification, $\Delta T_S$ at point 156 of curve 144, relative permeability will remain at the unity level 158 of curve 138. This unity level 158 will continue until a sufficient temperature drop excursion at the implanted sensor component is experienced, whereupon, as represented by knee 160 in curve 138, relative permeability then abruptly rises, as represented at curve portion 162, to reassume a high relative permeability, $\mu_N$ at time $t_{n+3}$ and as illustrated at the knee of 164 of curve 138. With a magnetic disturbance now being detectable by the magnetometer function 104 and probe or pick-up 106, at the next timed heating increment at time $t_{n+4}$, power again is applied for a fixed interval of heat application and the result is illustrated by curve 144 at region 166 showing a positive temperature slope extending to a slight thermal over-shoot at time $t_{n+5}$ a time condition wherein the sharp knee 168 of a Curie transition is witnessed at curve 138 to evoke a sharp drop in relative permeability as represented by curve portion 170. This fluctuating activity evokes the noted binary form of sensory response wherein magnetic field disturbance essentially is stopped and the disturbance termination is detected through pick-up 106 by magnetometer 104. As represented by sensor/tissue temperature curve 144 at region 172, the sensor/heater/tissue temperature then dwells in lower adjacency with the temperature setpoint $T_{SP}$ until the pre-model-based election of heat application interval is completed to define a thermal energy quantum of treatment to the given target tissue volume. It may be recalled that the Curie transition evoking this binary control of heat application is quite accurate, being within about 0.1° C. and 1° C. for a typical application.

If the power setting for the ACF heating assembly 94 is set only to a level which eventually will reach the setpoint, $T_{SP}$, sometimes referred to as a saturation level, then as the temperature curve 144 approaches the setpoint level, power will be on, for example, about 90% of the time. However, for typical applications, the power will be more than twice that saturation level in view of differences in the effect of the quantum of thermal energy applied. In the latter regard, vascularity in the region of the target tissue and the nature of that tissue itself will influence the effectiveness of the thermal energy introduction. Of course, this power level can be backed off as the tissue or sensor detected temperature reaches or approaches the setpoint value to avoid an over-shoot or excessive overshoot.

Figure 3:
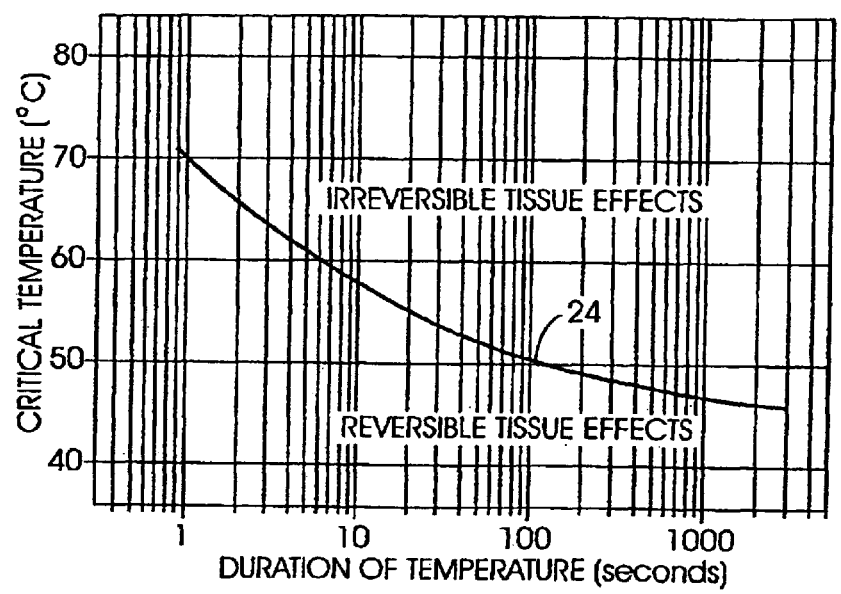
FIG. 3 is a generalized semi-log curve illustrating the temporal relationship between the duration of application of a given temperature to tissue with the value of critical temperatures.

Recalling the commentary provided in connection with the critical temperature curve 24 of FIG. 3, a form of proportional control is contemplated in addition to the intermitting approach of application of constant power followed by a quiescent measurement period. In this regard, increments of thermal energy for longer intervals can be employed at the commencement of development of a quantum of thermal energy and those increments can be diminished as the temperature setpoint is asymptotically reached as illustrated in connection with regions 156, 166 and 172 at curve 144.

Returning to FIG. 5, the user interactive functions of the control console 112 are addressed. Applied power levels are set by the user in conjunction with the apparatus 94 itself or may be preset at the time of manufacturer of apparatus. However, the control console then looks to a timing parameter for correctly establishing the energy quantum of thermotherapeutic application.

The control represented at console 112 is powered-on with a key switch 180, such a power-on condition being represented by the illumination of a green LED 182. While typically established by the manufacturer of the control 112, the duty cycles for the application of power or heat and the quiescent interval immediately following such heat application are shown as being electable by the user. Insertion of this operational criteria is provided at the switch combination shown generally at 184. The switches 184 include a heat interval input 186 and a corresponding sensor interrogation interval adjustment function 188. See the time interval ranges for $\delta t_1$ and $\delta t_2$ set forth in Table 1. With the duty cycles established, next, the timing aspects of the procedure are addressed in conjunction with a "Therapy Times" user input. Two times are set by the user, a therapy duration (TD) commencing with the attainment of setpoint temperature $T_{SP}$, and a maximum time to reach setpoint temperature ($TTT_{SP}$). Insertion of these times into the control 112 is carried out using up/down switches represented generally at 190 in conjunction with switch display 192 providing a visually perceptible visual time selection, for example, in minutes. Election between the setting of therapy duration (TD) and maximum time to setpoint temperature ($TTT_{SP}$) is made by throwing toggle switch 191 between its two election orientations.

The platform 52 or corresponding chair assemblage for supporting the patient 50 is adjusted for its motion parameters, particularly that of travel distance. It may be recalled that, in general, this travel may extend to as much as about 10 cm. The frequency of that travel preferably is pre-established by the manufacturer of the system. However, if desired, adjustment can be provided in conjunction with the control console 112. However, the extent of movement of platform 52 along a linear locus is established by up/down switches represented generally at 194 which are actuated in conjunction with observation of a digital display readout provided in centimeters as illustrated at 196. Oscillatory drive is initiated for the platform 52 by actuating the motor control circuit 78 via momentary on switch 198. Actuation of switch 198 will, in turn, cause the illumination of a green LED 200. The operator can stop this oscillation of platform 52 by actuation of momentary off switch 202.

In the course of setting up a therapy, certain associated interconnections will be made by the operator. The control system represented by the console 112 will respond to errors in that set-up procedure and provide visual cues as to the error involved and additionally will provide a prompt as to corrective action to be taken. That information is provided at a visual display 204. Display 204 also will provide a display of pertinent data concerning a completed therapy by operator actuation of momentary on-switch 206. That data also will be recorded automatically in data log memory.

During the course of setup and subsequent therapeutic operation of the system, an array of visual indicators as to the progress of the procedure as represented generally at 208 will provide confirmational outputs. In this regard, a table/chair ready indication is provided by illumination of green LED 210. The motor control 78 is configured with a motor status comparator which provides an on or enabled condition where the voltage of the motor control system exceeds or equals, for example, 3 volts. Next, the illumination of a green LED 211 indicates that an ACF heating assembly 94 switch located at that unit has been thrown to apply power. Additionally, it's illumination indicates that the magnetometer control 104 monitoring features have indicated that peak-to-peak variations of its control voltages are greater than a reference value.

LED 212, when illuminated, provides for an indication that magnetometer 104 is in a ready condition. In this regard, its power-on switch will have been actuated to an on condition and its peak-to-peak drive voltage will have equaled or exceeded a reference voltage value. Next, green LED 213 is illuminated to provide an indication that therapy is in progress, and green LED 214, when illuminated, indicates that the therapy duration has now been reached and therapy is completed. Finally, green LED 215 is illuminated to indicate that the target temperature or setpoint temperature, $T_{SP}$ (FIG. 7) has been reached. Once setpoint temperature is reached, this LED 215 will remain illuminated until the end of the therapy or until the stopping of the therapy.

Therapy is commenced with the user actuation of the momentary on start therapy switch 220. During the interval of the therapy, the elapsed time of therapy is indicated at display 222. That display may be reset to zero by actuation of momentary on switch 224. If, during the progress of therapeutic performance by the system, the operator deems it advisable to stop the therapy, then the stop therapy switch 226 is momentarily actuated and the therapy stopped red LED 228 is illuminated.

Concerning the general operation of the control function 112, it may be noted that unless the checking logic of the control system will have functioned to carry out the illumination of the "ready" LEDs 210–212, then the start therapy switch 220 will not be enabled. In general, error and prompt messages will remain at the display 204 where these startup conditions are not satisfied.

Figure 6:
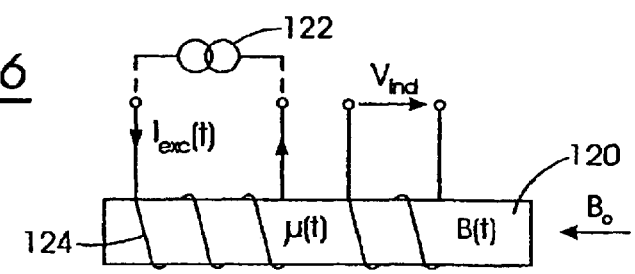
FIG. 6 is a schematic depiction of a fluxgate sensor.
Figure 8A:
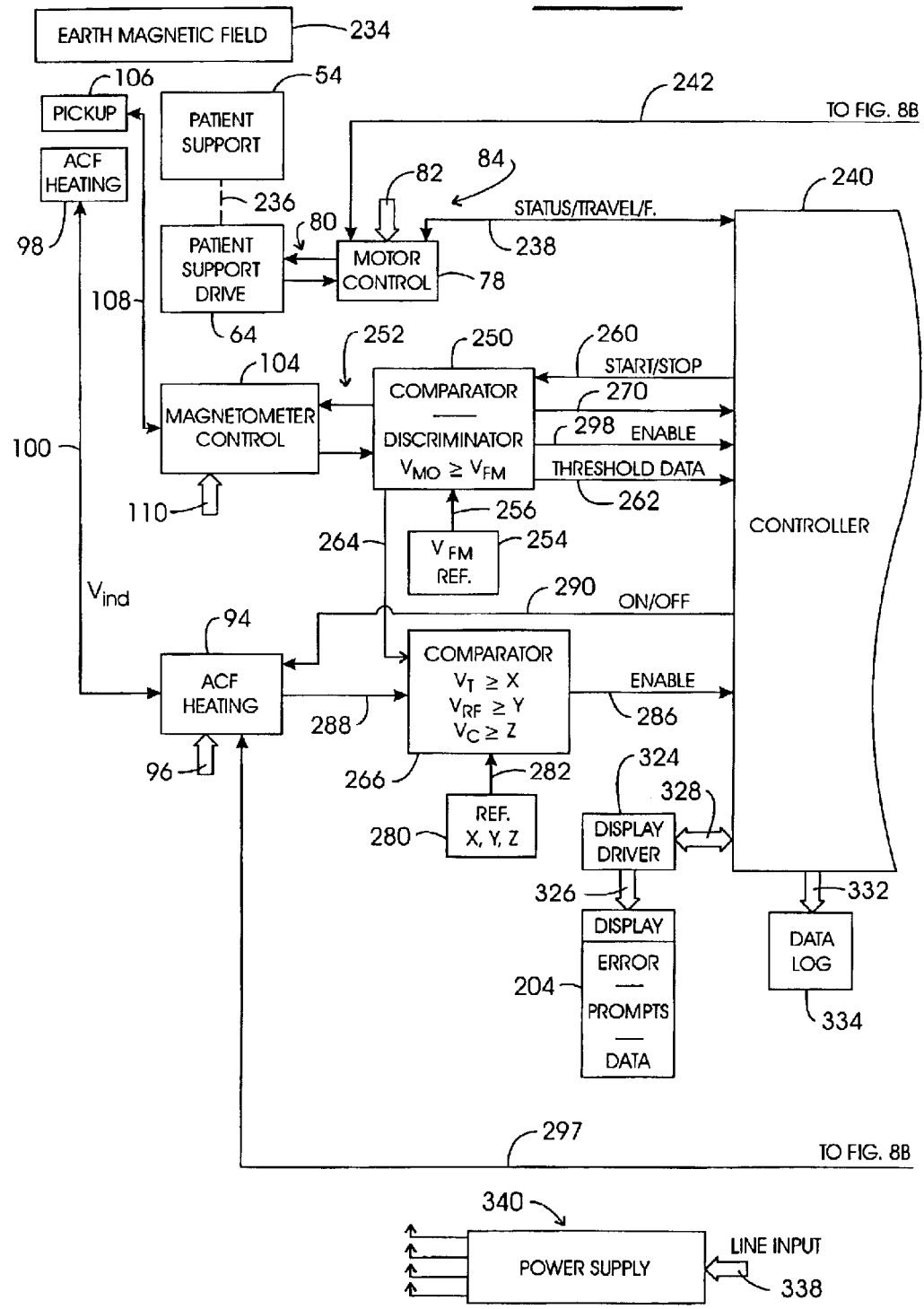

Referring to FIGS. 8A and 8B, which should be considered in connection with the labeling shown thereon, a more detailed representation of the system at hand is revealed. For the embodiment thus far described, the earth's magnetic field is employed in conjunction with the sensing aspects of the system. That magnetic field is represented in block form at 234 in adjacency with the patient support function represented in block form with the earlier numerical identification 54. In adjacency with the patient support function 54 there is shown the ACF heating coil or antenna represented in block form again with the number 98. The magnetometer pick-up 106, is similarly shown in block form with the same identifying numeration. Heater coil or antenna 98 again is represented as being coupled with the ACF heating assembly 94 via cable 100 and the pick-up 106 is shown associated with magnetometer control 104 in conjunction with earlier described cable 108 carrying the induced perturbation voltage $V_{ind}$ (FIG. 6). The patient drive support earlier described at 64 is represented in the instant figure in block form and its mechanical drive association with the patient support function 54 is represented by dashed line 236. Patient support drive function 54 again is shown in interactive communication with a motor control circuit represented at block 78. In addition to providing for a control over the extent of the locus of travel of the platform 52 and the frequency and related rate of its oscillation, the motor control 78 functions to carry out an enablement check as earlier described wherein its actuating circuit is tested for the presence of a confirming minimum voltage, $V_{MC}$ which will be greater than or equal to, for example, three volts. That data and assertion of the status check is sequentially controlled as represented by dual arrow 238 from a controller represented at block 240. Controller 240 may be implemented, for instance, as a programmable logic device (PLD) or may provide microprocessor-driven logic control over the system. Line input to the motor control 78 again is represented at arrow 82. Similarly, arrow 110 shows line input to magnetometer control 104 and arrow 96 shows such line input to the ACF heating assembly 94. Motor control 78 functions to actuate the motor driven patient support drive 64 initially upon the actuation of start switch 198 as represented by dual arrows 242 and 244. These arrows extend to start switch 198 as reproduced in block form herein. Similarly, a stop command is provided from stop switch 202, again represented in block form in the instant figure. The stop command is shown presented from dual arrow 242. The initial table ready status LED, as represented in block form with the earlier notation 210, is caused to be illuminated, when appropriate, in consequence of the status signals provided at line 238 to controller 240 and by virtue of input from the latter controller 240 thereto as represented at dual arrow 246. A similar energization of the presence of table oscillation LED 200 is provided from a status input via line 238 from motor controller 78 to controller 240 and consequent energization of the LED 200 as represented by dual arrow 248.

Magnetometer assembly 104 control is enabled from a comparator/discriminator circuit represented at block 250, the interactive relationship being represented in general by the arrow pair 252. Upon powering up of magnetometer assembly 104, the comparator carries out a determination as to whether its peak-to-peak drive voltage excursions $V_{MO}$ are equal to or exceed a reference voltage $V_{FM}$. That reference voltage is provided by a reference network represented at block 254 and arrow 256. Where that test is met, then an enable signal is provided to controller 240 as represented by arrow 258. The controller 240 additionally transmits start and stop commands to the circuit 250 as represented at arrow 260. The locus of travel distance supplied by the operator from up/down switch 194 is submitted to controller 240 as represented at arrow 243 while the corresponding display of the elected travel extent represented at corresponding block 196 is applied from controller 240 as represented at arrow 245. That information is supplied to the motor control function at block 78 as represented at dual arrow 238.

Where multiple implants, for example, combining a heater component and a sensor component are positioned within the target tissue volume, they may be identified, inter alia, by orientation as well as position. In the former regard, where the implants have a predominate lengthwise dimension, i.e., wherein their aspect ratio is less than unity, then their orientational aspect with respect to an impinging magnetic field will result in an alteration of the resultant perturbance-related amplitude detected by the magnetometer assembly 104. By submitting such amplitude data to a discriminator or window function, the location of these implant sensors can be confirmed. Under circumstances where it is desirable to utilize sensor implants exhibiting different temperature setpoints, the acquisition of these differing setpoint temperatures may be detected in correspondence with magnetometer output signal amplitudes, i.e., as signals representing lower temperatures and their associated amplitudes disappear, signals exhibiting a different amplitude representing a higher setpoint temperature will persist. Accordingly, threshold data can be supplied to the controller 240 from the comparator/discriminator function 250 as represented by arrow 262. Where the peak output, $V_{MO}$ satisfies the requirement of reference voltage 254, then the comparator 250 also provides an enable signal voltage $V_C$, as represented at arrow 264, to the comparator network 266 operationally associated with the ACF heating assembly 94.

Returning to controller 240, an enablement of the magnetometer control provides for the energization of the magnetometer ready LED 212 as represented at arrow 268. Binary signals representing the acquisition of Curie temperature are provided from the network 250 and magnetometer control 104 to the controller function 240 as represented at arrow 270. This, in turn, provides for the controller 240 energization of the target temperature reached LED 215 as represented at arrow 272 and corresponding block 215 as well as the commencement of time-out of therapy duration. Operator inputted or manufacturer established duty cycle data and, particularly, the interrogation interval input switch function 188 of switch grouping 184 is asserted to the controller as represented at arrow 274 extending from corresponding block 188.

ACF heating assembly 94 performs only upon the satisfaction of a triad of preliminary conditions. Initially, the enablement of the magnetometer control signal, $V_C$ as presented at line 264 must be present and verified as being greater than a reference voltage value, Z as derived from a reference network represented at block 280 and arrow 282. This comparison is provided at a comparator network represented at block 266. Next, the comparator network 266 determines a closure of ACF activation switch by determining that the corresponding signal, $V_{RF}$ is above a reference value, Y. Finally, the comparator determines the presence of a start therapy switch 220 activation by observing a resultant voltage output generation $V_T$ as being greater than reference voltage value, X. Upon the occurrence of these three enablement conditions, an enablement input is provided to controller 240 as represented at arrow 286. Inputs from the ACF heating apparatus 94 are provided to the comparator function 284 as represented at arrow 288 and a comparator verified on and off input to the ACF heating assembly 94 is provided from the controller 240 as represented at arrow 290.

Controller 240 responds with respect to the actuation of power on/off switch 180 as represented at arrow 292; responds to the start therapy switch 220 as represented at arrow 294; and responds to the stop therapy switch 226 actuation as represented at arrow 296. Heating interval, $\delta t_1$ information as provided either by the manufacturer or from switch 186 is supplied to the controller 240 as represented at arrow 298. Controller 240 responds to the above-noted actuation of on/off switch 180 as represented at arrow 292 to energize the on LED 182 as represented at arrow 300.

A timing network as represented at block 304 performs in concert with the controller function 240 as represented by dual arrow 306. Network 304 responds to the time selections from duration up/down switch 190 as represented at arrow 308, as well as to a reset input from the reset switch 224 as represented at arrow 310. That reset signal additionally is submitted to the controller 240 as represented by arrows 310 and 312. The output of time election switch 191 is submitted to the controller 240 as represented at arrow 309. Elected time data is supplied from the controller 240 to the display 192 as represented at arrow 314 and the therapy time elapsed data as retrieved from timing network 304 is supplied by the controller 240 to the therapy time elapsed display 222 as represented at arrow 316. Therapy in progress LED 213 is controlled from controller 240 as represented by arrow 322. The completion of therapy as is derived from timing network 304 is responded to by controller 240 to energize the therapy completed green LED 214 as represented at arrow 318. Correspondingly, the stop therapy input from switch 226 is asserted to controller 240 as represented at arrow 296. This provides for a corresponding reaction to energize the therapy stopped red LED 228 as represented at arrow 320. For safety purposes, the output of the stop therapy switch 226 also is simultaneously submitted to the ACF heating assembly 94 as represented by arrow 297.

The error, prompt and data display 204 is reproduced in the instant figure in block form with the same identifying numeration in conjunction with a display driver represented at block 324. Operative association between driver 324 and display 204 is represented at arrow 326 and the corresponding operational association between controller 240 and driver 324 is represented at arrow 328. By operator actuation of the display data switch 206, as represented at communications arrow 330, controller 240 reacts to provide corresponding visual data at display 204. Controller 240 also maintains a memory based data log as represented at arrow 332 and block 334. The data log retained data, of course, can be downloaded to paper or magnetic records. Power supply for requisite components of the control circuitry is represented at block 336 in conjunction with line input arrow 338 and regulated d.c. circuit power input as represented by an arrow array shown generally at 340.

The discourse now turns to discussion of the implanted sensor components as they may be intimately combined with implanted heater components or perform separately with or without such heater components. In an initial embodiment, the implant assumes a cylindrical form of dimension effective for implantation within a target tissue volume. In this regard, its configuration and dimensions should be suitable, for example, for percutaneous placement by utilizing a modified version of a hypodermic syringe. Thus, a minimally invasive implantation scheme is available to the practitioner. Looking to FIG. 9, the general shape of a combined sensor and heater implant 350 is shown with a cylindrical configuration. It may be noted that its length exceeds its diametric extent such that it will exhibit an aspect ratio of height or diametric extent divided by length of less than unity. This aspect ratio permits establishing an inclination with respect to encountered magnetic flux paths so as to provide an amplitude defined position or Curie transition temperature signature for a magnetometer readout. The operational and dimensional aspects of the implants described herein are summarized in Table 1.

Looking to FIG. 10, the implant 350 is seen to have a length, $L_1$ which will range, for example, from a minimum value of about 0.05 inch (1.3 mm) to about 4.0 inch (102 mm) and a preferred length range of from about 0.10 inch (2.5 mm) to about 2.0 inch (51 mm). The diametric extent, $D_1$ of implants 350 range from about 0.01 inch (0.25 mm) to about 0.50 inch (12.7 mm) and will fall within a preferred range of from about 0.02 inch (0.51 mm) to about 0.20 inch (5.08 mm). Note that implant 350 is shown in FIG. 10 to be formed of two right semi-cylindrical components, a sensor component 352 and a heater component 354. Components 352 and 354 are intimately joined together along their common flat boundary surfaces with a bonding agent 356. Thermal resistance, TR1, between the heater and sensor will be about 5° C./watt and preferably (TR2) about 0.5° C./watt. As discussed in conjunction with FIG. 2 above, the sensor component 352 is formed with a ferromagnetic material having a formulation exhibiting a Curie temperature based permeability transition of interest which exhibits an abrupt change in magnetic permeability, i.e., about a 20 to 1000 fold change over a relatively narrow range, for example, from about 0.1° C. to about 1° C. Recalling curve portion 156 in FIG. 7, $\Delta T_S$, the sensor temperature range about setpoint temperature $T_{SP}$ will be in a range extending from about 0.1° C. to about 10° C. and, preferably in a range extending from about 0.1° C. to about 3° C. The sensor component 352 is intimately coupled through the bonding agent 356 to the heater component 354 which, in turn, is a non-magnetic inductively energizable device formed, for example, of an austenitic stainless steel such as Type 316, titanium and titanium alloys and nitinol. The heater component 354 will exhibit a heater temperature range, $\Delta$Theater about the setpoint, $T_{SP}$ (FIG. 7) of from about 0.1° C. to about 20° C. and preferably from about 0.1° C. to about 3° C. This will provide or develop a tissue temperature range about the setpoint $T_{SP}$, $\Delta T_t$ from about 0.1° C. to about 8° C. and preferably in a range between about 0.1° C. and 3° C. Looking to FIG. 11, the semicylindrical diameters or heights of the sensor 352 and heater 354, are respectively indicated as $H_1$ and $H_2$. Those heights will fall within a range of from about 0.005 inch (0.13 mm) to about 0.25 inch (6.4 mm) and preferably within a range of from about 0.01 inch (0.25 mm) to about 0.10 inch (2.5 mm). Bonding agent 356 may be provided as adhesive such as a cyanoacrylate, acrylic or an epoxy adhesive, or a bonding agent such as a solder or a braze. In general, the adhesive or bonding agent will exhibit a thickness, $t_7$ of between about 0.0001 inch (0.0025 mm) and about 0.03 inch (0.75 mm) and, preferably, between about 0.001 inch (0.025 mm) and 0.015 inch (0.38 mm) and will establish the above-noted thermal resistance. The good thermal communication between the heater 354 and sensor 352 provides for desirable maintenance of the heater component 354 at temperatures close to the corresponding temperature of the sensor 352 as it is elevated toward a Curie transition temperature. The outer surface of the implant 350 may be covered with a biocompatible coating shown in the FIGS. 10–13 at 358. Coating 358 may be provided as a Parylene C (poly monochloro-p-xylylene) coating of thickness, $t_2$ ranging from about 0.001 inch (0.0025 mm) to about 0.010 inch (0.254 mm) and preferably between about 0.001 inch (0.025 mm) and about 0.003 inch (0.076 mm). Such coatings are available from organizations, such as Specialty Coating Systems, of Indianapolis, Ind.

Once implants as at 350 are accurately positioned within or in adjacency with targeted tissue, it is desirable that they remain in place. This follows, inasmuch as hyperthermia therapy typically will be repeated at given intervals for a multi-application treatment regimen. Advantageously re-implantation is not necessary. Of further benefit, typical surgical or biopsy procedures, for example, involving the breast call for the implantation of a radiographic marker. These markers are employed in subsequently occurring patient management procedures. The instant implants contribute the same radio-opaque marker function in subsequent patient management practice.

Referring to FIG. 9A, implant 350 reappears with its mutually bonded semi-cylindrical sensor component 352 and heater component 354. Note that mutually oppositely inwardly disposed tissue engagement implements in the form of barb-like projections 353a and 353b are fixed to and resiliently extend from heater component 354. When implant 350 is released into target tissue by an implantation instrument, (FIGS. 32 and 33), the implements 353a and 353b will spring outwardly into engagement with adjacent tissue. Connection of the implements 353a and 353b to implant 350 is facilitated by coupling with heater component 354. In this regard, connection may be carried out by welding or forming.

FIGS. 12 and 13 reveal an adaptation of the implant 350 wherein it is employable not only for the purpose of thermotherapy, and in particular hyperthermia applications, but it also carries a thermally activatable release agent coating shown at 360 to provide an adjunct therapy. By controlling or regulating such release with respect to the accurate temperatures made available with the instant system, multiple dosages of a release agent based therapeutic program may be achieved by the activation of the heating component 354 under the sensor 352 based control of the system at hand. Exemplary of such thermally activatable release agent coatings as may be provided at 360 are liposome and capsulated anti-tumor drugs as described in the following publication:

(39) Kong, G., et al., "Efficacy of Liposomes and Hyperthermia in Human Tumor Xenograft Model: Importance of Trigger Drug Release." *Cancer Research*, 60 (24): 6950–6957 (2000).

Another exemplary release agent coating includes a temperature-responsive polymeric micelle prepared using block copolymers of poly (N-isopropylacrylamide-b-butylmethacrylate) as discussed in publication (9) supra.

In one arrangement of this release agent embodiment, the thermally activated release agent coating is formulated to provide a controlled rate of release of an anti-tumor when the heater/sensor implant 350 reaches its pre-selected therapy temperature, for example, the temperature setpoint, $T_{SP}$, as discussed in connection with FIG. 7. The thickness of, $t_3$, of the thermally activatable release agent coating 360 may, for example, range from about 0.001 inch (0.025 mm) to about 0.20 inch (5.1 mm) and preferably between about 0.005 inch (0.13 mm) and about 0.10 inch (2.5 mm). Nominal release agent temperature ($T_{DRS}$) ranges will extend from about 39° C. to about 65° C. and preferably from about 41° C. to about 50° C.

The ferromagnetic sensing components of implants as at 350 generally are fabricated utilizing molded pressed powder technology. As such, they generally will exhibit adequate compressional strength but somewhat lower tensile strength. Thus, where they are incorporated in an embedded or clad heater/sensor combination it is preferred that the sensor component be internally disposed. However, it is essential that the surface of the sensor be exposed somewhat for appropriate reaction to the impinging magnetic field. Conversely, it is important that the surface of the heater component be readily exposed to, for example, E-field imposed activity to achieve requisite temperature development.

An embodiment for a heater/sensor implant structured having an outwardly disposed heater sleeve is shown in FIGS. 14–16 in general at 370. As represented in those figures. the implant 370 is configured having an internally disposed cylindrical sensor component 372 fashioned with the material as described in connection with sensor component 352 (supra). Cylindrical sensor component 372 is seen in FIG. 15 to have an outer surface 374 disposed along a central axis 373. Over the outer cylindrical surface 374 (FIGS. 15, 16) of component 372 there is positioned a heater component 376 formed of the material described in connection with heater component 354 (supra). Note in FIG. 14, however, that the heater component 376 is fashioned as a perforated sleeve which surrounds and is in good thermal communication with the cylindrical sensor component 372. Formed with a plurality of openings, certain of which are identified at 378, the sleeve-configured heater component 376 thus provides magnetic field access to the surface of sensor component 372, while being in intimate contact with adjacent tissue for heat transfer purposes and for response to inductively imposed E-fields. Openings 378 are seen to be arranged in a regular pattern, for the instant embodiment, of somewhat rectangular periphery. In this regard, FIG. 14 reveals that the openings 378 are configured with a height $W_6$ and a height-to-height inter opening spacing, $W_7$. FIG. 15 identifies a width dimension, $W_2$ for the openings 378 and a width-to-width spacing, $W_1$ for those openings. Additionally, the figure reveals that the sleeve-shaped heater component 376 exhibits a radial thickness, $t_1$. For the present embodiment, the cylindrical outer surface 374 of the sensor component 372 is coated with a biocompatible conformal coating 380. Biocompatible coating 380 may be provided in the same manner as coating 358 (supra) with thicknesses, $t_2$. A manufacturing approach for forming the implant 370 is to form the developed structure of the heater 376 into a cylinder by rolling, whereupon a welding step will complete the heater as a cylinder with a longitudinal seam. That perforate cylinder then is mounted upon the corresponding cylindrical sensor 372. It should be borne in mind that the conformal coating 380 described above can be applied over the combined heater and sensor implant assembly. This conformal coating, in addition to providing a very thin electrically insulative surface, additionally has been found functional as an effective adhesive joining medium.

As before, the alphanumerically identified dimensions and operational attributes are compiled in Table 1. Heater segment width, $W_1$ will be within a range from about 0.005 inch (0.13 mm) to about 0.25 inch (6.3 mm) and preferably within a range from about 0.010 inch (0.25 mm) to about 0.10 inch (2.5 mm). The distance between heater segments, $W_2$ will be within the same dimensioned ranges or dimension $W_1$. Further, the tabulated ranges for $\Delta T$ heater and $\Delta T$ sensor continues to be applicable as well as the values for thermal resistance, TR1 and TR2.

As discussed in connection with FIG. 9, re-installment of the implants 370 is not required for a succession of hyperthermia treatments, and the instant implants offer the added benefit of serving as radiographic markers for subsequent patient management practices.

Figure 14A:
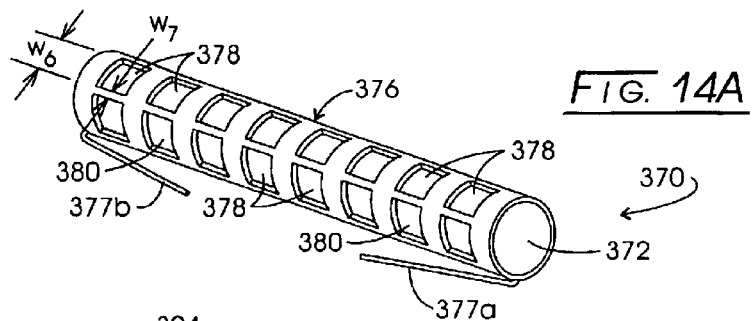
FIG. 14A is a perspective view of an implant configured in accordance with FIG. 14 but modified to incorporate extensible barb-like structures for migration avoidance.

Referring to FIG. 14A, implant 370 reappears with its mutually bonded cylindrical sensor component 372 and overlayed heater component 376. Note that heater component 376 is configured having resilient, integrally formed and outwardly extending tissue engagement implements in the form of barb-like projections 377a and 377b. When implant 370 is released into target tissue by an implantation instrument (FIGS. 32 and 33), the implements 377a and 377b will spring outwardly into engagement with adjacent tissue. This feature, combined with the perforate surface of implant 370 functions to avoid implant migration over an interval of successive therapy sessions, and subsequent patient management procedures.

Another embodiment for a combined sensor and heater implant is revealed in connection with FIGS. 19–21. Referring to FIG. 19, an implant represented generally at 384 is seen to have a sensor component 386, the surface 388 of which extends along axis 390 to define a right cylindrical configuration. As represented in FIGS. 20 and 21, that surface 388 may be coated with a biocompatible electrically insulative conformal coating 392 such as the "Parlyene" product described above having the noted thickness, $t_2$. The Curie transition temperature responsive sensor 386 is conjoined with a heater component represented generally at 394. Component 394 is formed as a continuous, generally open, helical or spiral sleeve herein configured as a band which is positioned in thermal exchange relationship about the cylindrical sensor surface 388. This intimate thermal exchange relationship between the heater component 394 and the sensor component 386 is revealed in FIG. 21. In general, the open spacing between the helically wound band components will have the earlier described spacing value $W_2$ and a band width corresponding with the earlier-described value $W_1$. Cylindrical sensor component 386 will have a diameter $D_1$ and a length L1 as earlier-described. Helically-shaped heater band 394 may be configured in the form of a helical spring formed either of flat wire construction in the manner shown in the instant figure or of wire of generally round cross-sectional configuration. In general, the helical heater component band 394, whether formed as a round spring or as a helical structure of rectangular cross-section as shown will be wound so that its inside diameter is slightly less than the outside diameter of the sensor surface 388 with or without the biocompatible conformal coating 392. For the assembly process, by temporarily partially unwinding the helical heater 394, its inside diameter will slightly increase such that it can be positioned securely over the sensor 386. As before, the electrically insulative conformal coating such as "Parlyene" may be applied with thickness, $t_2$, over the assembly of both heater 394 and sensor 386. Additionally, as before) at least the heater component and, more logically, the entire implant 384 may support a thermally activatable release agent coating effective to release an agent at the situs of the target tissue in conjunction with the heater component 394 achieving an induced temperature below or generally corresponding with the Curie transition temperature, $T_c$. The tabulated range for $\Delta T$ heater and $\Delta T$ sensor continue to be applicable to this embodiment, as well as the values for thermal resistance, TR1 and TR2. As discussed in connection with FIGS. 9 and 14 re-installment of the implants 384 is not required for a succession of hyperthermia treatments. An added benefit further is realized by subsequent utilization of the implants as radiographic markers in patient management procedures. For such procedures as well as for the initial succession of hyperthermia therapy successions, avoidance of implant migration from position is desired.

Figure 19A:
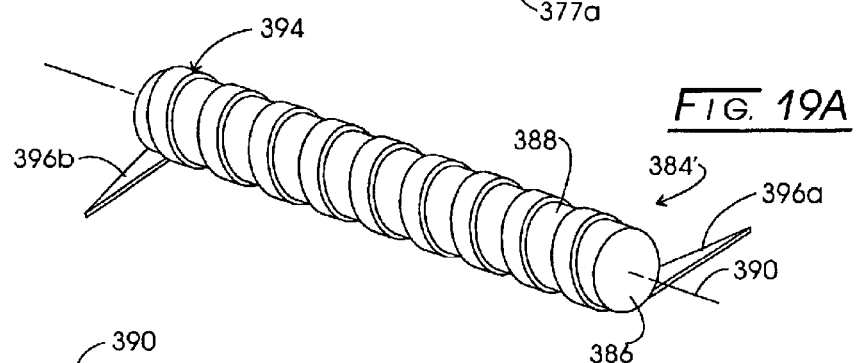
FIG. 19A is a perspective view of an implant configured in accordance with FIG. 19 but modified to incorporate extensible barb-like structures for migration avoidance.

Referring to FIG. 19A, implant 384 reappears at 384' with its mutually bonded cylindrical sensor component 386 and surface mounted heater component 394. Note that heater component 386 is configured having resilient, integrally formed and outwardly extending tissue engagement implements in the form of barb-like projections 396a and 396b. When implant 384 is released into target tissue by an implantation instrument (FIGS. 32 and 33), the implements 396a and 396b will move into engagement with adjacent tissue. This feature, combined with the helical shaped screw or bolt thread-like surface of implant 384' functions to avoid implant migration over an interval of successive therapy sessions and later patient management procedures.

Figure 19B:
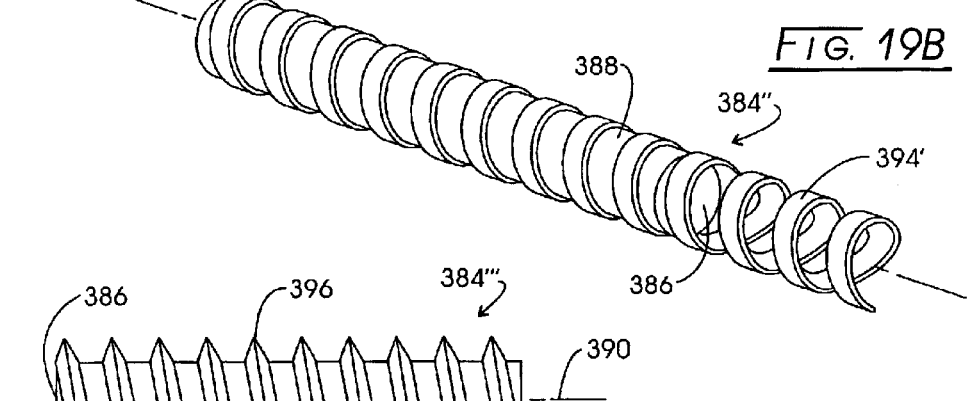
FIG. 19B is a perspective view of an implant configured in accordance with FIG. 19 but modified to provide a heater component as extending into a spiral tissue engaging implement.
Figure 19C:
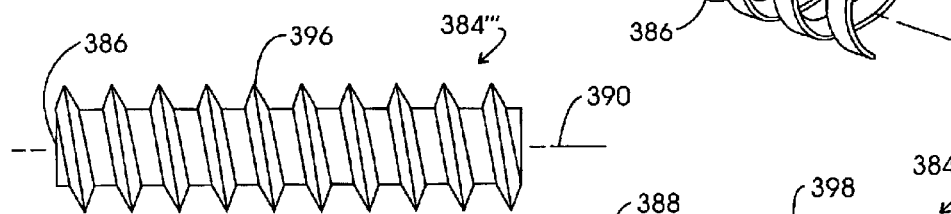
FIG. 19C is a perspective view of an implant configured in accordance with FIG. 19 but modified to incorporate a heater component configured as a screw thread for tissue engagement.
Figure 19D:
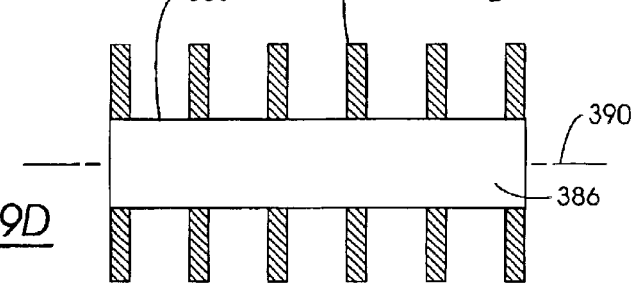
FIG. 19D is a perspective view of an implant having a sensor component configured in accordance with that of FIG. 19 but incorporating a heater component formed as a sequence of disk-like structures functioning to anchor the implant within tissue.

Looking to FIG. 19B, implant 384 reappears in general at 384" with cylindrical sensor component 386 and heater component 394. For this embodiment, the wire-like spiral heater component structure 394 has one end 394' extending outwardly beyond sensor component 386 forming a spirally-shaped tissue engaging implement for migration avoidance. Of course, such engaging implements can extend from either or both ends of sensor component 386. Turning to FIG. 19C another adaptation of implant 384 is represented in general at 384'''. Again, cylindrical sensor component 386 reappears, but joined with a heater component 396 formed as a screw thread configured somewhat coarsely for anchoring engagement with tissue. Referring to FIG. 19D, another adaptation of implant 384 is represented in general at 384''''. Again, cylindrical sensor component 386 reappears. However the heater component as shown at 398 is formed as a sequence of disk-like structures fixed to and extending outwardly from the surface 388 of sensor component 386. Implant 384'''' is configured for positioning in tissue intraoperatively, i.e., during an open surgical procedure prior to closure, the disk-shaped heater component structure providing a tissue engaging function in avoidance of implant migration.

Referring to FIGS. 22 and 23, another implant embodiment is represented generally at 400. Implant 400 is configured having a sensor component represented generally at 402 with a right cylindrical surface 404 disposed along an axis 406 between end portions or cylinder ends 408 and 410 (FIG. 23). The heater component for implant 400 is comprised of two cap-shaped heater components shown generally at 412 and 414. Each of the cap-shaped components 412 and 414 is formed having a cap end portion shown respectively at 416 and 418. These end portions are shown in FIG. 23 to have a thickness $t_4$.

FIG. 23 reveals that cap end portions 416 and 418 have a thickness $t_4$, which as tabulated herein will fall within a range of about 0.001 inch (0.025 mm) to about 0.20 inch (5.1 mm) and preferably within a range of about 0.003 inch (0.75 mm) to about 0.10 inch (2.5 mm). The cap end portions integrally extend and are formed with cap sleeve portions shown respectively at 420 and 422. Sleeve portions 420 and 422 will exhibit the earlier-described range of thicknesses, $t_1$. Cylindrical sensor component 402 may be coated as represented at coating 424 with an electrically insulative conformal coating such as the earlier-described "Parylene". The coating will have the thicknesses earlier-described as $t_2$. Cap-shaped components 412 and 414 are joined to the cylindrical sensor 404 utilizing a bonding agent 426. That bonding agent may be the same as that described earlier at 356 in connection with FIGS. 10 and 11. With the arrangement shown, a portion of the surface 404 of the sensor component 402 is exposed for interaction with confronting magnetic flux. That portion is identified by the cylindrical length or widthwise dimension $W_3$. As set forth in Table 1, the exposed length $W_3$ of the sensor component 402 may range from about 0.05 inch (1.3 mm) to about 4.0 inch (102 mm) and preferably will fall within the range of about 0.10 inch (2.5 mm) to about 2.0 inch (5.1 mm). The diameter of sensor component 402, $D_2$ as set forth in Table 1, will fall within a range of from about 0.01 inch (0.25 mm) to about 0.50 inch (12.7 mm) and preferably within a range of from about 0.020 inch (0.51 mm) to about 0.20 inch (5.1 mm). The length, $L_2$, of the overall implant 400 may, as represented in the Table, range from about 0.05 inch (1.3 mm) to about 4.0 inch (102 mm) and preferably will fall within a range of about 0.10 inch (2.5 mm) to about 2.0 inch (51 mm). Table 1 also sets forth ranges for ΔT heater or heater temperature around the setpoint, ΔT sensor or sensor temperature around the setpoint, $P_{heater}$ or instantaneous heating power generated within the heater, $T_{heater}$ or nominal hyperthermia temperature for the heater component, TR1, the nominal thermal resistance between the heater components and sensor components and TR2, the preferred thermal resistance between the heater component and the sensor component. These tabulated values and ranges of values are repeated for each of the embodiments. The heater cap components for 412 and 414 as well as the exposed portion of the sensor component 402 additionally may support a release agent coating which is thermally activatable under or below temperatures corresponding with the Curie transition temperature of the sensor component 402 thus providing an adjunct therapy in addition to the hyperthermal therapy achieved with the implant or implants as at 400. See the release agent temperature ranges $T_{DRS}$ in Table 1.

Multiple numbers of the sensor components described at 402 may be combined as represented at FIGS. 24–26. Looking to FIG. 24, implant 430 is seen to be comprised of sensor components as earlier-described at 402 and herein represented having respective surfaces 404a–404d extending along axis 432. Cap end portions identical to those described at 416 and 418 in FIGS. 22 and 23 are provided with the implant 430 as shown respectively at 416' and 418'. As illustrated in FIG. 25, these heater end cap components 416' and 418' have the same thickness dimensions, $t_4$. Retaining the serial assemblage of sensor components 402a–402d are three intermediate heater component sleeves 434–436. Sleeves 434–436 are configured with cylindrical outer sleeves shown respectively at 438–440 which are integrally formed in connection with inner cylindrically-shaped webs shown respectively at 442–444. The cylindrical outer sleeves 438–440 are provided having the earlier discussed thickness, $t_1$, and are arranged having a width, $W_5$, of from about 0.02 inch (0.51 mm) to about 0.5 inch (12.7 mm) and preferably within a range of from about 0.04 inch (1 mm) to about 0.2 inch (5.1 mm). Spacing between intermediate heater sleeves 434–436, as well as intermediate heater sleeves as at 434 and heater cap end portion 416' and intermediate heater sleeve 436 and heater cap end portion 418' is indicated as $W_4$. That dimension of exposed sensor length as set forth in Table 1 will range from about 0.05 inch (1.3 mm) to about 4.0 inch (102 mm) and preferably within a range of about 0.10 inch (2.5 mm) to about 2.0 inch (51 mm). The diametric extent of the sensor components 404a–404d will fall within the earlier-described ranges of values $D_2$. Sensor components 402a–402d are coupled with respective heater cap end portions 416' and 418' utilizing the bonding agent, for example, as described above in connection with FIG. 11 at 356. The bonding agent as represented in FIG. 25 at 446 also connects the sensor components 404a–404d with intermediate heater component sleeves 434–436 as illustrated.

Each of the sensor components 402a–402d may be coated with an electrically insulative conformal coating of thickness, $t_2$ such as the earlier-described "Parylene" as indicated at 448. This same conformal coating also may be employed to coat the entire implant 430. As noted earlier, such coatings provide an adhesive coupling contribution supporting the integrity of the multiple component arrangement. Table 1 sets forth ranges for ΔT heater or heater component temperature around the set point, ΔT sensor or sensor component temperature around the set point, $P_{heater}$ or instantaneous heating power generated within the heater component, $T_{heater}$ or nominal hyperthermia temperature for the heater component, TR1 the nominal thermal resistance between the heater components and sensor components, and TR2, the preferred thermal resistance between the heater component and the sensor component.

As is the case of all of the implant embodiments, the implant 430 may be utilized to support a thermally activatable release agent coating as shown at 450 in FIG. 26 which is effective to release an agent at the situs of the target tissue when the heater components 416', 418' and 434–436 achieve an induced temperature level generally corresponding with the elected temperature response of the sensor components 402a–402d which will exhibit a common Curie transition value. The thickness of the thermally activated release agent coating 450 in general, will average that described in connection with the dimension $t_3$, as discussed, for example, in conjunction with FIG. 12. Table 1 identifies nominal release agent temperature release ranges, $T_{DRS}$.

As discussed in connection with FIGS. 9, 14 and 19, reinstallment of the implants 430 is not required for a succession of hyperthermia treatments. An added benefit further is realized by subsequent utilization of the implants in patient management procedures. For such procedures as well as for the initial succession of hyperthermia therapy sessions avoidance of implant migration from position is desired.

Referring to FIG. 24A, implant 430 reappears with its linearly assembled compilation of sensor components 404a–04d, heater component sleeves 434–436 and heater component end caps now shown in primed fashion at 414' and 418'. Note that mutually oppositely inwardly disposed tissue engagement implements in the form of barb-like projections 428a and 428b are fixed to and resiliently extend from heater component end caps 416' and 418'. When implant 430 is released into target tissue by an implantation instrument (FIGS. 32 and 33), the implements 428a and 428b will spring outwardly into engagement with adjacent tissue. The discontinuous nature of the surface of implant 430 also contributes to an engaging relationship with tissue and the combined tissue engagement features serve to avoid implant migration over an interval of successive therapy successions and later patient management procedures.

In some applications of the instant system, the heating components may be dispensed with target tissue being, in effect, directly heated from the ACF heating assembly 94 and coil or antenna 98 as described in conjunction with FIG. 5 above. Sensor components, exhibiting requisite Curie temperature transition ranges which are quite narrow are retained with the embodiment of the procedure. Contributing to the effectiveness of this technique sans the presence of heater components is that aspect of tumor physiology wherein tumor will absorb heat differentially, i.e., to a greater extent with respect to normal surrounding healthy tissue. In this regard, while a quantum of thermal energy can be introduced to the tumor region, the surrounding adjacent normal tissue may be maintained at lower temperatures primarily due to the vascularity of that normal tissue. In the latter regard, the blood supply within normal tissue will have a tendency to remove thermal energy induced affectation. Conversely, tumor generally exhibits variational tissue characteristics with relatively poor blood profusion and varying but more enhanced tissue density. (See U.S. Pat. No. 5,099, 756).

FIGS. 27–30 look to the utilization of a sensor component only as the implant 92 as described in conjunction with FIG. 5. That implant then is utilized in conjunction with the heating of tissue at the target tissue volume from the ACF heating assembly 94 and associated coil or antenna 98. Such a sensor-dedicated implant is shown in FIG. 27 in general at 454, the implant being shown as a right cylinder, the surface 456 thereof being disposed about a centrally disposed axis 458. Implant 454 will exhibit the earlier-described desired Curie temperature transition ranges of quite narrow scope and is represented in cross-sectional format in FIG. 28. In the latter figure, the implant 454 is seen to be coated with an electrically insulative conformal coating such as "Parylene" as described above and shown at 460. Coating 460 additionally is shown to exhibit a thickness $t_2$, the ranges for which have been earlier described in connection with Table 1. Having a diametric extent of $D_1$ and a length shown as $L_1$, the dimensional ranges of which have been earlier-described, device 454 functions to monitor the heating of a target tissue volume as described at 90 in FIG. 5 and to provide the temperature information necessary to maintain the temperature of that target tissue volume within a narrow temperature range, $\Delta T_s$, about the setpoint for hyperthermia, $T_{SP}$, as described at dashed line 142 in connection with FIG. 7. That tissue temperature range about the setpoint will, for instance, extend from between about 0.1° C. and about 5° C. and preferably will fall within a range of from about 0.1° C. and 3° C. The implant 454 will exhibit a permeability based state change Curie transition within the earlier-described narrow range, for example, from about 0.1° C. to about 1° C. Table 1 describes $P_{tissue}$, the instantaneous heating power generated within tissue, as being within a range from about 0.2 to about 100 calories/second and preferably within a range from about 0.4 to about 25 calories/second.

FIGS. 30 and 31 illustrate an adaptation of the implant 454 wherein it supports a thermally activatable release agent coating 462. Coating 462 may be provided as earlier-described in conjunction with FIG. 12 and is seen to exhibit the earlier-described thickness, $t_3$, the ranges of which have been discussed above and are set forth in Table 1. In addition to this adjunct release agent therapy, the sensor implant 454, as in the earlier embodiments, may be employed for other adjunct therapies including the induction of heat shock proteins (HSPs). Additionally, the implant 454 may be utilized as a component of the "triple modality", radio-chemotherapy. See publication (10) supra. The ranges for nominal release agent dispersion temperature, $T_{DRS}$ are listed in Table 1.

Figure 32:
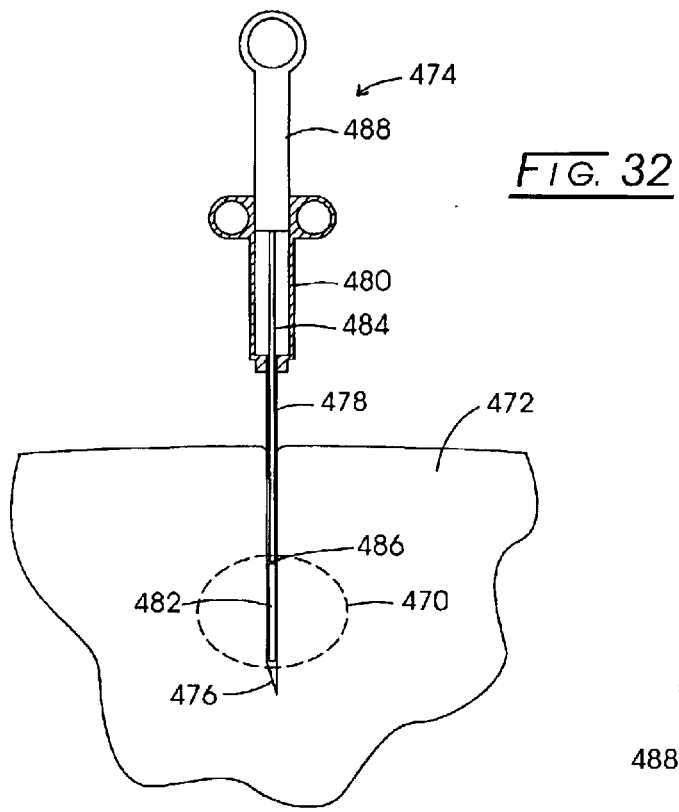
FIG. 32 is a schematic and sectional view of an implant locating instrument which may be used with the implants of the invention showing the instrument prior to releasing the implant in a targeted tissue volume.
Figure 33:
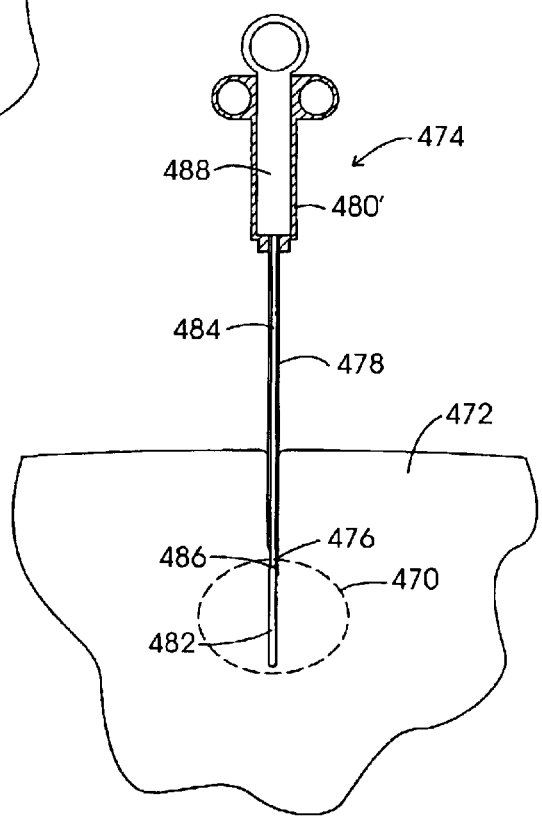
FIG. 33 is a schematic sectional view of the instrument of FIG. 32 showing the delivery of a sensor implant into a targeted tissue volume.
Figure 34B:
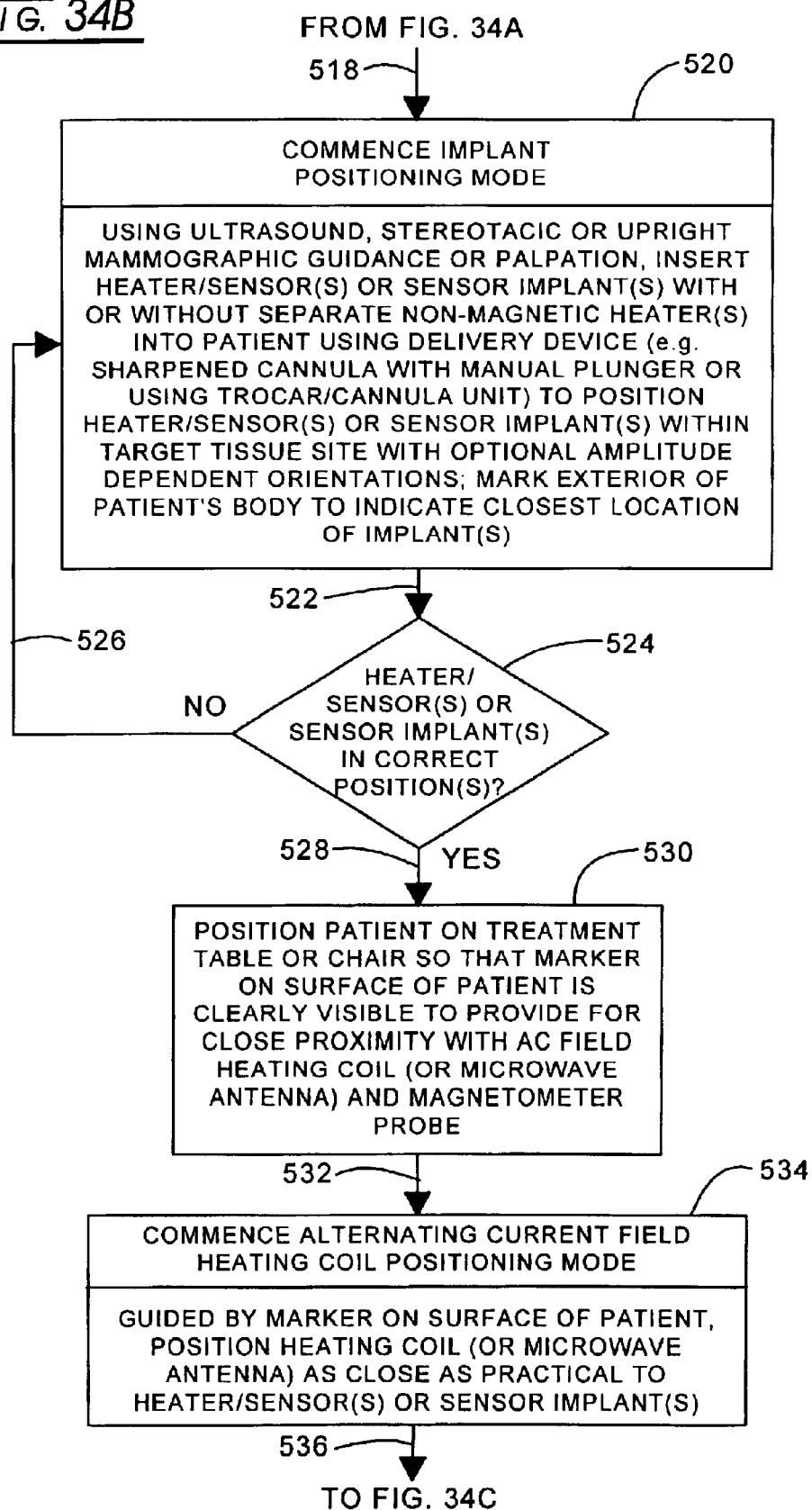
Figure 34D:
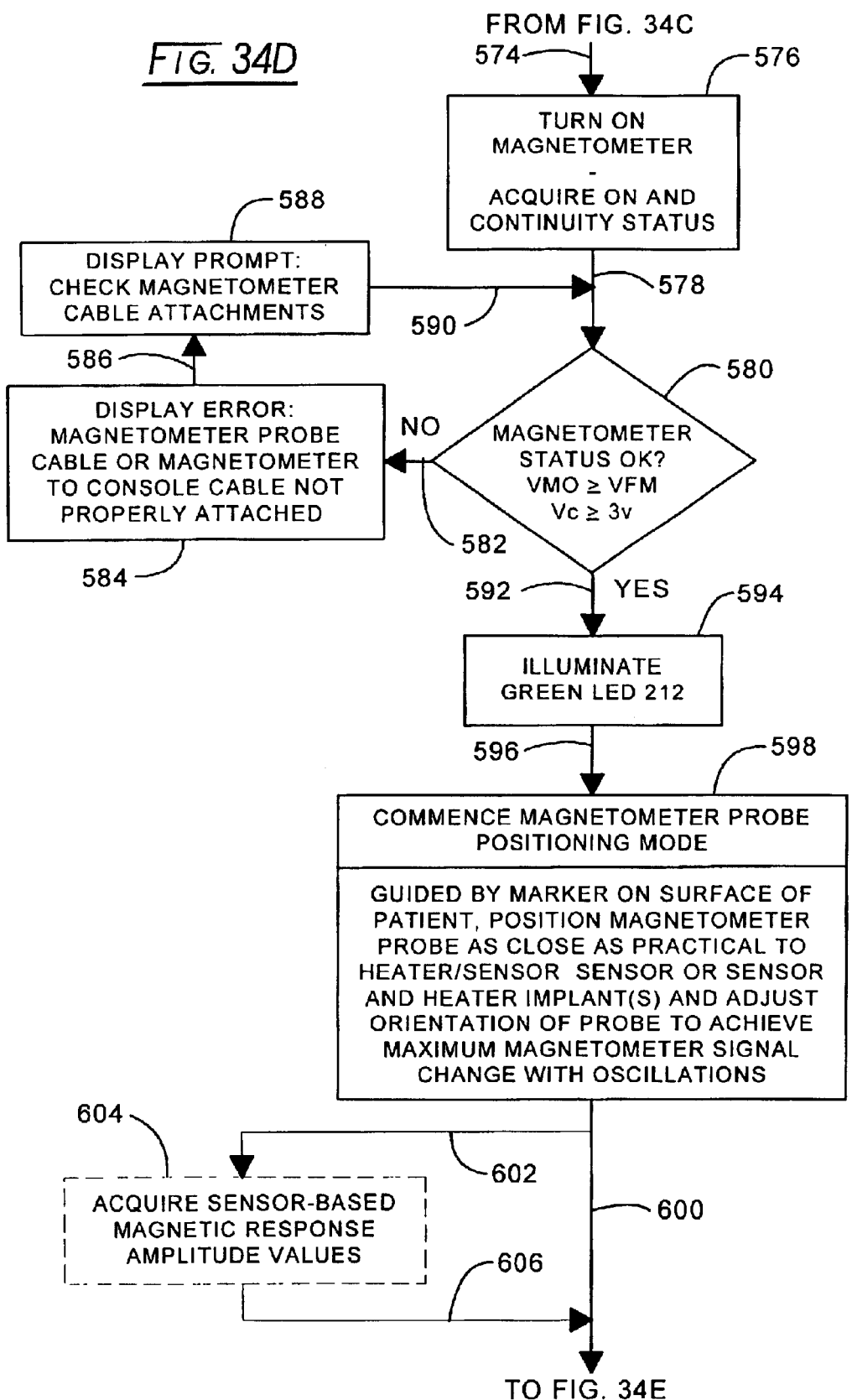
Figure 34E:
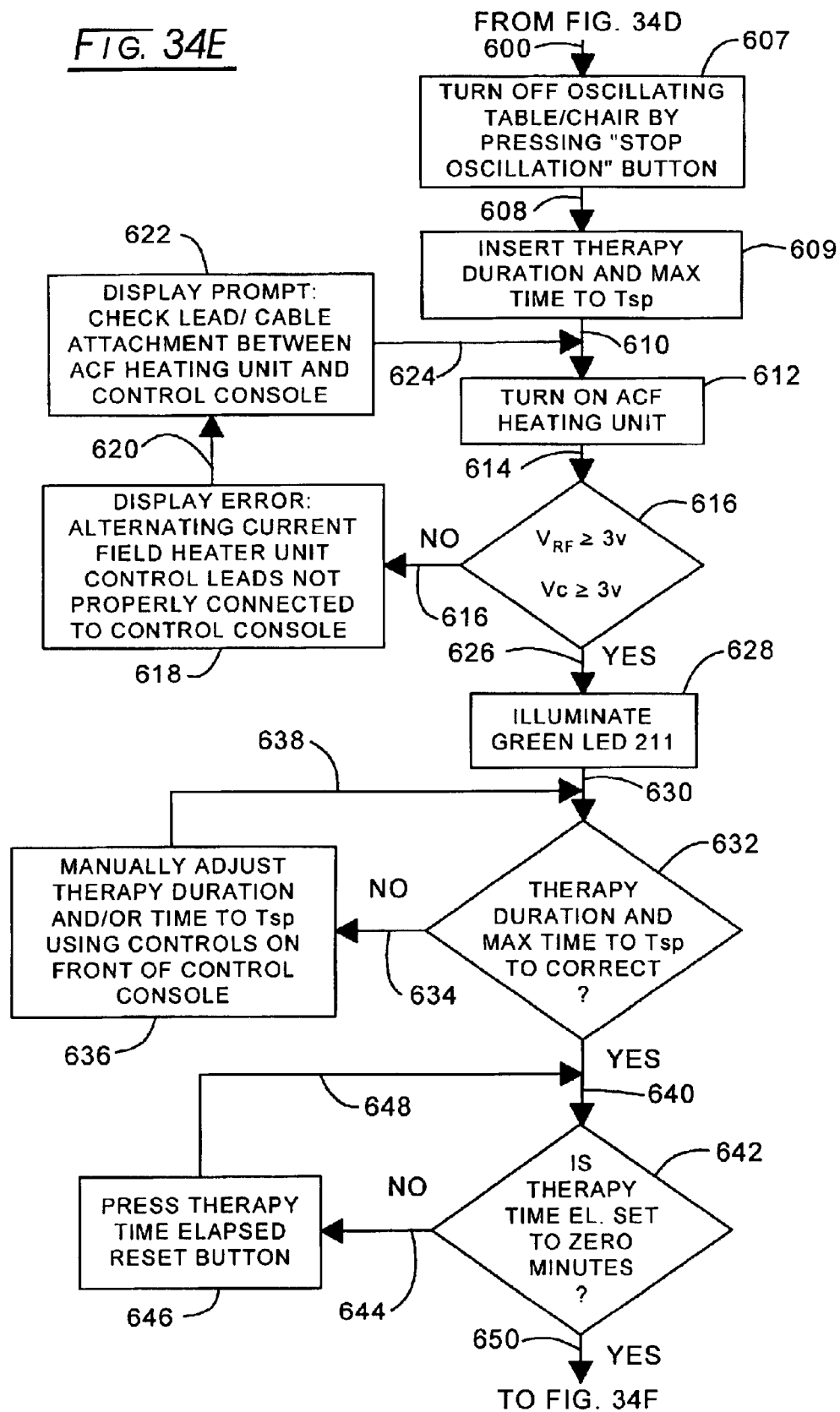
Figure 34F:
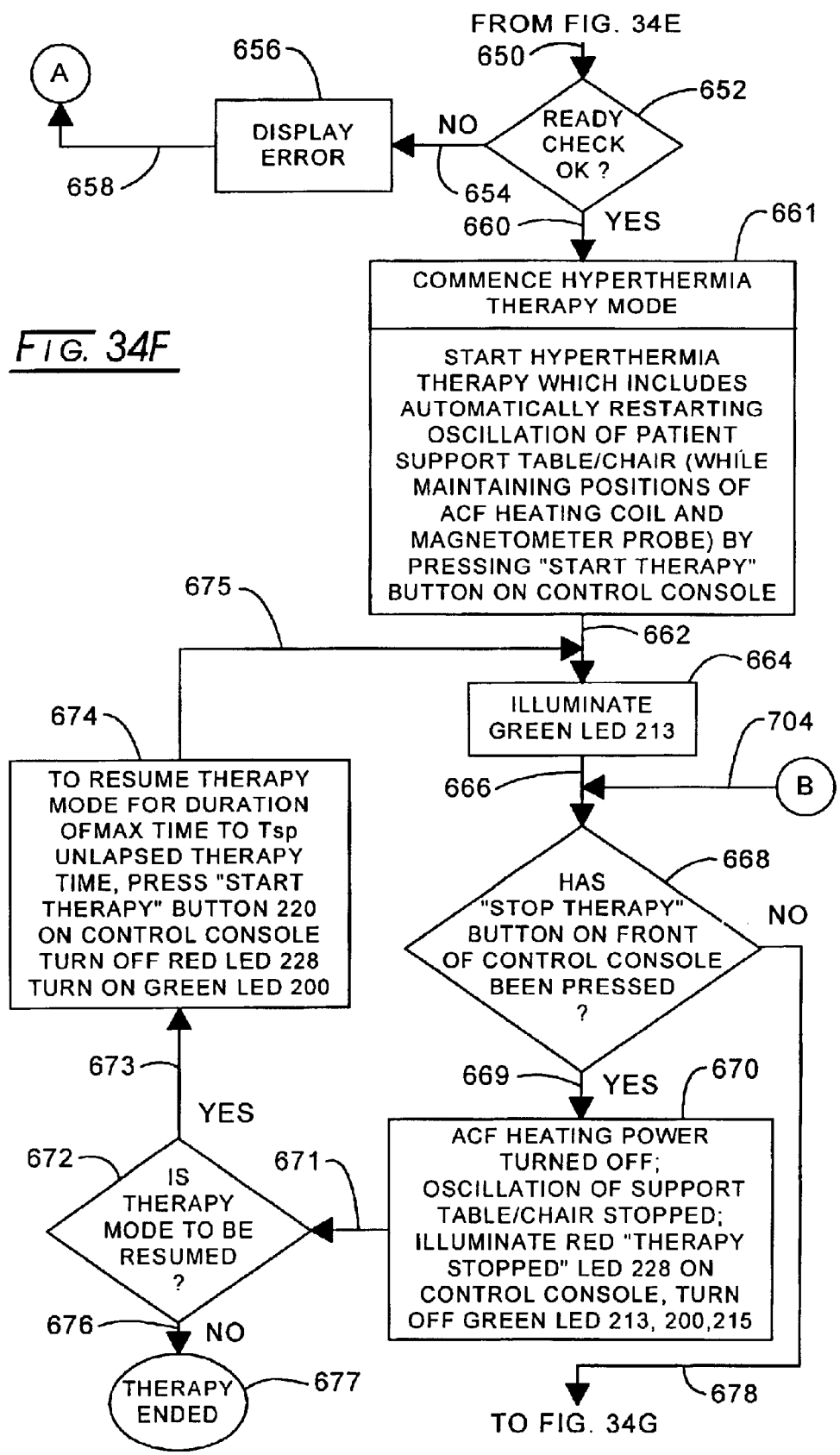
Figure 34G:
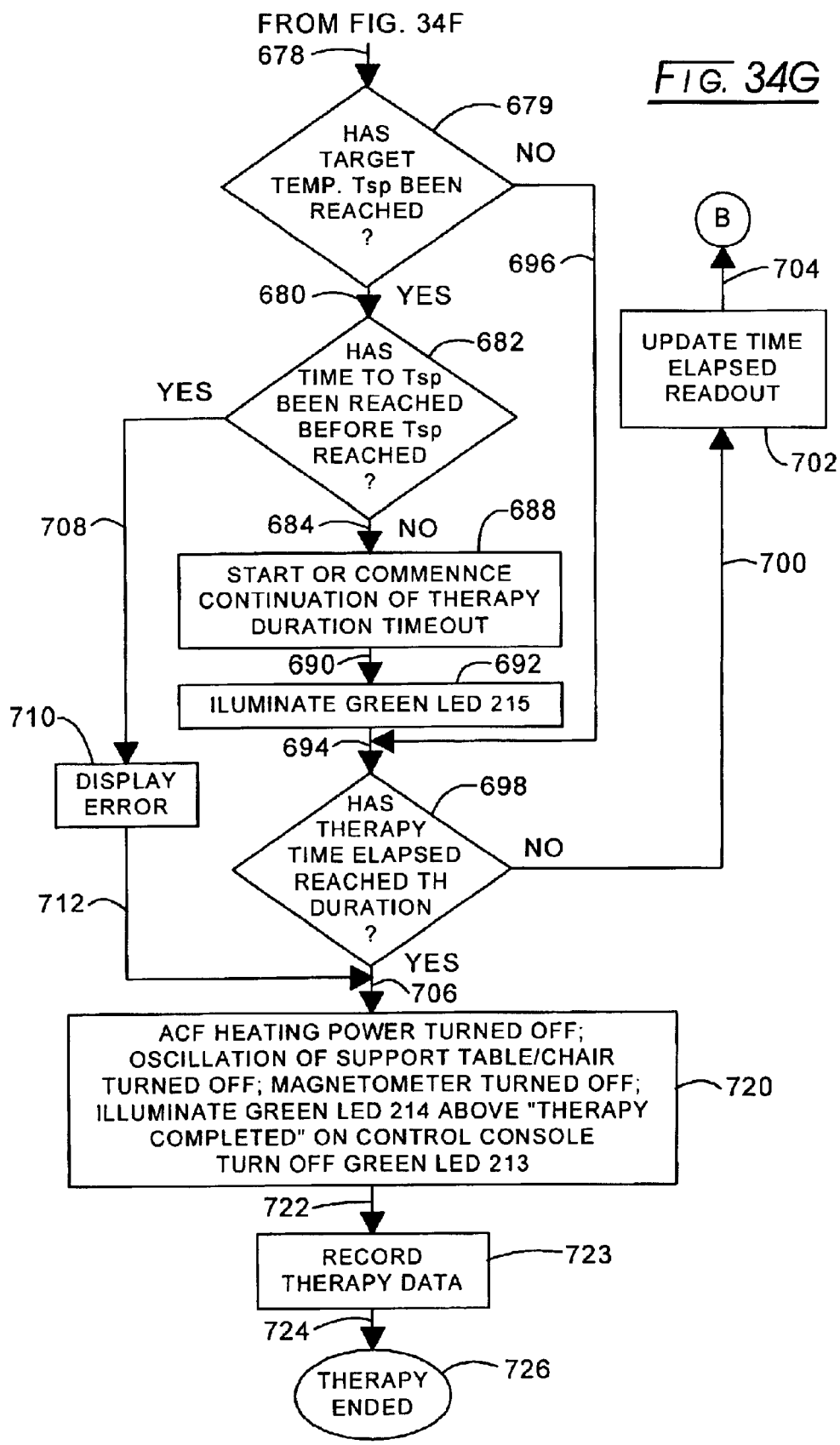

In general, the implants described in conjunction with FIGS. 9–30 may be positioned in target tissue utilizing a variation of syringe-hypodermic needle technology. FIGS. 32 and 33 generally, schematically represent one approach to implantation employing such technology. Radiographic, stereotactic, ultrasound or magnetic resonance imaging guidance methods or palpation are procedurally employed to accurately position an implant within a target tissue volume. Of particular interest, the implants may be positioned intra-operatively as an aspect of open surgical procedures. For instance, a most common approach to the treatment of cancer is that of tumor excision. Certain cases, for example, involving colorectal cancer will, upon gaining access to the abdominal cavity, reveal a substantially inoperative metastasis of the disease. Under such circumstances the surgical procedure typically is altered to a palliative one, for example, unblocking the colon and/or the incision is closed and other treatment modalities are considered.

However, with the instant system and method the surgeon is given an opportunity for deploying hyperthermia-based temperature control implants by direct access. Of special interest, colorectal cancers tend to metastasize through the lymph system. Accordingly, the implants can be intraoperatively positioned within lymph nodes to provide for the induction of HSPs at the node-retained cancer cells. Other sites of tumor similarly can be implanted. Following surgical closure, the hyperthermia therapy procedures described herein can be undertaken in mitigation of the metastasis. In general, practitioners employing the method herein described with respect to hyperthermia will elect to implant the most or more accessible target tissue volume.

A target tissue volume is represented in FIGS. 32 and 33 at 470 internally within the body 472 of a patient. The syringe-type insertion device represented generally at 474 is percutaneously or intraoperatively inserted within the body 472, piercing the skin where called for by virtue of the presence of a sharp tip 476 formed at the end of a needle 478. Needle 478 is fixed to a barrel or finger graspable housing 480 and removeably retains an elongate implant 482 within its internal core proximally from the tip 476. Immediately behind the implant 482 within the needle 478 is a plunger rod 484, the lower tip of which at 486 is in free abutment against the outwardly disposed end of implant 482 and which extends upwardly to a plunger handle 488. As is revealed, particularly, with respect to FIG. 33, once the sharpened tip 476 of the needle 478 has been properly positioned with respect to the target tissue volume 470, then a plunger rod 484 and associated handle 488 are stabilized positionally with respect to the body 472 and target tissue volume 470, whereupon housing 480 is retracted outwardly to the orientation shown at 480' in FIG. 33. This maneuver releases implant 482 at an appropriate location with respect to the target tissue volume 470. Implantation devices are described, for example, in U.S. Pat. No. 6,007,474.

As a prelude to considering detailed features of the procedure at hand, the discourse now turns to its aspects particularly with respect to heat shock phenomena. Previous research demonstrates that in vitro hyperthermia of cultured tumor cells can act as a vaccine against metastatic cancers. Hyperthermia of cultured cancer cells can partially denature proteins, induce HSPs, and lead to the presentment of intracellular peptides on the cell surface. Earlier work has isolated the antigen presenting HSPs and used these cell preparations as an autologous vaccine against syngeneic tumors. See:

(40) Tamura, Y., Peng, P., Liu, K., Daou, M. and Srivastava, P. K., "Immunotherapy of Tumors with Autologous Tumor-Derived Heat Shock Protein Preparations." *Science,* 278: 117–120 (1997).

The autologous cell vaccine described in Tamura presumably functions using heat shock to cause the presentment of intracellular cancer cell antigens. A subset of these cancer cell antigens represent aberrant proteins, and these aberrant proteins can be immunogenic. Once antigens derived from aberrant proteins unique to the cancer cell are presented to the cells of the immune system, then an immune response can occur. An immune response raised against aberrant proteins apparently does not trigger an auto-immune response, since only those cells which are syngeneic with the cancer cell would be likely to produce the antigen from the aberrant protein. An immune response so induced can be effective against syngeneic cancer cells and can activate the immune system against metastatic tumors too small to be otherwise detected.

In the present invention, rather than using invasive surgical techniques to excise a tumor and then produce a vaccine for that tumor by growing and heat-shocking the tumor in vitro, the tumor is heat shocked in situ, and tumor antigens are presented on the tumor cell surface. Heat-shock can cause the presentment of novel antigens on the cell surface. Presentment of novel peptides on the cell surface can induce immunogenicity. A cell which was previously not immunogenic, after heat shock, can thus become immuno genic. For additional background on immunogenicity induced via a heat-shock mechanism, See:

(41) Suto, R. & Srivastava, P. K., "A Mechanism for the Specific Immunogenicity of Heat Shock Protein-Chaperoned Peptides." *Science,* 269: 1585–1588 (1995).

(42) Wei., Y.-Q., Zhao, X., Kariya, Y., Fukata, H., Teshigawara, K., and Uchida, A., "Induction of Autologous Tumor Killing by Heat Treatment of Fresh Human Tumor Cells: Involvement of γδ T-cells and Heat Shock Protein 70." *Cancer Research,* 56: 1104–1110 (1996).

(43) Yanase, M., et al., "Antitumor Immunity Induction by Intracellular Hyperthermia Using Magnetite Cationic Liposomes." *Jpn. J. Cancer Res.,* 89: 775 (1998).

The present invention offers the advantages of reduction in the invasive nature of the therapy, as a tumor need not be removed from the body if the tumor responds to thermotherapy. Moreover, tumors which are otherwise inoperable because present surgical techniques do not allow their excision (e.g. certain brain tumors), could not be excised for in vitro treatment. By appropriate placement of the instant implant near or within targeted tumor, hyperthermia in situ can offer the same benefits as an autologous vaccine derived from excised, cultured cells. Additional complications caused by surgery and infection potential caused by reintroduction of tumor derived products can likewise be avoided.

The present approach also offers the thermal control aspect of being able to take advantage of different thermotherapy regimes, so that tumor cells, at different occasions can be induced to undergo heat shock, apoptosis or necrosis. A tumor may receive an implant and then be subjected to an initial round of mild thermotherapy, sufficient to induce only heat shock, but not apoptosis or necrosis. The initial therapeutic regime may be for a short duration (or at lower temperature, or both) designed to induce to a panel of heat shock proteins induced by only mild heat shock (e.g. activating HSF1 and HSP70). Referring to FIG. 3, the initial round of thermotherapy may be programmed to remain below the line 24, so that no irreversible tissue effects would occur. (An example of this regime would be a temperature elevation, $\Delta T=+4°$ C. for a duration of 45 minutes. This is achieved by selecting a target or setpoint temperature and therapy duration effective for the induction of HSP).

For a discussion of induction of the heat shock response following mild heat shock see:

(44) Morrison, A. J., Rush, S. J., and Brown, I. R., "Heat Shock Transcription Factors and the hsp70 Induction Response in Brain and Kidney of the Hyperthermic Rat During Postnatal Development" *Journal of Neurochemistry,* 75: 363–372 (2000).

(45) Neiland Thomas J. F., M. C. Agnes A. Tan, Monique Monnee-van Muijen, Frits Koning, Ada M. Kruisbeek, and Grada M. van Bleek, "Isolation of an Immunodonminant Viral Peptide that is Endogenously Bound to Stress Protein gp96/GRP94." *Proc. Nat'l Acad. Sci. USA,* 93: 6135–6139 (1996).

(46) Tanabe, M., Nakai, A., Kawazoe, Y., and Nagata, K. Different Thresholds in the Responses of Two Heat Shock Transcription Factors, HSF1 and HSF3." *Journal of Biological Chemistry,* 272: 15389–15395 (1997).

It should be noted that different tissues respond at differing rates to heat-shock, for instance brain tissue responds more rapidly than liver or muscle tissue. Though the response curve in FIG. 3 is a composite derived from several empirical observations, a thermotherapy regime suitable to induce HSP70 alone or HSP70 and HSP90 may be determined for individual tissues by those skilled in the art using well-known techniques for assaying gene expression. Individual tissues may not respond identically as depicted in FIG. 3, but empirical observations demonstrate that the response of tissues to thermotherapy follows the pattern illustrated by curve 24.

A second round of therapy, timed 10 days to 14 days later (in order to allow time for autologous adaptive immunity to begin to develop) may be for longer duration (which would not necessarily require the use of additional or different implants) for a higher temperature level. The subsequent round of therapy can be designed to induce a panel of heat shock proteins that are induced by more severe heat shock (e.g. activating HSF1 and inducing HSP70, activating HSF2 and inducing HSP90 and gp96). One example of this regime would be a setpoint temperature representing a $\Delta T=+4°$ C. for a duration of 90 minutes. Additional rounds of mild and moderate heat shock could be used to maximize tumor antigen presentation to immunoresponsive cells, and lead to an immune response to tumor cells, wherever they might reside in the body.

Advantages of initial moderate thermotherapy include minimization of damage to surrounding non-cancerous tissues, minimization of debilitating or damaging inflammatory responses, and maximizing the induction of immune response. For additional background discussing antigenicity of heat shocked cells see:

(47) Ito, A., Shinkai, M., Honda, H., Wakabayashi, T., Yoshida, J., and Kobayashi, T., "Augmentation of MHC Class I Antigen Presentation via Heat Shock Protein Expression by Hyperthermia." *Cancer Immunol. Immunother.,* 50: 515–522 (2001).

(48) Jolly, Caroline and Morimoto, Richard I., "Review: Role of the Heat Shock Response and Molecular Chaperones in Oncogenesis and Cell Death." *Journal of the National Cancer Institute,* 92 (19): pp 1564–1572 (Oct. 4, 2000).

(49) Melcher, A. Todryk, S, Hardwick, N., Ford, M., Jacobson, M., Vile, R. G., "Tumor Immunogenicity is Determined by the Mechanism of Cell Death via Induction of Heat Shock Protein Expression." *Nature Medicine,* 4 (5): 581–587 (1998).

After heat shock has been used to induce antigen presentation (e.g. by HSP70), a more severe thermotherapy regime could be implemented to induce apoptosis. Apoptotic cells may not allow presentation of antigens in the same manner as heat shocked cells, and therefore hold the possibility of inducing a different immune response that could offer protection against tumor cells that did not activate an immune response via mild heat shock. It is expected that thermotherapy sufficiently severe to induce apoptosis would be in the range depicted at or above the curve 24 in FIG. 3, with degradation of apoptotic cells producing irreversible tissue effects. One predicted example of this regime would be a setpoint temperature representing a $\Delta T=+8°$ C. for a duration of 90 minutes. Relative thermotherapy regimes capable of inducing apoptosis would need to be determined for different tissues using techniques well known to those skilled in the art of cell biology and molecular genetics. In addition, induction of apoptosis by temperature stress offers the possibility of tumor shrinkage arising from apoptosis of tumor cells. Induction of apoptosis in tumor cells offers the advantage of in situ shrinkage of tumor mass, at the same time as an immune response against tumor antigens is induced. For additional background discussing antigenicity of apoptotic cells see:

(50) Albert, M. L. et al., "Dendritic Cells Acquire Antigen from Apoptotic Cells and Induce Class I Restricted CTLs." *Nature,* 392: 86–89 (1998).

A subsequent round of thermotherapy can be used to induce necrosis of cancerous tissues. Thermotherapy sufficiently severe to induce necrosis would be in the range depicted above curve 24 in FIG. 3, producing irreversible tissue effects. One predicted example of a regime to induce tissue necrosis would be a setpoint temperature representing a $\Delta T=+15°$ C. for a duration of 90 minutes. Relative thermotherapy regimes capable of inducing necrosis would need to be determined for different tissues using techniques well known to those skilled in the art of cell biology and molecular genetics.

Necrotic cells are more immunogenic than typical apoptotic cells (note the inflammatory immune response activated by necrosis). See:

(51) Basu, Sreyashi, Binder, Robert J., Suto, Ryuichiro, Anderson, Kirstin M. and Srivastava, Pramod K., "Necrotic but not Apoptotic Cell Death Releases Heat Shock Proteins, Which Deliver a Partial Maturation Signal to Dendritic Cells and Activate the NF-κβ pathway." *International Immunology,* 12 (11): 1539–1546 (2000).

FIGS. 34A–34G present a block diagrammatic representation a procedure of the invention. In particular, the procedure looks, not only to the carrying out of the therapy with the purpose of achieving hyperthermia with respect to targeted tissue but also looks to the use of general thermal therapy procedures and associated controlled temperatures in time to evolve quanta of energy over time as above described optimizing the overall treatment of neoplastic tissue and other treatment systems including boney tissue repair, transplant support and viruses. Additionally, as discussed with the structuring of the implants earlier herein, adjunct therapies as chemotherapy can be provided with the system in a manner wherein release agents are dispersed non-invasively. This is carried out by temperature controlled application of radiative heat generating energy at prescribed agent application intervals. In general, for the former adjunct therapeutic approach, the thermotherapy is utilized to initially create reversible tissue effects by the application of energy in time quanta falling below the critical curve 24 described in conjunction with FIG. 3. Thereafter, quanta election may be selected to cause the tissue to be subjected to treatment above that critical curve to evoke denaturization or irreversible tissue effects. As noted earlier, the thermotherapy approach at hand also can be combined with radiation therapy or with a triple modality approach. (See publication 10).

Looking to FIG. 34A, the procedure is seen to commence at node 500 and line 502 leading to the determinations set forth at block 504. Those determinations provide for the election of target therapy temperature(s) for instance, for hyperthermia with HSP induction and susceptibility to adjunct therapies such as radiation therapy, chemotherapy. i.e., release agent dispersement by heat activation, bony tissue mending and the like. The procedure then continues as represented at line 506 and block 508 providing for the user selection of implant sensor (s) thermal responses based upon the elected target therapy setpoint temperature or temperatures. Particularly during hyperthermia treatments, the measurement of the actual temperature distribution in the tumor or immediately adjacent tissue is highly important. See publication (10) supra. With temperature elections having been made and sensor component/heater component configurations determined, then as represented at line 510 and block 512 the power level for the ACF heating assembly 94 is selected and set by the user. Where therapy such as the induction of heat shock proteins has been elected as the basic procedure, then as represented at line 513 and block 514 the user may evolve a maximum therapy duration at elected target temperature or temperatures to establish energy quanta of thermal application to the target tissue volume. The election of such maximum value(s) is made with respect to hyperthermia treatment to avoid generation of temperatures or temperature in time conditions falling above the critical curves as at 24 described in connection with FIG. 3. The procedure then continues as represented at line 515 and block 516 providing for the administration of general or local anesthetic agent as required. Then, as represented at line 518 and block 520, using one or more of the above-discussed imaging techniques, or as part of an intra operative procedure, the implant is inserted into or adjacent to the target tissue volume of the patient utilizing an implant device, for example, as discussed in connection with FIGS. 32 and 33. In connection with this implantation, where more than one implant sensor component is to be employed within the target tissue, then a positional magnetic flux response may be achieved by providing an orientation of the implant with respect to the direction of magnetic flux lines. In this regard, the orientation with respect to magnetic flux lines will effect the level of amplitude of the response of the magnetometer assembly 104. Such responses can be correlated to specific sensor component locations. Additionally, as part of this procedure, the exterior of the patient's body is marked to indicate the closest location of the implant or implants so as to facilitate the positioning of the radiative heating coil or antenna as well as to orient the pick-up structure of the magnetometer.

Next, the methodology provides a confirmational procedure as represented at line 522 and block 524 wherein the imaging and other such instrumentation are used for purposes of ascertaining if the implants are in the proper location with respect to the target tissue. Should the implant positioning not be appropriate, then as represented at loop line 526, the method reverts to the procedure described in connection with block 520. Upon an affirmative determination with respect to the query posed at block 524, then as represented at line 528 and block 530 the patient is positioned on the treatment support such as a table or chair so that the earlier located marker or outline on the surface of the patient is visible for the next step in the procedure. That step provides for locating the ACF heating coil or microwave antenna as well as the magnetometer probe at the proper locations with respect to the skin of the patient.

The procedure then continues as represented at line 532 and block 534 wherein, guided by the marker at the skin surface of the patient, the heating coil 98 or microwave antenna is positioned as close as practical with respect to the skin of the patient to sensor/heater implants. The method then continues as represented at line 536 which reappears in FIG. 34C extending to block 538 providing for turning on control 112 (switch 180 illuminating green LED 182). Then, as represented by line 540 and block 542, the operator selects the duty cycles. Reverting momentarily to FIG. 7, it may be recalled that the operator selects the interval, $\delta t_1$ during which interval the ACF heating assembly 94 is activated following which that assembly is deactivated to eliminate the potential for electrical noise phenomena and the like and an interval of interrogation or monitoring of the sensor implants, $\delta t_2$ follows. As described in connection with FIG. 5, the duty cycle election is undertaken with switch function 184. Table 1 sets forth ranges for these selections. $\delta t_1$ may range from about 0.01 to about 30 seconds and preferably from about 0.05 to about 5 seconds. $\delta t_2$ may range from about 0.005 to about 5 seconds and preferably from about 0.02 to about 1 second. Next, as represented by line 544 and block 546 the operator proceeds to select the extent of travel of the table or platform 52 or corresponding chair support. That selection is made at console 112, the operator actuating up/down switches 194 while observing the corresponding locus of travel shown at display 196. The program then continues as represented at line 548 which extends to block 550 providing for the acquisition of the enabling voltage value of the motor control 78. Following such acquisition, as represented at line 552 and block 554 a determination is made as to whether that enabling voltage $V_{mc}$ is greater than or equal to, for example, three volts. If the determination at block 554 is that the enabling voltage of the table control is not adequate, then as represented at line 556 and block 558, an error message is displayed at the display 204 (FIGS. 5 and 8A). The error, in general will indicate that the control leads 84 from the oscillation system are not properly attached to the console 112. The program then continues as represented at line 560 and block 562 wherein the display 204 outputs a display prompt, to wit: "check the lead/cable attachment". The program then reverts to line 548 as represented at line 564.

In the event of an affirmative determination with respect to the query posed at block 554, then as represented at line 566 and block 568 green LED 210 is illuminated (FIGS. 5 and 8B) and the procedure proceeds as represented at line 570 and block 572. In this regard, the operator carries out what in effect is a "check run" of the oscillation of platform 52 or chair or equivalent patient support. This check is initiated by actuating button switch 198 (FIGS. 5 and 8B). As the patient support assemblage 54 is activated, the procedure then evaluates the status of the magnetometer 104. Accordingly, as represented at line 574 and block 576 (FIG. 34D) the magnetometer 104 is turned on and the system acquires its on and continuity status information. The program then continues as represented at line 578 and block 580 wherein a determination is made as to whether the status of the magnetometer 104 is ok. In this regard, the peak-to-peak variation of the magnetometer output voltage, $V_{MO}$ is compared with a reference, $V_{FM}$. Where that condition obtains, then the enablement signal, $V_c$ is generated. This signal must be greater than or equal to, for example, three volts d.c. to be representative. In the event that the magnetometer status is not ok, then as represented at line 582 and block 584, an error condition is displayed at display 204 indicating that the magnetometer probe cable 108 or the cable 114 to console 112 is not properly attached. The program then continues as represented at line 586 and block 588 to display the prompt to the operator to check the magnetometer cable attachments. The program then returns as represented at line 590 to line 578.

Where the query posed at block 580 is responded to in the affirmative, then as represented at line 592 and block 594 green LED 212 at console 112 is illuminated and the program continues as represented at line 596 and block 598. At this juncture in the procedure, the operator will be positioning the magnetometer probe 106 as close as practical to the implants. This positioning will involve orientation of that probe to achieve a maximum magnetometer signal change with the oscillations of the platform 52. The program then continues as represented at line 600.

As an optional procedure, the instant system may utilize, the orientation of sensor components having a principal elongate dimension or, as noted above, an aspect ratio of less than unity such that when subjected to magnetic flux lines, for example, of the earth's magnetic field, the disturbance that evokes, if any, depending upon the state of permeability, will draw a response at magnetometer assembly 104, the amplitude of which will vary depending upon that orientation. Thus, by initially selectively orienting the sensor components, the magnetometer function may discern their location in a lateral, as it were, scanning aspect resulting from the oscillation of platform 52. In this regard, that aspect of interrogation is one generally normal to the longitudinal orientation of the probe component 106. Of course, probe orientation will be dependent upon the particular mechanism employed for that function. However, where sensor amplitude-based positional information is desired, then as represented by optional dashed line 602 and dashed block 604 the system will acquire sensor-based magnetic response amplitude values with respect to each implanted sensor. The program then reverts, as represented at dashed line 606 to line 600. Line 600 extends to block 607 (FIG. 34E) providing for the termination of the test run of the support assemblage 54. This is carried out by operator actuation of the stop button switch 202 on console 112 (FIGS. 5 and 8B).

The procedure continues as represented at line 608 and block 609 which provides for the operator switch-based selection of both therapy duration commencing with the attainment of setpoint temperature, $T_{SP}$ and the maximum allotted time to attain $T_{SP}$. Insertion of this temporal data is made with switches 190 and 191 in conjunction with the visual readout at numerical display 192.

The ACF heating assembly actuation next is addressed as represented at line 610 and block 612 providing that the ACF heating assembly 94 is turned on and, as represented at line 614 and block 616 a query is posed as to whether the ACF heating unit is enabled both by the development of a requisite on voltage level, $V_{RF}$ as being greater than or equal to three volts and the presence of the earlier-described magnetometer signal $V_c$ as being greater than or equal to three volts. If those ANDed conditions are not met, then as represented at line 616 and block 618 an error visual cue is displayed at display 204 indicating that the control leads 102 are not properly connected to the control console 112. The program then continues as represented at line 620 and block 622 to display a prompt advising the operator to turn off the ACF heating unit and check the cable attachment 102 extending to the console 112. The program then reverts to line 610 as represented at line 624.

Where the query posed at block 616 results in an affirmative determination, then as represented at line 626 and block 628 green LED 211 at console 112 is illuminated and the program continues as represented at line 630. Line 630 extends to the query posed at block 632 determining whether the duration for therapy and the maximum time allocated for reaching $T_{SP}$ have set to correct and intended intervals. These times are set by the operator employing the up/down switches 190 and election switch 191 in conjunction with display 192 on console 112. It may be recalled that for adjunct therapies to HSP induction such as the temperature controlled dispersion of chemotherapeutic release agents, proteins and/or combined radiation therapy, one or more levels of predetermined Curie transition temperatures may be utilized in conjunction with a corresponding sequence of sensor component containing implants. In the latter aspect, such therapy may involve maintenance of the quantum of thermal energy below critical curves as at 24 described in connection with FIG. 3. Where a time interval is incorrect, then as represented at line 634 and block 636 appropriate adjustment of control switches 190 and 191 is made and the program reverts to line 630 as represented at line 638. In general, therapy duration is timed commencing with the attainment of setpoint temperature, $T_{SP}$ for HSP-based procedures.

Where the query posed at block 632 is responded to in the affirmative, then as represented at line 640 and block 642 a determination is made as to whether the therapy time elapsed indicates zero minutes. This readout is provided at console 112 at display 222. In the event that that display does not register zero minutes, then as represented at line 644 and block 646 reset button switch 224 is actuated and the program continues as represented at lines 648 and 640. With the therapy time elapsed set at zero, the procedure continues as represented at line 650 and block 652 FIG. 34F). Block 652 reflects the activity of controller 240 (FIG. 8B) in carrying out a determination that the conditions established by the illumination of LEDs 210–212 at console 112 have been satisfied and the system is now ready to commence a thermal therapy mode. In the event that the ready check fails, then as represented at line 654 and block 656 an error cue is published at display 204 and, as represented at line 658 and node A the program reverts to line 548 to again consider the ready checks.

In the event the query posed at block 652 results in an affirmative determination, then as represented at line 660 and block 661 thermal therapy which may comprise hyperthermia therapy commences with the operator actuation of the start therapy button switch 220 at console 112. With this actuation, as represented at line 662 and block 664, the green LED 213 indicating that therapy is in progress at console 112 is illuminated and the procedure continues as represented at line 666 to the query at block 668. Therapy being underway, but setpoint temperature $T_{SP}$ not having been reached, the program determines whether or not the stop therapy button switch 226 at console 112 has been actuated. In the event that such an actuation occurred, then as represented at line 669 and block 670 the ACF heating assembly 94 is turned off as well as the motor control circuit 78 of the support assemblage 54. As a visual cue that the therapy is stopped, red LED 228 is illuminated and, correspondingly, green LEDs 200 and 213 are de-energized. The procedure then continues as represented at line 671 and block 672 wherein the operator determines whether or not the therapy mode is to be resumed. In the event that it is to be so resumed, then as represented at line 673 and block 679, to resume the therapy mode for the duration of the unlapsed therapy, the start therapy button switch 220 is actuated at control console 112 which, in turn, causes the turning off of red LED 228 and the turning on of green LEDs 200 and 213. This automatically restarts the platform 52 oscillation and the activation of the ACF heating assembly 94. As noted above, for HSP induction procedures, therapy duration is timed from the attainment of setpoint temperature, $T_{SP}$. If that setpoint value has not been reached in the presence of a stop command, the system, upon re-start, will proceed to derive $T_{SP}$ and then commence therapy duration time-out. The program then continues as represented at line 675 which extends to line 666.

Where the query posed at block 672 results in a determination that therapy is not to be resumed, then as represented at line 676 and node 677 the therapy is ended.

Returning to block 668, where a determination has been made that the stop therapy switch 226 has not been actuated, then as represented at line 678 and block 679 (FIG. 34G) a determination is made as to whether the target or set point temperature, $T_{SP}$, has been reached. This target temperature has been discussed in conjunction with dashed line 142 in connection with FIG. 7. See also the ranges for $T_{heater}$ in Table 1. Where the target or set point temperature has been reached, then as represented at line 680 and block 682 a determination is made as to whether the maximum allotted time for the system to reach the setpoint temperature, $T_{SP}$ has occurred before the target temperature, $T_{SP}$ has been reached. If that time limitation for acquiring setpoint temperature has not been reached at this juncture, then as represented at line 684 and block 688, the therapy duration timeout is commenced with the acquisition of setpoint temperature $T_{SP}$. As discussed above in connection with block 668 if the stop therapy button has been pressed and therapy has been resumed as discussed in connection with block 674, then a commencement of a continuation of the therapy duration interval is made. The program then continues as represented at line 690 and block 692 providing for the illumination of green LED 215 on console 112. The program then continues as represented at line 694. Where the target temperature has not been reached, then as represented at lines 696 and 694, the program continues to the query posed at block 698. Block 698 determines whether or not the therapy time elapsed as displayed at display 222 on console 112 has reached a therapy duration valuation. In the event that it has not, then as represented at line 700 and block 702, the time elapsed display 222 is updated and, as represented at line 704 the program reverts to line 666.

Returning to block 682, where the maximum time for reaching setpoint temperature, $T_{SP}$ has been reached before the attainment of setpoint temperature, then an error is at hand and is represented at line 708 and block 710, an error signal is visually displayed which may be accompanied by an acoustical cue. The program then continues as represented at line 712 to line 706.

Line 706 extends to block 720 which provides for the deactivation of the active components of the system. In this regard, the ACF heating assembly 94 is deactivated as is the magnetometer assembly 104. Control circuit 78 for the platform support assemblage 54 is deactivated. Therapy complete green LED 214 is illuminated and green LED 213 representing therapy in progress is de-energized. The program then continues as represented at line 722 and block 724 wherein pertinent data for the procedure parameters is recorded. It may be recalled that this data can be displayed at display 204 by the actuation of button switch 206. The procedure then continues as illustrated at line 724 extending to node 726 representing a therapy ended stage.

Figure 35:
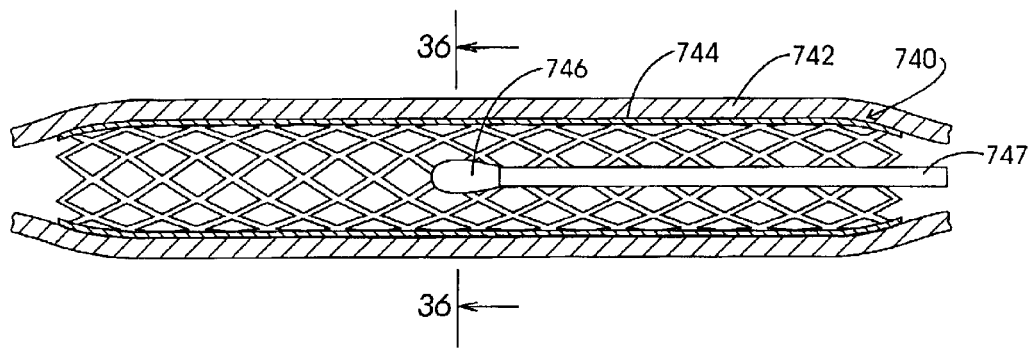
FIG. 35 is a sectional schematic representation of a prior art approach to applying thermotherapy to a stent imbedded in a blood vessel.
Figure 36:
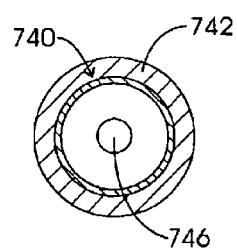
FIG. 36 is a sectional view taken through the plane 36—36 shown in FIG. 35.

Hyperthermia currently is employed for purpose of limiting restenosis at the location of implanted stents in blood vessels. In general, such stents, for example, may be utilized in percutaneous transluminal coronary angioplasty (PTCA) for purposes of avoiding a collapse of arteries subsequent to balloon implemented dilation. As in other thermotherapeutic procedures, necessary sensing of temperature heretofore has been carried out in an invasive manner. This prior approach is illustrated in connection with FIGS. 35 and 36. In the figures, a stent is shown generally at 740 as it is implanted within a blood vessel, the walls of which are shown at 742. Having a typical mesh-like structuring and cylindrical shape, the stent 742 is configured with an outwardly disposed cylindrical contact surface positioned in contact with the intima region of blood vessel 744. To apply thermotherapy, for example, by ACF heating from an external applicator, while assuring that accurate temperature control over the stent 740 is maintained, it is necessary to locate a transluminal catheter borne thermal sensor 746 within the stent structure 740. Sensor 746 may be provided, for example, as a thermister mounted at the tip of a catheter 747. As is apparent, this invasive positioning of the temperature sensor 746 is required each time the hyperthermia therapy is performed, a procedure which may be called for relatively often. In addition to the risk of this invasive positioning of the temperature sensor 746, the catherization of the patient involves a substantial cost. See the following publication in this regard:

(52) Stefanidas, C. et al., "Hyperthermia of Arterial Stent Segments by Magnetic Force: A New Method to Eliminate Intimal Hyperplasia." *Journal of the American College of Cardiology,* 37 (2) Supp. A: 2A–3A (2001). See additionally European Patent Application No. EP 1036574A1.

Figure 37:
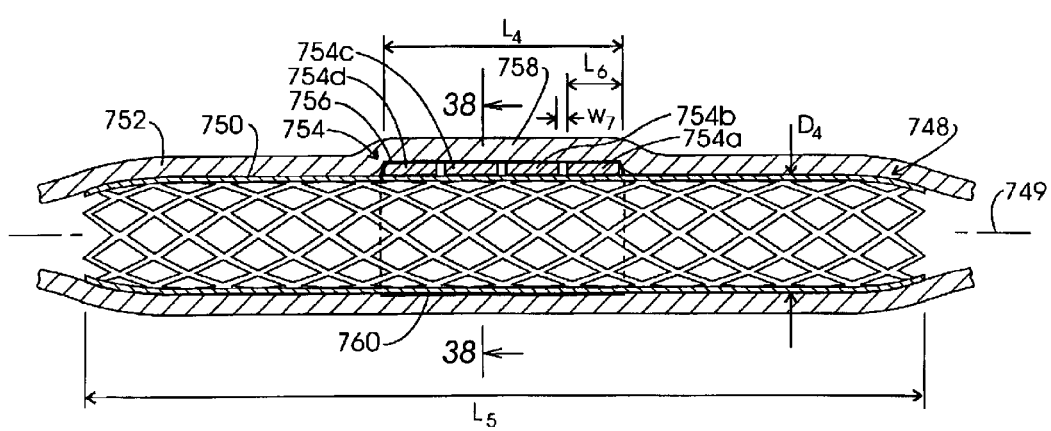
FIG. 37 is a schematic sectional representation of a combined stent and sensor component assembly according to the invention imbedded within a blood vessel.
Figure 38:
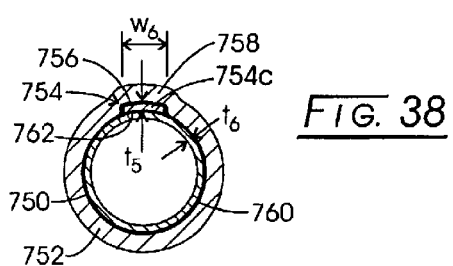
FIG. 38 is a sectional view taken through the plane 38—38 shown in FIG. 37.

FIGS. 37 and 38 illustrate an initial embodiment for a stent formed of non-magnetic material which can be heated from an externally applied energy source, for example by alternating current field heating and which initially incorporates an untethered temperature sensor which is fixed to it prior to implantation. Looking to FIGS. 37 and 38, the mesh-structured stent is represented generally at 748 extending about a central axis 749. Stent 748 will be formed of a non-magnetic inductively exercisable material, for example, austenitic stainless steel such as Type 316, titanium, titanium alloys and nitinol. Typically, stents are formed of a non-magnetic material inasmuch as they often will be located within the imaging field of highly magnetic devices such as MRI systems and the like. Typical stent structures are described in the following publications:

(53) *Interventional Vascular Product Guide,* Martin Dunitz, Ltd., London (1999).
(54) *Handbook of Coronary Stents,* 3rd ed., Martin Dunitz, Ltd., London (2000).

The mesh-like generally cylindrically-shaped stent 748 is seen to be implanted such that its outwardly disposed contact surface will have been urged into abutting and fixed intimate connection with the intima of blood vessel 752. Fixed in intimate thermal exchange relationship to this contact surface 750 at the central region of the stent 748 is an untethered temperature responsive component assembly represented generally at 754, the outwardly disposed surface of which at 756 is seen to slightly additionally distend blood vessel 752 at region 758. Sensor component assembly 754 is seen to be formed of four discrete components 754a–754d which, as in the earlier embodiments may be fashioned of a ferromagnetic material, i.e., a ferrite having a Curie temperature designed to provide a significant change in magnetic permeability, for example, a 20 to 1000 fold change over a relatively narrow range of temperature change, for example, between about 0.1° C. and about 1° C. The sensors 754a–754d are intimately bonded with the non-magnetic metallic stent 748 and their securement may be further assured by the positioning of a biocompatible flexible sheath or band 760 over the central portion of the stent 748 and over the outwardly disposed surfaces of the sensor component assembly 754. Band 760 may, for instance, be formed of a silicone elastomer, Dacron, Teflon, titanium, nitinol or a Type 316 stainless steel. Multiple temperature sensing components 754a–754d are used for the component assembly 754 in the interest of providing operational redundancy and for the purpose of providing a structural aspect wherein the sensor assembly 754 exhibits a flexibility called for to accommodate tortuous access through the vasculature of the body and placement, for example, of the stent 748 within a curved blood vessel as opposed to a vessel exhibiting more straight or uncurving characteristics. An intimate thermal exchange relationship is called for between the stent 748 and the untethered temperature responsive component 754. In this regard, the preferred thermal resistance, $TR_4$ between the stent 748 and the sensors 754a–754d will be about 0.5° C./watt, while the nominal thermal resistance, $TR_3$ will be about 5° C./watt. Providing a biocompatible electrically insulative conformal coating such as the earlier-described "Parylene" as shown at 762 in FIG. 38 is beneficial and promotes the adhesion of the components 754a–754d to the outer tissue contact surface 750 of stent 748. In general, stents as at 748 will have a length, $L_5$ of between about 0.12 inch (3 mm) and about 3 inches (76 mm) and preferably will fall within a length having a range of about 0.2 inch (5.1 mm) and about 2 inches (51 mm). For such stents, the sensor assembly 754 will have a length, $L_4$ of between about 0.06 inch (1.5 mm) and about 1.5 inch (38 mm) and preferably between about 0.1 inch (2.5 mm) and 1 inch (25.4 mm). The length, $L_6$ of each of the components 754a–754d will be between about 0.03 inch (0.76 mm) and about 0.75 inch (19 mm) and preferably will fall within a range of about 0.05 inch (1.3 mm) and about 0.5 inch (12.7 mm). The widthwise or circumferential extent, $W_6$ of the sensor components 754a–754d will fall in a range of about 0.01 inch (0.25 mm) and about 0.50 inch (12.7 mm) and preferably will fall within a range of about 0.03 inch (0.75 mm) and about 0.20 inch (5.1 mm). The thickness, $t_5$ of the components 754a–754d, as diametrically established in general will fall within a range of from about 0.01 inch (0.25 mm) to about 0.50 inch (12.7 mm) and preferably within a range of from about 0.03 inch (0.75 mm) to about 0.20 inch (5.1 mm). Spacing, $W_7$ for the gap extending between the stent sensor components 754a–754d will fall within the range of from about 0.005 inch (0.13 mm) to about 0.1 inch (2.5 mm) and preferably within a range of from about 0.01 inch (0.25 mm) to about 0.05 inch (1.3 mm). Flexible support band 760 will have a thickness, $t_6$ which will fall within a range of from about 0.0001 inch (0.0025 mm) to about 0.05 inch (1.3 mm) and preferably will fall within a range of from about 0.001 inch (0.025 mm) to about 0.03 inch (0.76 mm). Biocompatible coating 762 will have the earlier-described range of thicknesses, $t_2$.

The technique and instrumentation discussed in connection with FIGS. 5 through 8A and 8B essentially are repeated for the therapy assigned to limit restenosis utilizing stents as at 748. In this regard, looking to FIG. 39, the instrumentation and support equipment discussed in connection with FIG. 5 are illustrated in connection with a patient 770. Patient support components, heating components and sensing components which are repeated are shown with the same earlier presented numerical identification but in primed fashion. Note in the figure that stent 748 reappears adjacent the heart region 772 of patient 770. Heating component 98' extending from the ACF heating assemblage 94' is located in adjacency with the stent 748 and the pick-up 106' of magnetometer assembly 104' is positioned in external adjacency with the location of stent 748. Power is applied from the heating unit or assembly 94' on an intermittent basis as earlier-described in conjunction with FIG. 7 to permit a power input interval earlier-described at $\delta t_1$ followed by a measurement or interrogation interval earlier-described at $\delta t_2$. Time ranges for this intermitting remain as earlier identified at $\delta t_1$ and $\delta t_2$ in Table 1. The setpoint, $T_{SP}$ is established for restenosis therapy by design of the sensor component assembly 754 and the associated narrow Curie transition temperature. $\Delta T_S$ as described at 156 in FIG. 7 now termed $\delta T_{sent}$ or temperature range of the stent about the setpoint falls in a temperature range of nominally from about 0.1° C. to about 5° C. and preferably will fall within a range of about 0.1° C.

and 3° C. The instantaneous heating power generated within the stent 748, $P_{stent}$, will generally fall within a range of from about 0.05 calories/second to about 20 calories/second and preferably will be within a range of between about 0.1 calories/second and about 10 calories/second. As described in conjunction with FIG. 7, as Curie transition temperature is reached the permeability of the sensor component assembly 754 decreases somewhat dramatically, i.e., a 20 to 1000 fold change, whereupon power is terminated until temperature diminishes to evoke the heating patterns as have been discussed at 156, 166 and 172 in connection with FIG. 7. The nominal hyperthermia therapy temperature for stents such as at 748 ($T_{stent}$) will fall within a range of from about 39° C. to about 70° C. and preferably within a range from about 41° C. to about 50° C.

Figure 40:
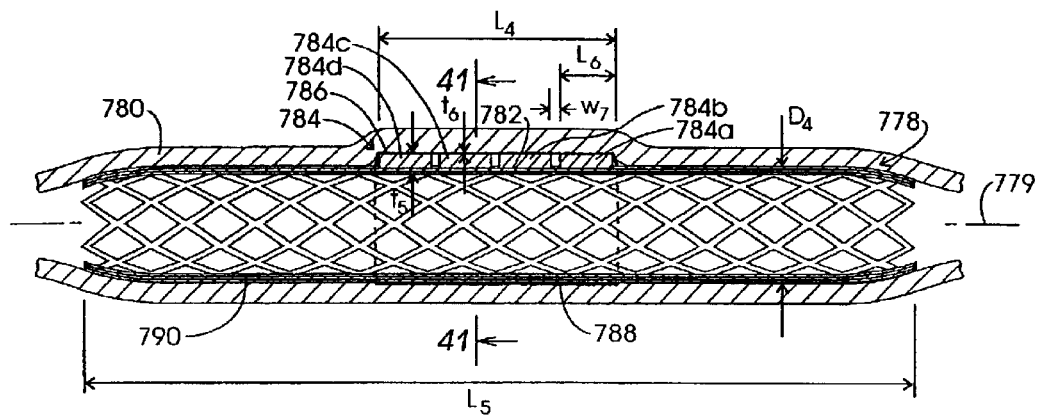
FIG. 40 is a sectional schematic view of a stent according to the invention incorporating a heat activated release agent coating and being shown imbedded within a blood vessel.
Figure 41:
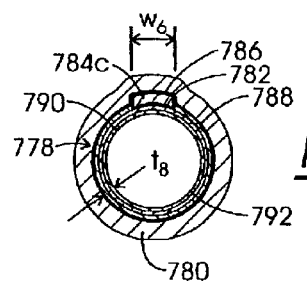
FIG. 41 is a sectional view taken through the plane 41—41 shown in FIG. 40.

The combined stent and unthethered sensor component assemblies discussed in conjunction with FIGS. 37 and 38 also may be utilized to implement a thermally activatable drug release feature. Referring to FIGS. 40 and 41, a stent represented generally at 778 is shown having been implanted within a blood vessel 780. Attached in intimate thermal exchange relationship with the outer contact surface 782 of stent 778 extending about a central axis 779 is a sensor component assembly represented generally at 784 which, as before, is formed of four untethered temperature responsive components 784a–784d which, along with the stent 778 are configured and spaced with the same dimensional and operational parameter ranges described in conjunction with FIGS. 37 and 38 and summarized in Table 1. Each of the temperature responsive components 784a–784d is fixed in thermal exchange relationship with the contact surface 782 present as the outwardly disposed surface of stent 778. The temperature responsive component assembly 784 is coated as before, by an electrically insulative conformal biocompatible coating 786 such as the earlier-described "Parylene" which further functions to aid in the securement of the four segments 784a–784d to surface 782. This securement further is enhanced by the flexible band or sheath 788 surmounting both the stent 778 and the sensor assembly 784. Band 788 is structured in the manner of earlier-described band 756. Note, however with the arrangement of FIGS. 40 and 41, that the inward surface 790 of stent 778 is coated with a thermally activatable drug release coating as shown at 792. The surface coating 792 is revealed in FIG. 41 as having a thickness, $t_8$ which may fall within a range of about 0.001 inch (0.025 mm) to about 0.20 inch (5.0 mm) and preferably will fall within a range of from about 0.005 inch (0.13 mm) to about 0.10 inch (2.5 mm). Such drugs may be provided, for example, as paclitaxel and the antibiotic Sirolimus as well as antithrombogenic agents such as heparin and the like. See the following publications in this regard:

(55) Simonsen, "Percutaneous intervention arena still expanding for heart disease." *Cardiovascular Device Update,* 7 (4): 2–5 (May 2001).

(56) "Drug-Coated Stents Poised for Growth", *Cardiovascular Device Update,;* 7 (9): 8–9 (September, 2001).

The nominal drug release temperature, $T_{DRS}$ will range from about 39° C. to about 65° C. and preferably from about 41° C. to about 50° C. Drug release coating 792 when non-invasively heated to a drug releasing temperature provides a controlled amount of a selected drug at the situs of the stent 778 to limit restenosis phenomena. Such a drug release process can be repeated at therapeutic intervals which may range from weeks to months to even years. Additionally, the coating may be activated in the event the patient's symptoms or diagnostic methods indicate that restenosis is occurring and progressing to the point that therapeutic intervention is warranted. Where hyperthermal therapy is combined with drug release activity, sensor segments or components 784*a*–784*d* may be assigned corresponding different setpoint or target temperatures (Curie transition temperatures).

The untethered temperature responsive component assemblies preferentially are positioned on the outer contact surface on the stent structure as described inasmuch as such location provides a factor of safety with respect to the adhesion of the individual components to that contact surface. Should the coupling be damaged, the sensor components are retained by the stent structure itself outside of luminal blood flow.

Figure 42:
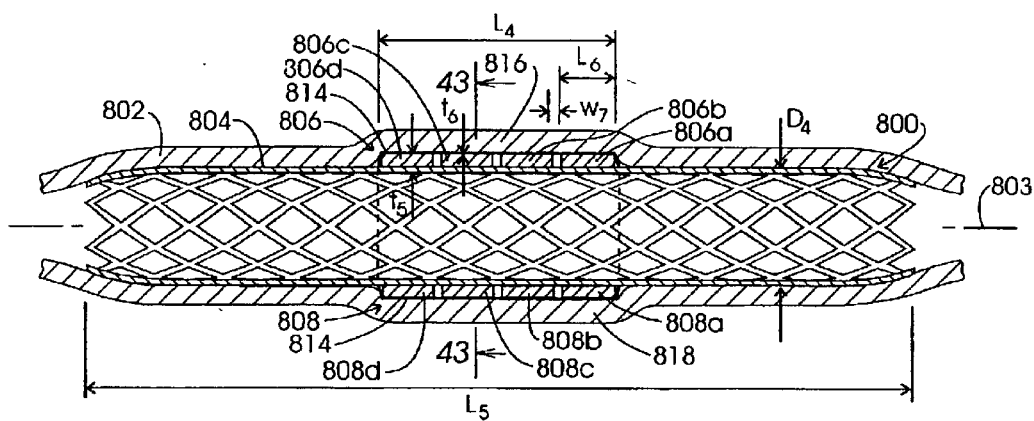
FIG. 42 is a schematic sectional view of another stent embodiment according to the invention, the device being shown embedded within a blood vessel.
Figure 43:
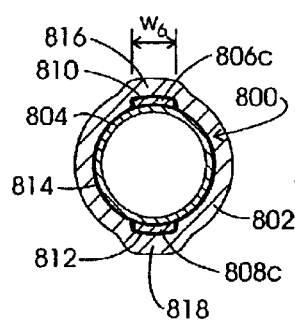
FIG. 43 is a sectional view taken through the plane 43—43 shown in FIG. 42.

This outboard positioning of the untethered temperature responsive component assemblies can be arranged with additional redundancy by mounting them, for instance, at diametrically opposite locations upon the stent contact or outer surface. FIGS. 42 and 43 present such an arrangement wherein the nonmagnetic material stent as represented generally at 800 is shown implanted within a blood vessel 802. As before, the stent 800 is formed about a central axis 803 with a generally mesh-like structuring having an outwardly disposed contact surface 804 of generally cylindrical configuration to which untethered temperature responsive component assemblies represented generally at 806 and 808 are mounted in intimate thermal exchange relationship. Assembly 806 is seen to be formed of discrete untethered temperature responsive components 806*a*–806*d* while, correspondingly, assembly 808 is formed of discrete untethered temperature responsive components 808*a*–808*d*. Each of these components is coated with an electrically insulative, conformal biocompatible material shown respectively at 810 and 812 in FIG. 43. That material, which may be the earlier-described "Parylene" further functions to enhance the bond between the assemblies 806 and 808 and the outer surface 804. Assemblies 806 and 808 further are secured to the outer surface 804 by a flexible band or sheath 814. Band 814 is structured in the manner of earlier-described band 756. As before, the figures reveal that the blood vessel 802 is diametrically enlarged at regions 816 and 818 to accommodate for the thicknesses of the assemblies 806 and 808. These assemblies and the stent structure 800 as well as coatings and the like will have the same dimensions and operational parameters as discussed above and summarized in Table 1.

As noted earlier, essentially all metallic stents which have been implanted are formed of nonmagnetic material in view of the potential involvement of highly magnetic imagining systems, e.g., MRI devices. As a consequence, those pre-implanted stents can be retrofitted in vivo with the temperature sensing aspects of the present invention to permit noninvasive therapeutic procedures for subsequent treatment of restenosis phenomena. The retrofitting approach, in effect, provides for the installation of a temperature responsive component containing stent-like structure diametrically expandable within the preexisting stent.

Figure 44:
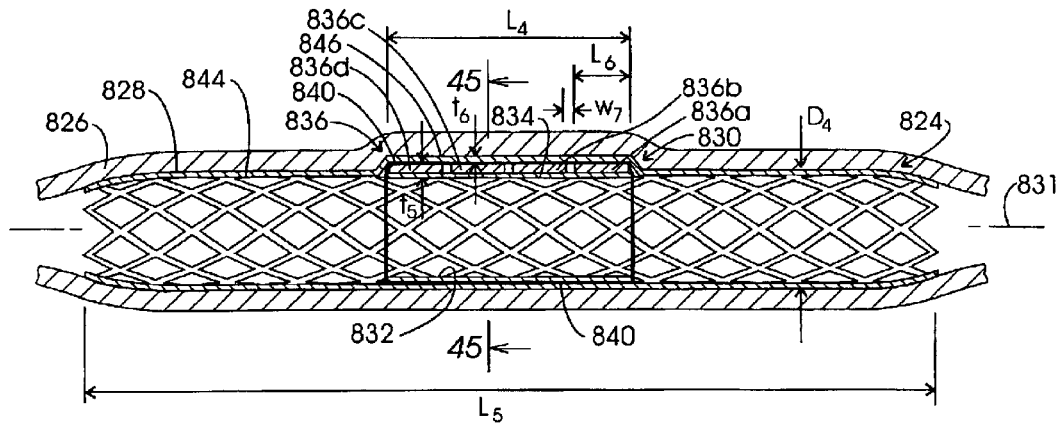
FIG. 44 is a sectional schematic view of a stent embedded in a blood vessel and having been retrofitted with a sensor assembly according to the invention.
Figure 45:
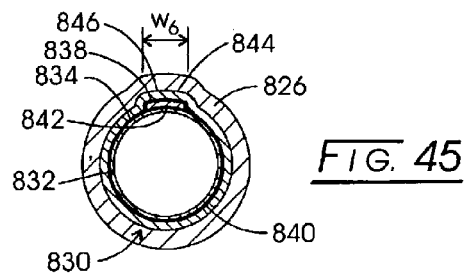
FIG. 45 is a sectional view taken through the plane 45—45 shown in FIG. 44.

Referring to FIGS. 44 and 45, an asymmetrical retrofitting design is illustrated. In the figure, a conventional nonmagnetic metal mesh stent is represented in general at 824 which has been previously implanted within a blood vessel 826. In this regard, note that the outwardly disposed surface 828 of the stent 824 is in contact with the intima of the vessel 826. The untethered temperature responsive component assembly carrying insert or support member is seen at 830 with a central axis 831 and having a generally cylindrical support member defining interiorly disposed surface 832 and an exterior surface 834 to which the untethered temperature responsive component assembly represented generally at 836 is bonded in thermal exchange relationship. Note, in this regard, that the assembly 36 is formed of four discrete temperature responsive components 836*a*–836*d*. In general the stent insert device may be formed with essentially the same mesh structuring and material as present in the previously implanted stent 824. Such mesh structuring is not shown in the figures in the interest of illustrational clarity. FIG. 45 shows that each of the components 836*a*–836*d* is coated with a biocompatible coating such as the earlier-described "Parylene" material. Additionally, the structural integrity of their attachment with the support member 830 is enhanced by a flexible band 840. Sensor carrying support member 830 is inserted within the preexisting stent 824 using balloon angioplasty procedures. In order to accommodate for the asymmetrical positioning of only a single sensor assembly 836, the member 830 is structured so that it is preferentially expandable in the region 842 (FIG. 45) immediately beneath the temperature responsive component assembly 836. Accordingly, upon balloon expansion during the placement of member 830, and its supported sensors, the region 842 will expand from an initial insertion diameter diametrically outwardly against the interior surface 844 of the preexisting stent 824 to create the crimping expansion of the contacting surface of that stent 824 as represented at region 846. Preferential expansion at sub-stent 830 region 842 can be provided by structuring the stent to be thinner at that region and/or the mesh structure opening size may be asymmetrically varied. Conventional characteristics again are identified in FIGS. 44 and 45 as $L_4$, $L_5$, $L_6$, $W_6$, $W_7$, $t_5$ and $t_6$. The dimensional ranges associated with these symbols remain as described above and as tabulated in Table 1. Similarly, the temperature range of the stent 824 around setpoint temperature, $\Delta T_{stent}$ remains as described above and tabulated. The instantaneous heating power generated within the stent, $P_{stent}$ remains as described above and set forth in Table 1 and the thermal resistance values between the stent and sensor assembly remain as described in connection with the identifiers $TR_3$ and $TR_4$ set forth above and in Table 1. Devices as at 830, in addition to being formed of biocompatible material, are formed of a material selected to avoid any Galvanic activity with the pre-existing stent, i.e., an agalvanic material.

Figure 46:
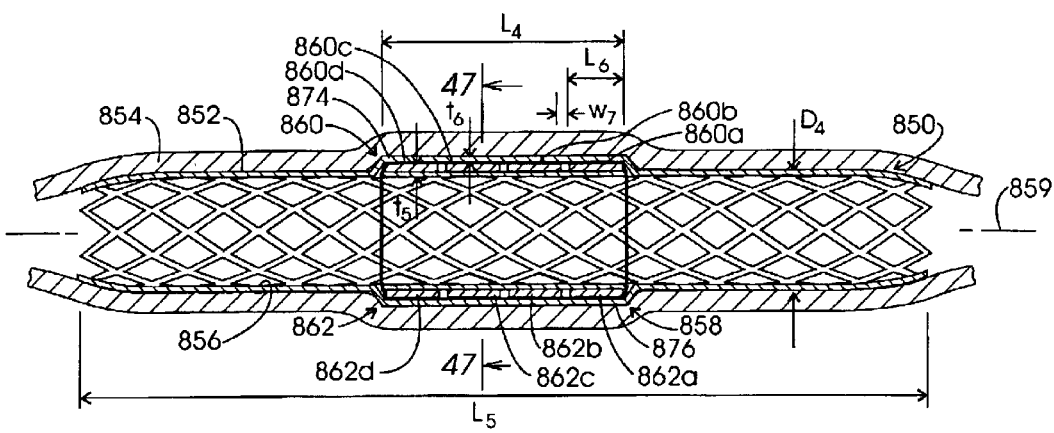
FIG. 46 is a sectional schematic view of a stent embedded within a blood vessel and showing a retrofit thereof with two sensor assemblies according to the invention.
Figure 47:
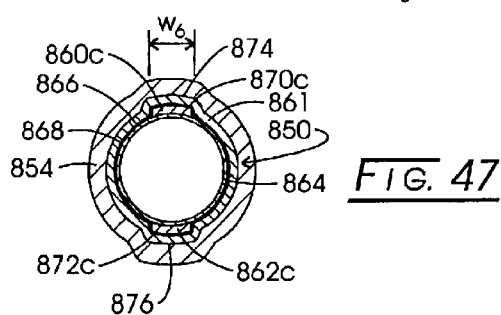
FIG. 47 is a sectional view taken through the plane 47—47 shown in FIG. 46.

Referring to FIGS. 46 and 47, a retrofitting or "stent within a stent" approach is illustrated wherein the untethered temperature responsive component assembly is symmetrically diametrically duplicated. In the figures, a pre-implanted nonmagnetic stent is represented generally at 850. As before, stent 850 has a mesh-type structure of generally cylindrical configuration, the cylindrical outer surface 852 of which is in abutting compressive engagement with the intima of blood vessel 854. In order to carry out a hyperthermia form of treatment for restenosis with the necessary highly accurate temperature control, a secondary stent or support member represented generally at 858 extending about a central axis 859 is implanted within the interior surface 856 of stent 850. Secondary stent 858 is formed of an expandable mesh material and functions to support diametrically oppositely disposed temperature sensor component assemblies represented generally at 860 and 862. To promote the flexibility of the support member stent 858, the temperature sensor component assemblies 860 and 862 are each formed of four ferrite sensing elements again exhibiting accurate and narrow Curie temperature transition phenomena. Assembly 860 is seen to be formed of ferrite sensors 860*a*–860*d*. As before, by utilizing such a sequence of the sensors, a modicum of flexibility is provided to aid in maneuvering the secondary stent 858 into position for connection with the primary stent 850. Assembly 862 is similarly fashioned with four sensor components exhibiting the same sharp Curie temperature transition phenomena and being shown at 862a–862d. Similar to the embodiment of FIGS. 44 and 45, the secondary stent 858 is configured with an internal wall formed of mesh material compatible with the material forming the primary stent 850. Such mesh structuring is not shown in FIG. 46 in the interest of illustrational clarity. The interior wall of device 898 wall is shown having an interior surface at 864 and an exterior surface 866 upon which the sensor component assemblies 860 and 862 are connected. To enhance this connection, a flexible band surmounts both the cylindrical exterior wall 866 and the assemblies 860 and 862. FIG. 43 reveals that each of the component assemblies 860 and 862 are connected. To enhance this connection, a flexible band surmounts both the cylindrical exterior wall 866 and the assemblies 860 and 862. FIG. 48 reveals that each of the components of the assemblies 860 and 862 are coated with an electrically insulative biocompatible conformal coating such as the earlier-described "Paryle" The coatings are revealed in FIG. 47 at 870c in conjunction with sensor component 860c and at 872c in conjunction with sensor component 862c. As before, the conformal coatings will have a thickness range identified earlier herein as, t2 and further set forth in Table 1. Sensor segments 860a–860d and 862a–862d are spaced apart a gap identified as $w_7$; each has an individual discrete length identified as $L_6$ and the assemblies 860 and 862 have lengths identified as $L_4$. Each of the components 860a–860d and 862a–862d have thicknesses identified as $t_5$ and widthwise dimensions as shown in FIG. 47 identified as $W_6$. All of these dimensions are tabulated in Table 1 and have been discussed above. Placement of the secondary stent 858 may be by balloon pressure to an extent creating the symmetrically disposed outward deformations in the wall of stent 850 as shown at 874 and 876. Those deformations generally will have the length $L_4$ while the overall length of the principal stent 850 will have length ranges identified as L5 in Table 1 and as described above.

By virtue of the intimate association of the secondary stent borne temperature sensor component assemblies 860 and 862 with the stent 850, $\Delta T_{stent}$, the temperature range of the stent 850 about the hyperthermia therapy set point may be maintained within the earlier-described range from about 0.1° C. to about 5° C. and preferably from about 0.1° C. to about 3° C. The intimate association also permits development of the nominal hyperthermia therapy temperature for the stent 850, $T_{stent}$ within the earlier-noted range of from about 39° C. to 70° C. preferably between about 43° C. and 48° C. A nominal stent heating temperature of 45° C. has been described in publication (52) supra.

See additionally the following publication:
(57) Thury, A., et al., "Initial Experience With Intravascular Sonotherapy For Prevention Of In-Stent Restenosis; Safety And Feasibility", J. of Am. College of Cardiology 37 (2) Supplement A. (2001).

In general the setpoint temperature, $T_{SP}$, is elected as being effective for inhibiting the proliferation of intimal hyperplasia growth following stent insult. The nominal thermal resistance between the retrofitted stent 850 and the sensor assemblies 860 and 862, $TR_3$ continues to be 5° C./watt and the preferred thermal resistance, $TR_4$ remains 0.5° C./watt. Because of the symmetry of positioning of the temperature sensor assemblies 860 and 862, a balloon evoked placement can be carried out without customized structuring of the secondary stent cylindrical wall as provided in conjunction with the embodiment shown in FIGS. 44 and 45.

The discourse now turns to the procedures associated with the embodiments described above in connection with FIGS. 39–47.

Looking to FIG. 48A, the initial phase of the procedure involves the positioning of a stent transluminally within the patient. That stent typically will be positioned as part of percutaneous transluminal coronary angioplasty (PTCA). For the instant method, the stent will incorporate an integral temperature sensing system and may further incorporate heat activatable drug components. Accordingly, the general procedure will involve the administration of a general or local anesthetic agent as indicated at block 890. Then, as represented at line 892 and block 894 the stent with integral sensor is positioned within the patient's blood vessel at the targeted location and, typically utilizing balloon procedures, the stent is deployed such that it is securely imbedded. Then the delivery catheter is removed from the patient and, as represented at line 896 and node 898 the stent positioning phase will have ended. It is subsequent to this phase, a time interval that may range from weeks to years that restenosis conditions may arise.

As an alternate to the procedure thus far described, the secondary stent approach described in conjunction with FIGS. 44–47 may be carried out as represented at block 900. With this procedure, a stent which has already been implanted is supplemented with temperature sensor components according to the invention by catheter placement and expansion within a preexisting stent.

Subsequent to the stent positioning phase the patient will be monitored for the occurrence of clinically significant restenosis. As represented at block 902 such checks may be carried out, for instance, using angiography, diagnostic ultrasound, x-ray, or MRI techniques. The procedure then continues as represented at line 904 and block 906 presenting a query as to whether or not evidence of restenosis is present. In the event that it is not, then as represented at line 908, block 910 and line 912 such checks are continued, the patient's cardiac/circulatory function being monitored on a periodical basis. Where evidence of restenosis does exist, then as represented at line 914 and block 916 thermal therapy according to the invention is commenced. As an initial step in the procedure, a marker is placed on the skin of the patient at a location selected for aiding in the positioning of the magnetometer probe 106' and the ACF heater coil 98'. As represented at line 918 and block 920 the patient is positioned on the table as at 52' or suitable chair so that the skin locative marker is clearly visible for the noted coil and probe orientation. Then, as represented at line 922 and block 924 the ACF heating coil positioning mode is commenced. In this regard, using the marker at the surface of the patient the heating coil 98' is located as close as practical to the location of the stent/sensor implant or implants. Then, as indicated by line 926 and block 928, the operator turns on the control feature by actuation of on/off switch 180' which, in turn, will cause the illumination of green LED 182'. Next, as represented at line 930 and block 932 the operator may select the duty cycles for activating the heater component and the magnetometer. While these intervals may be factory set, the operator may carry out the selection by utilizing switch function 184'. The procedure continues as represented at line 934 and block 936 wherein the operator selects the extent of travel of the table or platform 52' or a corresponding chair-type support. That selection is made by operator actuation of up/down switches 194' while observing any corresponding locus of travel value shown at display 196'. The program then continues as represented at line 938 which extends to block 940 providing for the acquisition of the enabling voltage value of the motor control 78'. Following such acquisition, as represented at line 942 and block 944, a determination is made as to whether that enabling voltage $V_{mc}$ is greater than or equal to three volts. If the determination at block 944 is that the enabling voltage of the table control is not adequate, then as represented at line 946 and block 948, an error message is displayed at the display 204'. The error, in general will indicate that the control leads 84' from the oscillation system are not properly attached to the console 112'. The program then continues as represented at line 950 and block 952 wherein the display 204' outputs a display prompt, to wit: "check the lead/cable attachment". The program then reverts to line 938 as represented at line 954.

Figure 39:
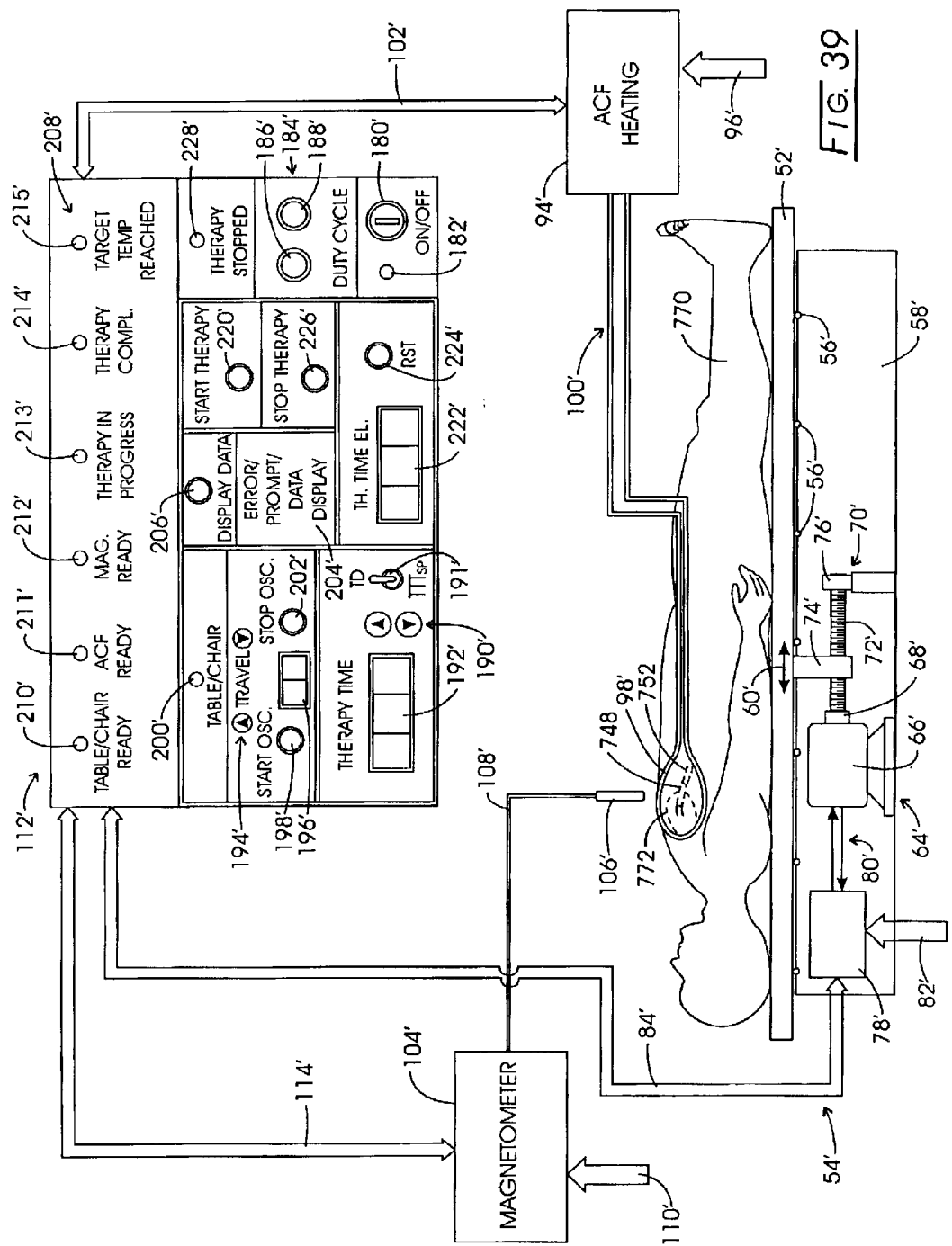
FIG. 39 is a schematic representation of a system according to the invention for utilization of stents formed according to the invention.

In the event of an affirmative determination with respect to the query posed at block 944, then as represented at line 956 and block 958 green LED 210' is illuminated and the procedure continues as represented at line 960 and block 962. In this regard, the operator carries out what in effect is a "check run" of the oscillation of platform 52'. This check is initiated by actuating button switch 198'. As the patient support assemblage 54' is activated, the procedure then evaluates the status of the magnetometer 104'. Accordingly, as represented at line 956 and block 958 the magnetometer 104' is turned on and the system acquires its on and continuity status information. The program then continues as represented at line 968 and block 970 wherein a determination is made as to whether the status of the magnetometer 104' is ok. In this regard, the peak-to-peak variation of the magnetometer output voltage, $V_{MO}$ is compared with a reference, $V_{FM}$. Where that condition obtains, then the enablement signal $V_c$ is generated. This signal must be greater than or equal to three volts d.c. to be representative. In the event that the magnetometer status is not ok, then as represented at line 972 and block 974 an error condition is displayed at display 204' indicating that the magnetometer probe cable 108' or cable 114' to console 112' is not properly attached. The program then continues as represented at line 976 and block 978 to display the prompt to the operator to check the magnetometer cable attachments. The program then returns as represented at line 980 to line 968.

Where the query posed at block 970 is responded to in the affirmative, then as represented at line 982 and block 984, green LED 212' at console 112' is illuminated and the program continues as represented at line 986 and block 988. At this juncture in the procedure, the operator will be positioning the magnetometer probe 106' as close as practical to the stent. This positioning will involve orientation of that probe to achieve a maximum magnetometer signal change with the oscillations of the platform 52'. The program then continues as represented at line 990. Line 990 extends to block 991 providing for the termination of the test run of the support assemblage 54'. This is carried out by operator actuation of the stop button switch 202' on console 112'. The procedure continues as represented at line 992 and block 993 which provides for operator selection of both therapy duration commencing with the attainment of setpoint temperature, $T_{SP}$, and the maximum allotted time to attain that temperature, $T_{SP}$. Selection is carried out by actuation of switches 190' and 191' in conjunction with the readout provided at display 192' (FIG. 39).

As represented at line 994 and block 996, the ACF heating assembly 94' is turned on, and as provided at line 998 and block 1000 a query is posed as to whether the ACF heating unit is enabled both by the development of a requisite on voltage level, $V_{RF}$ as being greater than or equal to three volts and the presence of the earlier-described magnetometer signal $V_c$ as being greater than or equal to three volts. If those ANDed conditions are not met, then as represented at line 1002 and block 1004 an error visual cue is displayed at display 204' indicating that the control leads 102' are not properly connected to the control console 112'. The program then continues as represented at line 1006 and block 1008 to display a prompt advising the operator to turn off the ACF heating unit and the cable attachment 102' extending to the console 112'. The program then reverts to line 994 as represented at line 1008.

Where the query posed at block 1000 results in an affirmative determination, then as represented at line 1012 and block 1014, green LED 211' is illuminated at console 112' and the program continues as represented at line 1016. Line 1016 extends to the query posed at block 1018 determining whether the duration for therapy and the maximum time allocated to reach $T_{SP}$ have been set to correct and intended values. Both intervals are set by the operator, employing the up/down switches 190' and election switch 191' in conjunction with display 192' on console 112'. The discussion associated with FIGS. 40 and 41 may be recalled with respect to the selection of therapy duration as to its function in providing a temperature controlled dispersion of chemotherapeutic or other release agents. One or more levels of predetermined Curie transition temperatures may be utilized in conjunction with a thermotherapy for restenosis per se and an adjunct dispersion of chemotherapeutic release agents. Where the therapy duration or time to $T_{SP}$ intervals are incorrect, then as represented at line 1020 and block 1022 appropriate adjustment at control switches 190' and 191' is made and the program reverts to line 1016 as represented at line 1024.

Where the query posed at block 1018 is responded to in the affirmative, then as represented at line 1026 and block 1028 a determination is made as to whether the therapy time elapsed indicates zero minutes. This readout is provided at console 112' at display 222'. In the event that display does not register zero minutes, then as represented at line 1030 and block 1032, reset button switch 224' is actuated and the program continues as represented at lines 1034 and 1036. Therapy time elapsed having been set at zero, the procedure continues as represented at line 1036 and block 1038. Block 1038 reflects the activity of controller 240 (FIG. 8B) in carrying out a determination that the conditions established by the illumination of LEDs 210'–212' at console 112' have been satisfied and the system now is ready to commence the thermotherapy mode. In the event that the ready check fails, then as represented at line 1040 and block 1042, an error cue is published at display 204' and, as represented at line 1044 and node A the program reverts to line 938 to again consider the ready checks.

In the event the query posed at block 1038 results in an affirmative determination, then as represented at line 1046 and block 1048 hyperthermia therapy is commenced with the operator actuation of the start therapy button switch 220' at console 112'. With this actuation, as represented at line 1050 and block 1052, the green LED 213' indicating that therapy is in progress at console 112' is illuminated and the procedure continues as represented at line 1054 to the query presented at block 1056. Therapy being underway, the program determines whether or not the stop therapy button switch 226' at console 112' has been actuated. In the event that such an actuation occurred, then as represented at line 1057 and block 1059, the ACF heating assembly 94' is turned off as well as the motor control circuit 78' of the support assemblage 54'. As a visual cue that the therapy is stopped, red LED 228' is illuminated and, correspondingly, green LEDs 200' and 213' are de-energized. The procedure then continues as represented at line 1060 and block 1061 wherein the operator determines whether or not the therapy mode is to be resumed. Where resumption is intended, then as represented at line 1060 and block 1061 the start therapy button switch 220' is actuated at control console 112' which, in turn, causes the turning off of red LED 228' and the turning on of green LEDs 200' and 213'. This automatically restarts the platform 52' oscillation and the re-activation of the ACF heating assembly 94'. The program then continues as represented at line 1064 which extends to line 1050. Where the query posed at block 1061 results in a determination that therapy is not to be resumed, then as represented at line 1065 and node 1066, the therapy is ended.

Returning to block 1056, where a determination has been made that the stop therapy switch 226' has not been actuated, then as represented at line 1067 and block 1068 a determination is made as to whether the target or setpoint temperature, $T_{SP}$ has been reached. This target temperature has been discussed in conjunction with dashed line 142 of FIG. 7. Where the target or setpoint temperature has been reached, then as represented at line 1070 and block 1072, a query is made as to whether the time to setpoint temperature, $T_{SP}$ has been reached or has elapsed before the setpoint temperature itself has been reached. In the event that it has not, then as represented at line 1074 and block 1076, a start of timing of duration of treatment or the commencement of a continuation of that therapy timing is effected. In the latter regard, should the stop therapy switch have been actuated and then therapy resumed as represented at block 1063, then timing will resume from the point where it had been interrupted.

The procedure then continues as represented at line 1078 and block 1080 providing for the illumination of green LED 215' on console 112'. The program then continues as represented at line 1082. Where the inquiry posed at block 1068 results in a negative determination, then as represented at line 1084 the program reverts to line 1082.

Line 1082 extends to the query posed at block 1086 wherein a determination is made as to whether the therapy time elapsed has reached the value of the preset therapy duration. Where that is not the case, then as represented at line 1088 and block 1090, the time elapsed readout 222' is updated and the program reverts as represented at line 1092 and node B to line 1054.

In the event the query posed at block 1086 results in an affirmative determination, then, as represented at line 1094 the therapy is completed and the procedure continues as represented at line 1094 and block 1108. Returning to the query at block 1072, where an affirmative determination has been made that the time to setpoint has elapsed before setpoint temperature is reached, then an error condition obtains and is represented at line 1096 and block 1098, an error is displayed at 204' on console 112' and the program reverts to line 1094 as represented at line 1100. Line 1194 extends to block 1108 which provides for the deactivation of the active components of the system. In this regard, the ACF heating assembly 94' is deactivated as is the magnetometer assembly 104'. Control circuit 78' for the platform support assembly 54' is deactivated. Therapy complete green LED 214' is illuminated and green LED 213' representing therapy in progress is de-energized. The program then continues as represented at line 1110 and block 1112 wherein pertinent data representing the procedure parameters is recorded. It may be recalled that this data can be displayed at display 204' by the actuation of button switch 206'. The procedure then continues as illustrated at line 1114 extending to node 1116 representing a therapy ended stage.

Figure 49:
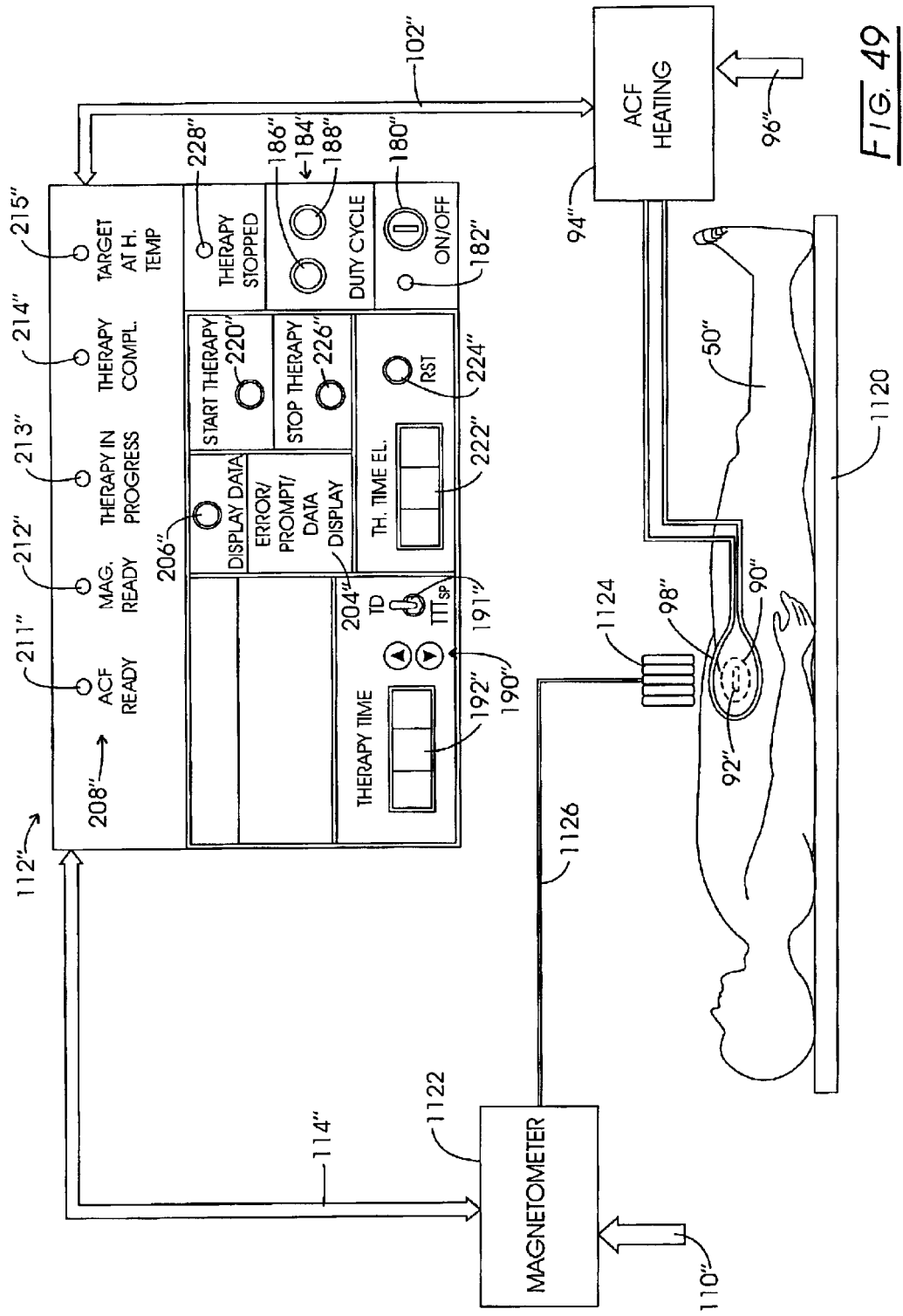
FIG. 49 is a schematic representation of another embodiment of the system of the invention showing the utilization of a stationary patient support in combination with a multichannel magnetometer having an array of pick-ups.

In the embodiments heretofore described, the patient has been supported upon a moveable platform or chair for the purpose of deriving a relative movement between the temperature sensor components and the magnetometer pick-up. However, this relative movement can be dispensed with, for example, through the utilization of an array of magnetometer pick-ups which is arranged as such that certain of the pick-ups within the array will intercept magnetic field flux lines affected by the sensor components while other somewhat adjacent pick-ups within the array will intercept magnetic field lines which are unaffected by a sensor component, i.e., the field lines will not have intercepted those components. Referring to FIG. 49, schematic representation of such an embodiment is provided. Because of the similarity of the embodiment of FIG. 49 with that earlier-described in connection with FIG. 5, items of commonality between these figures are identified in FIG. 49 with the same numeration as FIG. 5 but in double primed fashion. Removal of the oscillatory platform will be seen to result in a corresponding removal of certain control functions. In the figure, the patient 50" is shown in a supinate position on a stationary horizontal platform 1120. Other patient support structures may be employed such as modified chairs and the like. The target tissue volume of interest is again represented internally within the body of the patient 50" by a symbolically represented dashed boundary 90". Within this boundary 90" there is shown at least one temperature sensor or sensor/heater implant configured according to the invention as represented schematically at 92". As before, the implant 92" is untethered, having no electrical leads extending exteriorly of the patient 50".

Heating of the region of interest 90" under thermotherapy conditions and, in particular, hyperthermia conditions is provided from the alternating current field heating assembly represented at block 94". Line power input is represented as being directed to the assembly 94" at arrow 96". Substantially focused radiative heating is provided from the ACF heating assembly 94" by a typical coil-implemented heating component represented at 98" which is positioned in close proximity to the skin of patient 50" in the vicinity of a predetermined and earlier marked location of the target tissue volume 90". Association of the component 98" with the heating assembly 94" is represented schematically by line pair 100". Preferably, the component 98" may be associated with an induction heating assemblage operating at a lower frequency within the generally identified radio frequency range.

Now looking to the magnetometer-based detection of the earth magnetic field disturbances evoked by the state of permeability of the sensor component at implant 92", a magnetometer control assembly is represented at block 1122. Assembly 1122 is of a multichannel variety and performs in conjunction with the remotely disposed pick-up or multichannel array or probe 1124, the channels of which are oriented for discerning and/or differentiating magnet field flux lines as they may be affected by the implant or implants at 92". In effect, the magnetometer sensor array 1124 provides for the measurement of a two-dimensional pattern of magnetic field strength allowing the change in the field strength pattern to be detected as the ferromagnetic sensor 92" changes from a magnetic to a non-magnetic state—a change which occurs over a narrow temperature range (FIG. 2) around the intrinsic Curie temperature of the ferromagnetic material selected. The association of the multichannel probe or pick-up 1124 with the assembly 1122 is represented at cable 1126. Assembly 1122 is seen receiving line power as represented by arrow 110" and is controlled and provides outputs to a modified console mounted control assembly represented generally at 112" as indicated at arrow 114". It may be noted that the control assembly 112" does not incorporate the earlier-described table/chair control features, however, all other features described in connection with FIGS. 5, 8A and 8B are retained. While the magnetometer assembly 1122 may perform in conjunction with a synthetically generated magnet field, for the instant embodiment, the earth's magnetic field is employed in conjunction with the sensing approach. As before, the magnetometer assemblies for the instant applications generally will be configured in the manner of fluxgate sensors.

While the tissue heating function of assembly 94" may be carried out simultaneously with the temperature monitoring function of the magnetometer assembly 1122, such coincident operation necessarily requires that the monitoring function be effectively shielded or protected from electromagnetic interference. An approach to avoiding this interference is to intermit the operation of these assemblies in the manner described in connection with FIG. 7. In this regard, the heater assembly 94" is activated for the earlier-described interval $\delta t_1$ and the magnetometer 1122 is enabled subsequent to that time increment for an interrogation interval $\delta t_2$. Ranges for these delta values are set forth in Table 1.

The interactive control functions of the control console 112" are essentially identical to those described in connection with FIG. 5. Applied power levels are set by the user in conjunction with the apparatus 94" itself. However, the controls at console 112" then look to a timing parameter for correctly establishing the energy quantum of thermotherapeutic application. Console 112" is powered-on with a key switch 180", such a power-on condition being represented by the illumination of green LED 182". While typically established by the manufacturer of the control at console 112", the duty cycles for the application of power or heat in the quiescent interval immediately following such heat application is shown as being electable by the user. Insertion of this operational criteria is provided at the switch combination shown generally at 184". The switches 184" include a heat interval input 186" and a corresponding sensor interrogation interval adjustment function 188". As noted above, see the time interval ranges for $\delta_{t1}$ and $\delta_{t2}$ set forth in Table 1. With the duty cycles established, next, the total duration for a given therapy is inserted into the system utilizing up/down momentary depression switches as represented generally at 190" in combination with election switch 191" and a switch display 192", the latter feature providing a visibly perceptible visual time selection, for example, in minutes. Switch 191" provides for selection of Therapy Duration (TD) from the attainment of setpoint temperature and maximum time allocated for reaching $T_{SP}$ ($TTT_{SP}$).

In the course of setting up a therapy, certain associated interconnections will be made by the operator. The control system represented by the console 112" will respond to errors in that setup procedure and provide visual indicia as to error involved and additionally will provide a prompt as to corrective action to be taken. That information is provided at visual display 204". Display 204" also will provide a display of pertinent data concerning a completed therapy by operator actuation of momentary on switch 206". That data also will be recorded automatically in data log memory.

During the course of the setup and subsequent therapeutic operation of the system, an array of visual indicators as to the progress of the procedure as represented generally at 208" will provide confirmational outputs. In this regard, the illumination of green LED 211" indicates that an ACF heating assembly 94" switch located at that unit has been thrown to apply power. Additionally, its illumination indicates that the magnetometer control 1122 monitoring features have indicated that peak-to-peak variations of its control voltages are greater than a reference value. LED 212", when illuminated, provides for an indication that magnetometer 1122 is in a ready condition. In this regard, its power-on switch will have been actuated to an on condition and its peak-to-peak voltage will have equaled or exceeded a reference voltage value. Next, green LED 213" is illuminated to provide an indication that therapy is in progress, and green LED 214", when illuminated, indicates that the therapy duration now has been reached and therapy is completed. Finally, green LED 215" is illuminated to indicate that the target temperature or setpoint temperature $T_{SP}$ (FIG. 7) has been reached and therapy duration commences to be timed out. Once setpoint temperature is reached, this LED 215" will remain illuminated until the end of the therapy or upon stopping of the therapy.

Therapy is commenced with the user actuation of the momentary on start therapy switch 220". During the interval of the therapy, the time elapsed for therapy commencing with the attainment of setpoint temperature, $T_{SP}$ is indicated at display 222". That display may be reset to zero by actuation of momentary on switch 224". If, during the progress of the therapeutic performance of the system, the operator deems it advisable to stop the therapy, then the stop therapy switch 226" is actuated momentarily and the therapy stop red LED 228" is illuminated.

Concerning the general operation of the control function at console 112", it may be noted that unless the checking logic of the control system will have functioned to carry out the illumination of the "ready" LED (s) 211"–212", then the start therapy switch 220" will not be enabled. In general, error and prompt messages will remain at the display 204" where the start-up conditions are not satisfied. The control system represented at console 112" is configured as described above in connection with FIGS. 8A and 8B with the earlier-noted table oscillation related functions deleted.

FIGS. 50A–50E present a block diagrammatic representation of procedure of the invention associated with the arrangement of FIG. 49.

Figure 50A:
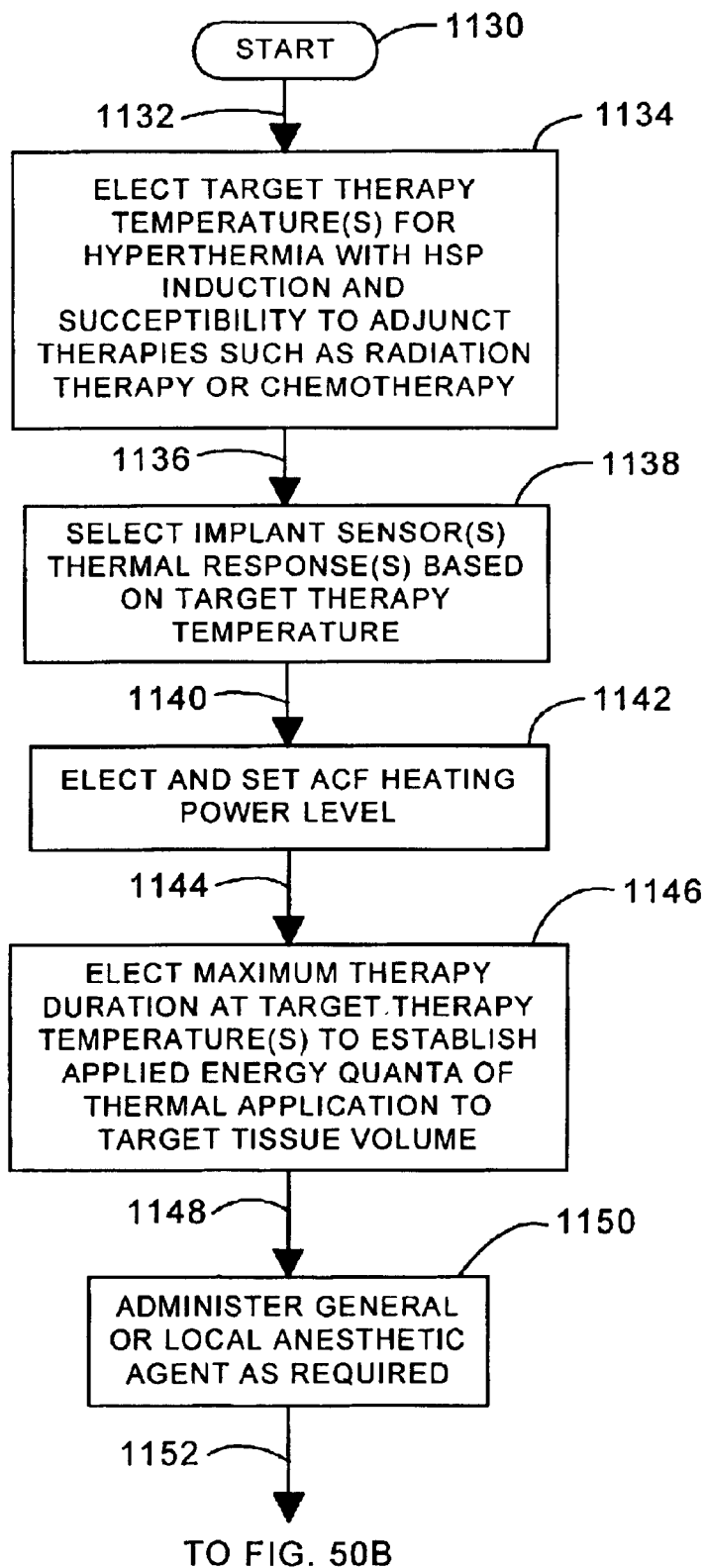
Figure 50B:
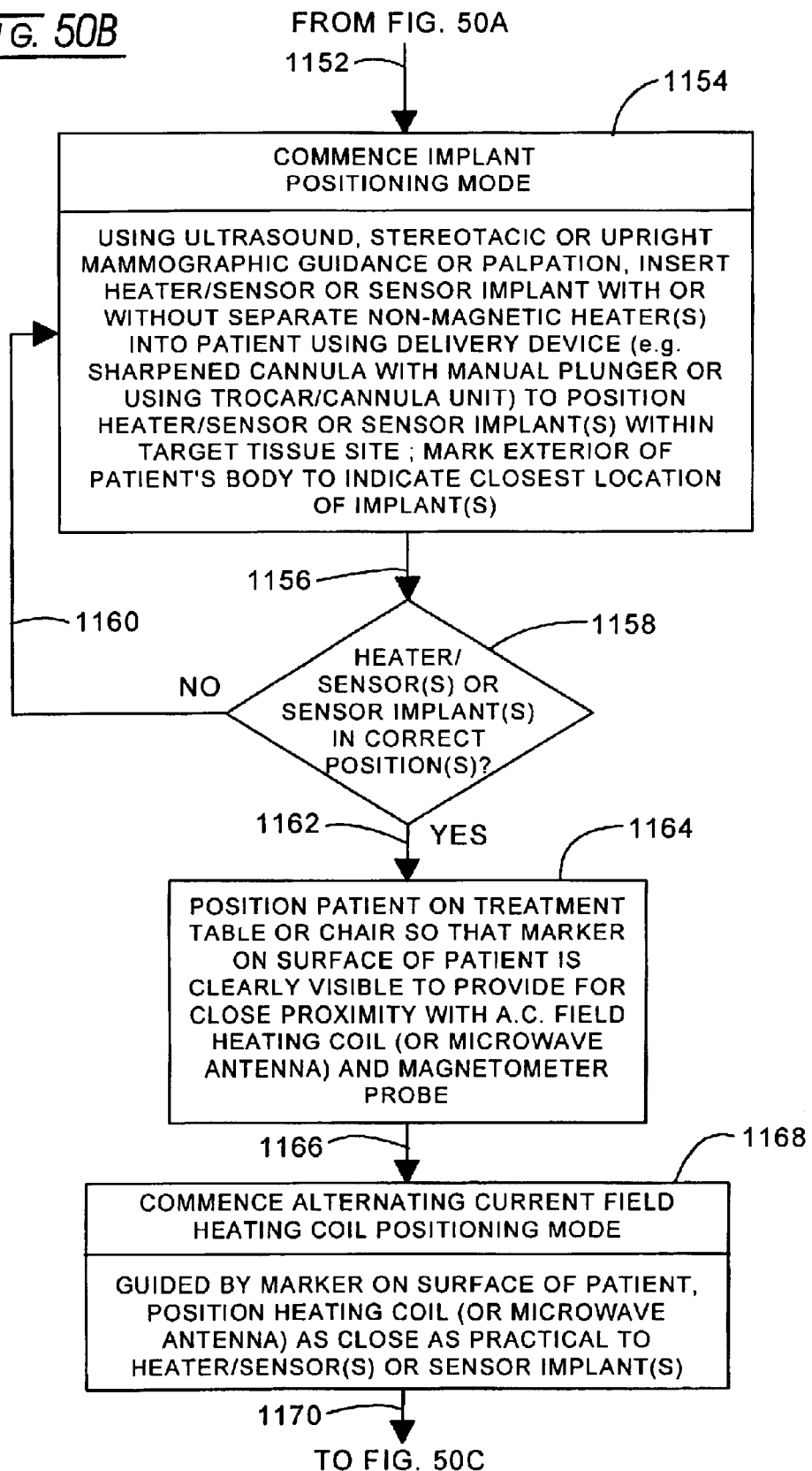
Figure 50E:
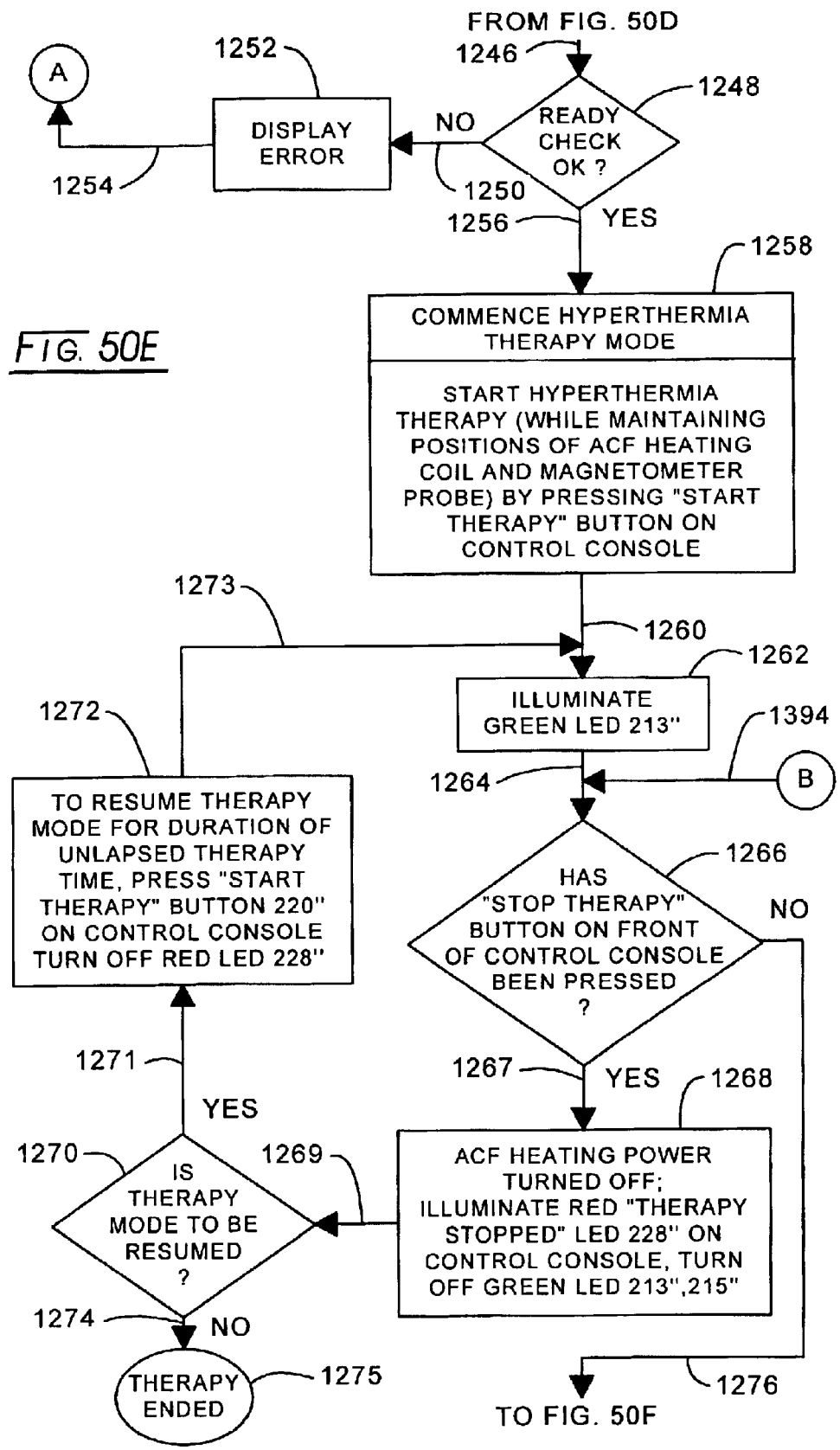

Looking to FIG. 50A, the procedure is seen to commence at node 1130 and line 1132 leading to the determinations set forth at block 1134. Those determinations provide for the election of target therapy temperature(s) for instance, for hyperthermia with (HSP) induction and susceptibility to adjunct therapies such as chemotherapy, i.e., release agent dispersion by heat activation, boney tissue mending or the like. The procedure then continues as represented at line 1136 and block 1138 providing for the user selection of implant sensor (s) thermal responses based upon the elected target therapy setpoint temperature or temperatures. With temperature elections having been made and sensor component/heater component configuration determined, then as represented at line 1140 and block 1142 the power level for the ACF heating assembly 94" is selected and set by the user. Where the therapy will include the induction of heat shock proteins, then, as represented at line 1144 and block 1146 the user may evolve a maximum therapy duration at elected target temperature or temperatures to establish an energy quanta of thermal application to the target tissue volume. The election of such maximum values is made to avoid generation of temperatures or temperature in time conditions falling above critical curves as at 24 described in connection with FIG. 3 and to maximize induction of HSPs. The procedure then continues as represented at line 1148 and block 1150 providing for the administration of general or local anesthetic agent as required. Then, as represented at line 1152 and block 1154, using one or more of the above-discussed imaging techniques, the implant is inserted into or adjacent to the target tissue volume of the patient utilizing an implant device, for example, as discussed in connection with FIGS. 32 and 33. As part of this procedure, the exterior of the patient's body is marked to indicate the closest location of the implant or implants so as to facilitate the positioning of the radiative heating coil or antenna as well as to orient the pick-up structure 1124 of the magnetometer assembly 1122. As discussed above, the implants may be installed as part of an intraoperative surgical procedure.

Next, the method provides a confirmational procedure as represented at line 1156 and block 1158 wherein the imagining and other such instrumentation are used for purposes of ascertaining if the implants are in the proper location with respect to the target tissue. Should the implant positioning not be appropriate, then as represented at loop line 1160, the method reverts to the procedure described in connection with block 1154. Upon an affirmative determination with respect to the query posed at block 1158, then as represented at line 1162 and block 1164 the patient is positioned on the treatment support 1120 so that the earlier located marker or outline on the surface of the patient is visible for the next step in the procedure. That step provides for locating the ACF heating coil or microwave antenna as well as the magnetometer probe 1124 at the proper locations with respect to the skin of the patient. The procedure then continues as represented at line 1166 and block 1168 wherein, guided by the marker at the skin surface of the patient, the heating coil 98" or microwave antenna is positioned as close as practical with respect to the skin of the patient to the sensor/heater implant(s). The method then continues as represented at line 1170 extending to block 1172 providing for turning on control console 112" by actuating switch 180" to, in turn, illuminate green LED 182". Then, as represented by line 1174 and block 1176, the operator selects the duty cycles. It may be recalled that duty cycle ranges, $\delta t_1$ and $\delta t_2$ are set forth in Table 1. As described in conjunction with FIG. 49, duty cycle election is undertaken with switch function 184". Next, as represented by line 1178 and block 1180 the procedure evaluates the status of the magnetometer. In this regard, the magnetometer is turned on and the system acquires its on and continuity status information. The program then continues as represented at line 1182 and block 1184 wherein a determination is made as to whether the status of the magnetometer 1122 is ok. In this regard, the peak-to-peak variation of the magnetometer output voltage, $V_{MO}$ is compared with a reference, $V_{FM}$. Where that condition obtains, then the enablement signal, $V_c$ is generated. This signal must be greater than or equal to, for example, three volts d.c. to be representative. In the event that the magnetometer status is not ok, then as represented at line 1186 and block 1188, an error condition is displayed at display 204" indicating that the magnetometer probe cable 1126 or the cable 114" to console 112" is not properly attached. Continuing the program, as represented at line 1190 and block 1192 a prompt is displayed to the operator to check the magnetometer cable attachments. The program then returns as represented at line 1194 to line 1178.

Where the query posed at block 1184 is responded to in the affirmative, then as represented at line 1196 and block 1198 green LED 212" at console 112" is illuminated and the program continues as represented at line 1200 and block 1202. At this juncture in the procedure, the operator will be positioning the magnetometer probe 1124 as close as practical to the implant(s) in order to obtain a maximum magnetometer signal channel differentiation.

The procedure continues as represented at line 1203 and block 1204 which provides for operator selection of both therapy duration commencing with the attainment of setpoint temperature, $T_{SP}$, and the maximum allotted time to attain that temperature, $T_{SP}$. Selection is carried out by actuation of switches 190" and 191" in conjunction with the readout provided at display 192". (FIG. 49).

The ACF heating assembly actuation next is addressed as represented at line 1205 and block 1206 providing that the ACF heating assembly 94" is turned on and, as represented at line 1208 and block 1210, a query is posed as to whether the ACF heating unit is enabled both by the development of a requisite voltage level, $V_{RF}$ as being greater than or equal to, for example, three volts and the presence of the earlier-described magnetometer signal $V_c$ as being greater than or equal to, for example, three volts. If those ANDed conditions are not met, then as represented at line 1212 and block 1214 an error visual cue is displayed at display 204" indicating that the control leads 102" are not properly connected to the control console 112". The program then continues as represented at line 1216 and block 1218 to display a prompt advising the operator to turn off the ACF heating unit and check the cable attachment 102" extending to the console 112". The program then reverts to line 1204 as represented at line 1220.

Where the query posed at block 1210 results in an affirmative determination, then as represented at line 1222 and block 1224, green LED 211'" is illuminated and the program continues as represented at line 1226. Line 1226 extends to the query posed at block 1228 determining whether the duration for therapy and maximum time to achieve setpoint temperature have been set to correct and intended values. The times are set by the operator employing the up/down switches 190" in conjunction with election switch 191" and display 192" on console 112". It may be recalled that for such activities as the temperature controlled dispersion of release agents (see FIGS. 40, 41), one or more levels of predetermined Curie transition temperatures may be utilized in conjunction with a corresponding sequence of sensor component containing implants. In the latter aspect, such therapy may involve maintenance of the quantum of thermal energy below critical curves as at 24 described in connection with FIG. 3. Where the therapy duration is incorrect, then as represented at line 1230 and block 1232 appropriate adjustment of the control switches 190" and 191" is made and the program reverts to line 1226 as represented at line 1234.

Where the query posed at block 1228 is responded to in the affirmative, then as represented at line 1236 and block 1238 a determination is made as to whether the therapy time elapsed indicates zero minutes. This readout is provided at console 112" at display 222". In the event that this display does not register zero minutes, then as represented at line 1240 and block 1242, reset button switch 224" is actuated and the program continues as represented at lines 1244 and 1236. With the therapy time elapsed set at zero, the procedure continues as represented at line 1246 and block 1248. Block 1248 reflects the activity of controller 240 (FIG. 8B) in carrying out a determination that the conditions established by the illumination of LEDs 211"–212" at console 112" have been satisfied and the system now is ready to commence a thermal therapy mode. In the event the ready check fails, then as represented at line 1250 and block 1252 an error cue is published at display 204" and, as represented at line 1254 and node A the program reverts to line 1178 to again consider the ready checks. In this regard node A and line 1254 reappears adjacent line 1178.

In the event the query posed at block 1248 results in an affirmative determination, then as represented at line 1256 and block 1258 thermotherapy which may comprise hyperthermia therapy commences with the operator actuation of the start therapy button switch 220" at console 112". With this actuation, as represented at line 1260 and block 1262, the green LED 213" indicating that therapy is in progress at console 112" is illuminated and the procedure continues as represented at line 1264 to the query at block 1266. Therapy being underway, the program determines whether or not the stop therapy button switch 226" at console 112" has been actuated. In the event that such an actuation occurred, then as represented at line 1267 and block 1268, the AC Field heating assembly is turned off. As a visual cue that the therapy is stopped, red LED 228" is illuminated and, correspondingly, green LED 213" is de-energized. The procedure then continues as represented at line 1269 and block 1270 wherein the operator determines whether or not the therapy mode is to be resumed. In the event that it is to be so resumed, then as represented at line 1271 and block 1272, in order to resume the therapy mode for the duration of the unlapsed therapy, the start therapy switch 220" is actuated at control console 112" which, in turn, causes the turning off of red LED 228". This automatically activates the ACF heating assembly 94". The program then continues as represented at line 1273 which extends to line 1260.

Where the query posed at block 1270 results in a determination that therapy is not to be resumed, then as represented at line 1274 and node 1275 the therapy is ended.

Returning to block 1266, where a determination has been made that the stop therapy switch 226" has not been actuated, then as represented at line 1276 and block 1277, a determination is made as to whether the target or setpoint temperature, $T_{SP}$, has been reached. This target temperature has been discussed in conjunction with dashed line 142 in connection with FIG. 7. Refer additionally to the ranges provided in conjunction with $T_{heater}$ set forth in Table 1. When the target or setpoint temperature has been reached, then as represented at line 1278 and block 1280, the program determines whether the maximum time assigned for attaining setpoint temperature has been reached before the setpoint temperature has been attained. Where that conflict is not at hand, then as represented at line 1281 and block 1282, the therapy duration timeout is started or its earlier commencement is continued following the actuation of the start therapy button as discussed in connection with block 1272. The program then continues as represented at line 1284 to block 1285 providing for the illumination of the green LED 215" on console 112". The program continues as represented at line 1286. Where the target temperature has not been reached then, as represented at lines 1287 and 1286 the program continues to the query posed at block 1288. That query determines whether or not the therapy time elapsed as displayed at display 222" on console 112" has reached a therapy duration valuation. In the event that it has not, then as represented at line 1290 and block 1292 the time elapsed display 222" is updated and, as represented at line 1294 and node B the program reverts to line 1264. Node B reappears with line 1294 adjacent line 1264. Where the therapy time elapsed corresponds with the therapy duration time, then the program continues as represented at line 1298. Returning to block 1280, where the maximum time assigned for the system to reach setpoint temperature has elapsed prior to a setpoint temperature being reached, then as represented at line 1300 and block 1302, an error cue is displayed and the program continues as represented at lines 1304 and 1298. Line 1298 extends to block 1320 which provides for the deactivation of the active components of the system. In this regard, the ACF heating assembly 94" is deactivated as is the magnetometer assembly 1122. Therapy complete green LED 214" is illuminated and green LED 213" representing therapy in progress is de-energized. The program then continues as represented at line 1322 and block 1324 wherein pertinent data for the procedure parameters is recorded. It may be recalled that this data can be displayed at display 204" by the actuation of button switch 206". The procedure then continues as illustrated at line 1326 extending to node 1328 representing a therapy ended stage.

Figure 51:
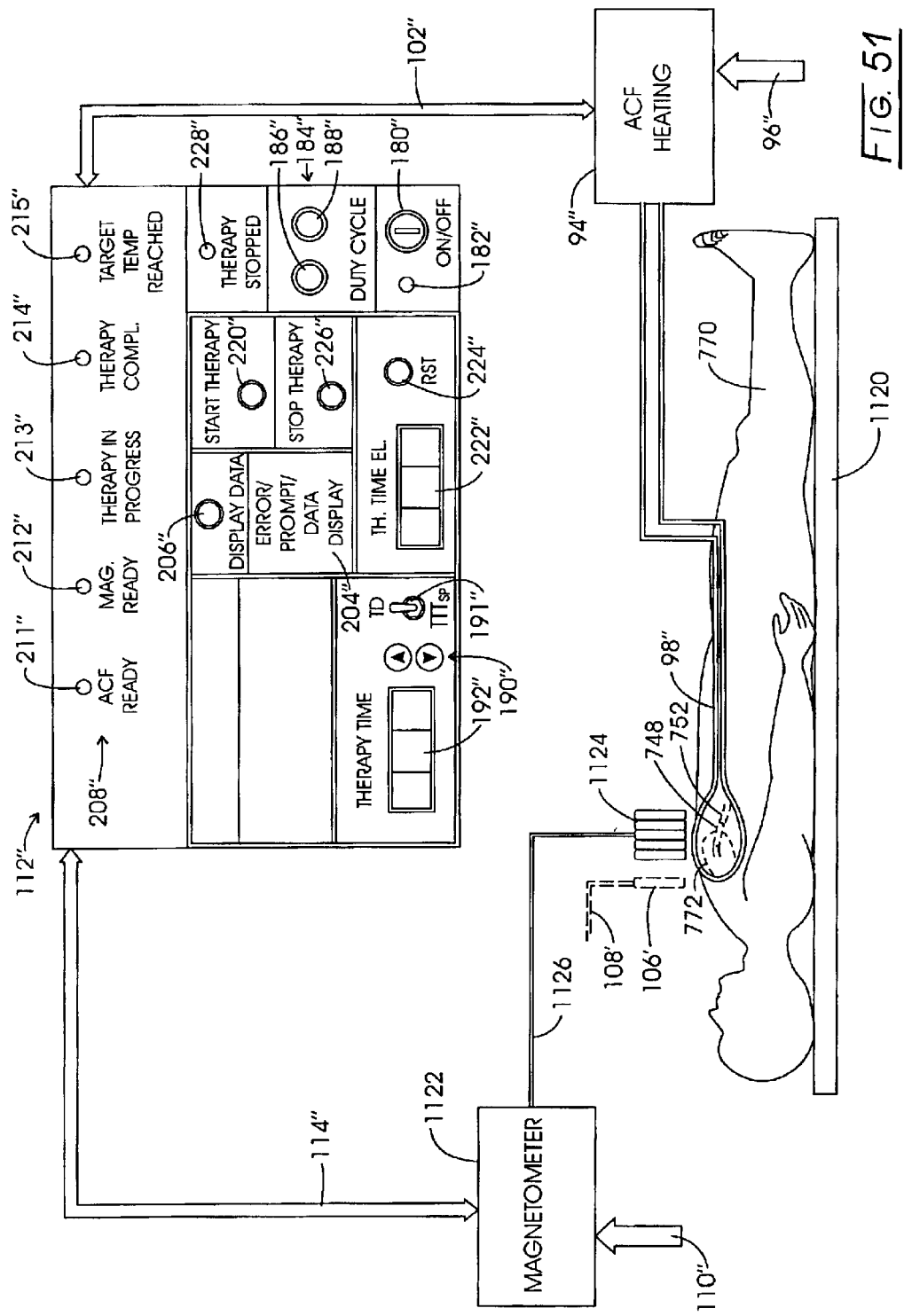
FIG. 51 is a diagram showing a system of the invention wherein the patient is held stationary and a stent is thermally treated utilizing a multichannel magnetometer with an array of pick-ups, the diagram further showing an alternative arrangement utilizing a single channel magnetometer and pick-up and relying upon relative movement of the sensor by virtue of adjacent heartbeat activity.

The utilization of an array of magnetometer pick-ups in the manner described in connection with FIG. 49 also finds applicability to the treatment of restenosis as discussed earlier in connection with FIG. 39 et seq. Referring to FIG. 51, patient 770 reappears from FIG. 39 being supported in a supinate position from stationary platform 1120 which reappears from FIG. 49. The heart of patient 770 is shown at 772 along with a coronary artery 752 incorporating a stent formed according to the invention at 748 (FIGS. 37–38). Control console 112" reappears from FIG. 49 as does the associated ACF heating assembly 94". Substantially focused heating is provided from the heating assembly 94" by a coil-implemented heating component represented at 98" which is positioned in close proximity to the skin of the patient 770 adjacent the stent 748. As before, the component 98" preferably is associated with an induction heating assemblage operating at a relatively lower frequency with respect to the generally identified radiofrequency range. Magnetometer 1122 in combination with cable 1126 and pick-up array 1124 reappear from FIG. 49. As described above in connection with FIG. 49, assembly 1122 is of a multichannel variety and performs in conjunction with a corresponding multichannel array or probe 1124, the channels of which are oriented for discerning and/or differentiating magnetic field flux lines as they may be affected by the sensors affixed to the stent 748. Array 1124 and associated multichannel magnetometer 1122 provide for the measurement of a two-dimensional pattern of magnet field strengths allowing the change in the field strength pattern to be detected as the ferromagnetic sensor(s) at the stent 748 changes from a magnetic to a non-magnetic state, a change which occurs over a narrow temperature range (FIG. 2) around the intrinsic Curie temperature of the ferromagnetic material selected. As before, it may be noted that the control assembly 112" does not incorporate the earlier-described table/chair control features, however, however, all the other features described in connection with FIGS. 5, 8A and 8B are retained. For the instant embodiment, the earth's magnetic field is employed in conjunction with the temperature sensing approach.

Figure 52A:
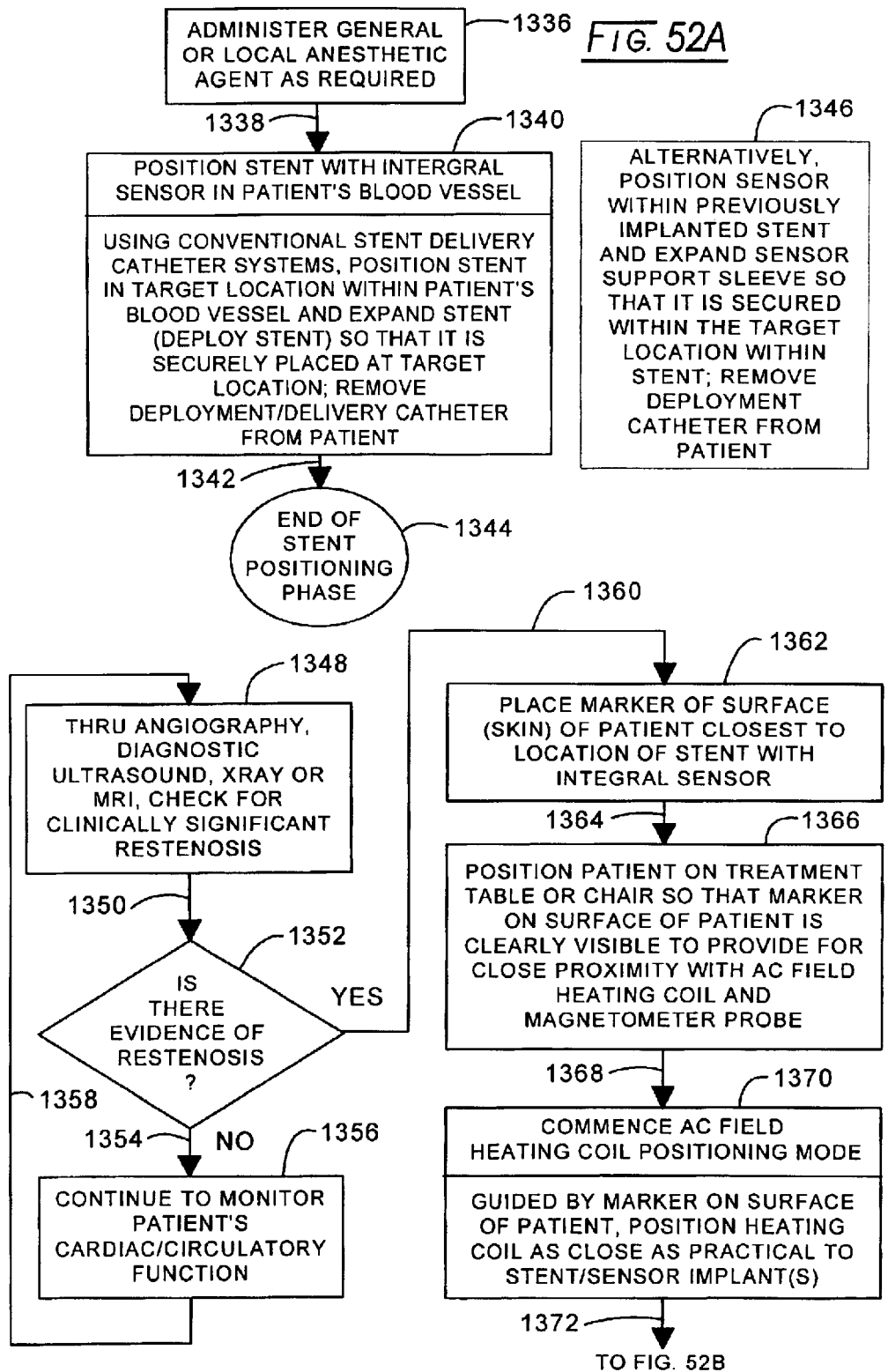

The discourse now turns to the procedure and control associated with the embodiments described in connection with FIG. 51 as well as FIGS. 37–38 and 40–47. Looking to FIG. 52A the initial phase of the procedure involves the positioning of a stent transluminally within the patient. That stent typically will be positioned as part of percutaneous transluminal coronary angioplasty (PTCA). For the instant method, the stent will incorporate an integral temperature sensing system and may further incorporate heat activatable drug components. The stent positioning phase involves the administration of a general or local anesthetic agent as indicated at block 1336. Then, as represented at line 1338 and block 1340 the stent with integral sensor is positioned within the patient's blood vessel at the targeted location, and, typically utilizing balloon procedures, the stent is deployed such that it is securely imbedded at the intima of the blood vessel. Then the delivery catheter is removed from the patient and, as represented at line 1342 and node 1344 the stent positioning phase will have ended. Subsequent to this implantation restenosis may arise within a time interval that may range from weeks to years.

As an alternate to the procedure thus far described, the secondary stent approach described in conjunction with FIGS. 44–47 may be carried out as represented at block 1346. With this procedure, a stent which has already been implanted is supplemented with temperature sensor components according to the invention by catheter placement and expansion within that preexisting stent.

Subsequent to the stent positioning phase the patient will be monitored for the occurrence of clinically significant restenosis. As represented at block 1348 such checks may be carried out, for instance, using angiography, diagnostic ultrasound, x-ray, or MRI techniques. The procedure then continues as represented at line 1350 and block 1352, where a query is presented as to whether or not evidence of restenosis is present. In the event that it is not, then as represented at line 1354, block 1356 and line 1358, such checks are continued, the patient's cardiac/circulatory function being monitored on a periodic basis. Where evidence of restenosis does exist, then as represented at line 1360 thermotherapy according to the invention is commenced. Looking to block 1362 a marker initially is placed on the skin of the patient at a location selected for aiding in the positioning of the magnetometer probe array 1124 and the inductive heater coil 98". As represented at line 1364 and block 1366, the patient is positioned on the stationary table or chair as at 1120 so that the skin located marker is clearly visible for the noted coil and probe orientation. Then, as represented at line 1368 and block 1370 the heating coil positioning mode is commenced. In this regard, using the marker at the surface of the patient, the heating coil 98" is located as close as practical to the location of the stent/sensor implant. Then, as indicated by line 1372 and block 1374, the operator turns on the control console 112" by actuation of on/off switch 180" which, in turn, will cause the illumination of green LED 182". Next, as represented at line 1376 and block 1378 the operator may select the duty cycles for activating the heater assembly and the magnetometer. While these intervals may be factory set, the operator may carry out selection by utilizing switch function 184". It may be recalled that duty cycle ranges $\delta t_1$ and $\delta t_2$ are set forth in Table 1.

Next, as represented by line 1380 and block 1382 the procedure evaluates the status of the magnetometer. In this regard, the magnetometer 1122 is turned on and the system acquires its on and continuity status information. The program then continues as represented at line 1384 and block 1386 wherein a determination is made as to whether the status of the magnetometer 1122 is ok. In this regard, the peak-to-peak variation of the magnetometer output voltage is compared with a reference, $V_{FM}$. Where that condition obtains, then the enablement signal, $V_c$ is generated. This signal must be greater than or equal to, for example, three volts d.c. to be representative. In the event that the magnetometer status is not ok, then as represented at line 1388 and block 1390 an error condition is displayed at display 204" indicating that the magnetometer probe cable 1126 or the cable 114" to console 112" is not properly attached. The program then continues as represented at line 1392 and block 1394 to display a prompt to the operator to check the magnetometer cable attachments. The program then returns as represented at line 1396 to line 1380.

Where the query posed at block 1386 is responded to in the affirmative, then as represented at line 1398 and block 1400 green LED 212" at console 112" is illuminated and the program continues as represented at line 1402 and block 1404. At this juncture in the procedure, the operator will be positioning the magnetometer array-type probe 1124 as close as practical to the stent 748 in order to obtain a maximum magnetometer signal channel differentiation.

The procedure continues as represented at line 1406 and block 1407 which provides for operator selection of both therapy duration commencing with the attainment of set-point temperature, $T_{SP}$, and the maximum time allotted to attain that temperature. Selection is carried out by actuation of switches 190" and 191" in conjunction with the readout provided at display 192" (FIG. 51).

The ACF heating assembly 94" actuation next is addressed as represented at line 1408 and block 1409. Upon turning on the heating unit, as represented at line 1410 and block 1412 a query is posed as to whether the ACF heating unit is enabled both by the development of a requisite voltage level, $V_{RF}$ as being greater than or equal to, for example, three volts and the presence of the earlier-described magnetometer signal $V_c$ as being greater than or equal to, for example, three volts. If those ANDed conditions are not met, then as represented at line 1414 and block 1416 an error visual cue is displayed at display 204" indicating that the control leads 102" are not properly connected to the control console 112". The program then continues as represented at line 1418 and block 1420 to display a prompt advising the operator to turn off the ACF heating unit and check the cable attachment 102" extending to the console 112". The program then reverts to line 1408 as represented at line 1422.

Where the query posed at block 1412 results in an affirmative determination, then as represented at line 1424 and block 1426, green LED 211" is illuminated and the program continues as represented at line 1428. Line 1428 extends to the query posed at block 1430 determining whether the duration for therapy and the maximum time to achieve setpoint temperature have been set to correct and intended values. These times are set by the operator employing the up/down switches 190" and election switch 191" in conjunction with display 192" on console 112". It may be recalled that for such activities as the temperature controlled heating dispersion of chemotherapeutic and the like release agents as discussed in connection with FIGS. 40 and 41, one or more levels of predetermined Curie transition temperatures may be utilized in conjunction with a corresponding sequence of stent containing sensor components. Where the therapy duration is incorrect, then as represented at line 1432 and block 1434 appropriate adjustment of the control and election switches 190" and 191" is made and the program reverts to line 1428 as represented at line 1436.

Figure 52B:
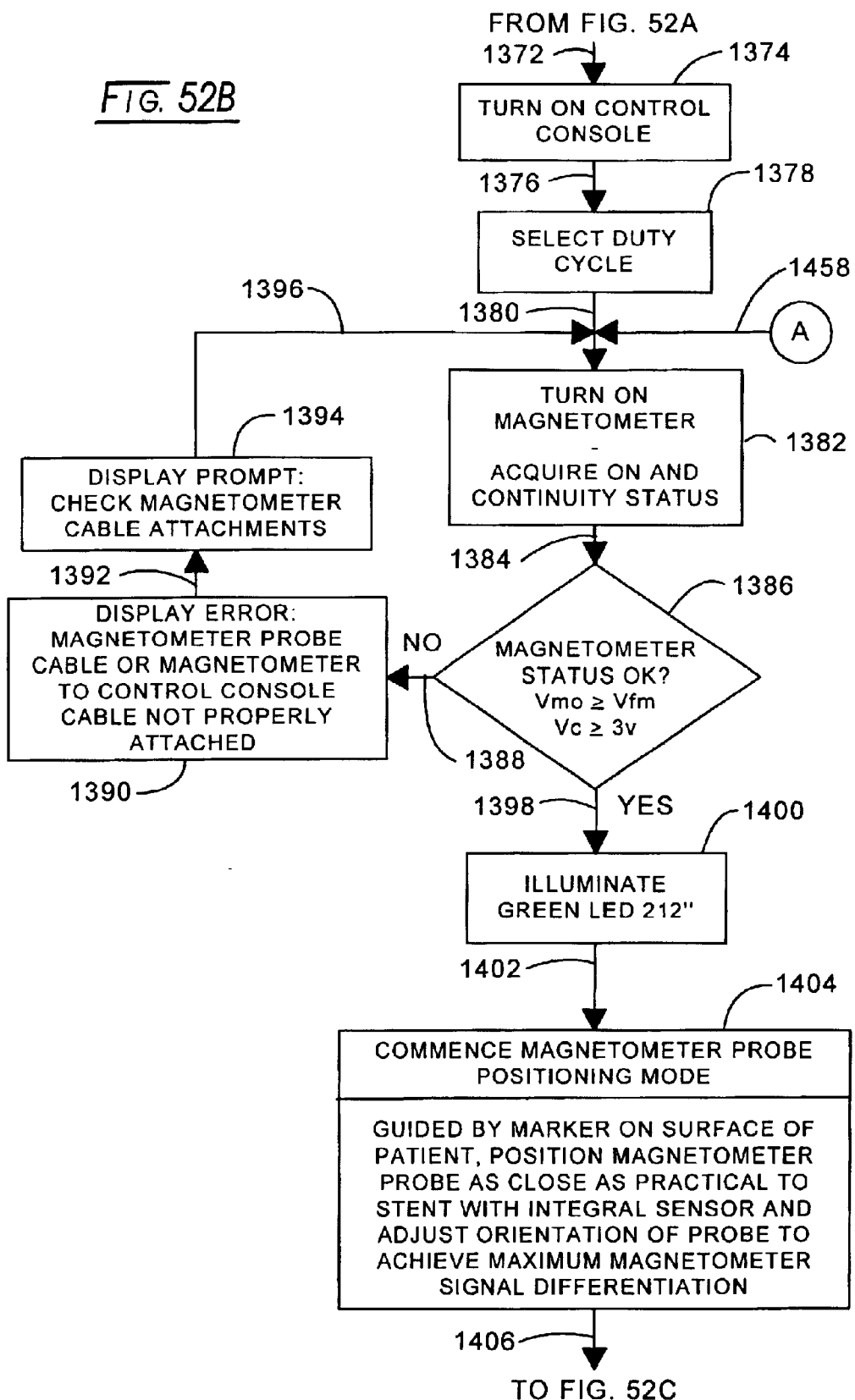
Figure 52C:
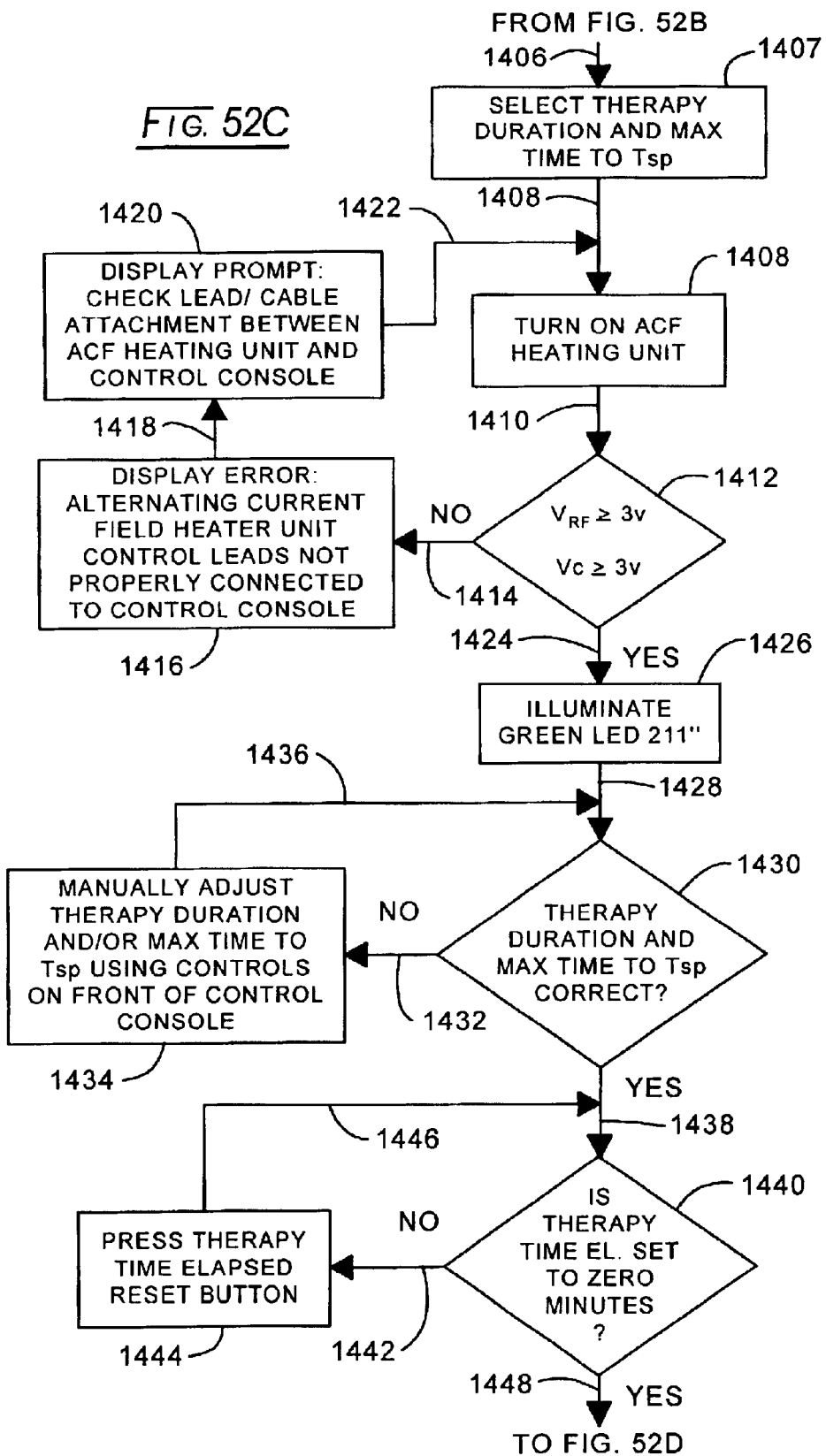

When the query posed at block 1430 is responded to in the affirmative, then as represented at line 1438 and block 1440 a determination is made as to whether the therapy time elapsed indicates zero minutes. This readout is provided at console 112" at display 222". In the event that this display does not register zero minutes, then as represented at line 1442 and block 1444, reset button switch 224" is actuated and the program continues as represented at lines 1446 and 1438. With the therapy time elapsed set at zero, the procedure continues as represented at line 1448 and block 1450. Block 1450 reflects the activity of controller 240 (FIGS. 8A–8B) in carrying out a determination that the conditions established by the illumination of LEDs 211"–212" at console 112" have been satisfied and the system now is ready to commence a thermotherapy mode. In the event the ready check fails, then as represented at line 1452 and block 1454 an error cue is published at display 204" and the program reverts as represented at line 1456 and node, A. Node A reappears in FIG. 52B in conjunction with line 1458 extending to line 1380. Accordingly, the program is reentered to again consider the ready checks.

In the event the query posed at block 1450 results in an affirmative determination, then as represented at line 1460 and block 1462 thermotherapy which may comprise hyperthermia therapy commences with the operator actuation of the start therapy button switch 220" at console 112". With this actuation, as represented at line 1464 and block 1466 the green LED 213" is energized indicating that therapy is in progress and the procedure continues as represented at line 1468 to the query at block 1470. Therapy being underway, the program determines whether or not the stop therapy button switch 226" at console 112" has been actuated. In the event that such an actuation occurred, then as represented at line 1471 and block 1472, the AC field heating assembly is turned off. As a visual cue that the therapy is stopped, red LED 228" is illuminated and, correspondingly, green LED 213" is de-energized. The procedure then continues as represented at line 1473 and block 1474 wherein the operator determines whether or not the therapy mode is to be resumed. In the event it is to be so resumed, then as represented at line 1475 and at block 1476 therapy is resumed for the remaining duration of unlapsed therapy or maximum time allotted to reach setpoint temperature, $T_{SP}$, by actuating the start therapy switch 220" at control console 112". This actuation, in turn, causes the turning off of red LED 228" and automatically activates the AC field heating assembly 94". The program then continues as represented at line 1477 which extends to line 1464.

Where the query posed at block 1474 results in a determination that therapy is not to be resumed, then as represented at line 1478 and node 1479 the therapy is ended.

Returning to block 1470, where a determination has been made that the stop therapy switch 226" has not been actuated, then as represented at line 1480 and block 1481, a determination is made as to whether the target or setpoint temperature $T_{SP}$ has been reached. This target temperature has been discussed in conjunction with dashed line 142 in connection with FIG. 7. Refer additionally to the ranges provided in conjunction with $T_{stent}$ set forth in Table 1. When the target or setpoint temperature has been reached, then as represented at line 1482 and block 1484, a query is made as to whether the maximum time allocated to reaching setpoint temperature $T_{SP}$ has elapsed before that setpoint temperature has been reached. In the event of a negative determination, then as represented at line 1486 and block 1488, the program starts or commences continuation of the therapy duration. In this regard, therapy at setpoint temperature may have been underway within a proper time format before the actuation of the stop therapy switch as discussed in connection with block 1470. On the other hand, the target temperature having been reached, the therapy duration as elected by the operator may commence at this point. The program then continues as represented at line 1490 and block 1492 which provides for the illumination of green LED 215" representing target temperature having been reached and the program continues as represented at line 1494. When the target temperature has not been reached, then as represented at lines 1496 and 1494, the program proceeds to query at block 1498. That query determines whether or not the therapy time elapsed as displayed at display 222" on console 112" has reached a therapy duration valuation. In the event that it has not, then as represented at line 1500 and block 1502 the time elapsed display 222" is updated and, as represented at line 1504 and node B the program reverts to line 1468. Node B and line 1504 reappear adjacent line 1468. Where the query posed at block 1498 is answered in the affirmative, then as represented at line 1506 and block 1522 the system enters a mode deactivating the active components of the system. In this regard, the ACF heating assembly 94" is deactivated as is the magnetometer assembly 1122. Therapy complete green LED 214" is illuminated and green LED 213" representing therapy in progress is de-energized.

Where the query posed at block 1484 results in an affirmative determination that the allocated maximum time to reach setpoint has elapsed before that setpoint has actually been reached, then an error condition is at hand and is represented at line 1508 and block 1510, an error condition is displayed at display 204" and the program continues as represented at lines 1512 and 1506 to the shutdown procedures as above described at block 1522. The program continues as represented at line 1524 and block 1526 wherein pertinent data for the procedure parameters is recorded. It may be recalled that this data can be displayed at display 204" by actuation of button switch 206". The procedure then continues as illustrated at line 1528 extending to node 1530 representing a therapy ended stage.

Returning to FIG. 51, another embodiment of the instant invention which involves a stationary patient may be carried out through the utilization of a moving sensor component. In particular, where the stent 748 is within a coronary artery adjacent to the heart 772 the stent and its associated temperature sensor will be caused to move by virtue of the beating of heart 772. Accordingly, the magnetometer assembly and probe described respectively at 104' and 106' in connection with FIG. 39 may be utilized as illustrated in phantom. A single channel magnetometer as described at 94' may be employed in this arrangement of a stationary patient and moving stent/sensor combination.

Figure 53:
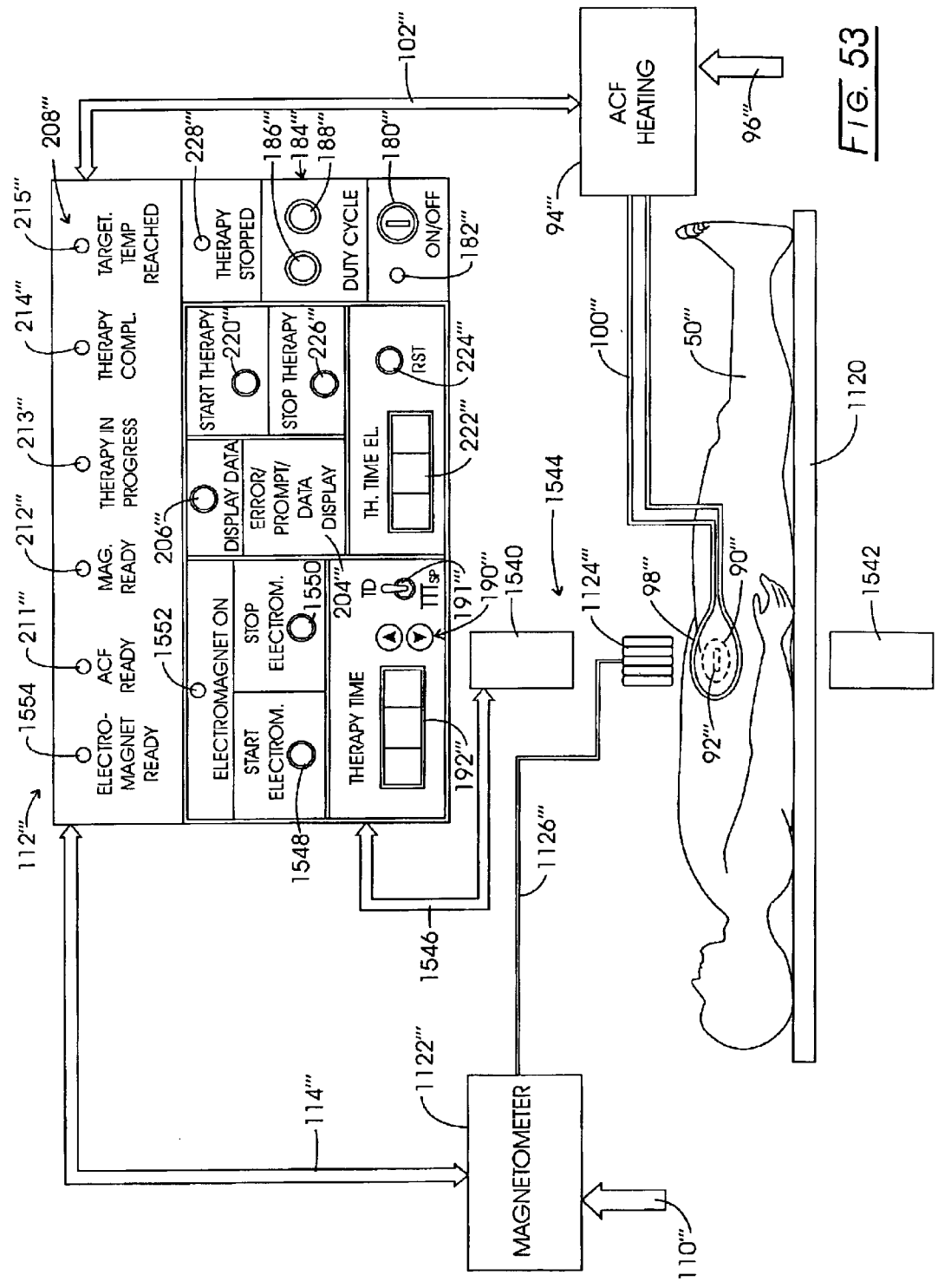
FIG. 53 is a schematic diagram of a system according to the invention wherein the patient remains stationary while a multichannel magnetometer evaluates an implant in combination with an electromagnetically generated magnetic field.

The system and method thus far presented has utilized the earth's magnetic field in conjunction with the temperature sensors and magnetometer instrumentation. However, the magnetic field may be applied utilizing an electromagnet. FIGS. 53 through 55 illustrate this approach. In FIG. 53, a multichannel magnetometer arrangement with a pick-up array and a stationary patient support is employed in the manner described in connection with FIG. 49. Accordingly, the component identifying numeration is imported from that figure but in triple primed fashion. However, disposed about the implant region of interest 90''' are electromagnet poles 1540 and 1542 of an electromagnet assembly represented generally at 1544. Control over the electromagnet 1544 is represented by the dual arrow 1546 extending to the control console 112'''. Console 112''' incorporates all of the components described in connection with console 112" shown in FIG. 51. However, the console may be observed to incorporate a start electromagnet button switch 1548 and a corresponding stop electromagnet switch 1550. When the electromagnet 1544 is in an energized or on state, a green LED 1552 is illuminated. Additionally within the LED array 208''' there is interposed a green electromagnet ready LED 1554.

Figure 54A:
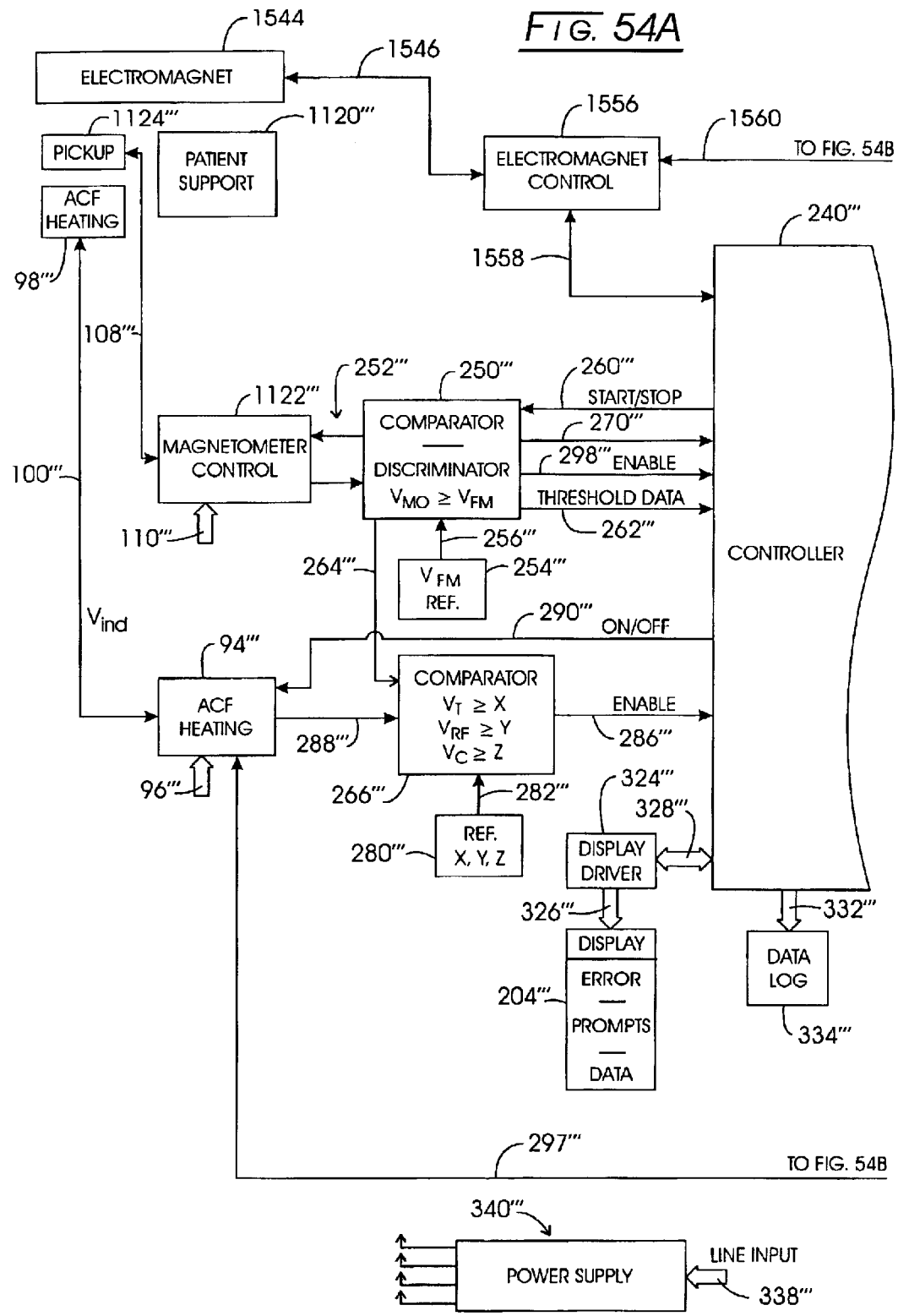
Figure 55A:
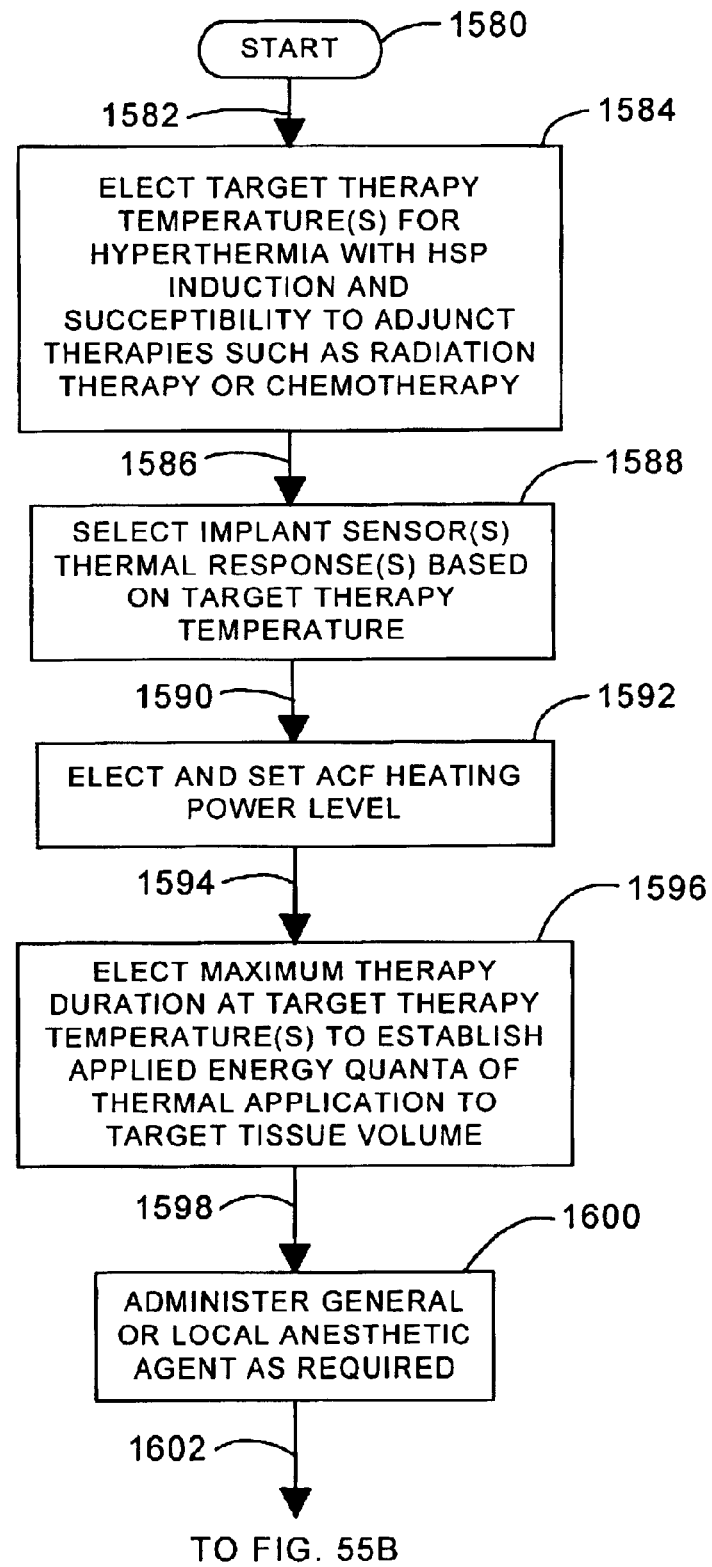
Figure 55C:
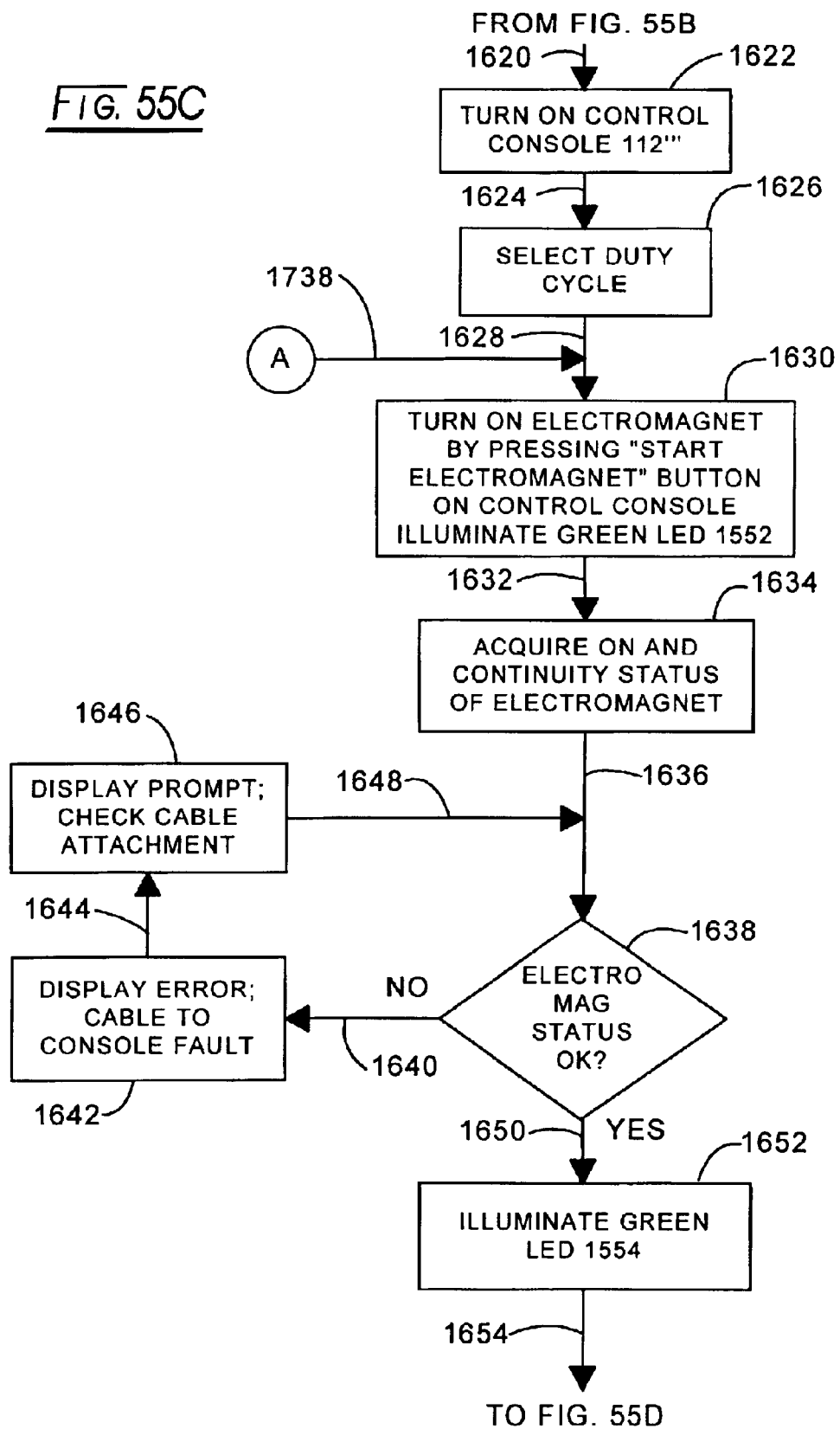
Figure 55D:
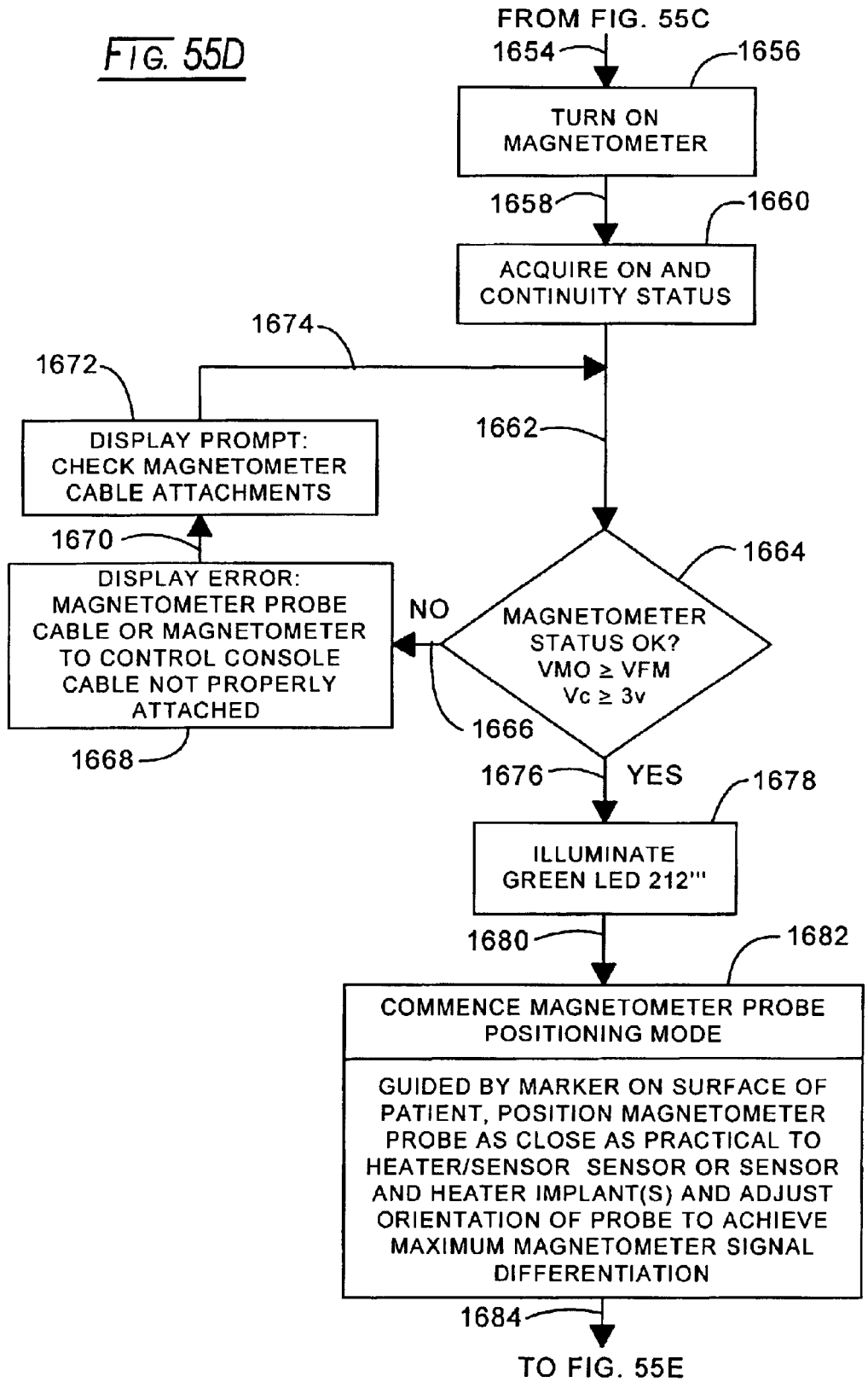
Figure 55E:
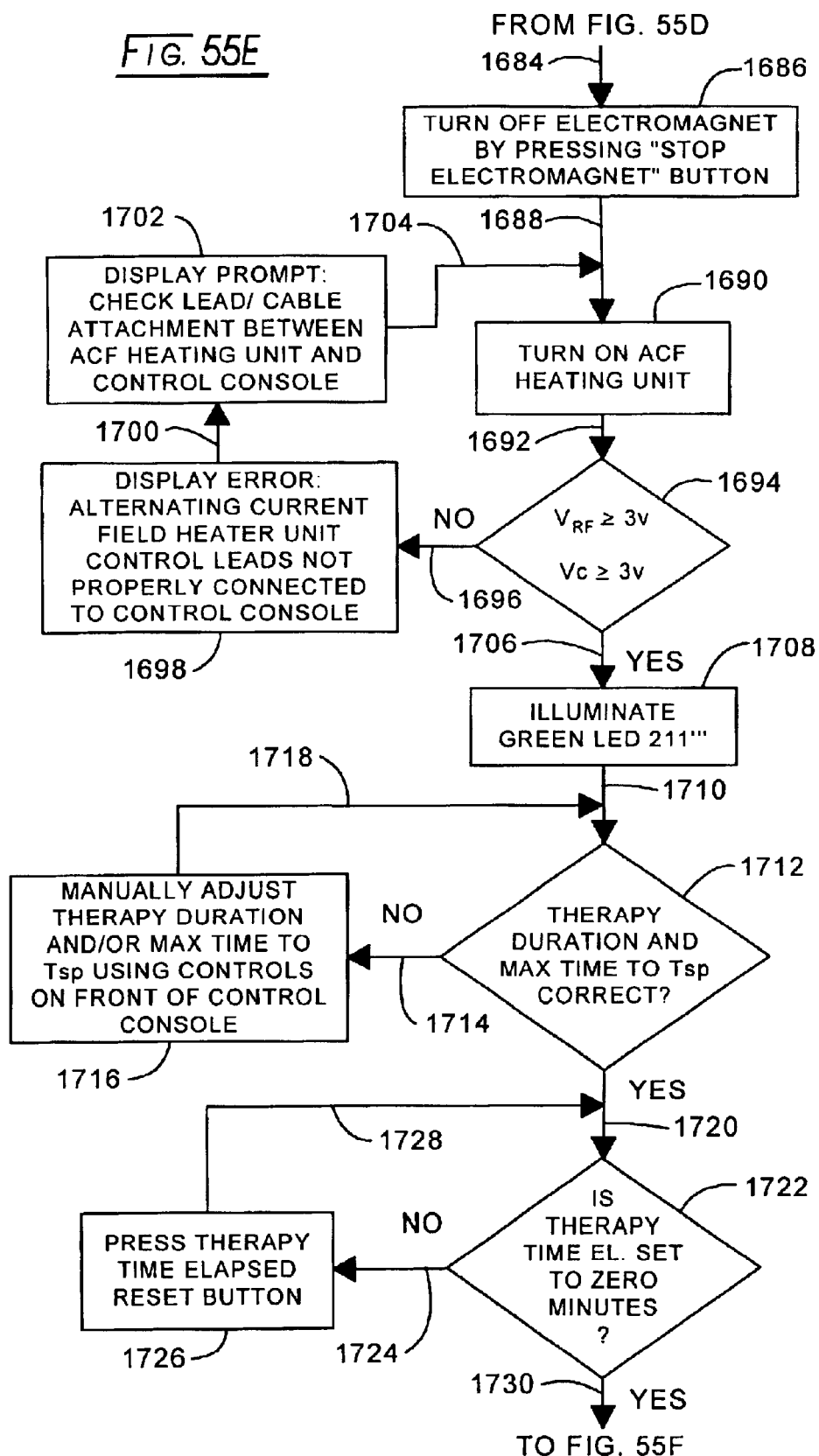
Figure 55G:
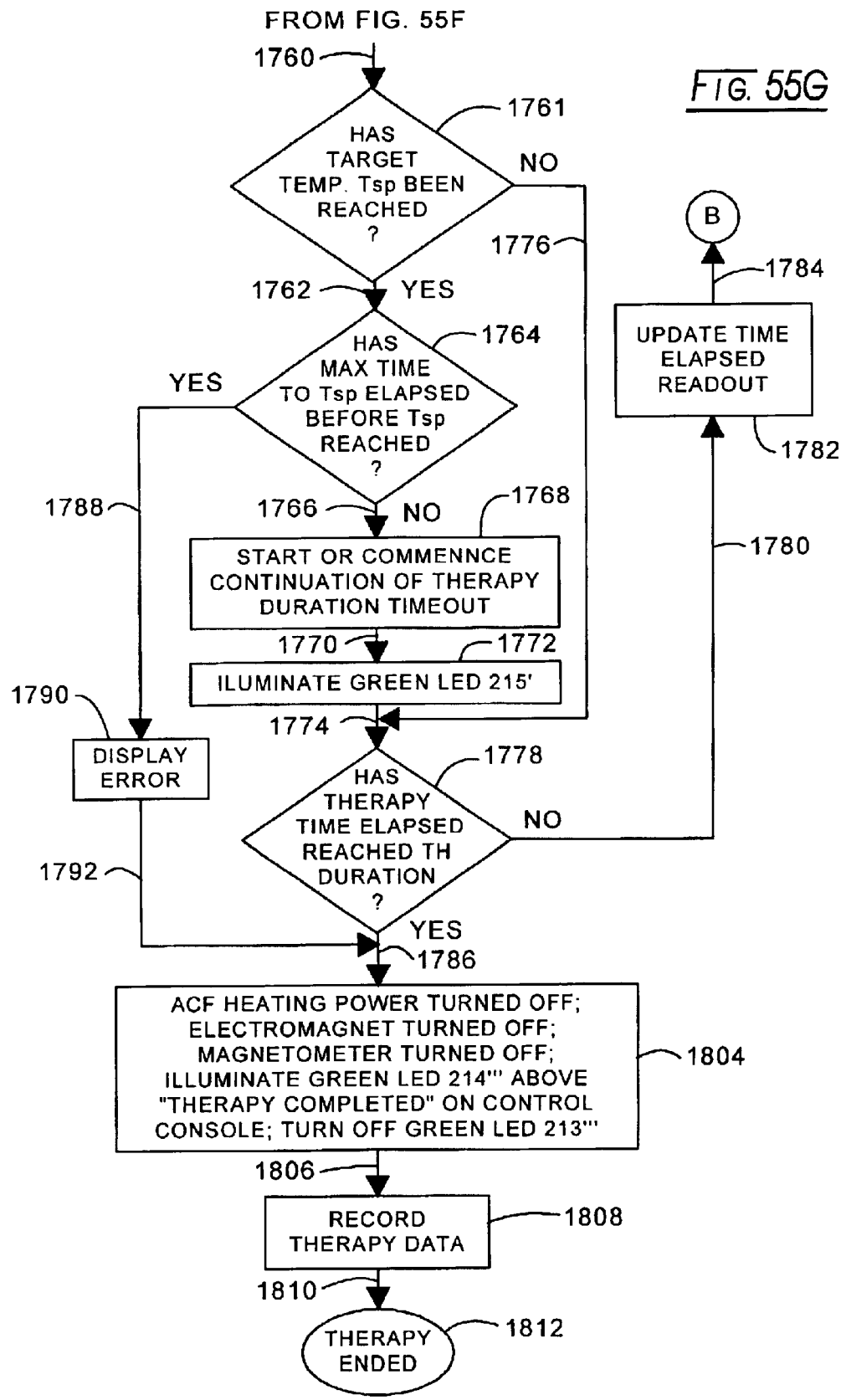

Looking to FIGS. 54A and 54B which should be considered in accordance with the labeling thereon, the components earlier-described in conjunction with FIGS. 8A and 8B are reproduced but in triple primed fashion. The figure differs from FIGS. 8A and 8B in that the motor control and patient support drive functions along with associated cueing and switching are removed and the electromagnet 1544 is now represented in block form with that same identifying numeration. In FIG. 54A the electromagnet 1544 is shown interactively controlled as represented at arrow 1546 by an electromagnet control network represented at block 1556. Block 1556 is shown interactively controlled from the controller 240''' as represented by arrow 1558. Control 1556 receives stop and start commands as represented at arrows 1560 and 1562 extending to corresponding switch blocks 1550 and 1548. FIG. 54B further reveals "EM ready" LED 1554 being coupled for energization from controller 240''' as represented at arrow 1564. Similarly, the "EM on" LED 1552 is programably energized from controller 240''' as represented at arrow 1566.

Referring to FIGS. 55A–55G, a block diagrammatic representation of the control and procedure is set forth for the embodiment employing a magnetic field generated by an electromagnet. The procedure commences in connection with FIG. 55A at node 1580 and line 1582 leading to the determinations at block 1594. Those determinations provide for the election of target therapy temperature (s), for instance, for hyperthermia with heat shock protein (HSP) induction. Additionally, the thermotherapy may be selected for combination with such adjunct therapies as radiation therapy and/or chemotherapy by release agent dispersion by heat activation. The procedure then continues as represented at line 1586 and block 1588 providing for the user selection of implant sensor (s) thermal responses based upon the elected target therapy setpoint temperature or temperatures. With temperature elections having been made and sensor component/heater component configurations determined, then as represented at line 1590 and block 1592 the power level for the ACF heating assembly 94''' is selected and set by the user. For the induction of heat shock proteins, as represented at line 1594 and block 1596 the user may select a maximum therapy duration at elected target temperature or temperatures to establish energy quanta of thermal application to the target tissue volume. An election of such maximum values is made to avoid generation of temperatures or temperature in time conditions falling above the critical curve as at 24 described in connection with FIG. 3. The procedure then continues as represented at line 1598 and block 1600 providing for the administration of general or local anesthetic agent as required. Then, as represented at line 1602 and block 1604, using one or more of the above-discussed imaging techniques, the implant is inserted percutaneously or intraoperatively into or adjacent to the target tissue volume of the patient utilizing an implant device, for example, as discussed in connection with FIGS. 32 and 33. As in the earlier embodiments, the orientation of the implant may be considered, particularly where more than one is being employed. Additionally, as part of this procedure, the exterior of the patient's body is marked to indicate the closest location of the implant or implants so as to facilitate the positioning of the ACF heating coil or antenna as well as to orient the pick-up structure of the magnetometer.

Next, the method provides a confirmational procedure as represented at line 1606 and block 1608 wherein imaging and other such instrumentation are used for the purpose of ascertaining if the implants are in the proper location with respect to the target tissue. Should the implant positioning not be appropriate, then as represented at loop line 1610, the method reverts to the procedure described in connection with block 1604. Upon an affirmative determination with respect to the query posed at block 1608, then as represented at line 1612 and block 1614 the patient is positioned on the treatment support such as the table 1120 so that the earlier-located marker or outline on the surface of the patient is visible for the next step in the procedure. Next, as represented at line 1616 and block 1618 the heating coil positioning mode ensues wherein the ACF heating coil or antenna is located at a proper location with respect to the skin of the patient. The procedure then continues as represented at line 1620 and block 1622 providing for turning on the console 112''' (switch 180''' illuminating green LED 182'''). Then, as represented by line 1624 and block 1626, the operator selects the duty cycles. It may be recalled that duty cycle ranges $\delta t_1$ and $\delta t_2$ are set forth in Table 1. As described in conjunction with the FIG. 53, duty cycle election is undertaken with switch function 184'''. Next, as represented by line 1628 and block 1630 electromagnet 1544 is turned on by momentarily pressing the start electromagnetic button switch 1548 on console 112'''. This will cause the green LED 1552 to become illuminated. The procedure then continues as represented at line 1632 and block 1634 providing for acquiring the on and continuity status of the electromagnet 1540. This information is derived as described in conjunction with block 1556 and controller 240''' in FIG. 54A. With this information at hand, then as represented at line 1636 and block 1638 a determination is made as to whether the status of the electromagnet 1540 is ok. In the event that it is not, then as represented at line 1640 and block 1642 an error cue is displayed corresponding with a cable to console fault. Then, as represented at line 1644 and block 1646 a prompt is published at display 204''' advising the operator to check the cable 1546. The program then loops to line 1636 as represented at line 1648. In the event the query posed at block 1638 indicates that the electromagnet 1540 is ok, then as represented at line 1650 and block 1652, green LED 1554 on console 112''' is illuminated. Next as represented at line 1654 and block 1656 the magnetometer 1122''' is turned on and, as represented at line 1658 and block 1660, the system acquires the on and continuity status of the magnetometer. The program then continues as represented at line 1662 and block 1664 wherein a determination is made as to whether the status of the magnetometer 1122''. is ok. In this regard, the peak-to-peak variation of the magnetometer output voltage, $V_{MO}$ is compared with a reference, $V_{FM}$. Where that condition obtains, then the enablement signal $V_c$ is generated. This signal, for example, must be greater than or equal to three volts d.c. to be representative. In the event that the magnetometer status is not ok, then as represented at line 1666 and block 1668, an error condition is displayed at display 204''' indicating that the magnetometer probe cable 1126''' or the cable 114''' to console 112'' is not properly attached. The program then continues as represented at line 1670 and block 1672 to display a prompt to the operator to check the magnetometer cable attachments. The program then returns as represented at line 1674 to line 1662.

Where the query posed at block 1664 is responded to in the affirmative, then as represented at line 1676 and block 1678, green LED 212''' at console 112''' is illuminated and the program continues as represented at line 1680 and block 1682. At this juncture in the procedure, the operator will be positioning the magnetometer probe 1124''' as close as practical to the implant (s) in order to obtain a maximum magnetometer signal channel differentiation.

The ACF heating assembly actuation next is addressed as represented at line 1684 and block 1686 providing for turning off the electromagnet 1544 by actuating the stop button switch 1550 on console 112'''.

The ACF heating assembly actuation next is addressed as represented at line 1688 and block 1690 providing that the ACF heating assembly 94''' is turned on and, as represented at line 1692 and block 1694 a query is posed as to whether the ACF heating unit is enabled both by the development of a requisite voltage level, $V_{RF}$ as being greater than or equal to three volts and the presence of the earlier-described magnetometer signal $V_c$ as being greater than or equal to three volts. If those ANDed conditions are not met, then as represented at line 1696 and block 1698 an error visual cue is provided at display 204''' indicating that the control leads 102'41 are not properly connected to the control console 112'''. The program then continues as represented at line 1700 and block 1702 to display a prompt advising the operator to turn off the ACF heating unit and check the cable attachment 102''' extending to the console 112'''. The program then reverts to line 1688 as represented at line 1704.

Where the query posed at block 1694 results in an affirmative determination, then as represented at line 1706 and block 1708, green LED 211''' is illuminated and the program continues as represented at line 1710. Line 1710 extends to the query posed at block 1712 determining whether the duration for therapy and maximum time allotted for reading setpoint temperature $T_{SP}$ have been set to correct and intended intervals. These intervals are set by the operator employing the up/down switches 190''' and election switch 191''' in conjunction with display 192''' on console 112'''. Where the therapy duration is incorrect, then as represented at line 1714 and block 1716 appropriate adjustment of the control switches 190''' and 191''' is made and the program reverts to line 1710 as represented at line 1718.

Where the query posed at block 1712 is responded to in the affirmative, then as represented at line 1720 and block 1722 a determination is made as to whether the therapy time elapsed indicates zero minutes. This readout is provided at console 112''' at display 222'''. In the event that this display does not register zero minutes, then as represented at line 1724 and block 1726, reset button switch 224''' is actuated and the program continues as represented at lines 1728 and 1720. With the therapy time remaining set at zero, the procedure continues as represented at line 1730 and block 1732. Block 1732 reflects the activity of controller 240''' (FIGS. 54A, 54B) in carrying out a determination that the conditions established by the illumination of LEDs 1554, 211''' and 212''' at console 112''' have been satisfied and the system now is ready to commence a thermotherapy mode. In the event the ready check fails, then as represented at line 1734 and block 1736 an error cue is published at display 204''' and, as represented at line 1738 and node A the program reverts to line 1628. In the latter regard, node A and line 1738 reappear adjacent line 1628.

In the event the query posed at block 1732 results in an affirmative determination, then as represented at line 1740 and block 1742 thermotherapy, which generally will comprise hyperthermia therapy, commences with the operator actuation of the start therapy button switch 220''' at console 112'''. With this actuation, electromagnet 1544 automatically is restarted, ACF heater unit 96''' and the magnetometer 1122''' are activated. Such actuation of the switch 220''', will, as represented at line 1744 and block 1746 provide for the illumination of green LED 213''' indicating that therapy is in progress. The procedure then continues as represented at line 1748 to the query at block 1750 determining whether or not the stop therapy button switch 226''' at console 112''' has been actuated. In the event such actuation has occurred, then as represented at line 1751 and block 1752 the AC field heating power assembly is turned off; electromagnet 1544 is stopped; green LED 213''' is turned off and red LED 228''' is illuminated as a visual cue that the therapy has been stopped. The procedure then continues as represented at line 1753 and block 1754 at which juncture the operator determines whether or not therapy is to be resumed. In the event that it is to be so resumed, then as represented at line 1755 and block 1756, in order to resume the therapy mode for the duration of the unlapsed therapy, the start therapy switch 220''' is actuated at control console 112''' which, in turn, causes the turning off of red LED 228'''. The start therapy switch actuation automatically activates the ACF heating assembly 94''' as well as the automatic restarting of the electromagnet 1544. The program then continues as represented at line 1757 which extends to line 1744.

Where the query posed at block 1758 results in a determination that therapy is not to be resumed, then as represented at line 1758 and node 1759 the therapy is ended.

Returning to block 1750, where a determination has been made that the stop therapy switch 226" has not been actuated, then as represented at line 1760 and block 1761, a query is made as to whether the target setpoint temperature $T_{SP}$ has been reached. This target temperature has been discussed in conjunction with dashed line 142 in connection with FIG. 7. Refer additionally to the ranges provided in conjunction with $T_{heater}$ set forth in Table 1. When the target or setpoint temperature has been reached, then as represented at line 1762 and block 1764 a determination is made as to whether the maximum time allotted to reach the setpoint temperature $T_{SP}$ has elapsed before that setpoint temperature has been reached. In the event that is not the situation, then as represented at line 1766 and block 1768, the program starts or commences continuation of therapy duration. In this regard, inasmuch as target temperature has been reached, if this is the first time it has been reached, then the system starts such therapy duration. However, if the setpoint temperature had been earlier reached, then the therapy duration continues for its originally allotted interval. The program then continues as represented at lines 1770 and block 1772. Block 1772 provides for the illumination of green LED 215''' serving as an indication that target temperature has been reached. The program then continues as represented at line 1774 and block 1778 wherein a query is posed determining whether or not the therapy time elapsed has reached the selected therapy duration valuation. In the event that it has not, then as represented at line 1780 and block 1782 the time elapsed display 222''' is updated as represented at line 1784 and node B, the program reverts to line 1748. In the latter regard, it may be noted that node B and line 1784 appear in adjacency with line 1748.

Where the query posed at block 1778 results in an affirmative determination, then the program continues as represented at line 1786 and block 1804. Returning to block 1764, in the event that the maximum time allocated for reaching target temperature $T_{SP}$, has elapsed before the setpoint temperature has been reached, then an error condition obtains and is represented at line 1788 and block 1790 an error is displayed at display 204''' and the program continues as represented at lines 1792 and 1786 to block 1804. Block 1804 provides for the deactivation of the active components of the system. In this regard, the ACF heating power system is turned off; electromagnet 1544 is turned off; magnetometer 1122''' is turned off; therapy completed green LED 214''' is illuminated; and green LED 213''' representing therapy in progress is de-energized. The program then continues as represented at line 1806 and block 1808 wherein pertinent data for the procedure parameters is recorded. It may be recalled that this data can be displayed at display 204''' by the actuation of button switch 206'''. The procedure then continues as illustrated at line 1810 extending to node 1812 representing a therapy ended stage.

TABLE 1

| Parameter | Description | Minimum | Maximum | Preferred Minimum | Preferred Maximum | Units |
|---|---|---|---|---|---|---|
| $D_1$ | diameter of sensor (cylinder shaped) | 0.01 (0.25) | 0.50 (12.7) | 0.02 (0.51 mm) | 0.20 (5.1 mm) | inch (mm) |
| $D_2$ | diameter of sensor (cylinder shaped) | 0.01 (0.25) | 0.50 (12.7) | 0.02 (0.51 mm) | 0.20 (5.1 mm) | inch (mm) |
| $\Delta T_{heater}$ | heater temperature range around setpoint | 0.1 | 20 | 0.1 | 3 | degree C. |
| $\Delta T_{sensor}$ | sensor temperature range around setpoint | 0.1 | 10 | 0.1 | 3 | degree C. |
| $\delta T_1$ | tissue temperature range around setpoint | 0.1 | 8 | 0.1 | 3 | degree C. |
| $\delta T_{stent}$ | temperature range of stent around setpoint | 0.1 | 5 | 0.1 | 3 | degree C. |
| $\delta t_1$ | heater turn on period | 0.01 | 30 | 0.05 | 5 | seconds |
| $\delta t_2$ | heater turn off period (magnetometer sampling period) | 0.005 | 5 | 0.02 | 1 | seconds |
| $f_1$ | Frequency range | 10 K | 10 M | | | Hertz |
| $H_1$ | semicylindrical diameter of height of sensor | 0.005 (0.13) | 0.25 (6.4) | 0.010 (0.25) | 0.10 (2.5) | inch (mm) |
| $H_2$ | semicylindrical diameter of height of heater | 0.005 (0.13) | 0.25 (6.4) | 0.010 (0.25) | 0.10 (2.5) | inch (mm) |
| $L_1$ | legnth of Implantable heater/sensor | 0.05 (1.3) | 4.0 (1.02) | 0.10 (2.5) | 2.0 (51) | inch (mm) |
| $L_2$ | length of Implantable heater/sensor | 0.05 (1.3) | 4.0 (102) | 0.10 (2.5) | 2.0 (51) | inch (mm) |
| $L_3$ | length of Implantable heater/sensor | 0.05 (1.3) | 4.0 (102) | 0.10 (2.5) | 2.0 (51) | inch (mm) |
| $L_4$ | length of stent sensor | 0.06 (1.5) | 1.5 (38) | 0.1 (2.5) | 1 (25.4) | inch (mm) |
| $L_5$ | length of stent | 0.12 (3) | 3 (76) | 0.2 (5.1) | 2 (51) | inch (mm) |
| $L_6$ | length of stent sensor segment | 0.03 (.78) | 0.75 (19) | 0.05 (1.3) | 05 (12.7) | inch (mm) |
| $P_{stent}$ | Instantaneous heating power generated within stent | 0.05 | 20 | 0.1 | 10 | calories/second |
| $P_{heater}$ | Instantaneous heating power generated within heater | 0.05 | 20 | 0.1 | 10 | calories/second |
| $P_{tissue}$ | Instantaneous heating power generated within tissue | 0.2 | 100 | 0.4 | 25 | calories/second |
| $t_1$ | thickness of heater | 0.001 (0.025) | 0.20 (5.1) | 0.003 (0.075) | 0.10 (2.5) | inch (mm) |
| $t_2$ | thickness of biocompatible coating | 0.0001 (0.0025) | 0.05 (1.3) | 0.001 (0.025) | 0.03 (0.76) | inch (mm) |
| $t_3$ | thickness of thermally activatable drug release compound | 0.001 (0.025) | 0.20 (5.1) | 0.005 (0.13) | 0.10 (2.5) | inch (mm) |
| $t_4$ | thickness of end cap | 0.001 (0.025) | 0.20 (5.1) | 0.003 (0.075) | 0.10 (2.5) | inch (mm) |
| $t_5$ | thickness (diameter) of stent sensor | 0.01 (0.25) | 0.50 (12.7) | 0.03 (0.75) | 0.20 (5.1) | inch (mm) |
| $t_6$ | thickness of stent sensor support band | 0.0001 (0.0025) | 0.05 (1.3) | 0.001 (0.025) | 0.03 (0.76) | inch (mm) |
| $t_7$ | thickness of adhesive layer | 0.0001 (0.0025) | 0.03 (0.75) | 0.001 (0.025) | 0.015 (0.38) | inch (mm) |
| $t_8$ | thickness of thermally activatable drug release compound | 0.001 (0.025) | 0.20 (5.0) | 0.005 (0.13) | 0.10 (2.5) | inch (mm) |
| $T_{heater}$ | nominal hyperthermia therapy temperature for heater | 39 | 70 | 40 | 48 | degree C. |
| $T_{stent}$ | nominal hyperthermia therapy temperature for stent | 39 | 70 | 43 | 47 | degree C. |
| $T_{ID}$ | target tissue implant temperature range for infectious disease | | | 40 | 45 | degree C. |
| $T_{BONE}$ | target tissue implant temperature range for boney tissue repair | | | 39 | 41 | degree C. |
| $T_{DRS}$ | nominal release agent temperature | 39 | 85 | 41 | 50 | degree C. |

TABLE 1-continued

| Parameter | Description | Minimum | Maximum | Preferred Minimum | Preferred Maximum | Units |
|---|---|---|---|---|---|---|
| $TR_1$ | thermal resistance between heater and sensor | 5 | | | | degree C./watt |
| $TR_2$ | thickness of thermally activatable drug release compound | 0.5 | | | | degree C./watt |
| $TR_3$ | thermal resistance between stent and sensor | 5 | | | | degree C./watt |
| $TR_4$ | preferred thermal resistance between stent and sensor | 0.5 | | | | degree C./watt |
| $W_1$ | width of heater segment | 0.005 (0.13) | 0.25 (6.3) | 0.010 (0.25) | 0.10 (2.5) | inch (mm) |
| $W_2$ | distance between heater segments | 0.005 (0.13) | 0.25 (6.3) | 0.010 (0.25) | 0.10 (2.5) | inch (mm) |
| $W_3$ | exposed length of sensor | 0.05 (1.3) | 4.0 (102) | 0.10 (2.5) | 2.0 (51) | inch (mm) |
| $W_4$ | exposed length of sensor | 0.05 (1.3) | 4.0 (102) | 0.10 (2.5) | 2.0 (51) | inch (mm) |
| $W_5$ | width of heater coupling | 0.02 (0.51) | 0.5 (12.7) | 0.04 (1) | 0.2 (5.1) | inch (mm) |
| $W_6$ | width (or diameter) of stent sensor | 0.01 (0.25) | 0.50 (12.7) | 0.03 (0.75) | 0.20 (5.1) | inch (mm) |
| $W_7$ | gap between stent sensor segments | 0.005 (0.13) | 0.1 (2.5) | 0.01 (0.25) | 0.05 (1.3) | inch (mm) |

As is apparent, the sensor and/or sensor/heater component combination of the invention as combined with a magnetometer based temperature evaluation approach provides the highly desirable, untethered, in vivo thermal treatment of tissue. Such tissue may include bone matter, i.e., boney tissue. In this regard, the sensors may be attached to a bone repair implant or support component such as a rod, plate or screw allowing such an implant then to be raised to a controlled and slightly elevated temperature, for example, in a range of from about 39° C. to about 41° C. The heating can be accomplished by already existing approaches, such as by microwave radiation, or ultrasound. Such mild but targeted and accurately controlled temperature elevations serve to accelerate the rate of bone growth and/or fusion necessary to ultimate bone repair. The untethered nature of the sensors as discussed above, permits an essentially non-invasive repetition of these therapies.

In another embodiment of the invention, a sensor/heater component combination, allows controlled heating of the region directly surrounding a boney injury, wound or tumor site. In this regard, the sensor/heater component combination may be attached to a bone repair implant or support component or a number of sensor/heater component combinations could be placed adjacent to the area to be treated. The sensor/heater component combination allows an implant or the tissue adjacent to sensor/heater component to be heated, raised to a controlled and slightly elevated temperature, with the absolute temperature range depending on a number factors, including but not limited to, the initial body temperature, the duration of heating used, and the stage of healing of the boney tissue, and such additional factors as discussed previously herein.

Implantation of sensors and/or sensor/heater component combination minimizes the potential for infection present with tethered bone stimulation implants, which are susceptible to infection at the site of the tether. Nor does the tissue immediately adjacent to an injured bone need be exposed by invasive surgery. The minimally invasive implantation of the sensor/heater component allows the sensor/heater component combination to remain in place for an extended treatment period. The sensor/heater component combination can be placed such that the target tissue is directly heated.

Additional advantages of the sensor/heater component combination, whether used alone, or in conjunction with other heating mechanisms is the ability to readily determine the temperature of the target boney tissue, which cannot be easily done with existing untethered bone growth stimulators. Due to cytotoxic effects if the tissue is overheated, which could damage boney tissue, the ability to monitor the temperature of the target tissue allows therapy that maximizes the therapeutic benefit by maintaining the target tissue in the chosen therapy temperature range.

Hyperthermia can be used as a means for inducing immunity or for treating diseases caused by infectious agents. Particularly for chronic infections that are recalcitrant to treatment with drugs or other existing therapies, an infected individual's immune system could be activated by using hyperthermia to induce infected cells to present immunogenic peptides. In this regard, the sensor/heater component of the present invention could be implanted in tissue that harbors the pathogen. Heating of the tissue sufficient to induce heat shock, as previously described, would cause infected cells to present immunogenic peptides derived from the infectious agent, thus activating the immune system. Those tissues or organs with relatively high numbers of infected cells would be preferred targets for the hyperthermia. Examples of targets include, but are not limited to, the liver or spleen for *Mycobacterium tuberculosis* infections; lymph nodes for Human Immunodeficiency Virus infections; the liver for *Plasmodium* or hepatitis virus infections.

The present invention is superior to currently available methods for inducing immunity to infectious agents using HSPs because it offers more precise temperature control of the heat shock than whole organism hyperthermia; focuses the induction of the immune system on a subset of the peptides presented by whole organism hyperthermia; induces an immune response against the actual infectious agent present in the organism, rather than against a non-specific agent that exogenous purified vaccines would produce; and can be used to treat acute infection for which no effective therapy is available.

Since certain changes may be made in the above-described apparatus, method and system without departing from the scope of the invention herein involved, it is intended that all matter contained in the description thereof or shown in the accompanying drawings shall be interpreted as illustrative and not in a limiting sense.

What is claimed is:

1. A system for thermally treating a target tissue within the body of a patient, comprising:
   a tetherless implant located internally within said patient, positioned in thermally responsive relationship with said target tissue and having an extra body discernable response condition when at a predetermined target temperature level;
   a heating assembly actuable to apply alternating current field based heat-inducing energy to said target tissue to an extent effective to elevate the temperature of tissue toward said target temperature level and de-actuable to terminate said application of thermal energy;
   an implant monitor located externally of said body and responsive when enabled, to said tetherless implant response condition to provide a monitor condition corresponding with said response condition; and
   a control assembly responsive to said monitor conditions to actuate said heating assembly in a manner effective to attain said target temperature level.

2. The system of claim 1 in which:
   said implant transitions from an initial condition to said response condition when at said predetermined target temperature level; and
   said implant monitor is responsive, when enabled, to said tetherless implant response condition to provide monitor conditions corresponding with said initial and response conditions.

3. The system of claim 2 in which said control assembly is responsive to a said monitor condition corresponding with said implant initial condition to actuate said heating assembly and is responsive to a said monitor condition corresponding with said implant response condition to de-actuate said heating assembly.

4. The system of claim 3 in which said control assembly is responsive to said monitor conditions to maintain said implant at a temperature within a range about said target temperature extending from about 0.1° C. to about 10° C.

5. The system of claim 3 in which said control assembly is responsive to said monitor conditions to maintain said implant at a temperature within a range about said target temperature extending from about 0.1° C. to about 3° C.

6. The system of claim 3 in which:
   said target tissue is boney tissue; and
   said tetherless implant member predetermined target temperature level is within a range of about 39° C. to about 41° C.

7. The system of claim 3 in which;
   said tetherless implant comprises a ferromagnetic material exhibiting a Curie transition temperature substantially corresponding with said target temperature level;
   said implant monitor comprises a magnetometer having a first monitor condition in the presence of a magnetic field confrontation with said implant when said implant temperature is below said Curie transition temperature and having a second monitor condition when said implant is at a temperature corresponding with said Curie transition temperature.

8. The system of claim 7, in which said implant monitor has said first monitor condition in the presence of an earth's magnetic field confrontation with said implant member.

9. The system of claim 7 in which said implant monitor further comprises an electromagnet having first and second poles arranged with respect to said patient to apply a magnetic field across said implant.

10. The system of claim 7 in which said control assembly is responsive in the presence of said first monitor condition to actuate said heating assembly, and is responsive in the presence of said second monitor condition to de-actuate said heating assembly and to enable said implant monitor.

11. The system of claim 3 in which said control assembly is configured for partitioning, in time, the actuation of said heating assembly and said enablement of said implant monitor to avoid deleterious electromagnetic interference with said implant monitor.

12. The system of claim 7 in which:
   said control assembly is responsive to said first monitor condition to actuate said heating assembly for a first interval of time, is responsive at the termination of said first interval of time to de-actuate said heating assembly and to enable said implant monitor for a second interval of time less than said first interval of time, and is responsive at the termination of said second internal of time in the presence of said first monitor condition to actuate said heating assembly for said first interval of time.

13. The system of claim 12 in which:
   said first interval of time of actuating said heating assembly is within a range from about 0.01 second to about 30 seconds.

14. The system of claim 12 in which:
   said first interval of time of actuating said heating assembly is within a range from about 0.05 second to about 5 seconds.

15. The system of claim 12 in which:
   said second interval of time during which said implant monitor is enabled is from about 0.005 second to about 5 seconds.

16. The system of claim 12 in which:
   said second interval of time during which said implant monitor is enabled is from about 0.02 second to about 1 second.

17. The system of claim 12 in which said heating assembly is an inductive heating assembly actuable to apply inductively derived heat-inducing energy to said target tissue.

18. The system of claim 2 in which said tetherless implant member is configured for commencing said transition to said response condition when at a temperature level within about 0.1° C. to about 1.0° C. of said predetermined target temperature level.

19. The system of claim 18 in which said tetherless implant predetermined target temperature level is within a range of about 39° C. to about 70° C.

20. The system of claim 18, in which said tetherless implant predetermined target temperature level is within a range of about 40° C. to about 48° C.

21. The system of claim 18 in which said control assembly is responsive to said monitor conditions to maintain said heater implant at a temperature within a range about said target temperature extending from about 0.1° C. to about 10° C.

22. The system of claim 18 in which said control assembly is responsive to said monitor conditions to maintain said heater implant at a temperature within a range about said target temperature level extending from about 0.1° C. to about 3° C.

23. The system of claim 1 further comprising:
   a tetherless heater implant located internally within said patient in thermal exchange relationship with said target tissue and responsive to said heating assembly applied heat inducing energy to elevate the temperature of said target tissue in adjacency therewith toward said target temperature level.

24. The system of claim 23 in which said heater implant is formed of non-magnetic material.

25. The system of claim 2 in which:
said control assembly is responsive to said monitor condition corresponding with said implant initial condition to actuate said heating assembly for a first interval of time, is responsive at the termination of said first interval of time to de-actuate said heating assembly and to enable said implant monitor, and is responsive to defer dis-enablement of said implant monitor and associated actuation of said heating assembly in the presence of a said monitor condition corresponding with said response condition.

26. The system of claim 2 in which:
said control assembly is responsive to said monitor condition corresponding with said implant initial condition to actuate said heating assembly for a first interval of time, is responsive at the termination of said first interval of time to de-actuate said heating assembly and to enable said implant monitor for a second interval of time less than said first interval of time, and is responsive at the termination of said second interval of time in the presence of said monitor condition corresponding with said implant initial condition to actuate said heating assembly for said first interval of time.

27. The system of claim 26, in which:
said first interval of time of actuating said heating assembly is within a range from about 0.01 second to about 30 seconds.

28. The system of claim 26 in which:
said first interval of time of actuating said heating assembly is within a range from about 0.05 second to about 5 seconds.

29. The system of claim 26 in which:
said second interval of time during which said implant monitor is enabled is from about 0.005 second to about 5 seconds.

30. The system of claim 26 in which:
said second interval of time during which said implant monitor is enabled is from about 0.02 second to about 1 second.

31. The system of claim 1 in which said implant comprises:
a ferromagnetic component having a geometrically, volumetrically defined shape effective for untethered implantation within tissue, at least a portion of the surface of which is exposed to said target tissue and exhibiting a Curie transition temperature corresponding with said target temperature level; and
a heater component having a geometrically volumetrically defined shape effective for untethered implantation at said target tissue, formed of non-magnetic material and located in adjacency with said ferromagnetic component.

32. The system of claim 31 in which said implant monitor comprises a magnetometer having a first monitor condition in the presence of a magnetic field confrontation with said implant when said implant exhibits a temperature below said Curie transition temperature and having a second monitor condition when said implant member exhibits a temperature at said Curie temperature.

33. The system of claim 32 in which said control assembly is configured for partitioning, in time, the actuation of said heating assembly and said enablement of said implant monitor to avoid deleterious electromagnetic interference with said implant monitor.

34. The system of claim 2 in which:
said implant is ferromagnetic exhibiting a Curie transition temperature range corresponding with said target temperature level, said response condition being derived as a low value of relative magnetic permeability, and said initial condition being derived as a higher value of relative magnetic permeability at temperature below said Curie transition temperature range; and
said implant monitor is a magnetometer having a pick-up responsive to magnetic field perturbations positioned adjacent said patient at a location effective for determining said initial and response conditions to derive said monitor conditions.

35. The system of claim 34 further comprising:
an oscillatory support for said patient;
said magnetic field is the earth's magnetic field; and
said pick-up has a single channel and is stationary with respect to the movement of said oscillatory support.

36. The system of claim 34 in which said Curie transition temperature range is from about 0.1° C. to about 1° C.

37. The system of claim 34 in which said Curie transition temperature range is from about 0.1° C. to about 5° C.

38. The system of claim 34 further comprising:
an oscillatory support for said patient;
an electromagnet having poles positioned to establish a said magnetic field within a region interceptible by said implant; and
said pick-up has a single channel and is stationary with respect to the movement of said oscillatory support.

39. The system of claim 34 in which said magnetometer is of a multi-channel variety, said pick-up is a multi-channel array pick-up, and is stationary with respect to said patient.

40. The system of claim 39 further comprising an electromagnet having poles positioned to establish said magnetic field within a region interceptible by said implant.

41. The system of claim 34 in which said control assembly is responsive to a first said monitor condition corresponding with said implant initial condition higher values of relative magnetic permeability to actuate said heating assembly for a heating interval of time, is responsive at the end of said heating interval to de-actuate said heating assembly and enable said implant monitor for an interrogation interval of time less than said heating interval of time, and is responsive at the termination of said interrogation interval of time in the presence of said first monitor condition to actuate said heating assembly.

42. The system of claim 41 in which said heating interval is within a range of time of from about 0.01 second to about 30 seconds.

43. The system of claim 41 in which said heating interval is within a range of time of from about 0.05 second to about 5 seconds.

44. The system of claim 41 in which said interrogation interval is within a range of time of from about 0.005 second to about 5 seconds.

45. The system of claim 41 in which said interrogation interval is within a range of time of from about 0.05 second to about 5 seconds.

46. The system of claim 41 in which said control assembly is responsive to a second said monitor condition corresponding with said implant response condition lower value of relative magnetic permeability present during a given interrogation interval to defer actuation of said heating assembly and continue the enablement of said implant monitor until the occurrence of said first monitor condition.

47. An implant for employment in developing a setpoint related thermotherapy temperature at a target tissue, comprising:

an untethered ferromagnetic material sensor component dimensioned for minimally invasive implantation at said target tissue and configured for confronting the flux of a magnetic field extending along said target tissue, said sensor component having a relative magnetic permeability characteristic normally disturbing said magnetic field and exhibiting an abrupt drop in said relative permeability toward a unity value at a Curie transition occurring within a temperature range, $\Delta T_c$, about said setpoint temperature of about 0.1° C. to about 5.0° C., said abrupt drop effecting a termination of said magnetic field disturbance as a remotely discernable indication of the attainment of said setpoint temperature; and a non-magnetic heater component in heat exchange relationship with said sensor component and dimensioned with said sensor component for effecting said minimally invasive implantation at said target tissue.

48. The implant of claim 47 in which said sensor component is coupled in heat exchange relationship with said heater component to define a union therebetween exhibiting a thermal resistance of about 5° C./watt.

49. The implant of claim 47 in which said sensor component is coupled in heat exchange relationship with said heater component to define a union therebetween exhibiting a thermal resistance of about 0.5° C./watt.

50. The implant of claim 47 in which the tissue engagable surfaces of said sensor component and said heater component are coated with an electrically insulative biocompatible conformal layer.

51. An implant for employment in developing a setpoint related thermotherapy temperature at a target tissue, comprising:

an untethered ferromagnetic material sensor component dimensioned for minimally invasive implantation at said target tissue and configured for confronting the flux of a magnetic field extending along said target tissue, said sensor component having a relative magnetic permeability characteristic normally disturbing said magnetic field and exhibiting an abrupt drop in said relative permeability toward a unity value at a Curie transition occurring within a temperature range, $\Delta T_c$, about said setpoint temperature of about 0.1° C. to about 5.0° C. said abrupt drop effecting a termination of said magnetic field disturbance as a remotely discernable indication of the attainment of said setpoint temperature an expandable generally cylindrical non-magnetic support member having an outer surface generally extending along a control axis, having an insertion diameter of extent permitting its insertion within a non-magnetic stent when said stent is implanted within a blood vessel and formed of a biocompatible material agalvanic with respect to said stent;

said sensor component is fixed to said support member; and said support member being expandable along said insertion diameter when having been inserted within said stent to an extent effecting a fixed engagement therewith and effective when said stent is heated to derive a thermal exchange relationship therewith.

52. The implant of claim 51 in which said sensor component is coated with an electrically insulative biocompatible conformal layer.

53. The implant of claim 51 in which said sensor component is fixed to said support member outer surface.

54. The implant of claim 51 in which an assembly of at least two of said sensor components are fixed to said support member.

55. The implant of claim 53 further comprising a non-magnetic flexible band agalvanic with respect to said stent and surmounting said outer surface and said sensor component said band being expandable generally along said insertion diameter within said stent.

56. The implant of claim 51 in which at least a first assembly of two said sensor components are fixed to said support member in generally parallel alignment with said central axis in mutually spaced apart relationship.

57. The implant of claim 56 in which:

said first assembly of two sensor components is fixed to said support member outer surface; and further comprising a non-magnetic flexible band agalvanic with respect to said stent and surmounting said outer surface and said first two sensor components, said band being expendable generally along said insertion diameter within said stent.

58. The implant of claim 56 in which said first assembly of sensor components is coated with an electrically insulative biocompatible conformal layer.

59. The implant of claim 56 in which at least a second assembly of two said sensor components is fixed to said support member diametrically oppositely from said first assembly of two sensor components.

60. The implant of claim 59 in which:

said first and second assemblies of sensor components are fixed to said support member outer surface; and further comprising a non-magnetic flexible band agalvanic with respect to said stent and surmounting said outer surface and said first and second assemblies of two sensor components, said band being expandable generally along said insertion diameter within said stent.

61. The implant of claim 59 in which said first and second assemblies of sensor components are coated with an electrically insulative biocompatible conformal layer.

62. An implant for employment in developing a setpoint related thermotherapy temperature at a target tissue, comprising:

an untethered ferromagnetic material sensor component dimensioned for minimally invasive implantation at said target tissue and configured for confronting the flux of a magnetic field extending along said target tissue, said sensor component having a relative magnetic permeability characteristic normally disturbing said magnetic field and exhibiting an abrupt drop in said relative permeability toward a unity value at a Curie transition occurring within a temperature range, $\Delta T_c$, about said setpoint temperature of about 0.1° C. to about 5.0° C. said abrupt drop effecting a termination of said magnetic field disturbance as a remotely discernable indication of the attainment of said setpoint temperature; and a non-magnetic stent having a generally cylindrical configuration with an outer surface and central axis, expandable generally diametrically from an insertion diameter to luminally engage a blood vessel and formed of a material heatable from a remote, extra body applied alternating current field heating source; and said sensor component is coupled in intimate thermal exchange relationship with said stent.

63. The implant of claim 62 in which said sensor component is coated with an electrically insulative biocompatible conformal layer.

64. The implant of claim 62 in which said sensor component is fixed to said stent outer surface.

65. The implant of claim 64 further comprising:
a non-magnetic flexible band agalvanic with respect to said stent and surmounting said stent outer surface and said sensor, said band being generally diametrically expandable with said stent.

66. The implant of claim 64 further comprising:
a thermally activatable release agent layer supported by said stent and effective to disperse when said stent is at an induced temperature below or generally corresponding with said temperature range, $\Delta T_c$.

67. The implant of claim 62 in which said sensor component is coupled in intimate thermal relationship with said stent to define a union exhibiting a thermal resistance of about 5° C./watt.

68. The implant of claim 62 in which said sensor component is coupled in intimate thermal relationship with said stent to define a union exhibiting a thermal resistance of about 0.5° C./watt.

69. The implant of claim 62 which an assembly of at least two of said sensor components is coupled with said stent.

70. The implant of claim 62 in which at least a first assembly of two said sensor components are coupled with said stent in generally parallel alignment with said central axis in mutually spaced apart relationship.

71. The implant of claim 70 in which:
said first assembly of two sensor components are coupled with said stent outer surface; and
further comprising a non-magnetic flexible band agalvanic with respect to said stent and surmounting said stent outer surface and said first two sensor components.

72. The implant of claim 70 in which at least a second assembly of at least two said sensor components are coupled with said stent diametrically oppositely from said first assembly of two sensor components.

73. The implant of claim 72 in which:
said first and second assemblies of sensor components are fixed to said stent outer surface; and
further comprising a non-magnetic flexible band agalvanic with respect to said stent and surmounting said outer surface and said first and second assemblies of two sensor components, said band being expandable generally diametrically with said stent.

74. Stent apparatus for positioning within the body of a patient comprising:
a metal stent structure having a contact surface configured for abutting engagement with tissue of said patient and formed with material responsive to an alternating current field based energy applied externally of said body to elevate in temperature; and
an untethered temperature responsive component assembly fixed in thermal exchange relationship with said metal stent structure and having a response condition at a hyperthermia based temperature level which is discernable externally of said body.

75. The stent apparatus of claim 74 in which said temperature responsive component assembly is fixed to said metal stent structure contact surface.

76. The stent apparatus of claim 74 in which the thermal resistance between said stent structure and said temperature responsive component is less than about 5° C./watt.

77. The stent apparatus of claim 74 in which said untethered temperature responsive component is configured having a said response condition when at said temperature within a range of about 0.1° C. and about 1.0° C. from said hyperthermia based temperature.

78. The stent apparatus of claim 74 in which said metal stent structure is non-magnetic, and said untethered temperature responsive component is ferromagnetic, having a Curie temperature transition when at a temperature within about 0.1° C. and about 1.0° C. of said hyperthermia based temperature level.

79. The stent apparatus of claim 75 further comprising a flexible securement band agalvanic with respect to said metal stent structure and tensionally surmounting said metal stent structure and said temperature responsive component assembly.

80. The stent apparatus of claim 74 in which said temperature responsive component is coated with a biocompatible electrically insulative conformal layer.

81. The stent apparatus of claim 75 in which:
said metal stent structure is generally cylindrically shaped; and
said untethered temperature responsive component assembly comprises a first discrete temperature responsive component fixed to said contact surface, and a second discrete temperature responsive component fixed to said contact surface at a location generally diametrically opposite from the location of said first discrete temperature responsive component.

82. The stent apparatus of claim 81 including a flexible securement band tensionally surmounting said metal stent structure and said temperature responsive component assembly.

83. The stent apparatus of claim 74 further comprising a thermally activatable release agent coating extending over said metal stent structure, effective to limit restenosis when dispersed at said hyperthermia based temperature level.

84. An implant for employment in developing a thermotherapy setpoint temperature at a target tissue when disposed in thermal exchange relationship therewith, comprising:
an untethered temperature sensor component dimensioned for minimally invasive implantation at said target tissue and having an extra body discernable response condition when at said setpoint temperature; and
a non-magnetic heater component in heat exchange relationship with said sensor component and dimensioned with said sensor component for effecting said minimally invasive implantation at said target tissue.

85. The implant of claim 84 in which said sensor component is coupled in heat exchange relationship with said heater component to define a union therebetween exhibiting a thermal resistance of about 5° C./watt.

86. The implant of claim 84 in which said sensor component is coupled in heat exchange relationship with said heater component to define a union therebetween exhibiting a thermal resistance of about 0.5° C./watt.

87. A system for thermally treating a target tissue within the body of a patient, comprising:
a tetherless implant located internally within said patient, positioned in thermally responsive relationship with said target tissue and transitioning from an initial condition to an extra body discernable response condition when at a predetermined target temperature level;
a heating assembly actuable to apply alternating current field based heat-inducing energy to said target tissue to an extent effective to elevate the temperature of tissue toward said target temperature level and de-actuable to terminate said application of thermal energy;

an implant monitor located externally of said body and responsive when enabled, to said tetherless implant response condition to provide monitor conditions corresponding with said initial and response conditions; and a control assembly having an operator input receiving input data including said predetermined target temperature level, the time interval duration of therapy application at said target temperature level, said operator input including an operator actuable start therapy input and an operator actuable stop therapy input, said control assembly comprising a controller responsive to said start therapy input to effect controlled actuation of said heating assembly and controlled enablement of said implant monitor, responsive to a said monitor condition corresponding with said extra body discernable response condition to commence time-out of said time interval duration of therapy application at said target temperature level, responsive at the completion of said time interval to de-actuate said heating assembly, and responsive to said stop therapy input to de-actuate said heating assembly.

88. The system of claim 87 in which:

said control assembly controller is responsive to a said start therapy input occurring subsequently to a stop therapy input within a given therapeutic procedure to recommence controlled actuation of said heating assembly and is further responsive to a said monitor condition corresponding with said response condition to carry out timing of said time interval duration of therapy application at said target temperature level.

89. The system of claim 87 in which:

said control assembly operator input data includes a maximum time input corresponding with a maximum time allotted to reach said target temperature level commencing with said actuation of said heating assembly, said control assembly includes a time cuing alert actuable to provide an operator perceptible cuing output, and said controller is responsive to said maximum time input and said time interval duration of therapy to actuate said cuing device upon the occurrence of a time-out of said maximum time-out prior to the occurrence of a time-out of said time interval duration of therapy.

90. The system of claim 87 in which:

said control assembly includes an implant monitor enablement check network having a monitor fault output when said implant monitor is inoperative and a monitor fault cue alert readout actuable to provide an operator perceptible monitor fault cue; and said controller is responsive to said enablement check network monitor fault output to actuate said monitor fault cue alert readout.

91. The system of claim 87 in which:

said control assembly includes a heater assembly enablement check network having a heater fault output when said heater assembly is inoperative and a heater fault cue alert readout actuable to provide an operator perceptible heater fault cue; and said controller is responsive to said heater fault output to actuate said heater fault cue alert readout.

92. The system of claim 87 in which said control assembly further comprises:

a data log assembly for recording in memory for each procedure carried out by said control assembly, patient identification, and said input data.

93. The system of claim 87 in which:

said tetherless implant comprises a ferromagnetic material exhibiting a Curie transition temperature substantially corresponding with said target temperature level;

said implant monitor comprises a magnetometer having a first monitor condition in the presence of a magnetic field confrontation with said implant when said implant temperature is below said Curie transition temperature and having a second monitor condition when said implant is at a temperature corresponding with said Curie transition temperature; and said control assembly controller is responsive to said first monitor condition to actuate said heating assembly for a first interval of time, is responsive at the termination of said first interval of time to de-actuate said heating assembly and to enable said implant monitor for a second interval of time less than said first interval of time, and is responsive at the termination of said second internal of time in the presence of said first monitor condition to actuate said heating assembly for said first interval of time.

94. The system of claim 87 in which:

said control assembly is responsive to said monitor condition corresponding with said implant initial condition to actuate said heating assembly for a first interval of time, is responsive at the termination of said first interval of time to de-actuate said heating assembly and to enable said implant monitor, and is responsive to defer dis-enablement of said implant monitor and associated actuation of said heating assembly in the presence of a said monitor condition corresponding with said response condition.

95. The system of claim 87 in which:

said control assembly is responsive to said monitor condition corresponding with said implant initial condition to actuate said heating assembly for a first interval of time, is responsive at the termination of said first interval of time to de-actuate said heating assembly and to enable said implant monitor for a second interval of time less than said first interval of time, and is responsive at the termination of said second interval of time in the presence of said monitor condition corresponding with implant initial condition to actuate said heating assembly for said first interval of time.

96. The system of claim 93, in which:

said first interval of time of actuating said heating assembly is within a range from about 0.01 second to about 30 seconds.

97. The system of claim 93 in which:

said first interval of time of actuating said heating assembly is within a range from about 0.05 second to about 5 seconds.

98. The system of claim 93 in which:

said second interval of time during which said implant monitor is enabled is from about 0.005 second to about 5 seconds.

99. The system of claim 93 in which:

said second interval of time during which said implant monitor is enabled is from about 0.02 second to about 1 second.

100. The system of claim 87 in which:

said control assembly controller is responsive to said monitor condition corresponding with said implant initial condition to actuate said heating assembly for a first interval of time, is responsive at the termination of said first interval of time to de-actuate said heating assembly and to enable said implant monitor, and is responsive to defer dis-enablement of said implant monitor and associated actuation of said heating assembly in the presence of a said monitor condition corresponding with said response condition.

101. The system of claim 87 in which:

said control assembly controller is responsive to said monitor condition corresponding with said implant initial condition to actuate said heating assembly for a first interval of time, is responsive at the termination of said first interval of time to de-actuate said heating assembly and to enable said implant monitor for a second interval of time less than said first interval of time, and is responsive at the termination of said second interval of time in the presence of said monitor condition corresponding with implant initial condition to actuate said heating assembly for said first interval of time.

102. The system of claim 87 in which:

said control assembly further comprises a visually perceptible display responsive to a readout input to provide a visual display; and said control assembly controller is responsive to a said monitor condition corresponding with said extra body discernable response condition to commence time-out of said time interval duration of therapy and derive said readout inputs corresponding therewith.

* * * * *